United States Patent
Luck et al.

(10) Patent No.: US 9,175,304 B2
(45) Date of Patent: Nov. 3, 2015

(54) DROUGHT TOLERANT PLANTS AND RELATED CONSTRUCTS AND METHODS INVOLVING GENES ENCODING SELF-INCOMPATIBILITY PROTEIN RELATED POLYPEPTIDES

(75) Inventors: Stanley Luck, Wilmington, DE (US); Jeffrey Mullen, Maple Plain, MN (US); Hajime Sakai, Newark, DE (US); Scott V. Tingey, Wilmington, DE (US); Robert Wayne Williams, Hockessin, DE (US)

(73) Assignees: E I DU PONT DE NEMOURS AND COMPANY, Wilmington, DE (US); PIONEER HI-BRED INTERNATIONAL INC., Johnston, IA (US)

(*) Notice: Subject to any disclaimer, the term of this patent is extended or adjusted under 35 U.S.C. 154(b) by 612 days.

(21) Appl. No.: 13/501,462

(22) PCT Filed: Oct. 5, 2010

(86) PCT No.: PCT/US2010/051418
§ 371 (c)(1),
(2), (4) Date: Apr. 12, 2012

(87) PCT Pub. No.: WO2011/046772
PCT Pub. Date: Apr. 21, 2011

(65) Prior Publication Data
US 2012/0204288 A1    Aug. 9, 2012

Related U.S. Application Data

(60) Provisional application No. 61/251,982, filed on Oct. 15, 2009.

(51) Int. Cl.
*C12N 15/82* (2006.01)

(52) U.S. Cl.
CPC .................. *C12N 15/8273* (2013.01)

(58) Field of Classification Search
None
See application file for complete search history.

(56) References Cited

U.S. PATENT DOCUMENTS 6,855,866 B1   2/2005  Weterings et al.

FOREIGN PATENT DOCUMENTS

| EP | 1033045 A2 | 6/2000 |
| EP | 2543735 A1 | 9/2013 |

OTHER PUBLICATIONS

Hillbrecht et al. Retrotransposons and siRNA have a role in the evolution of desiccation tolerance leading to resurrection of the plant Craterostigma plantagineum. New Phytologist, vol. 179, No. 3, pp. 877-887.*

Furini et al. High level transcription of a member of a repeated gene family confers dehydration tolerance to callus tissue of Craterostigma plantagineum. EMBO J., vol. 16, No. 12, 1997, pp. 3599-3608.*

Smith-Espinoza et al. Identification of further Craterostigma plantagineum cdt mutants affected in abscisic acid mediated desiccation tolerance. Molecular Genetics and Genomics, vol. 274, No. 4, 2005, pp. 364-372.*

Murfett et al. S-RNase expressed in transgenic Nicotiana causes S-allele-specific pollen rejection. Nature. Feb. 10, 1994;367(6463):563-6.*

Whisstock J.C. et al. Prediction of protein function from protein sequence and structure. Q Rev Biophys. Aug. 2003;36(3):307-40.*

J. S. Boyer, Plant Productivity and Environment, Science, Oct. 29, 1982, pp. 443-448, vol. 218.

Elizabeth A. Bray, Molecular Responses to Water Deficit, Plant Physiol., 1993, pp. 1035-1040, vol. 103.

M. M. Chaves and M. M. Oliveira, Mechanisms underlying plant resilience to water deficits: prospects for water-saving agriculture, Journal of Experimental Botany, Nov. 2004, pp. 2365-2384, vol. 55, No. 407.

C. J. Smith-Espinoza et al., Identification of further Craterostigma plantagineum cdt mutants affected in abscisic acid mediated desiccation tolerance, Mol. Gen. Genomics, 2005, pp. 364-372, vol. 274.

Humphrey C. Foote At Al., Cloning and expression of a distinctive class of self-incompatibility (S) gene from Papaver rhoeas L., Proc. Natl. Acad. Sci. USA, Mar. 1994, pp. 2265-2269, vol. 91.

Antonella Furini et al., High level transcription of a member of a repeated gene family confers dehyfration tolerance to callus tissue of Craterostigma plantagineum, The EMBO Journal, 1997, pp. 3599-3608, vol. 16, No. 12.

Antonella Furini, CDT retroelement, Plant Signaling & Behavior, Dec. 2008, pp. 1129-1131, vol. 3, No. 12.

Tobia Hilbricht et al., Retrotransposons and siRNA have a role in the evolution of desiccation tolerance leading to resurrection of the plant Craterostigma plantagineum, New Phytologist, 2008, pp. 877-887, vol. 179.

Daniel P. Matton et al., Self-incompatibility: How Plants avoid illegitimate offspring, Proc. Natl. Acad. Sci. USA, Mar. 1994, pp. 1992-1997, vol. 91.

S. Ramanjulu et al., Drought- and desiccation-induced modulation of gene expression in plants, Plant, Cell and Environment, 2002, pp. 141-151.

Kazuo Shinozaki and Kazuko Yamaguchi-Shinozaki, Gene Expression and Signal Transduction in Water-Stress Response, Plant Physiol., 1997, pp. 327-334, vol. 115.

Kazuo Shinozaki et al., Regulatory network of gene expression in the drought and cold stress responses, Current Opinion in Plant Biology, 2003, pp. 410-417, vol. 6.

Kazuko Yamaguchi-Shinozaki et al., Organization of cis-acting regulatory elements in osmotic- and cold-stress-responsive promoters, TRENDS in Plant Science, Feb. 2005, pp. 88-93, vol. 10, No. 2.

(Continued)

*Primary Examiner* — Cynthia Collins

(57) ABSTRACT

Isolated polynucleotides and polypeptides and recombinant DNA constructs useful for conferring drought tolerance, compositions (such as plants or seeds) comprising these recombinant DNA constructs, and methods utilizing these recombinant DNA constructs. The recombinant DNA construct comprises a polynucleotide operably linked to a promoter that is functional in a plant, wherein said polynucleotide encodes an SIPR polypeptide.

14 Claims, 21 Drawing Sheets

(56) References Cited

OTHER PUBLICATIONS

Michael F. Thomashow, Plant Cold Acclimation: Freezing Tolerance Genes and Regulatory Mechanisms, Annu. Rev. Plant Physiol. Plant Mol. Biol. 1999, pp. 571-599, vol. 50.

Babu Valliyodan and Henry T. Nguyen, Understanding regulatory networks and engineering for enhanced drought tolerance in plants, Current Opinion in Plant Biology, 2006, pp. 189-195, vol. 9.

Basia Vinocur and Arie Altman, Recent advances in engineering plant tolerance to abiotic stress: achievements and limitations, Current Opinion in Biotechnology, 2005, pp. 123-132, vol. 16.

Wangxia Wang et al., Plant responses to drought, salinity and extreme temperatures: towards genetic engineering for stress tolerance, Planta, 2003, pp. 1-14, vol. 218.

D. Weigel At Al., Activation Tagging in Arabidopsis, Plant Physiology, Apr. 2000, pp. 1003-1013, vol. 122.

M. J. Wheeler et al., Genomic organization of the Papaver rhoeas self-incompatibility $S_1$ locus, Journal of Experimental Botany, Jan. 2003, pp. 131-139, vol. 54, No. 380.

Liming Xiong and Jian-Kang Zhu, Abiotic stress signal transduction in plants: Molecular and genetic perspectives, Physiologia Plantarum, 2001, pp. 152-166, vol. 112.

Jian-Kang Zhu et al., Molecular Aspects of Osmotic Stress in Plants, Critical Reviews in Plant Sciences, 1997, pp. 253-277, vol. 16:3.

National Center for Biotechnology Information Gl No. 30689649, A. Theologis et al., Jan. 22, 2014, Sequence and analysis of chromosome 1 of the plant Arabidopsis thaliana, Accession No. NM_179378.

National Center for Biotechnology Information Gl No. 30689650, A. Theologis et al., Jan. 22, 2014, Sequence and analysis of chromosome 1 of the plant Arabidopsis thaliana, Accession No. NP_849709.

National Center for Biotechnology Information Gl No. 145362293, A. Theologis et al., Jan. 22, 2014, Sequence and analysis of chromosome 1 of the plant Arabidopsis thaliana, Accession No. NM_202188.

National Center for Biotechnology Information Gl No. 42571653, A. Theologis et al., Jan. 22, 2014, Sequence and analysis of chromosome 1 of the plant Arabidopsis thaliana, Accession No. NP_973917.

National Center for Biotechnology Information Gl No. 79318656, A. Theologis et al., Jan. 22, 2014, Sequence and analysis of chromosome 1 of the plant Arabidopsis thaliana, Accession No. NM_001036018.

National Center for Biotechnology Information Gl No. 79318657, A. Theologis et al., Jan. 22, 2014, Sequence and analysis of chromosome 1 of the plant Arabidopsis thaliana, Accession No. NM_001031095.

National Center for Biotechnology Information Gl No. 18396056, A. Theologis et al., Jan. 22, 2014, Sequence and analysis of chromosome 1 of the plant Arabidopsis thaliana, Accession No. NM_102443.

National Center for Biotechnology Information Gl No. 18396057, A. Theologis et al., Jan. 22, 2014, Sequence and analysis of chromosome 1 of the plant Arabidopsis thaliana, Accession No. NP_564262.

National Center for Biotechnology Information Gl No. 18416755, Jan. 22, 2014, Accession No. NM_121244.

National Center for Biotechnology Information Gl No. 15239857, Jan. 22, 2014, Accession No. NP_196767.

National Center for Biotechnology Information Gl No. 79315207, Jan. 22, 2014, M. Salanoubat et al., Sequence and analysis of chromosome 3 of the plant Arabidopsis thaliana, Accession No. NM_001035789.

National Center for Biotechnology Information Gl No. 79315208, Jan. 22, 2014, M. Salanoubat et al., Sequence and analysis of chromosome 3 of the plant Arabidopsis thaliana, Accession No. NM_001030866.

National Center for Biotechnology Information Gl No. 297850998, E. Bakker et al., The basis of rapid genome size change in Arabidopsis, Jun. 11, 2010, Accession No. XP002893380.

National Center for Biotechnology Information Gl No. 270257654, O. Jaillon et al., The grapevine genome sequence suggests ancestral hexaploidization in major angiosperm phyla, May 16, 2010, Accession No. FN_596747.

National Center for Biotechnology Information Gl No. 270257838, O. Jaillon et al., The grapevine genome sequence suggests ancestral hexaploidization in major angiosperm phyla, Nov. 25, 2009, Accession No. CBI_39880.

National Center for Biotechnology Information Gl No. 3766801, Apr. 1, 2002, Accession No. AU_030911.

E. A. Bray et al., In Biochemistry and Molecular Biology of Plants, 2000, Edited by B. B. Buchannan et al., Amer. Soc. Plant Biol. pp. 1158-1249 (book not included).

National Center for Biotechnology Information Gl No. 224118733, G. A. Tuskan et al., Feb. 26, 2009, Accession No. XM_002331397.

National Center for Biotechnology Information Gl No. 224118734, G. A. Tuskan et al., Feb. 26, 2009 Accession No. XP_002331433.

International Search Report—PCT/US2010/051418.

* cited by examiner

FIG. 12

| | 1 | 2 | 3 | 4 | 5 | 6 | 7 | 8 | 9 | 10 | 11 | 12 | 13 | 14 | 15 | |
|---|---|---|---|---|---|---|---|---|---|---|---|---|---|---|---|---|
| 15 | 66.4 | 72.2 | 76.5 | 84.1 | 26.7 | 31.5 | 100.0 | 22.2 | 24.2 | 84.1 | 26.7 | 30.1 | 25.5 | 25.2 | | 15 |
| 14 | 25.2 | 28.1 | 26.7 | 26.7 | 30.4 | 23.7 | 24.4 | 29.6 | 33.3 | 26.7 | 30.4 | 22.2 | 34.8 | | 167.3 | 14 |
| 13 | 26.4 | 25.2 | 27.8 | 25.8 | 36.0 | 21.1 | 25.8 | 29.2 | 29.8 | 25.8 | 36.0 | 19.3 | | 112.6 | 183.5 | 13 |
| 12 | 30.0 | 32.5 | 31.8 | 35.8 | 24.7 | 61.8 | 35.8 | 21.5 | 20.5 | 35.8 | 24.7 | | 146.8 | 147.5 | 113.9 | 12 |
| 11 | 27.9 | 26.7 | 24.7 | 24.7 | 100.0 | 22.7 | 24.7 | 27.1 | 28.0 | 24.7 | | 122.1 | 99.0 | 120.6 | 144.4 | 11 |
| 10 | 59.3 | 60.9 | 80.1 | 100.0 | 24.7 | 36.4 | 62.3 | 20.8 | 25.8 | | 185.4 | 152.9 | 271.0 | 296.0 | 15.4 | 10 |
| 9 | 27.1 | 27.2 | 25.8 | 25.8 | 28.0 | 22.4 | 25.2 | 32.6 | | 191.1 | 134.5 | 185.9 | 117.7 | 104.3 | 161.1 | 9 |
| 8 | 24.3 | 23.6 | 21.5 | 20.8 | 27.1 | 21.5 | 25.0 | | 104.1 | 286.0 | 133.0 | 171.9 | 132.3 | 121.4 | 175.2 | 8 |
| 7 | 56.4 | 55.6 | 62.9 | 62.3 | 24.7 | 31.8 | | 173.5 | 282.0 | 40.0 | 140.9 | 89.2 | 195.0 | 152.3 | 0.0 | 7 |
| 6 | 29.3 | 29.8 | 33.1 | 36.4 | 22.7 | | 94.8 | 150.8 | 144.2 | 122.3 | 119.0 | 42.2 | 131.9 | 136.8 | 110.5 | 6 |
| 5 | 27.9 | 26.7 | 24.7 | 24.7 | | 119.0 | 140.9 | 133.0 | 134.5 | 185.4 | 0.0 | 122.1 | 99.0 | 120.6 | 144.4 | 5 |
| 4 | 59.3 | 60.9 | 80.1 | | 185.4 | 122.3 | 40.0 | 296.0 | 191.1 | 0.0 | 185.4 | 152.9 | 271.0 | 296.0 | 15.4 | 4 |
| 3 | 60.0 | 60.3 | | 23.1 | 208.0 | 129.8 | 40.0 | 246.0 | 217.0 | 23.1 | 208.0 | 152.9 | 362.0 | 246.0 | 28.7 | 3 |
| 2 | 82.9 | | 61.9 | 61.9 | 220.0 | 122.5 | 40.7 | 135.1 | 140.9 | 61.9 | 220.0 | 112.9 | 276.0 | 285.0 | 28.7 | 2 |
| 1 | | 18.6 | 60.0 | 66.2 | 233.0 | 145.3 | 43.9 | 140.9 | 140.9 | 66.2 | 233.0 | 119.0 | 186.7 | 220.0 | 37.1 | 1 |
| | 1 | 2 | 3 | 4 | 5 | 6 | 7 | 8 | 9 | 10 | 11 | 12 | 13 | 14 | 15 | |

Percent Identity

SEQ ID 18.pro
SEQ ID 20.pro
SEQ ID 22.pro
SEQ ID 24.pro
SEQ ID 26.pro
SEQ ID 28.pro
SEQ ID 30.pro
SEQ ID 32.pro
SEQ ID 34.pro
SEQ ID 35.pro
SEQ ID 36.pro
SEQ ID 37.pro
SEQ ID 38.pro
SEQ ID 39.pro
SEQ ID 40.pro

ID POLYPEPTIDES

CROSS REFERENCE TO RELATED APPLICATIONS

This application is a 371 national stage entry of International Application No. PCT/US10/51418, filed Oct. 5, 2010, now expired, which claims the benefit of U.S. Provisional Application No. 61/251982, filed Oct. 15, 2009, now expired, the entire content of each is herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named "20120412_BB1724USPCT_SEQListing" created on Sep. 28, 2010, and having a size of 305 kilobytes and is filed concurrently with the specification. The sequence listing contained in this ASCII formatted document is part of the specification and is herein incorporated by reference in its entirety.

FIELD OF THE INVENTION

The field of invention relates to plant breeding and genetics and, in particular, relates to recombinant DNA constructs useful in plants for conferring tolerance to drought.

BACKGROUND OF THE INVENTION

Abiotic stress is the primary cause of crop loss worldwide, causing average yield losses of more than 50% for major crops (Boyer, J. S. (1982) Science 218:443-448; Bray, E. A. et al. (2000) In Biochemistry and Molecular Biology of Plants, Edited by Buchannan, B. B. et al., Amer. Soc. Plant Biol., pp. 1158-1249). Among the various abiotic stresses, drought is the major factor that limits crop productivity worldwide. Exposure of plants to a water-limiting environment during various developmental stages appears to activate various physiological and developmental changes. Understanding of the basic biochemical and molecular mechanism for drought stress perception, transduction and tolerance is a major challenge in biology. Reviews on the molecular mechanisms of abiotic stress responses and the genetic regulatory networks of drought stress tolerance have been published (Valliyodan. B., and Nguyen, H. T., (2006) Curr. Opin. Plant Biol. 9:189-195; Wang, W., at al. (2003) Planta 218:1-14); Vinocur, B., and Altman, A. (2005) Curr. Opin. Biotechnol, 16:123-132; Chaves, M. M., and Oliveira, M. M. (2004) J. Exp. Bat. 55:2365-2384; Shinozaki, K., et al. (2003) Curr. Opin. Plant Biol. 6:410-417; Yamaguchi-Shinozaki, K., and Shinozaki, K. (2005) Trends Plant Sci. 10:88-94).

Earlier work on molecular aspects of abiotic stress responses was accomplished by differential and/or subtractive analysis (Bray, E. A. (1993) Plant Physiol. 103:1035-1040; Shinozaki, K., and Yamaguchi-Shinozaki, K. (1997) Plant Physiol. 115:327-334; Zhu, J.-K. et al. (1997) Crit. Rev. Plant Sci. 16:253-277; Thomashow, M. F. (1999) Annu. Rev. Plant Physiol. Plant Mol. Biol. 50:571-599). Other methods include selection of candidate genes and analyzing expression of such a gene or its active product under stresses, or by functional complementation in a stressor system that is well defined (Xiang, L., and Zhu, J.-K. (2001) Physiologia Plantarum 112:152-166). Additionally, forward and reverse genetic studies involving the identification and isolation of mutations in regulatory genes have also been used to provide evidence for observed changes in gene expression under stress or exposure (Xiang, L., and Zhu, J.-K. (2001) Physiologia Plantarum 112:152-166).

Activation tagging can be utilized to identify genes with the ability to affect a trait. This approach has been used in the model plant species *Arabidopsis thaliana*(Weigel, D., et al. (2000) Plant Physiol. 122:1003.-1013). Insertions of transcriptional enhancer elements can dominantly activate and/or elevate the expression of nearby endogenous genes. This method can be used to select genes involved in agronomically important phenotypes, including stress tolerance.

SUMMARY OF THE INVENTION

The Present Invention Includes:

In one embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NOS: 18, 20, 22, 24, 26, 28, 30, 32 or 34 and wherein said plant exhibits increased drought tolerance when compared to a control plant not comprising said recombinant DNA construct.

In another embodiment, a method of increasing drought tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NOS: 18, 20, 22, 24, 26, 28, 30, 32 or 34; (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct; and optionally, (c) obtaining a progeny plant derived from the transgenic plant, wherein said progeny plant comprises in its genome the recombinant DNA construct and exhibits increased drought tolerance when compared to a control plant not comprising the recombinant DNA construct.

In another embodiment, a method of evaluating drought tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NOS; 18, 20, 22, 24, 26, 28, 30, 32 or 34; (b) regenerating a transgenic plant from the regenerable plant cell after step (a), wherein the transgenic plant comprises in its genome the recombinant DNA construct; and (c) evaluating the transgenic plant for drought tolerance compared to a control plant not comprising the recombinant DNA construct; and optionally, (d) obtaining a progeny plant derived from the transgenic plant, wherein the progeny plant comprises in its genome the recombinant DNA construct; and optionally, (e) evaluating the progeny plant for drought tolerance compared to a control plant not comprising the recombinant DNA construct.

In a further embodiment, a method of evaluating drought tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NOS: 18, 20, 22, 24, 26, 28, 30, 32 or 34; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for drought tolerance compared to a control plant not comprising the recombinant DNA construct.

In another embodiment, the present invention includes any of the methods of the present invention wherein the plant is a maize plant or a soybean plant.

In another embodiment, the present invention includes an isolated polynucleotide comprising: (a) a nucleotide sequence encoding a Self-Incompatibility Related Polypeptide (SIPR) polypeptide, wherein the polypeptide has an amino acid sequence of at least 90% or 95% sequence identity, based on the Clustal V method of alignment, when compared to one of SEQ ID NOS: 18, 20, 22, 24, 26, 28, 30, 32 or 34, or (b) a full complement of the nucleotide sequence, wherein the full complement and the nucleotide sequence consist of the same number of nucleotides and are 100% complementary. The polypeptide may comprise the amino acid sequence of SEQ ID NOS: 18, 20, 22, 24, 26, 28, 30, 32 or 34. The nucleotide sequence may comprise the nucleotide sequence of SEQ ID NOS: 17, 19, 21, 23, 25, 27, 29, 31 or 33.

In another embodiment, the present invention concerns a recombinant DNA construct comprising any of the isolated polynucleotides of the present invention operably linked to at least one regulatory sequence, and a cell, a plant, and a seed comprising the recombinant DNA construct.

In another embodiment, the present invention includes a vector comprising any of the isolated polynucleotides of the present invention.

In another embodiment, the present invention concerns a cell, plant or seed comprising any of the recombinant DNA constructs of the present invention. The cell may be eukaryotic, e.g., a yeast, insect or plant cell, or prokaryotic, e.g., a bacterium.

BRIEF DESCRIPTION OF THE DRAWINGS AND SEQUENCE LISTING

The invention can be more fully understood from the following detailed description and the accompanying drawings and Sequence Listing which form a part of this application.

Figure 1:
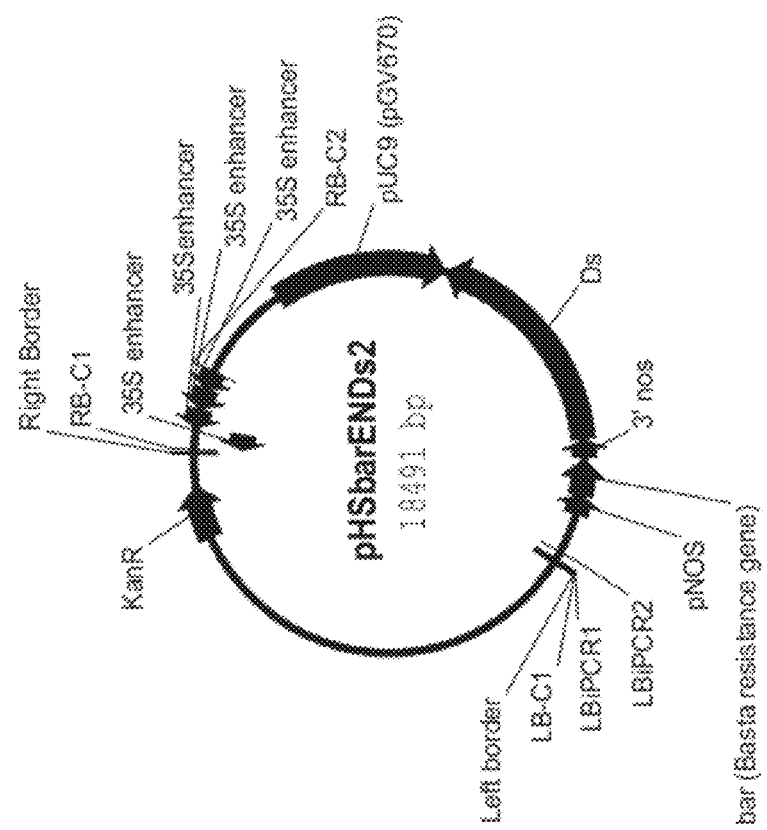
FIG. 1 shows a schematic of the pHSbarENDs2 activation tagging construct (SEQ ID NO: 1) used to make the *Arabidopsis* populations.

FIGS. 11A-11J present an alignment of the amino acid sequences of SIPR polypeptides set forth in SEQ ID NOS: 18, 20, 22, 24, 26, 28, 30, 32, 34-40.

FIG. 12 presents the percent sequence identities and divergence values for each sequence pair presented in FIG. 11A-11J.

SEQ ID NO: 1 is the nucleotide sequence of the pHSbarENDs2 activation tagging vector.

SEQ ID NO: 2 is the nucleotide sequence of the GATEWAY® donor vector pDONR™/Zeo.

SEQ ID NO: 3 is the nucleotide sequence of the GATEWAY® donor vector pDONR™221.

SEQ ID NO:4 is the nucleotide sequence of pBC-yellow, a destination vector for use with *Arabidopsis*.

SEQ ID NO:5 is the nucleotide sequence of PHP27840, a destination vector for use with soybean.

SEQ ID NO:6 is the nucleotide sequence of PHP23236, a destination vector for use with Gaspe Flint derived maize lines.

SEQ ID NO:7 is the nucleotide sequence of PHP10523 (Komari et al., *Plant J.* 10:165-174 (1996); NCBI General Identifier No. 59797027).

SEQ ID NO:8 is the nucleotide sequence of PHP23235, a destination vector for use with Gaspe Hint derived lines.

SEQ ID NO:9 is the nucleotide sequence of PHP28647, a destination vector for use with maize inbred-derived lines.

SEQ ID NO:10 is the nucleotide sequence of the attB1 site.

SEQ ID NO:11 is the nucleotide sequence of the attB2 site.

SEQ ID NO:12 is the nucleotide sequence of the At1g26797-5'attB forward primer, containing the attB1 sequence, used to amplify the At1g26797 protein-coding region.

SEQ ID NO:13 is the nucleotide sequence of the At1g26797-3'attB reverse primer, containing the attB2 sequence, used to amplify the At1g26797 protein-coding region.

SEQ ID NO:14 is the nucleotide sequence of the VC062 primer, containing the T3 promoter and attB1 site, useful to amplify cDNA inserts cloned into a BLUESCRIPT® II SK(+) vector (Stratagene).

SEQ ID NO: 15 is the nucleotide sequence of the VC063 primer, containing the T7 promoter and attB2 site, useful to amplify cDNA inserts cloned into a BLUESCRIPT® II SK(+) vector (Stratagene).

SEQ ID NO: 16 is the nucleotide sequence of PHP29634 (also called DV11), a destination vector for use with Gaspe Flint derived maize lines.

SEQ ID NO: 17 corresponds to NCBI GI No. 30689649, which is the nucleotide sequence from locus At1g26797 encoding an *Arabidopsis* self-incompatibility related polypeptide (*Arabidopsis thaliana*).

SEQ ID NO: 18 corresponds NCBI GI NO. 30689650, which is the amino acid sequence encoded by SEQ ID NO: 17 (*Arabidopsis thaliana*).

SEQ ID NO: 19 corresponds to NCBI GI No. 145362293, which is the nucleotide sequence from the locus At1g26798 (*Arabidopsis thaliana*).

SEQ ID NO: 20 corresponds to NCBI GI No. 42571653, which is the amino acid sequence encoded by the nucleotide sequence of SEQ ID NO: 19 (*Arabidopsis thaliana*).

SEQ ID NO: 21 corresponds to NCBI GI No, 79318656, which is the nucleotide sequence from the locus At1g26796 (*Arabidopsis thaliana*).

SEQ ID NO: 22 corresponds to NCBI GI No. 79318657, which is the amino add sequence encoded by the nucleotide sequence of SEQ ID NO: 21 (*Arabidopsis thaliana*).

SEQ ID NO: 23 corresponds to NCBI GI No. 18396056, which is the nucleotide sequence from the locus At1g26795 (*Arabidopsis thaliana*).

SEQ ID NO: 24 corresponds to NCBI GI No, 18396057, which is the amino acid sequence encoded by the nucleotide sequence of SEQ ID NO: 23 (*Arabidopsis thaliana*).

SEQ ID NO: 25 corresponds to NCBI GI No. 18416755, which is the nucleotide sequence from the locus At5g12060 (*Arabidopsis thaliana*).

SEQ ID NO: 26 corresponds to NCBI GI No. 15239857, which is the amino acid sequence encoded by the nucleotide sequence of SEQ ID NO: 25 (*Arabidopsis thaliana*).

SEQ ID NO: 27 corresponds to NCBI GI No. 79315207, which is the nucleotide sequence from the locus At3g55677 (*Arabidopsis thaliana*).

SEQ ID NO: 28 corresponds to NCBI GI No. 79315208, which is the amino acid sequence encoded by the nucleotide sequence of SEQ ID NO: 27 (*Arabidopsis thaliana*).

SEQ ID NO: 29 corresponds to an *Arabidopsis lyrata* sequence, encoding a DTP10 polypeptide (*Arabidopsis lyrata* subsp. *lyrata*). It encodes a truncated form of the publicly available *Arabidopsis lyrata* sequence presented in NCBI GI No. 297850998.

SEQ ID NO: 30 corresponds to the amino acid sequence encoded by the nucleotide sequence of SEQ ID NO: 29 (*Arabidopsis lyrata* subsp. *lyrata*). It is a truncated form of the sequence presented in NCBI GI NO. 297850998.

SEQ ID NO: 31 corresponds to NCBI GI No. 224118733, which is a nucleotide sequence encoding a DTP10 polypeptide (*Populus trichocarpa*).

SEQ ID NO: 32 corresponds to NCBI GI No. 224118734, which is the amino acid sequence encoded by the nucleotide sequence of SEQ ID NO: 31 (*Populus trichocarpa*).

SEQ ID NO: 33 corresponds to nucleotides 3234493-3234978 of NCBI GI NO: 270257654 (*Vitis vinifera*).

SEQ ID NO: 34 corresponds to NCBI GI No. 270257838, which is the amino acid sequence encoded by the nucleotide sequence of SEQ ID NO: 33 (*Vitis vinifera*).

SEQ ID NO: 35 is the amino add sequence presented in SEQ ID NO: 18685 of EP Patent Publication No. EP1033405 (*Arabidopsis thaliana*).

SEQ ID NO: 36 is the amino acid sequence presented in SEQ ID NO: 49855 of EP Patent Publication No. EP2152891 (*Arabidopsis thaliana*).

SEQ ID NO: 37 is the amino acid sequence presented in SEQ ID NO: 226 of EP Patent Publication No. EP1033405 (*Arabidopsis thaliana*).

SEQ ID NO: 38 is the amino acid sequence presented in SEQ ID NO: 9 of U.S. Pat. No. 6,855,866 (*Arabidopsis thaliana*).

SEQ ID NO: 39 is the amino acid sequence presented in SEQ ID NO: 12314 of EP Patent Publication No. EP2152891 (*Arabidopsis thaliana*).

SEQ ID NO: 40 corresponds to NCBI GI No. 297850998 (*Arabidopsis lyrata* subsp. *lyrata*).

The sequence descriptions and Sequence Listing attached hereto comply with the rules governing nucleotide and/or amino acid sequence disclosures in patent applications as set forth in 37 C.F.R. §1.821-1825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 4:345-373 (1984) which are herein incorporated by reference. The symbols and format used for nucleotide and amino acid sequence data comply with the rules set forth in 37 C.F.R. §1.822.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As Used Herein:

The terms "AT-Self-incompatibilty protein related polypeptide", "AT-SIPR polypeptide", "AT-Drought Tolerant Phenotype 10 polypeptide" and "AT-DTP10 polypeptide" are used interchangeably herein and refer to an *Arabidopsis thaliana* protein encoded by the *Arabidopsis thaliana* locus At1g26797.

The terms "Self-incompatibilty protein related polypeptide", "SIPR polypeptide", "Drought Tolerant Phenotype 10 polypeptide" and "DTP10 polypeptide" are used interchangeably herein and refer to homologs of At-DTP10.

"Self-incompatibility protein-related polypeptides" refers to a family of proteins that are related to the self-incompatibility protein S1 of Papaver Rhoeas. (Foote H C, Ride J P, Franklin-Tong V E, Walker E A, Lawrence M J, Franklin F C; Proc Natl Acad Sci USA 1994; 91:2265-2269. Cloning and expression of a distinctive class of self-incompatibility (S) gene from *Papaver rhoeas* L.).

Self-Incompatibility (SI) is the incapability of apparently healthy plants to produce seed when self-pollinated. This inhibition of self-fertilization in some flowering plants occurs by a recognition mechanism wherein the plants are able to distinguish between self and non-self pollen. SI systems in most flowering plants are controlled by a single multi-allele locus termed the S-locus. In Papaver Rhoeas the SI response takes place at the stigma surface and is mediated by a complex signaling cascade involving a transient increase in Ca2+ and protein phopshorylation. This response is initiated following interaction between S-proteins secreted by the stigma and their cognate receptors in the pollen tube. The S-proteins are small, signaling molecules that can presumably bind to a receptor on the pollen, leading to intracellular signaling that ultimately leads to inhibition of pollen tube growth. The function of the SIPR proteins in *Arabidopsis thaliana* is not known, since it is a self-fertilizing plant (Mallen at al *Proc. Natl. Acad. Sci.*, 1994, vol. 91, pp 1992-1997; Foote et al. *Proc. Natl. Acad. Sci.*, 1994, vol. 91, pp. 2265-2269; Wheeler et al., *J. Exp. Botany*, 2003, vol. 54 (380), pp. 131-139).

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Agronomic characteristic" is a measurable parameter including but not limited to, greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, early seedling vigor and seedling emergence under low temperature stress.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques.

"Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry done" and "entry vector" are used interchangeably herein.

"Regulatory sequences" refer to nucleotide sequences located upstream (5' non-coding sequences), within, or downstream (3' non-coding sequences) of a coding sequence, and which influence the transcription. RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632). A "mitochondrial signal peptide" is an amino acid sequence which directs a precursor protein into the mitochondria (Zhang and Glaser (2002) *Trends Plant Sci* 7:14-21).

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press Cold Spring Harbor, 1989 (hereinafter "Sambrook").

Turning Now to the Embodiments:

Embodiments include isolated polynucleotides and polypeptides, recombinant DNA constructs useful for conferring drought tolerance, compositions (such as plants or seeds) comprising these recombinant DNA constructs, and methods utilizing these recombinant DNA constructs.

Isolated Polynucleotides and Polypeptides:

The present invention includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. The polypeptide is preferably an SIPR polypeptide.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34. The polypeptide is preferably an SIPR polypeptide.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to 17, 19, 21, 23, 25, 27, 29, 31 or 33; or (ii) a full complement of the nucleic acid sequence of (i). Any of the foregoing isolated polynucleotides may be utilized in any recombinant DNA constructs (including suppression DNA constructs) of the present invention. The isolated polynucleotide preferably encodes an SIPR polypeptide.

Recombinant DNA Constructs and Suppression DNA Constructs:

In one aspect, the present invention includes recombinant DNA constructs (including suppression DNA constructs).

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to 16, 18, 20, 22, 24, 26, 28, 30 or 32; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide encodes an SIPR polypeptide. The SIPR polypeptide may be from *Arabidopsis thaliana*, *Zea mays*, *Glycine max*, *Glycine tabacina*, *Glycine soja* and *Glycine tomentella*.

In another aspect, the present invention includes suppression DNA constructs.

A suppression DNA construct may comprise at least one regulatory sequence (e.g., a promoter functional in a plant) operably linked to (a) all or part of: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34, or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an SIPR polypeptide; or (c) all or part of: (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to 16, 18, 20, 22, 24, 26, 28, 30 or 32, or (ii) a full complement of the nucleic acid sequence of (c)(i). The suppression DNA construct may comprise a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing, "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest. Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5° non-coding sequence, 3° non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

Another variation describes the use of plant viral sequences to direct the suppression of proximal mRNA encoding sequences (POT Publication No, WO 98/36083 published on Aug. 20, 1998).

RNA interference refers to the process of sequence-specific post-transcriptional gene silencing in animals mediated by short interfering RNAs (siRNAs) (Fire et al., *Nature* 391: 806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. In the case of lin-4 and let-7, the target sites are located in the 3' UTRs of the target mRNAs (Lee et al., *Cell* 75:843-854 (1993); Wightman et al., *Cell* 75:855-862 (1993); Reinhart et al., *Nature* 403:901-906 (2000); Slack et al., *Mol. Cell* 5:659-669 (2000)), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros, *Dev. Biol.* 216:671-680 (1999)). On the other hand, recent evidence suggests that miRNAs can in some cases cause specific RNA cleavage of the target transcript within the target site, and this cleavage step appears to require 100% complementarity between the miRNA and the target transcript (Hutvagner and Zamore, *Science* 297:2056-2060 (2002); Llave et al., *Plant Cell* 14:1605-1619 (2002)). It seems likely that miRNAs can enter at least two pathways of target gene regulation: (1) protein downregulation when target complementarity is <100%; and (2) RNA cleavage when target complementarity is 100%. MicroRNAs entering the RNA cleavage pathway are analogous to the 21-25 nt short interfering RNAs (siRNAs) generated during RNA interference (RNAi) in animals and post-transcriptional gene silencing (PTGS) in plants, and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al., *Plant Cell* 14:1605-1619 (2002); Park et al., *Curr. Biol.* 12:1484-1495 (2002); Rhoades et al., *Cell* 110:513-520 (2002)), and thus it appears that plant miRNAs have higher overall complementarity with their putative targets than do animal miRNAs. Most of these predicted target transcripts of plant miRNAs encode members of transcription factor families implicated in plant developmental patterning or cell differentiation.

Regulatory Sequences:

A recombinant DNA construct (including a suppression DNA construct) of the present invention may comprise at least one regulatory sequence.

A regulatory sequence may be a promoter.

A number of promoters can be used in recombinant DNA constructs of the present invention. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga et al. (1999) Nature Biotechnol. 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812 (1985)); rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include soybean Kunitz trypsin inhibitor (Kti3, Jofuku and Goldberg, Plant Cell 1:1079-1093 (1989)), patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259: 149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori. T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., Bio/Technology 7:L929-932 (1989)), bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current invention include the following: 1) the stress-inducible RD29A promoter (Kasuga et al. (1999) Nature Biotechnol. 17:287-91); 2) the barley promoter, B22E; expression of B22E is specific to the pedicel in developing maize kernels ("Primary Structure of a Novel Barley Gene Differentially Expressed in Immature Aleurone Layers". Klemsdal, S. S. et al., Mol. Gen. Genet. 228(1/2):9-16 (1991)); and 3) maize promoter, Zag2 ("Identification and molecular characterization of ZAG1, the maize homolog of the *Arabidopsis* floral homeotic gene AGAMOUS", Schmidt, R. J. et al., Plant Cell 5(7):729-737 (1993); "Structural characterization, chromosomal localization and phylogenetic evaluation of two pairs of AGAMOUS-like MADS-box genes from maize", Theissen et al. Gene 156(2):155-166 (1995); NCBI GenBank Accession No. X80206)). Zag2 transcripts can be detected 5 days prior to pollination to 7 to 8 days after pollination ("DAP"), and directs expression in the carpel of developing female inflorescences and Ciml which is specific to the nucleus of developing maize kernels. Ciml transcript is detected 4 to 5 days before pollination to 6 to 8 DAP. Other useful promoters include any promoter which can be derived from a gene whose expression is maternally associated with developing female florets.

Additional promoters for regulating the expression of the nucleotide sequences of the present invention in plants are stalk-specific promoters. Such stalk-specific promoters include the alfalfa S2A promoter (GenBank Accession No. EF030816; Abrahams et al., Plant Mol. Biol. 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in the current invention may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (Genbank accession number EF030817), and the constitutive promoter GOS2 from Zea mays. Other promoters include root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1BIO promoter (WO06055487, published May 26, 2006), the CRWAQ81 (WO05035770, published Apr. 21, 2005) and the maize ZRP2.47 promoter (NCBI accession number: U38790; GI No. 1063664).

Recombinant DNA constructs of the present invention may also include other regulatory sequences, including but not limited to, translation leader sequences, introns, and polyadenylation recognition sequences. In another embodiment of the present invention, a recombinant DNA construct of the present invention further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, Mol. Cell Biol. 8:4395-4405 (1988); Callis et al., *Genes Dev.* 1:1183-1200 (1987).

Any plant can be selected for the identification of regulatory sequences and SIPR genes to be used in recombinant DNA constructs of the present invention. Examples of suitable plant targets for the isolation of genes and regulatory sequences would include but not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblally pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yarns, and zucchini.

Compositions:

A composition of the present invention is a plant comprising in its genome any of the recombinant DNA constructs (including any of the suppression DNA constructs) of the present invention (such as any of the constructs discussed above). Compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley or millet.

The recombinant DNA construct may be stably integrated into the genome of the plant.

Particularly embodiments include but are not limited to the following:

1. A plant (for example, a maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34, and wherein said plant exhibits increased drought tolerance when compared to a control plant not comprising said recombinant DNA construct. The plant may further exhibit an alteration of at least one agronomic characteristic when compared to the control plant.

2. A plant (for example, a maize or soybean plant) comprising in its genome a recombinant DNA construct comprising a polynucleotide operably linked to at least one regulatory sequence, wherein said polynucleotide encodes an SIPR polypeptide, and wherein said plant exhibits increased drought tolerance when compared to a control plant not comprising said recombinant DNA construct. The plant may further exhibit an alteration of at least one agronomic characteristic when compared to the control plant.

3. A plant (for example, a maize or soybean plant) comprising in its genome a recombinant DNA construct comprising a polynucleotide operably linked to at least one regulatory sequence, wherein said polynucleotide encodes an SIPR polypeptide, and wherein said plant exhibits an alteration of at least one agronomic characteristic when compared to a control plant not comprising said recombinant DNA construct.

4. A plant (for example, a maize or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34, and wherein said plant exhibits an alteration of at least one agronomic characteristic when compared to a control plant not comprising said recombinant DNA construct.

5. A plant (for example, a maize or soybean plant) comprising in its genome a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an SIPR polypeptide, and wherein said plant exhibits an alteration of at least one agronomic characteristic when compared to a control plant not comprising said suppression DNA construct.

6. A plant (for example, a maize or soybean plant) comprising in its genome a suppression DNA construct comprising at least one regulatory element operably linked to all or part of (a) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34, or (b) a full complement of the nucleic acid sequence of (a), and wherein said plant exhibits an alteration of at least one agronomic characteristic when compared to a control plant not comprising said suppression DNA construct.

7. Any progeny of the above plants in embodiments 1-6, any seeds of the above plants in embodiments 1-6, any seeds of progeny of the above plants in embodiments 1-6, and cells from any of the above plants in embodiments 1-6 and progeny thereof.

In any of the foregoing embodiments 1-7 or any other embodiments of the present invention, the SIPR polypeptide may be from *Arabidopsis thaliana, Zea mays, Glycine max, Glycine tabacina, Glycine soja* or *Glycine tomentella*.

In any of the foregoing embodiments 1-7 or any other embodiments of the present invention, the recombinant DNA construct (or suppression DNA construct) may comprise at least a promoter functional in a plant as a regulatory sequence.

In any of the foregoing embodiments 1-7 or any other embodiments of the present invention, the alteration of at least one agronomic characteristic is either an increase or decrease.

In any of the foregoing embodiments 1-7 or any other embodiments of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, early seedling vigor and seedling emergence under low temperature stress. For example, the alteration of at least one agronomic characteristic may be an increase in yield, greenness or biomass.

In any of the foregoing embodiments 1-7 or any other embodiments of the present invention, the plant may exhibit the alteration of at least one agronomic characteristic when compared, under water limiting conditions, to a control plant not comprising said recombinant DNA construct (or said suppression DNA construct).

"Drought" refers to a decrease in water availability to a plant that, especially when prolonged, can cause damage to the plant or prevent its successful growth (e.g., limiting plant growth or seed yield).

"Drought tolerance" is a trait of a plant to survive under drought conditions over prolonged periods of time without exhibiting substantial physiological or physical deterioration.

"Increased drought tolerance" of a plant is measured relative to a reference or control plant, and is a trait of the plant to survive under drought conditions over prolonged periods of time, without exhibiting the same degree of physiological or physical deterioration relative to the reference or control plant grown under similar drought conditions. Typically, when a transgenic plant comprising a recombinant DNA construct or suppression DNA construct in its genome exhibits increased drought tolerance relative to a reference or control plant, the reference or control plant does not comprise in its genome the recombinant DNA construct or suppression DNA construct.

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates.

A drought stress experiment may involve a chronic stress (i.e., slow dry down) and/or may involve two acute stresses (i.e., abrupt removal of water) separated by a day or two of recovery. Chronic stress may last 8-10 days. Acute stress may last 3-5 days. The following variables may be measured during drought stress and well watered treatments of transgenic plants and relevant control plants:

The variable "% area chg_start chronic-acute2" is a measure of the percent change in total area determined by remote visible spectrum imaging between the first day of chronic stress and the day of the second acute stress The variable "% area chg_start chronic-end chronic" is a measure of the percent change in total area determined by remote visible spectrum imaging between the first day of chronic stress and the last day of chronic stress The variable "% area chg_start chronic-harvest" is a measure of the percent change in total area determined by remote visible spectrum imaging between the first day of chronic stress and the day of harvest The variable "% area chg_start chronic-recovery24 hr" is a measure of the percent change in total area determined by remote visible spectrum imaging between the first day of chronic stress and 24 hrs into the recovery (24 hrs after acute stress 2)

The variable "psii_acute1" is a measure of Photosystem II (PSII) efficiency at the end of the first acute stress period. It provides an estimate of the efficiency at which light is absorbed by PSII antennae and is directly related to carbon dioxide assimilation within the leaf.

The variable "psii_acute2" is a measure of Photosystem II (PSII) efficiency at the end of the second acute stress period. It provides an estimate of the efficiency at which light is absorbed by PSII antennae and is directly related to carbon dioxide assimilation within the leaf.

The variable "fv/fm_acute1" is a measure of the optimum quantum yield (Fv/Fm) at the end of the first acute stress-(variable fluorescence difference between the maximum and minimum fluorescence/maximum fluorescence)

The variable "fv/fm_acute2" is a measure of the optimum quantum yield (Fv/Fm) at the end of the second acute stress-(variable flourescence difference between the maximum and minimum fluorescence/maximum fluorescence)

The variable "leaf rolling_harvest" is a measure of the ratio of top image to side image on the day of harvest.

The variable "leaf rolling_recovery24 hr" is a measure of the ratio of top image to side image 24 hours into the recovery.

The variable "Specific Growth Rate (SGR)" represents the change in total plant surface area (as measured by Lemna Tec Instrument) over a single day ($Y(t)=Y0*e^{r*t}$). $Y(t)=Y0*e^{r*t}$ is equivalent to % change in $Y/\Delta t$ where the individual terms are as follows: $Y(t)$=Total surface area at t; $Y0$=Initial total surface area (estimated); $r$=Specific Growth Rate $day^{-1}$, and $t$=Days After Planting ("DAP")

The variable "shoot dry weight" is a measure of the shoot weight 96 hours after being placed into a 104° C. oven The variable "shoot fresh weight" is a measure of the shoot weight immediately after being cut from the plant The Examples below describe some representative protocols and techniques for simulating drought conditions and/or evaluating drought tolerance.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to a control or reference plant).

One of ordinary skill in the art would readily recognize a suitable control or reference plant to be utilized when assessing or measuring an agronomic characteristic or phenotype of a transgenic plant in any embodiment of the present invention in which a control plant is utilized (e.g., compositions or methods as described herein). For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct) (i.e., the progeny not comprising the recombinant DNA construct (or the suppression DNA construct) is the control or reference plant).

2. Introgression of a recombinant DNA construct (or suppression DNA construct) into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the first hybrid line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct (or suppression DNA construct)). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (OAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods:

Methods include but are not limited to methods for increasing drought tolerance in a plant, methods for evaluating drought tolerance in a plant, methods for altering an agronomic characteristic in a plant, methods for determining an alteration of an agronomic characteristic in a plant, and methods for producing seed. The plant may be a monocotyledonous or dicotyledonous plant, for example, a maize or soybean plant. The plant may also be sunflower, sorghum, canola, wheat, alfalfa, cotton, rice, barley or millet. The seed is may be a maize or soybean seed, for example, a maize hybrid seed or maize inbred seed.

Methods include but are not limited to the following:

A method for transforming a cell comprising transforming a cell with any of the isolated polynucleotides of the present invention. The cell transformed by this method is also included. In particular embodiments, the cell is eukaryotic cell, e.g., a yeast, insect or plant cell, or prokaryotic, e.g., a bacterium.

A method for producing a transgenic plant comprising transforming a plant cell with any of the isolated polynucleotides or recombinant DNA constructs of the present invention and regenerating a transgenic plant from the transformed plant cell. The invention is also directed to the transgenic plant produced by this method, and transgenic seed obtained from this transgenic plant.

A method for isolating a polypeptide of the invention from a cell or culture medium of the cell, wherein the cell comprises a recombinant DNA construct comprising a polynucleotide of the invention operably linked to at least one regulatory sequence, and wherein the transformed host cell is grown under conditions that are suitable for expression of the recombinant DNA construct.

A method of altering the level of expression of a polypeptide of the invention in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the polypeptide of the invention in the transformed host cell.

A method of increasing drought tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34; and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased drought tolerance when compared to a control plant not comprising the recombinant DNA construct.

A method of increasing drought tolerance in a plant, comprising: (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34, or (ii) a full complement of the nucleic acid sequence of (a)(i); and (b) regenerating a transgenic plant from the regenerable plant cell after step (a), wherein the transgenic plant comprises in its genome the suppression DNA construct and exhibits increased drought tolerance when compared to a control plant not comprising the suppression DNA construct. The method may further comprise (c) obtaining a progeny plant derived from the transgenic plant, wherein said progeny plant comprises in its genome the suppression DNA construct and exhibits increased drought tolerance when compared to a control plant not comprising the suppression DNA construct.

A method of increasing drought tolerance in a plant, comprising: (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an SIPR polypeptide; and (b) regenerating a transgenic plant from the regenerable plant cell after step (a), wherein the transgenic plant comprises in its genome the suppression DNA construct and exhibits increased drought tolerance when compared to a control plant not comprising the suppression DNA construct. The method may further comprise (c) obtaining a progeny plant derived from the transgenic plant, wherein said progeny plant comprises in its genome the suppression DNA construct and exhibits increased drought tolerance when compared to a control plant not comprising the suppression DNA construct.

A method of evaluating drought tolerance in a plant, comprising (a) introducing into a regenerable plant cell a recombinant DNA construct comprising a polynucleotide operably linked to at least on regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34; (b) regenerating a transgenic plant from the regenerable plant cell after step (a), wherein the transgenic plant comprises in its genome the recombinant DNA construct; and (c) evaluating the transgenic plant for drought tolerance compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for drought tolerance compared to a control plant not comprising the recombinant DNA construct.

A method of evaluating drought tolerance in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34, or (ii) a full complement of the nucleic acid sequence of (a)(i); (b) regenerating a transgenic plant from the regenerable plant cell after step (a), wherein the transgenic plant comprises in its genome the suppression DNA construct; and (c) evaluating the transgenic plant for drought tolerance compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for drought tolerance compared to a control plant not comprising the suppression DNA construct.

A method of evaluating drought tolerance in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an SIPR polypeptide; (b) regenerating a transgenic plant from the regenerable plant cell after step (a), wherein the transgenic plant comprises in its genome the suppression DNA construct; and (c) evaluating the transgenic plant for drought tolerance compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for drought tolerance compared to a control plant not comprising the suppression DNA construct.

A method of evaluating drought tolerance in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34; (b) regenerating a transgenic plant from the regenerable plant cell after step (a), wherein the transgenic plant comprises in its genome the recombinant DNA construct; (c) obtaining a progeny plant derived from said transgenic plant, wherein the progeny plant comprises in its genome the recombinant DNA construct; and (d) evaluating the progeny plant for drought tolerance compared to a control plant not comprising the recombinant DNA construct.

A method of evaluating drought tolerance in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34, or (ii) a full complement of the nucleic acid sequence of (a)(i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) evaluating the progeny plant for drought tolerance compared to a control plant not comprising the suppression DNA construct.

A method of evaluating drought tolerance in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an SIPR polypeptide; (b) regenerating a transgenic plant from the regenerable plant cell after step (a), wherein the transgenic plant comprises in its genome the suppression DNA construct; (c) obtaining a progeny plant derived from the transgenic plant, wherein the progeny plant comprises in its genome the suppression DNA construct; and (d) evaluating the progeny plant for drought tolerance compared to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least on regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34; (b) regenerating a transgenic plant from the regenerable plant cell after step (a), wherein the transgenic plant comprises in its genome said recombinant DNA construct; and (c) determining whether the transgenic plant exhibits an alteration in at least one agronomic characteristic when compared, optionally under water limiting conditions, to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration in at least one agronomic characteristic when compared, optionally under water limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34, or (ii) a full complement of the nucleic acid sequence of (i); (b) regenerating a transgenic plant from the regenerable plant cell after step (a), wherein the transgenic plant comprises in its genome the suppression DNA construct; and (c) determining whether the transgenic plant exhibits an alteration in at least one agronomic characteristic when compared, optionally under water limiting conditions, to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration in at least one agronomic characteristic when compared, optionally under water limiting conditions, to a control plant not comprising the suppression DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an SIPR polypeptide; (b) regenerating a transgenic plant from the regenerable plant cell after step (a), wherein the transgenic plant comprises in its genome the suppression DNA construct; and (c) determining whether the transgenic plant exhibits an alteration in at least one agronomic characteristic when compared, optionally under water limiting conditions, to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration in at least one agronomic characteristic when compared, optionally under water limiting conditions, to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34; (b) regenerating a transgenic plant from the regenerable plant cell after step (a), wherein the transgenic plant comprises in its genome said recombinant DNA construct; (c) obtaining a progeny plant derived from said transgenic plant, wherein the progeny plant comprises in its genome the recombinant DNA construct; and (d) determining whether the progeny plant exhibits an alteration in at least one agronomic characteristic when compared, optionally under water limiting conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%. 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32 or 34, or (ii) a full complement of the nucleic acid sequence of (i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration in at least one agronomic characteristic when compared, optionally under water limiting conditions, to a control plant not comprising the suppression DNA construct.

A method of determining an alteration of an agronomic characteristic in a plant, comprising (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes an SIM polypeptide; (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration in at least one agronomic characteristic when compared, optionally under water limiting conditions, to a control plant not comprising the suppression DNA construct.

A method of producing seed (for example, seed that can be sold as a drought tolerant product offering) comprising any of the preceding methods, and further comprising obtaining seeds from said progeny plant, wherein said seeds comprise in their genome said recombinant DNA construct (or suppression DNA construct).

In any of the preceding methods or any other embodiments of methods of the present invention, in said introducing step said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present invention, said regenerating step may comprise the following: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, early seedling vigor and seedling emergence under low temperature stress. The alteration of at least one agronomic characteristic may be an increase in yield, greenness or biomass.

In any of the preceding methods or any other embodiments of methods of the present invention, the plant may exhibit the alteration of at least one agronomic characteristic when compared, under water limiting conditions, to a control plant not comprising said recombinant DNA construct (or said suppression DNA construct).

In any of the preceding methods or any other embodiments of methods of the present invention, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant invention.

The introduction of recombinant DNA constructs of the present invention into plants may be carried out by any suitable technique, including but not limited to direct DNA uptake, chemical treatment, electroporation, microinjection, cell fusion, infection, vector-mediated DNA transfer, bombardment, or *Agrobacterium*-mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

EXAMPLES

The present invention is further illustrated in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Creation of an *Arabidopsis* Population with Activation-Tagged Genes

An 18.5-kb T-DNA based binary construct was created, pHSbarENDs2 (FIG. 1; SEQ ID NO:1), that contains four multimerized enhancer elements derived from the Cauliflower Mosaic Virus 35S promoter (corresponding to sequences −341 to −64, as defined by Odell at al., Nature 313:810-812 (1985)). The construct also contains vector sequences (pUC9) and a polylinker to allow plasmid rescue, transposon sequences (Ds) to remobilize the T-DNA, and the bar gene to allow for glufosinate selection of transgenic plants. In principle, only the 10.8-kb segment from the right border (RB) to left border (LB) inclusive will be transferred into the host plant genome. Since the enhancer elements are located near the RB, they can induce cis-activation of genomic loci following T-DNA integration.

*Arabidopsis* activation-tagged populations were created by whole plant *Agrobacterium* transformation. The pHSbarENDs2 construct was transformed into *Agrobacterium tumefaciens* strain C58, grown in LB at 25° C. to OD600 H ~1.0. Cells were then pelleted by centrifugation and resuspended in an equal volume of 5% sucrose/0.05% Silwet L-77 (OSI Specialties, Inc). At early bolting, soil grown *Arabidopsis thaliana* ecotype Col-0 were top watered with the *Agrobacterium* suspension. A week later, the same plants were top watered again with the same *Agrobacteriurn* strain in sucrose/Silwet. The plants were then allowed to set seed as normal. The resulting T1 seed were sown on soil, and transgenic seedlings were selected by spraying with glufosinate (Finale®; AgrEvo; Bayer Environmental Science). A total of 100,000 glufosinate resistant T1 seedlings were selected. T2 seed from each line was kept separate.

Example 2

Screens to Identify Lines with Enhanced Drought Tolerance

Quantitative Drought Screen: From each of 96,000 separate T1 activation-tagged lines, nine glufosinate resistant T2 plants are sown, each in a single pot on Scotts® Metro-Mix® 200 soil. Flats are configured with 8 square pots each. Each of the square pots is filled to the top with soil. Each pot (or cell) is sown to produce 9 glufosinate resistant seedlings in a 3×3 array.

The soil is watered to saturation and then plants are grown under standard conditions (i.e., 16 hour light, 8 hour dark cycle; 22° C.; −60% relative humidity). No additional water is given.

Digital images of the plants are taken at the onset of visible drought stress symptoms. Images are taken once a day (at the same time of day), until the plants appear dessicated. Typically, four consecutive days of data is captured.

Color analysis is employed for identifying potential drought tolerant lines. Color analysis can be used to measure the increase in the percentage of leaf area that falls into a yellow color bin. Using hue, saturation and intensity data ("HSI"), the yellow color bin consists of hues 35 to 45.

Maintenance of leaf area is also used as another criterion for identifying potential drought tolerant lines, since *Arabi*-

*dopsis* leaves wilt during drought stress. Maintenance of leaf area can be measured as reduction of rosette leaf area over time.

Leaf area is measured in terms of the number of green pixels obtained using the LemnaTec imaging system. Activation-tagged and control (e.g., wild-type) plants are grown side by side in flats that contain 72 plants (9 plants/pot). When wilting begins, images are measured for a number of days to monitor the wilting process. From these data wilting profiles are determined based on the green pixel counts obtained over four consecutive days for activation-tagged and accompanying control plants. The profile is selected from a series of measurements over the four day period that gives the largest degree of wilting. The ability to withstand drought is measured by the tendency of activation-tagged plants to resist wilting compared to control plants.

LemnaTec HTSBonitUV software is used to analyze CCD images. Estimates of the leaf area of the *Arabidopsis* plants are obtained in terms of the number of green pixels. The data for each image is averaged to obtain estimates of mean and standard deviation for the green pixel counts for activation-tagged and wild-type plants. Parameters for a noise function are obtained by straight line regression of the squared deviation versus the mean pixel count using data for all images in a batch. Error estimates for the mean pixel count data are calculated using the fit parameters for the noise function. The mean pixel counts for activation-tagged and wild-type plants are summed to obtain an assessment of the overall leaf area for each image. The four-day interval with maximal wilting is obtained by selecting the interval that corresponds to the maximum difference in plant growth. The individual wilting responses of the activation-tagged and wild-type plants are obtained by normalization of the data using the value of the green pixel count of the first day in the interval. The drought tolerance of the activation-tagged plant compared to the wild-type plant is scored by summing the weighted difference between the wilting response of activation-tagged plants and wild-type plants over day two to day four; the weights are estimated by propagating the error in the data. A positive drought tolerance score corresponds to an activation-tagged plant with slower wilting compared to the wild-type plant. Significance of the difference in wilting response between activation-tagged and wild-type plants is obtained from the weighted sum of the squared deviations.

Lines with a significant delay in yellow color accumulation and/or with significant maintenance of rosette leaf area, when compared to the average of the whole flat, are designated as Phase 1 hits. Phase 1 hits are re-screened in duplicate under the same assay conditions. When either or both of the Phase 2 replicates show a significant difference (score of greater than 0.9) from the whole flat mean, the line is then considered a validated drought tolerant line.

Example 3

Identification of Activation-Tagged Genes

Genes flanking the T-DNA insert in drought tolerant lines are identified using one, or both, of the following two standard procedures: (1) thermal asymmetric interlaced (TAIL) PCR (Liu et al., (1995), *Plant J.* 8:457-63); and (2) SAIFF PCR (Siebert et al., (1995) *Nucleic Acids Res.* 23:1087-1088). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and *Arabidopsis* genomic sequence.

Once a tag of genomic sequence flanking a T-DNA insert is obtained, candidate genes are identified by alignment to publicly available *Arabidopsis* genome sequence.

Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic FOR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 4A

Identification of Activation-Tagged SIPR Gene

An activation-tagged line (No. 104159) showing drought tolerance was further analyzed. DNA from the line was extracted, and genes flanking the T-DNA insert in the mutant line were identified using SAIFF PCR (Siebert et al., *Nucleic Acids Res.* 23:1087-1088 (1995)). A PCR amplified fragment was identified that contained T-DNA border sequence and *Arabidopsis* genomic sequence. Genomic sequence flanking the T-DNA insert was obtained, and the candidate gene was identified by alignment to the completed *Arabidopsis* genome. For a given T-DNA integration event, the annotated gene nearest the 35S enhancer elements/T-DNA RB was the candidate for gene that is activated in the line. In the case of line 104159, the T-DNA landed in the codon sequence of At1g26796 (NCBI GI NO. 3766801) with the 35S enhancer elements pointing towards the candidate gene At1g26797 (SEQ ID NO: 17; NCBI GI No. 30689649), encoding an SIPR polypeptide (SEQ ID NO: 18; NCBI GI No. 30689650).

Example 4B

Assay for Expression Level of Candidate Drought Tolerance Genes

A functional activation-tagged allele should result in either up-regulation of the candidate gene in tissues where it is normally expressed, ectopic expression in tissues that do not normally express that gene, or both.

Expression levels of the candidate genes in the cognate mutant line vs. wild-type are compared. A standard RT-PCR procedure, such as the QuantiTect® Reverse Transcription Kit from Qiagen®, is used. RT-PCR of the actin gene is used as a control to show that the amplification and loading of samples from the mutant line and wild-type are similar.

Assay conditions are optimized for each gene. Expression levels are checked in mature rosette leaves. If the activation-tagged allele results in ectopic expression in other tissues (e.g., roots), it is not detected by this assay. As such, a positive result is useful but a negative result does not eliminate a gene from further analysis.

Example 5

Validation of *Arabidopsis* Candidate Gene At1g126797 (SIPR Polypeptide) via Transformation into *Arabidopsis*

Candidate genes can be transformed into *Arabidopsis* and overexpressed under the 35S promoter. If the same or similar phenotype is observed in the transgenic line as in the parent activation-tagged line, then the candidate gene is considered to be a validated "lead gene" in *Arabidopsis*.

The candidate *Arabidopsis* SIPR gene (A11 g26797; SEQ ID NO; 17; NCBI GI No. 30689649) was tested for its ability to confer drought tolerance in the following manner.

Figure 4:
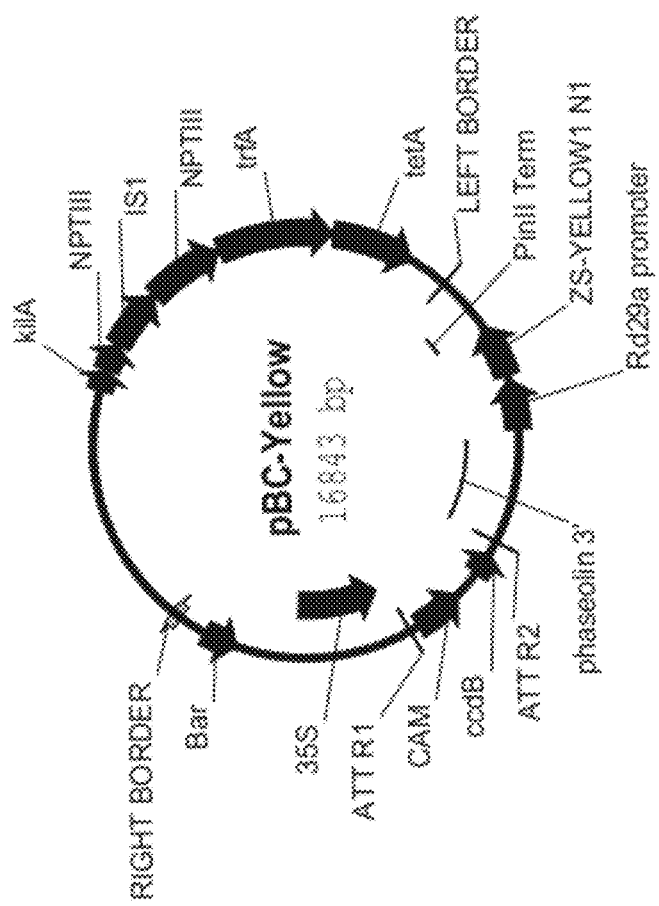
FIG. 4 shows a map of the vector pBC-yellow (SEQ ID NO: 4), a destination vector for use in construction of expression vectors for *Arabidopsis*. The attR1 site is at nucleotides 11276-11399 (complementary strand); the attR2 site is at nucleotides 9695-9819 (complementary strand).

A 16.8-kb T-DNA based binary vector, called pBC-yellow (SEQ ID NO:4; FIG. 4), was constructed with a 1.3-kb 35S promoter immediately upstream of the INVITROGEN™ GATEWAY®C1 conversion insert. The vector also contains the RD29a promoter driving expression of the gene for ZS-Yellow (INVITROGEN™), which confers yellow fluorescence to transformed seed.

The At1g26797 cDNA protein-coding region was amplified by RT-PCR with the following primers:

```
(1)  At1g26797-5'attB forward primer
     (SEQ ID NO: 12):
     ggggacaagtttgtacaaaaaagcaggctccatgctaatcaca
     gttctag (2)  At1g26797-3'attB reverse primer
     (SEQ ID NO: 13):
     ggggaccactttgtacaagaaagctgggtcagtcaatctctaa
     gatgtcc
```

The forward primer contains the attB1 sequence (ACAAGTTTGTACAAAAAAGCAGGCT; SEQ ID NO:10) and a consensus Kozak sequence (CAACA) adjacent to the first 19 nucleotides of the protein-coding region, beginning with the ATG start codon, of said cDNA.

The reverse primer contains the attB2 sequence (ACCACTTTGTACAAGAAAGCTGGGT; SEQ ID NO:11) adjacent to the reverse complement of the last 21 nucleotides of the protein-coding region, beginning with the reverse complement of the stop codon, of said cDNA.

Figure 2:
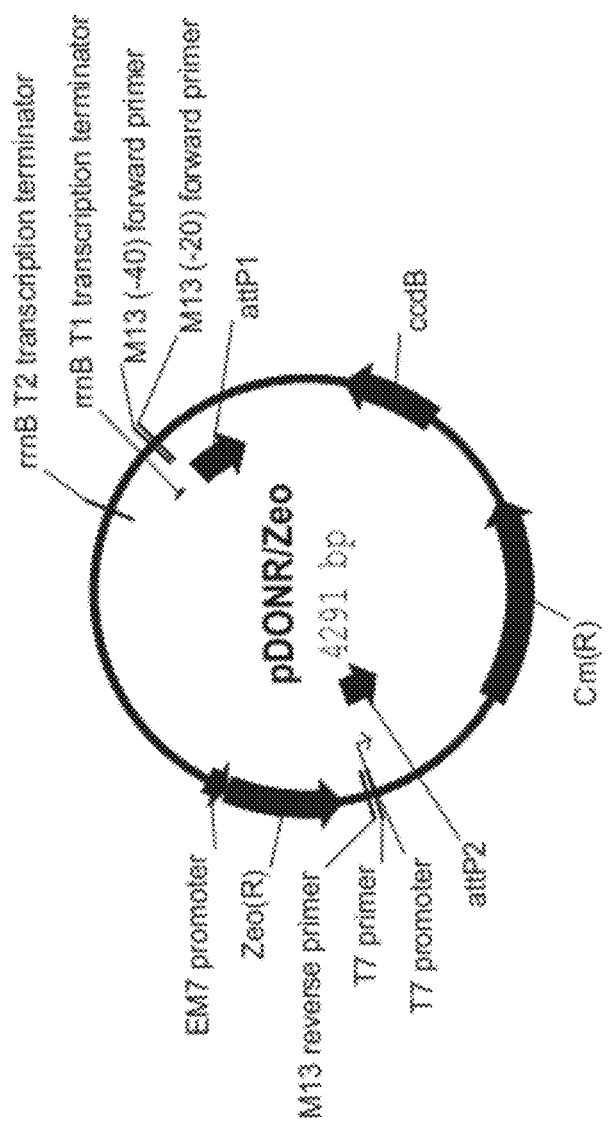
FIG. 2 shows a map of the vector pDONR™/Zeo (SEQ ID NO: 2). The attP1 site is at nucleotides 570-801; the attP2 site is at nucleotides 2754-2985 (complementary strand).

Using the INVITROGEN™ GATEWAY® CLONASE™ technology, a BP Recombination Reaction was performed with pDONR™/Zeo (SEQ ID NO:2; FIG. 2). This process removed the bacteria lethal ccdB gene, as well as the chloramphenicol resistance gene (CAM) from pDONR™/Zeo and directionally cloned the PCR product with flanking attB1 and attB2 sites creating an entry clone, PHP32324. This entry clone was used for a subsequent LR Recombination Reaction with a destination vector, as follows.

A 16.8-kb 1-DNA based binary vector (destination vector), called pBC-yellow (SEQ ID NO:4; FIG. 4), was constructed with a 1.3-kb 35S promoter immediately upstream of the INVITROGEN™ GATEWAY® C1 conversion insert, which contains the bacterial lethal ccdB gene as well as the chloramphenicol resistance gene (CAM) flanked by attR1 and attR2 sequences. The vector also contains the RD29a promoter driving expression of the gene for ZS-Yellow (INVITROGEN™), which confers yellow fluorescence to transformed seed. Using the INVITROGEN™™ GATEWAY® technology, an LR Recombination Reaction was performed on the PHP32324 entry clone, containing the directionally cloned PCR product, and pBC-yellow. This allowed for rapid and directional cloning of the candidate gene behind the 35S promoter in pBC-yellow to create the 35S promoter: At1g26797 expression construct, pBC-Yellow-At1g26797.

Applicants then introduced the 35S promoter::At1g26797 expression construct into wild-type *Arabidopsis* ecotype Col-0, using the same *Agrobacterium*-mediated transformation procedure described in Example 1. Transgenic T1 seeds were selected by yellow fluorescence, and T1 seeds were plated next to wild-type seeds and grown under water limiting conditions. Growth conditions and imaging analysis were as described in Example 2. R was found that the original drought tolerance phenotype from activation tagging could be recapitulated in wild-type *Arabidopsis* plants that were transformed with a construct where At1g26797 was directly expressed by the 35S promoter. The drought tolerance score, as determined by the method of Example 2, was 1.934.

Example 6

Preparation of cDNA Libraries and Isolation and Sequencing of cDNA Clones cDNA libraries may be prepared by any one of many methods available. For example, the cDNAs may be introduced into plasmid vectors by first preparing the cDNA libraries in UNI-ZAP™ XR vectors according to the manufacturer's protocol (Stratagene Cloning Systems, La Jolla, Calif.). The UNI-ZAP™ XR libraries are converted into plasmid libraries according to the protocol provided by Stratagene. Upon conversion, cDNA inserts will be contained in the plasmid vector pBLUESCRIPT®. In addition, the cDNAs may be introduced directly into precut BLUESCRIPT®II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBLUESCRIPT® plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) Science 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (GIBCO BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI PRISM® dye-terminator ReadyReaction mix) outward from the transposition event site, utilizing unique primers specific to the binding sites within the transposon.

Sequence data is collected (ABI PRISM® Collections) and assembled using Phred and Phrap (Ewing et al. (1998) *Genome Res.* 8:175-185; Ewing and Green (1998) *Genome Res.* 8:186-194). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al. (1998) *Genome Res.* 8:195-202).

In some of the clones the cDNA fragment may correspond to a portion of the 3'-terminus of the gene and does not cover the entire open reading frame. In order to obtain the upstream information one of two different protocols is used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBLUESCRIPT® vector using a commercial kit and following the manufacturers protocol. This kit is selected from many available from several vendors including INVITROGEN™ (Carlsbad, Calif.), Promega Biotech (Madison, Wis.), and GIBCO-BRL (Gaithersburg, Md.). The plasmid DNA is isolated by alkaline lysis method and submitted for sequencing and assembly using Phred/Phrap, as above.

Example 7

Identification of cDNA Clones cDNA clones encoding the polypeptide of interest can be identified by conducting BLAST (Basic Local Alignment Search Tool; Altschul et al. (1993) *J. Mol. Biol.* 215:403-410: see also the explanation of the BLAST algorithm on the world wide web site for the National Center for Biotechnology Information at the National Library of Medicine of the National Institutes of Health) searches for similarity to amino acid sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The DNA sequences from clones can be translated in all reading frames and compared for similarity to all publicly available protein sequences contained in the "nr" database using the BLASTX algorithm (Gish and States (1993) *Nat. Genet.* 3:266-272) provided by the NCBI. The polypeptides encoded by the cDNA sequences can be analyzed for similarity to all publicly available amino acid sequences contained in the "nr" database using the BLASTP algorithm provided by the National Center for Biotechnology Information (NCBI). For convenience, the P-value (probability) or the E-value (expectation) of observing a match of a cDNA-encoded sequence to a sequence contained in the searched databases merely by chance as calculated by BLAST are reported herein as "pLog" values, which represent the negative of the logarithm of the reported P-value or E-value. Accordingly, the greater the pLog value, the greater the likelihood that the cDNA-encoded sequence and the BLAST "hit" represent homologous proteins.

ESTs sequences can be compared to the Genbank database as described above. ESTs that contain sequences more 5- or 3-prime can be found by using the BLASTN algorithm (Altschul et al (1997) *Nucleic Acids Res.* 25:3389-3402.) against the DUPONT™ proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described above. Homologous genes belonging to different species can be found by comparing the amino acid sequence of a known gene (from either a proprietary source or a public database) against an EST database using the TBLASTN algorithm. The TBLASTN algorithm searches an amino acid query against a nucleotide database that is translated in all 6 reading frames. This search allows for differences in nucleotide codon usage between different species, and for codon degeneracy.

Example 8

Characterization of cDNA Clones Encoding SIPR Polypeptides

Shown in Table 1 (non-patent literature) and Table 2 (patent literature) are the BLASTP results for the *Arabidopsis* SIPR polypeptide (SEQ ID NO: 18) and its homologs (SEQ ID NOS: 20, 22, 24, 26, 28, 30, 32 and 34) described herein. SEQ ID NO: 30 is encoded by SEQ ID NO; 29, and is a truncated version of the publicly available *Arabidopsis lyrata* sequence presented in NCBI GI No. 297850998.

Also shown are the percent sequence identity values for each pair of amino acid sequences:

TABLE 1

BLASTP Results for SIPR polypeptides

| Sequence (Amino Acid) (SEQ ID NO) | Reference (SEQ ID NO) | BLASTP pLog of E-value | Percent Sequence Identity |
|---|---|---|---|
| SEQ ID NO: 30 | NCBI GI NO: 297850998 (SEQ ID NO: 40) | >180 | 100 |

TABLE 2

BLASTP Results for SIPR polypeptides

| Sequence (Amino-Acid) (SEQ ID NO) | Reference (SEQ ID NO) | BLASTP pLog of E-value | Percent Sequence Identity |
|---|---|---|---|
| At1g26797 (SEQ ID NO: 18) | SEQ ID NO: 18685 of EP1033405 (SEQ ID NO: 35) | 97 | 59.3 |
| At1g26798 (SEQ ID NO: 20) | SEQ ID NO: 18685 of EP1033405 (SEQ ID NO: 35) | 105 | 60.9 |
| At1g26796 (SEQ ID NO: 22) | SEQ ID NO: 18685 of EP1033405 (SEQ ID NO: 35) | 150 | 80.1 |
| At1g26795 (SEQ ID NO: 24) | SEQ ID NO: 18685 of EP1033405 (SEQ ID NO: 35) | >180 | 100 |
| At5g12060 (SEQ ID NO: 26) | SEQ ID NO: 49855 of EP2152891 (SEQ ID NO: 36) | >180 | 100 |
| At3g55677 (SEQ ID NO: 28) | SEQ ID NO: 226 of EP1033405 (SEQ ID NO: 37) | 139 | 61.8 |
| SEQ ID NO: 30 | SEQ ID NO: 18685 of EP1033405 (SEQ ID NO: 35) | 112 | 62.3 |
| NCBI GI NO: 224118734 (SEQ ID NO: 32) | SEQ ID NO: 9 of US6855866 (SEQ ID NO: 38) | 15.34 | 29.2 |
| NCBI GI NO: 270257838 (SEQ ID NO: 34) | SEQ ID NO: 12314 of EP2152891 (SEQ ID NO: 39) | 39 | 24.2 |

FIGS. 11A-11J present an alignment of the amino acid sequences of SIPR polypeptides set forth in SEQ ID NOS: 18, 20, 22, 24, 26, 28, 30, 32, 34-40.

FIG. 12 presents the percent sequence identities and divergence values for each sequence pair presented in FIGS. 11A-11J.

Sequence alignments and percent identity calculations were performed using the Megalign® program of the LASERGENE® bioinformatics computing suite (DNAS-TAR® Inc., Madison, Wis.). Multiple alignment of the sequences was performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

Example 9

Preparation of a Plant Expression Vector Containing a Homolog to the *Arabidopsis* Lead Gene Sequences homologous to the *Arabidopsis* SIPR polypeptide can be identified using sequence comparison algorithms such as BLAST (Basic Local Alignment Search Tool; Altschul et al., J. Mol. Biol. 215:403-410 (1993); see also the explanation of the BLAST algorithm on the world wide web site for the National Center for Biotechnology Information at the National Library of Medicine of the National Institutes of Health). Sequences encoding homologous SIPR polypeptides can be PCR-amplified by either of the following methods.

Method 1 (RNA-based): If the 5' and 3' sequence information for the protein-coding region of a gene encoding a SIPR polypeptide homolog is available, gene-specific primers can be designed as outlined in Example 5. RT-PCR can be used with plant RNA to obtain a nucleic acid fragment containing the protein-coding region flanked by attB1 (SEQ ID NO:10) and attB2 (SEQ ID NO:11) sequences. The primer may contain a consensus Kozak sequence (CAACA) upstream of the start codon.

Method 2 (DNA-based): Alternatively, if a cDNA clone is available for a gene encoding a SIPR polypeptide homolog, the entire cDNA insert (containing 5 and 3' non-coding regions) can be PCR amplified. Forward and reverse primers can be designed that contain either the attB1 sequence and vector-specific sequence that precedes the cDNA insert or the attB2 sequence and vector-specific sequence that follows the cDNA insert, respectively. For a cDNA insert cloned into the vector pBulescript SK+, the forward primer VC062 (SEQ ID NO: 14) and the reverse primer VC063 (SEQ ID NO: 15) can be used.

Methods 1 and 2 can be modified according to procedures known by one skilled in the art. For example, the primers of Method 1 may contain restriction sites instead of attB1 and attB2 sites, for subsequent cloning of the PCR product into a vector containing attB1 and attB2 sites. Additionally, Method 2 can involve amplification from a cDNA clone, a lambda clone, a BAC clone or genomic DNA.

Figure 3:
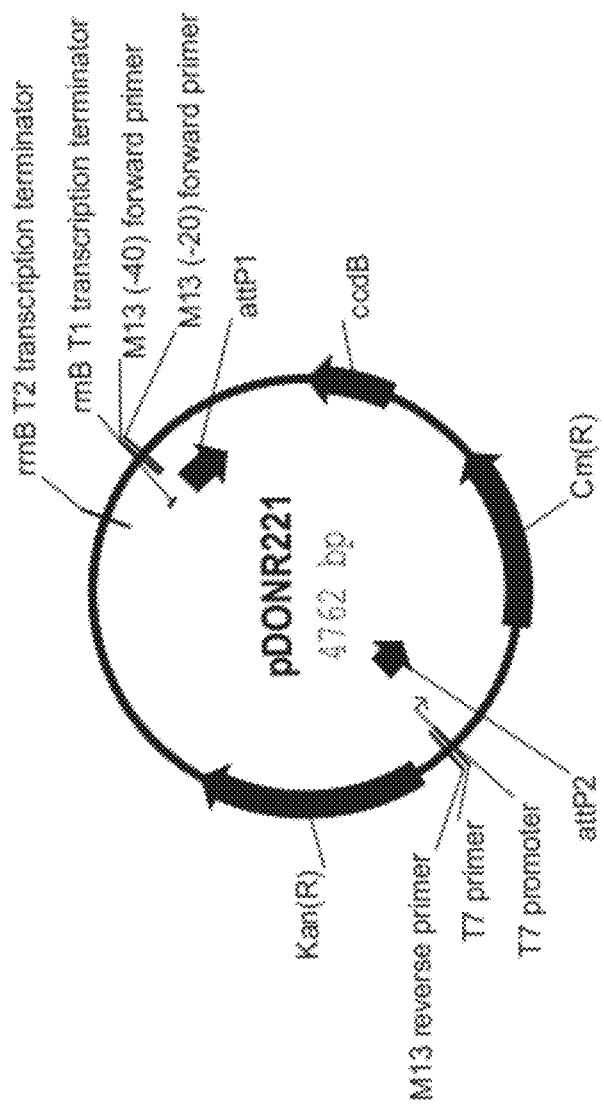
FIG. 3 shows a map of the vector pDONR™221 (SEQ ID NO: 3). The attP1 site is at nucleotides 570-801; the attP2 site is at nucleotides 2754-2985 (complementary strand).

A PCR product obtained by either method above can be combined with the GATEWAY® donor vector, such as pDONR™/Zeo (INVITROGEN™; FIG. 2; SEQ ID NO:2) or pDONR™221 (INVITROGEN™; FIG. 3; SEQ ID NO:3), using a BP Recombination Reaction. This process removes the bacteria lethal ccdB gene, as well as the chloramphenicol resistance gene (CAM) from pDONR™221 and directionally clones the PCR product with flanking attB1 and attB2 sites to create an entry clone. Using the INVITROGEN™ GATEWAY®, CLONASE™ technology, the sequence encoding the homologous SIPR polypeptide from the entry clone can then be transferred to a suitable destination vector, such as pBC-Yellow (FIG. 4; SEQ ID NO:4), PHP27840 (FIG. 5; SEQ ID NO:5) or PHP23236 (FIG. 6; SEQ ID NO:6), to obtain a plant expression vector for use with *Arabidopsis*, soybean and corn, respectively.

Figure 5:
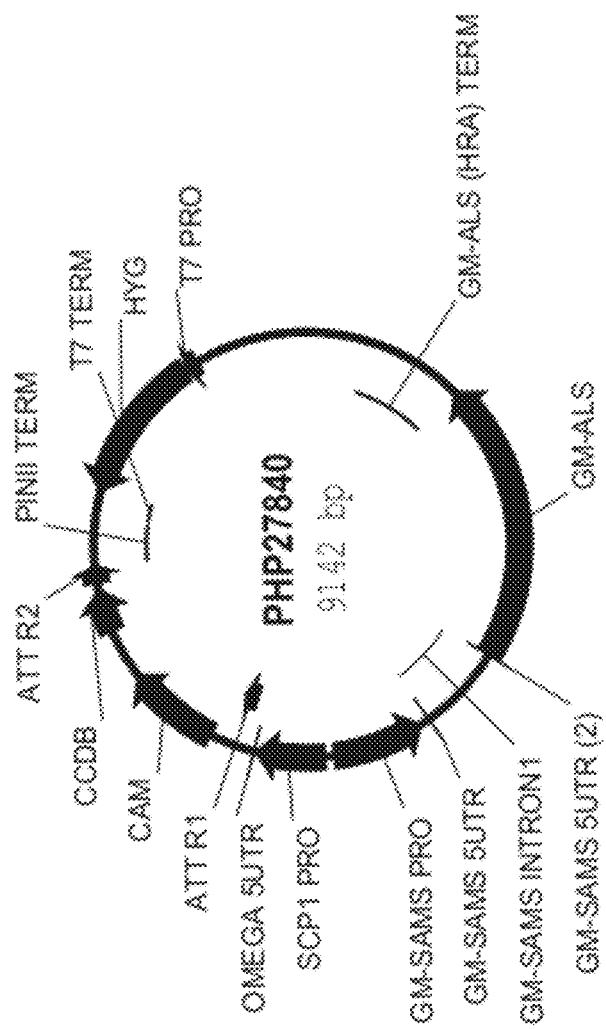
FIG. 5 shows a map of PHP27840 (SEQ ID NO: 5), a destination vector for use in construction of expression vectors for soybean. The attR1 site is at nucleotides 7310-7434; the attR2 site is at nucleotides 8890-9014.
Figure 6:
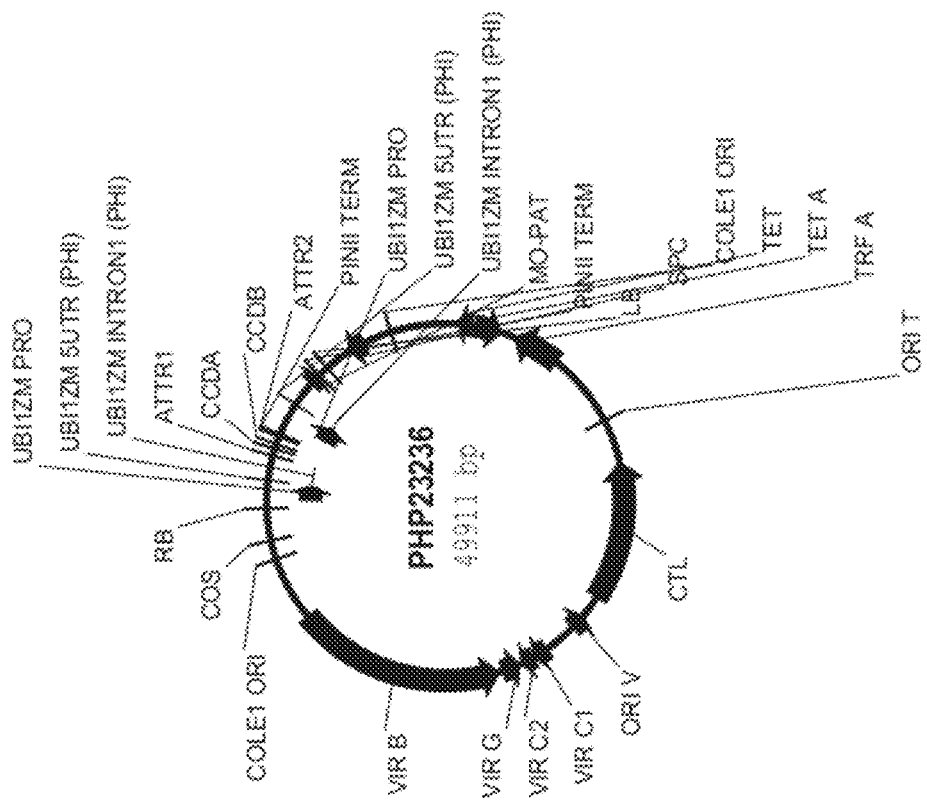
FIG. 6 shows a map of PHP23236 (SEQ ID NO: 6), a destination vector for use in construction of expression vectors for Gaspe Flint derived maize lines. The attR1 site is at nucleotides 2006-2130; the attR2 site is at nucleotides 2899-3023.

The attP1 and attP2 sites of donor vectors pDONR™/Zeo or pDONR™221 are shown in FIGS. 2 and 3, respectively. The attR1 and attR2 sites of destination vectors pBC-Yellow, PHP27840 and PHP23236 are shown in FIGS. 4, 5 and 6, respectively.

Alternatively a MultiSite GATEWAY® LR recombination reaction between multiple entry clones and a suitable destination vector can be performed to create an expression vector.

Example 10

Preparation of Soybean Expression Vectors and Transformation of Soybean with Validated *Arabidopsis* Lead Genes Soybean plants can be transformed to overexpress a validated *Arabidopsis* lead gene or the corresponding homologs from various species in order to examine the resulting phenotype.

The same GATEWAY® entry clone described in Example 5 can be used to directionally clone each gene into the PHP27840 vector (SEQ ID NO:5; FIG. 5) such that expression of the gene is under control of the SCP1 promoter.

Soybean embryos may then be transformed with the expression vector comprising sequences encoding the instant polypeptides. Techniques for soybean transformation and regeneration have been described in International Patent Publication WO 2009/006276, the contents of which are herein incorporated by reference.

T1 plants can be subjected to a soil-based drought stress. Using image analysis, plant area, volume, growth rate and color analysis can be taken at multiple times before and during drought stress. Overexpression constructs that result in a significant delay in wilting or leaf area reduction, yellow color accumulation and/or increased growth rate during drought stress will be considered evidence that the *Arabidopsis* gene functions in soybean to enhance drought tolerance.

Soybean plants transformed with validated genes can then be assayed under more vigorous field-based studies to study yield enhancement and/or stability under well-watered and water-limiting conditions.

Example 11

Transformation of Maize with Validated *Arabidopsis* Lead Genes Using Particle Bombardment Maize plants can be transformed to overexpress a validated *Arabidopsis* lead gene or the corresponding homologs from various species in order to examine the resulting phenotype.

The same GATEWAY® entry clone described in Example 5 can be used to directionally clone each gene into a maize transformation vector. Expression of the gene in the maize transformation vector can be under control of a constitutive promoter such as the maize ubiquitin promoter (Christensen et al., (1989) *Plant Mol. Biol.* 12:619-632 and Christensen et al., (1992) *Plant Mol. Biol.* 18:675-689)

The recombinant DNA construct described above can then be introduced into corn cells by particle bombardment. Techniques for corn transformation by particle bombardment have been described in International Patent Publication WO 2009/006276, the contents of which are herein incorporated by reference.

T1 plants can be subjected to a soil-based drought stress. Using image analysis, plant area, volume, growth rate and color analysis can be taken at multiple times before and during drought stress. Overexpression constructs that result in a significant delay in wilting or leaf area reduction, yellow color accumulation and/or increased growth rate during drought stress will be considered evidence that the *Arabidopsis* gene functions in maize to enhance drought tolerance.

Example 12

Electroporation of *Agrobacterium tumefaciens* LBA4404

Figure 7:
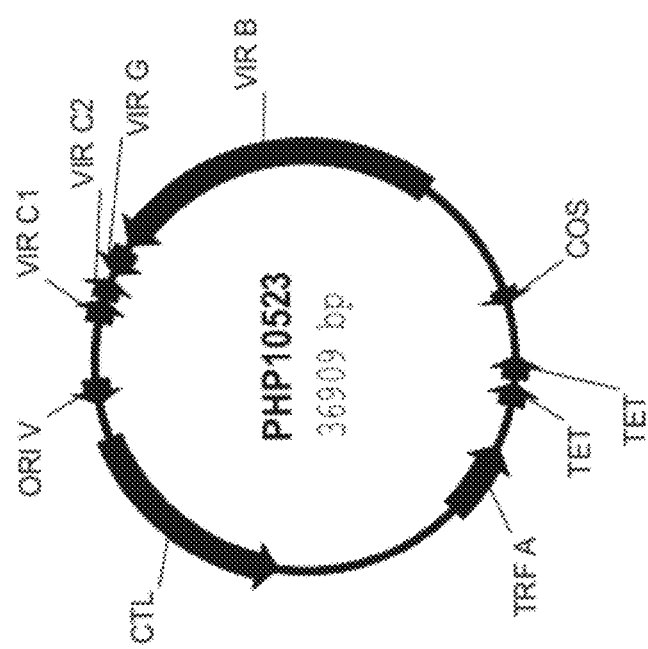
FIG. 7 shows a map of PHP10523 (SEQ ID NO: 7), a plasmid DNA present in *Agrobacterium* strain LBA4404 (Komari et al., *Plant* 10:165-174 (1996); NCBI General Identifier No. 59797027).

Electroporation competent cells (40 µL), such as *Agrobacterium tumefaciens* LBA4404 containing PHP10523 (FIG. 7; SEQ ID NO:7), are thawed on ice (20-30 min). PHP10523 contains VIR genes for 1-DNA transfer, an *Agrobacterium* low copy number plasmid origin of replication, a tetracycline resistance gene, and a Cos site for in vivo DNA bimolecular recombination. Meanwhile the electroporation cuvette is chilled on ice. The electroporator settings are adjusted to 2.1 kV. A DNA aliquot (0.5 µL parental DNA at a concentration of 0.2 µg-1.0 µg in low salt buffer or twice distilled $H_2O$) is mixed with the thawed *Agrobacterium tumefaciens* LBA4404 cells while still on ice. The mixture is transferred to the bottom of electroporation cuvette and kept at rest on ice for 1-2 min. The cells are electroporated (Eppendorf electroporator 2510) by pushing the "pulse" button twice (ideally achieving a 4.0 millisecond pulse). Subsequently, 0.5 mL of room temperature 2×YT medium (or SOC medium) are added to the cuvette and transferred to a 15 mL snap-cap tube (e.g., FALCON™ tube). The cells are incubated at 28-30° C., 200-250 rpm for 3 h.

Aliquots of 250 µL are spread onto plates containing YM medium and 50 µg/mL spectinomycin and incubated three days at 28-30 C. To increase the number of transformants one of two optional steps can be performed:

Option 1: Overlay plates with 30 µl of 15 mg/mL rifampicin. LBA4404 has a chromosomal resistance gene for rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on plates containing AB minimal medium and 50 µg/mL spectinomycin for isolation of single colonies. The plates are incubated at 28° C. for two to three days. A single colony for each putative co-integrate is picked and inoculated with 4 mL of 10 g/L bactopeptone, 10 g/L yeast extract, 5 g/L sodium chloride and 50 mg/L spectinomycin. The mixture is incubated for 24 h at 28° C. with shaking. Plasmid DNA from 4 mL of culture is isolated using Qiagen® Miniprep and an optional Buffer PB wash. The DNA is eluted in 30 µL. Aliquots of 2 µL are used to electroporate 20 µL of DH10b+20 µL of twice distilled $H_2O$ as per above. Optionally a 15 µL aliquot can be used to transform 75-100 µL of INVITROGEN™ Library Efficiency DH5α. The cells are spread on plates containing LB medium and 50 µg/mL spectinomycin and incubated at 37° C. overnight.

Three to four independent colonies are picked for each putative co-integrate and inoculated 4 mL of 2×YT medium (10 g/L bactopeptone, 10 yeast extract, 5 g/L sodium chloride) with 50 µg/mL spectinomycin. The cells are incubated at 37° C. overnight with shaking. Next, isolate the plasmid DNA from 4 mL of culture using QIAprep® Miniprep with optional Buffer PB wash (elute in 50 µL). Use 8 for digestion with SalI (using parental DNA and PHP10523 as controls). Three more digestions using restriction enzymes BamHI, EcoRI, and HindIII are performed for 4 plasmids that represent 2 putative co-integrates with correct SalI digestion pattern (using parental DNA and PHP10523 as controls). Electronic gels are recommended for comparison.

Example 13

Transformation of Maize Using *Agrobacterium*

Maize plants can be transformed to overexpress a validated *Arabidopsis* lead gene or the corresponding homologs from various species in order to examine the resulting phenotype.

*Agrobacterium*-mediated transformation of maize is performed essentially as described by Zhao et al. in Meth. Mol. Biol. 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium innoculation, co-cultivation, resting, selection and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg./L L-cysteine is critical for recovering stable transgenic events.

3. Selection of Putative Transgenic Events:

To each plate of PHI-D medium in a 100×15 mm Petri dish, 10 embryos are transferred, maintaining orientation and the dishes are sealed with parafilm. The plates are incubated in darkness at 28° C. Actively growing putative events, as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 µE from cool white or equivalent fluorescent lamps). In seven to ten days, regenerated plants, about 10 cm tall, are potted in horticultural mix and hardened-off using standard horticultural methods.

Media for Plant Transformation:

1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 µM acetosyringone (filter-sterilized).
2. PHI-B: PHI-A without glucose, increase 2,4-D to 2 mg/L, reduce sucrose to 30 g/L and supplement with 0.85 mg/L silver nitrate (filter-sterilized), 3.0 g/L Gelrite®, 100 µM acetosyringone (filter-sterilized), pH 5.8.
3, PHI-C: PHI-B without Gelrite® and acetosyringonee, reduce 2,4-D to 1.5 mg/L and supplement with 8.0 g/L agar, 0.5 g/L 2-[N-morpholino]ethane-sulfonic acid (MES) buffer, 100 mg/L carbenicillin (filter-sterilized).
4. PHI-D: PH-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat, No. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L Gelrite®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected.

Furthermore, a recombinant DNA construct containing a validated *Arabidopsis* gene can be introduced into an elite maize inbred line either by direct transformation or introgression from a separately transformed line.

Transgenic plants, either inbred or hybrid, can undergo more vigorous field-based experiments to study yield enhancement and/or stability under water limiting and water non-limiting conditions.

Subsequent yield analysis can be done to determine whether plants that contain the validated *Arabidopsis* lead gene have an improvement in yield performance (under water limiting or non-limiting conditions), when compared to the control (or reference) plants that do not contain the validated *Arabidopsis* lead gene. Specifically, water limiting conditions can be imposed during the flowering and/or grain fill period for plants that contain the validated *Arabidopsis* lead gene and the control plants. Plants containing the validated *Arabidopsis* lead gene would have less yield loss relative to the control plants, for example, at least 25% less yield loss, under water limiting conditions, or would have increased yield relative to the control plants under water non-limiting conditions.

Example 14A

Preparation of *Arabidopsis* Lead Gene (At1g26797) Expression Vector for Transformation of Maize Using INVITROGEN's™ GATEWAY® technology, an LR Recombination Reaction was performed with an entry clone (PHP32324) and a destination vector (PHP28647) to create the precursor plasmid PHP32330. The vector PHP32330 contains the following expression cassettes:

1. Ubiquitin promoter::moPAT::PinII terminator; cassette expressing the PAT herbicide resistance gene used for selection during the transformation process.
2. LTP2 promoter::DS-RED2::PinII terminator; cassette expressing the DS-RED color marker gene used for seed sorting.
3. Ubiquitin promoter::At-SIPR::PinII terminator; cassette overexpressing the gene of interest, *Arabidopsis* SIPR polypeptide.

Example 14B

Transformation of Maize with the *Arabidopsis* Lead Gene (At1g26797) Using *Agrobacterium*

The SIPR polypeptide expression cassette present in vector PHP32330 can be introduced into a maize inbred line, or a transformable maize line derived from an elite maize inbred line, using *Agrobacterium*-mediated transformation as described in Examples 12 and 13.

Vector PHP32330 can be electroporated into the LBA4404 *Agrobacterium* strain containing vector PHP10523 (FIG. 7; SEQ ID NO:7) to create the co-integrate vector PHP32412. The co-integrate vector is formed by recombination of the 2 plasmids, PHP32330 and PHP10523, through the COS recombination sites contained on each vector. The co-integrate vector PHP32412 contains the same 3 expression cassettes as above (Example 14A) in addition to other genes (TET, TET, TRFA, ORI terminator, CTL, ORI V, VIR C1, VIR C2, VIR G, VIR B) needed for the *Agrobacterium* strain and the *Agrobacterium*-mediated transformation.

Example 15

Figure 8:
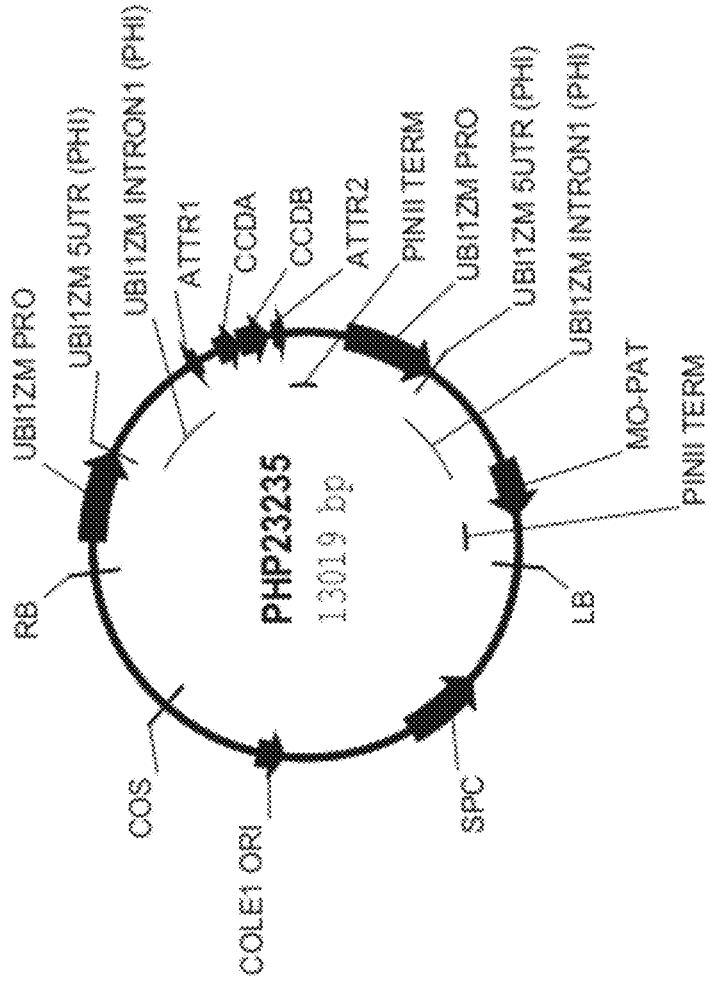
FIG. 8 shows a map of PHP23235 (SEQ ID NO: 8), a destination vector for use with Gaspe Flint derived maize lines.
Figure 9:
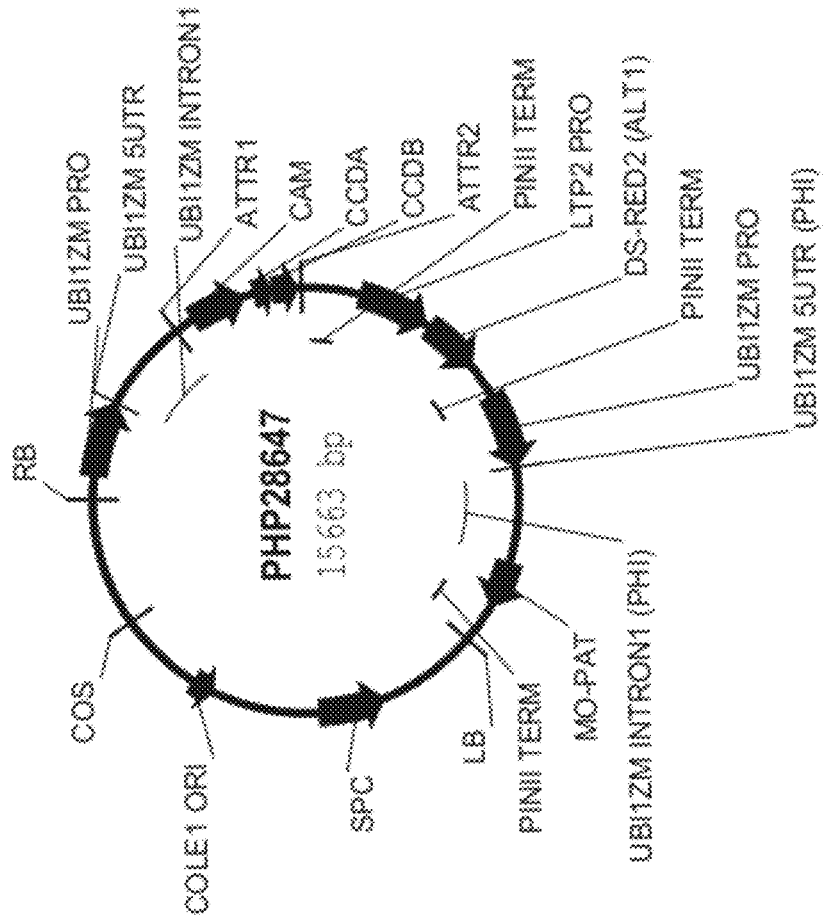
FIG. 9 shows a map of PHP28647 (SEQ ID NO: 9), a destination vector for use with maize inbred-derived lines. The attR1 site is at nucleotides 2289-2413; the attR2 site is at nucleotides 3869-3993.
Figure 10:
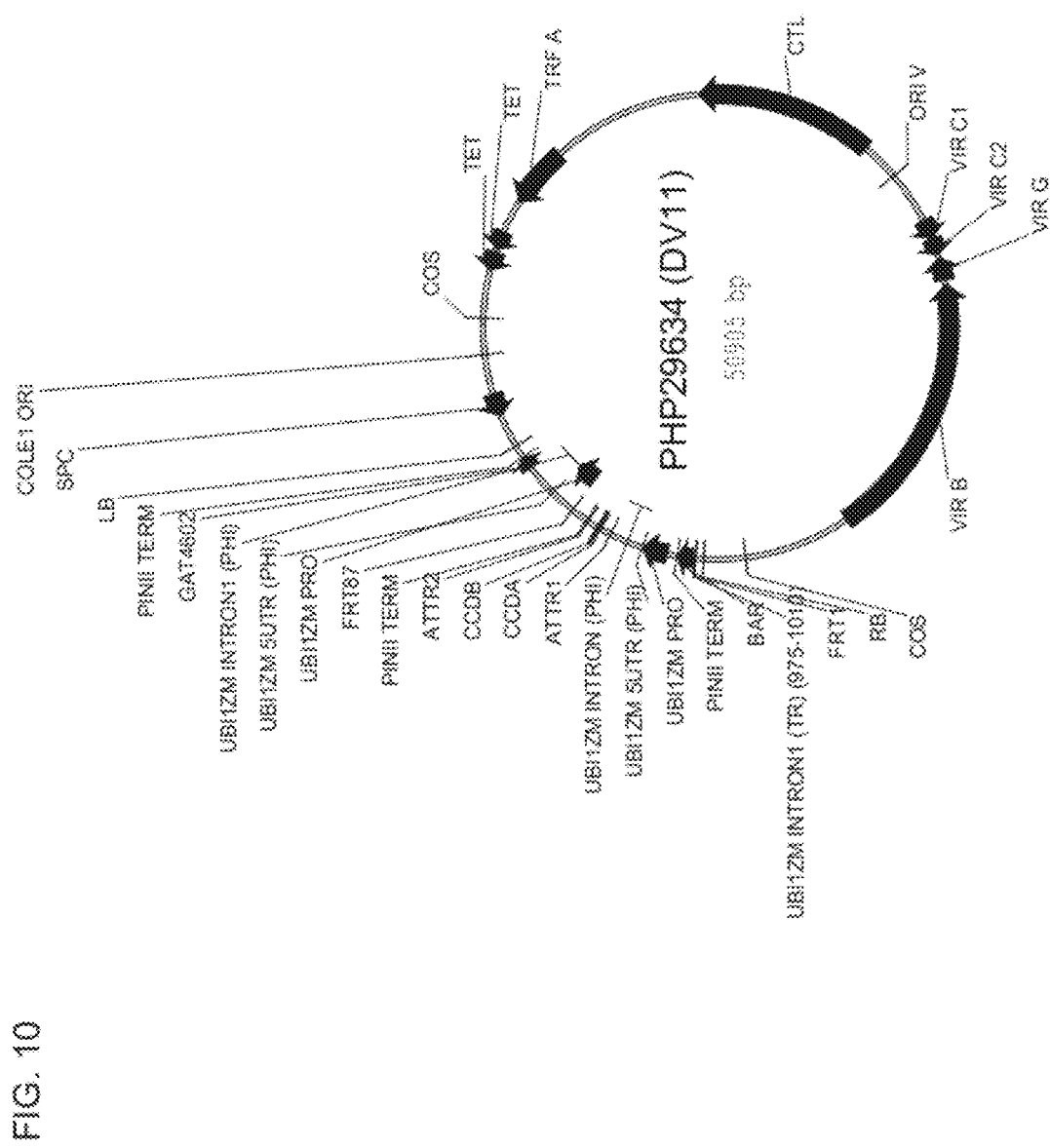
FIG. 10 shows a map of PHP29634 (SEQ ID NO: 16), a destination vector for use in construction of expression vectors for Gaspe Flint derived maize lines.
Figure 11A:
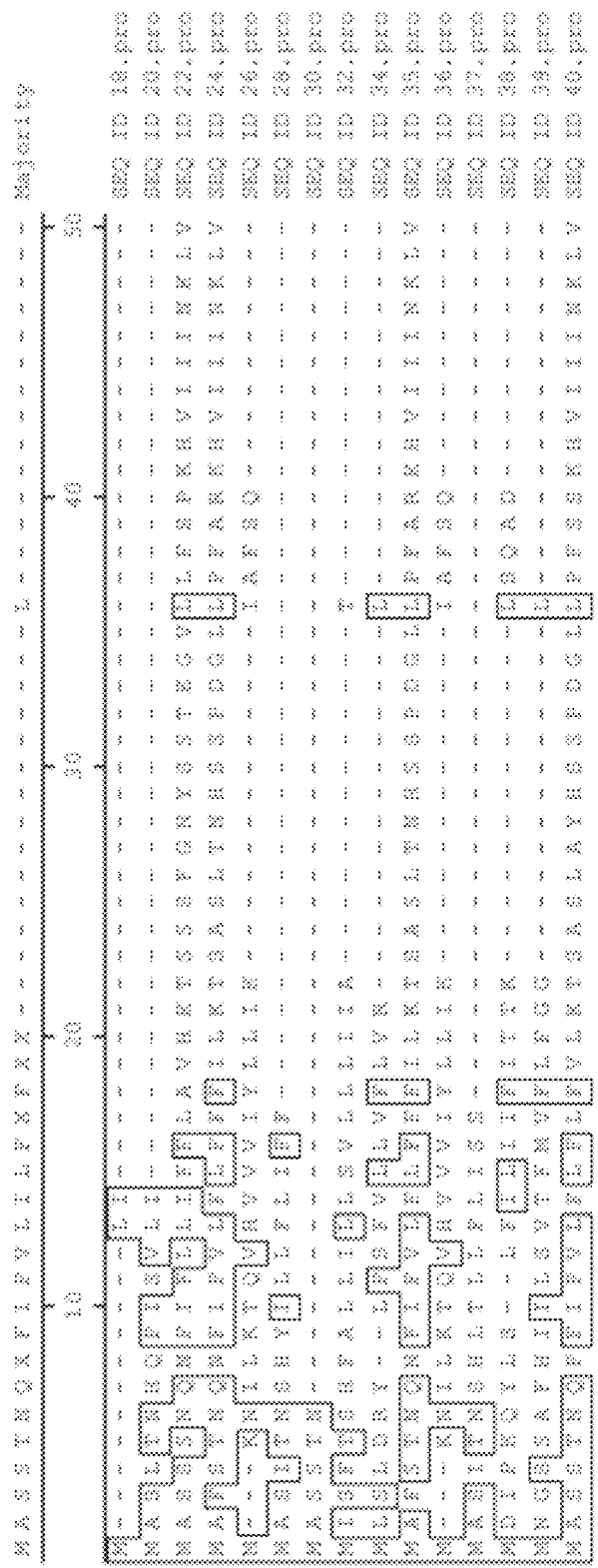
Figure 11B:
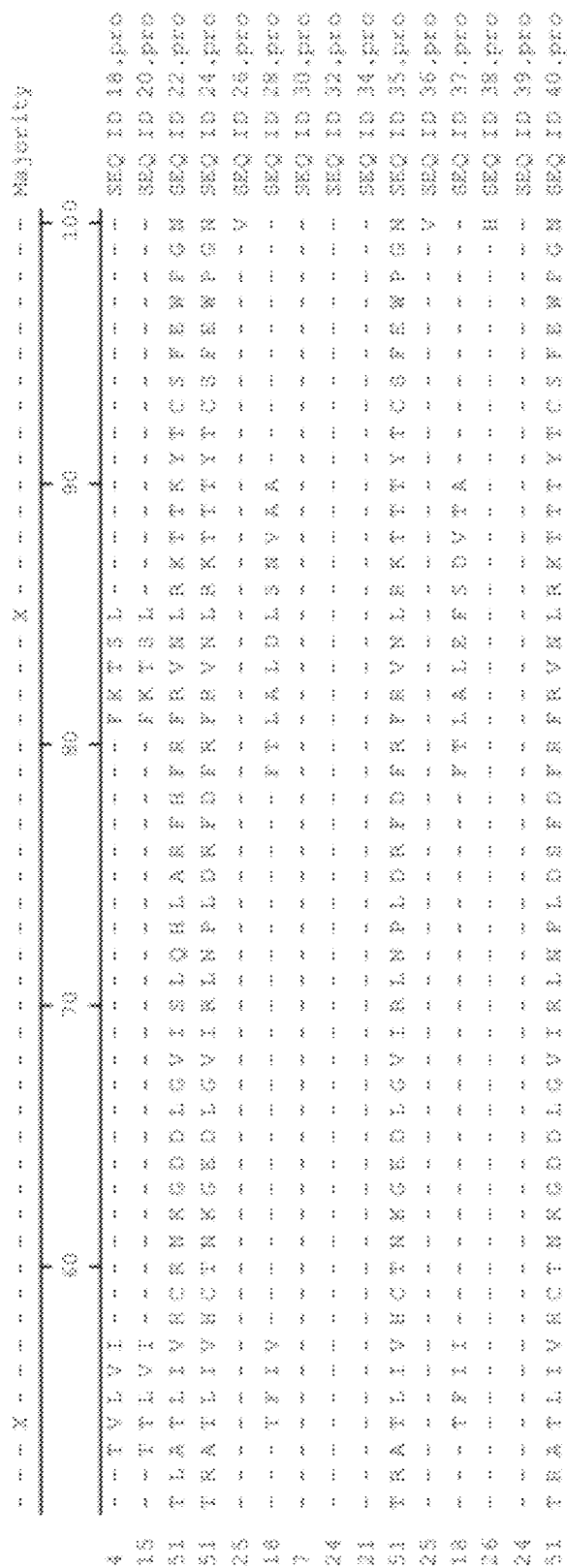
Figure 11C:
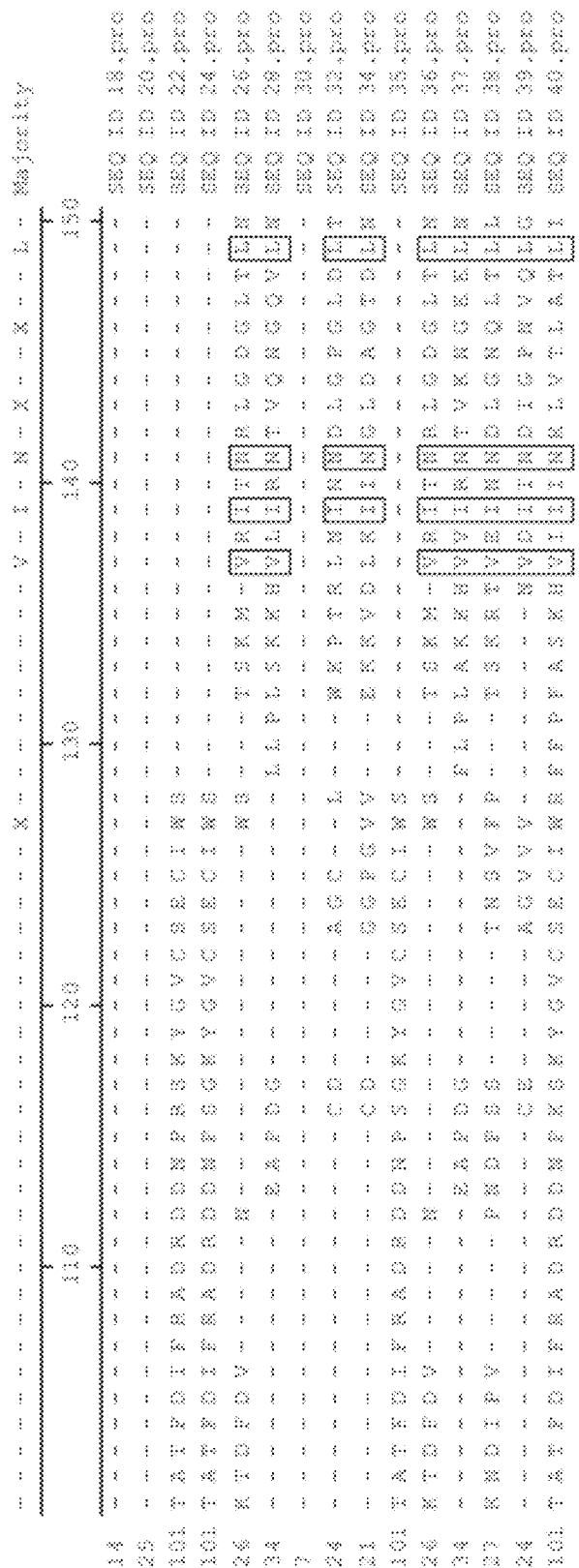
Figure 11D:
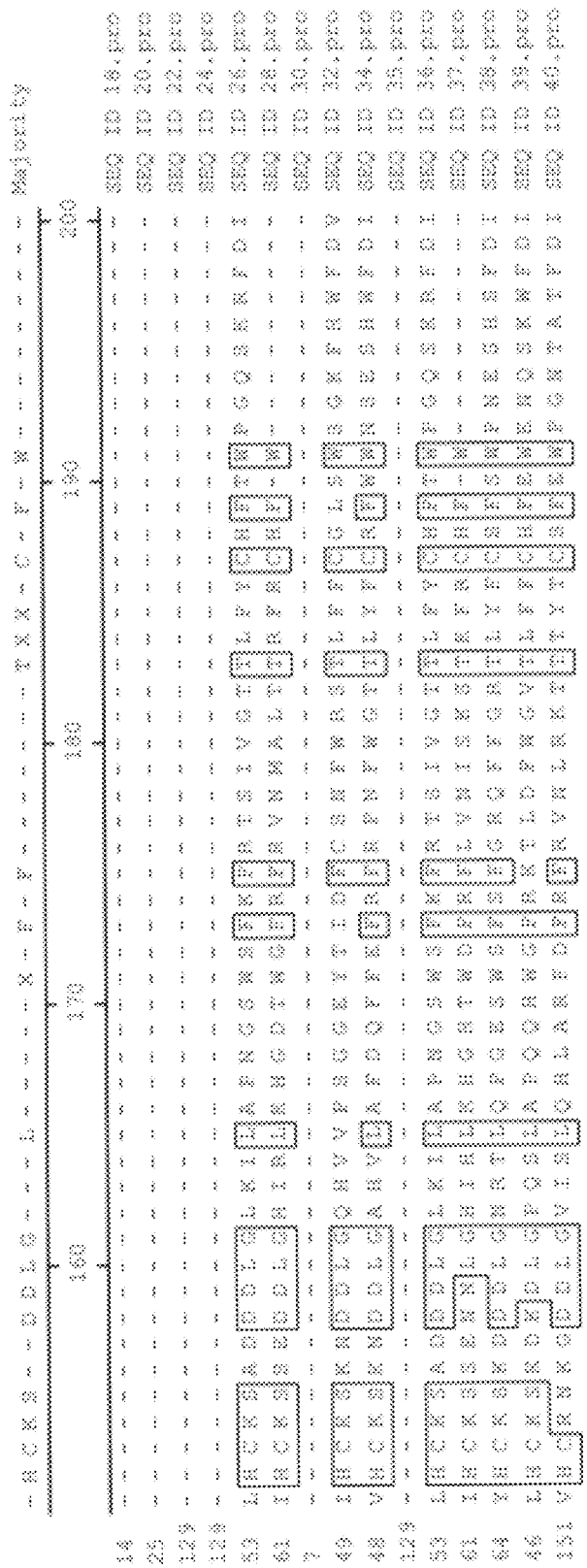
Figure 11E:
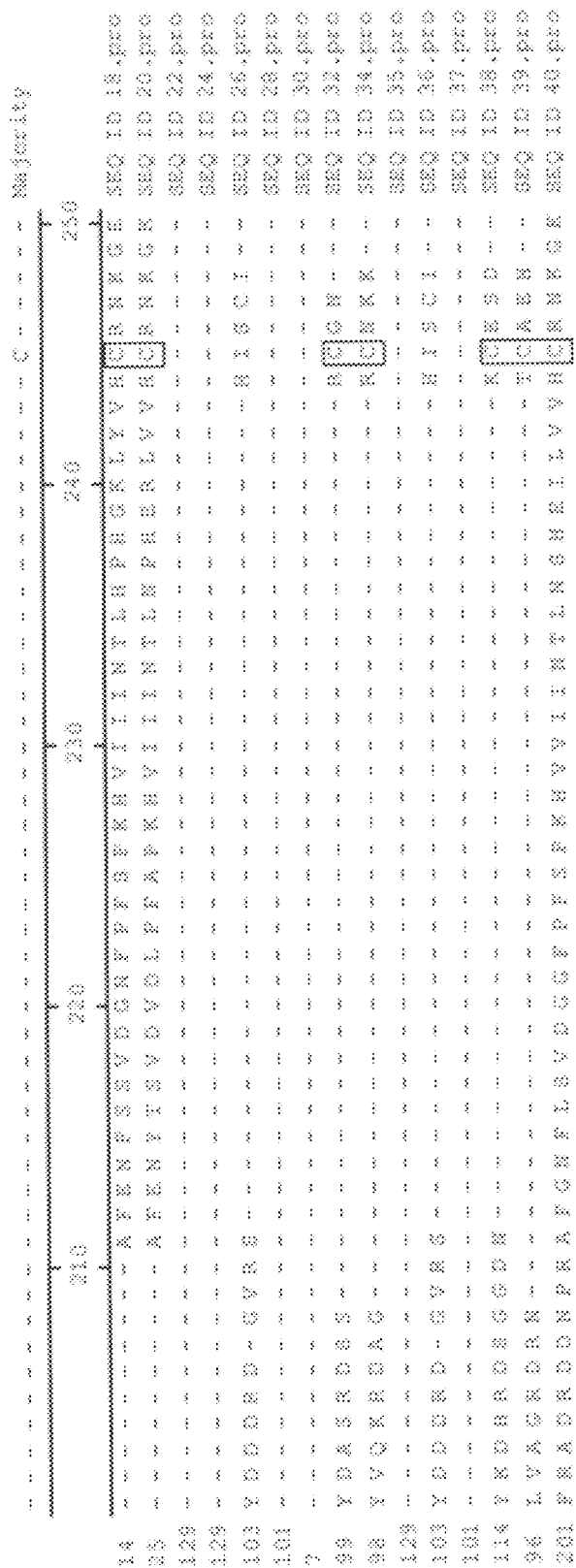
Figure 11F:
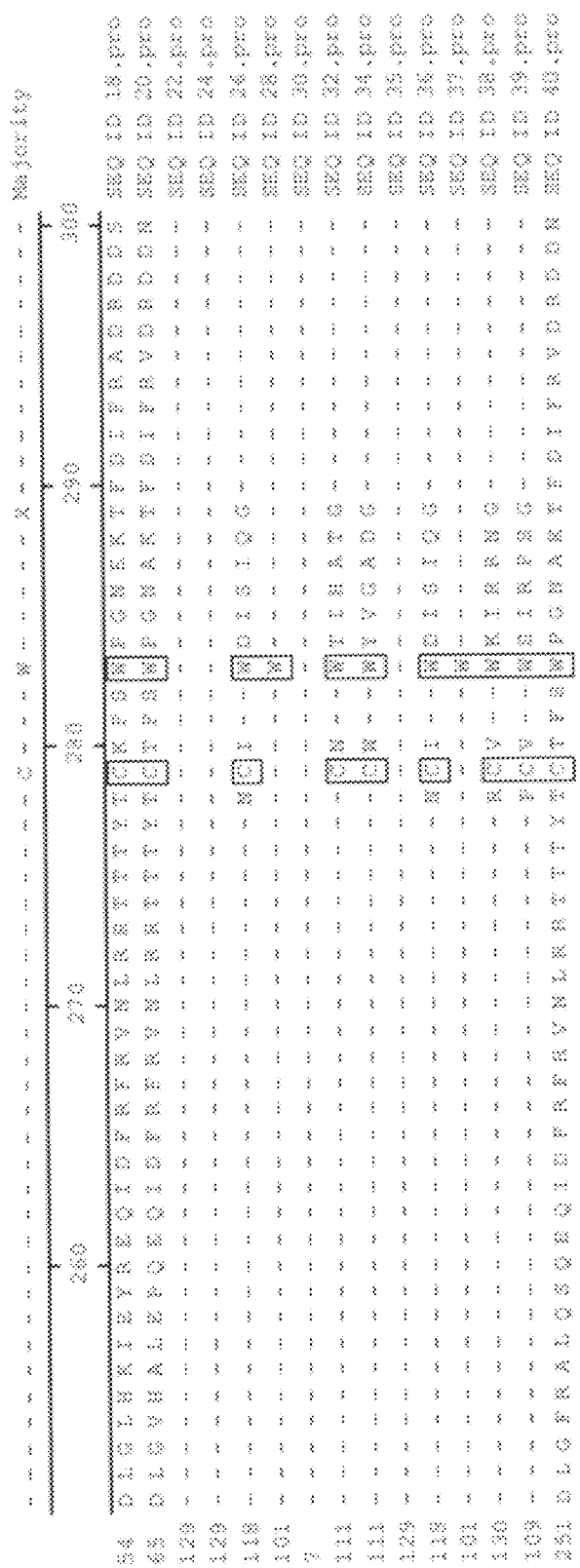
Figure 11G:
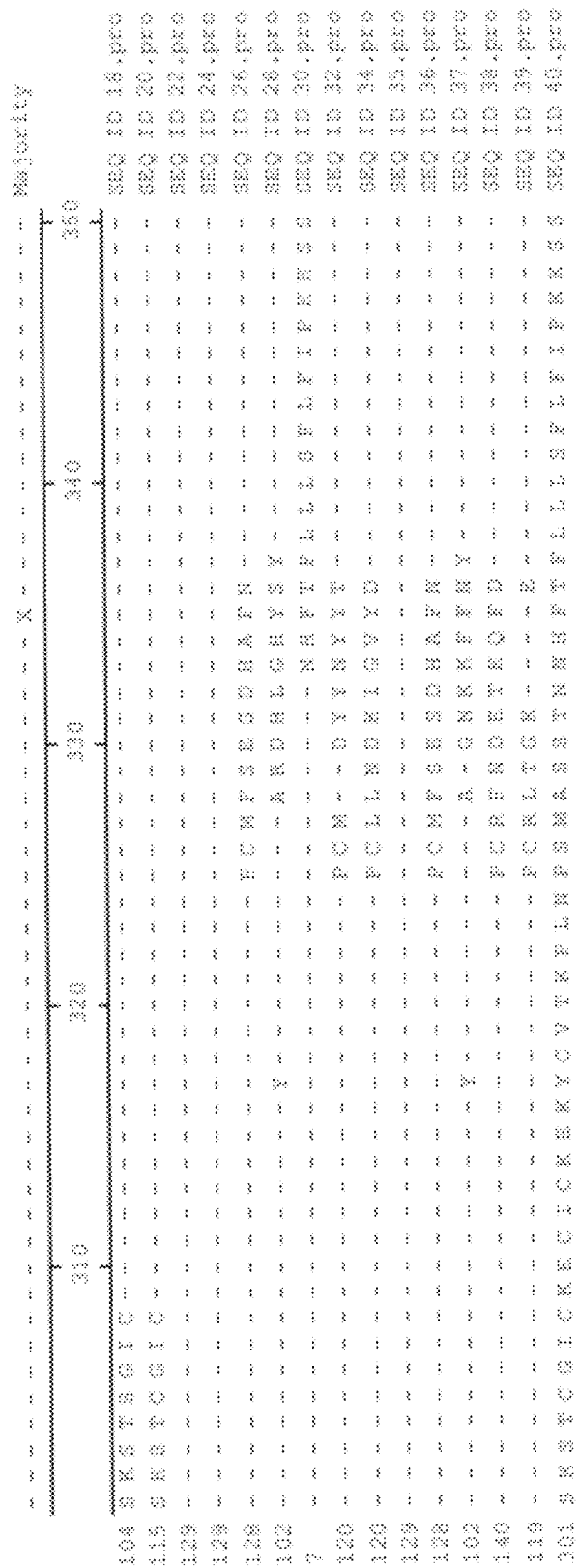
Figure 11H:
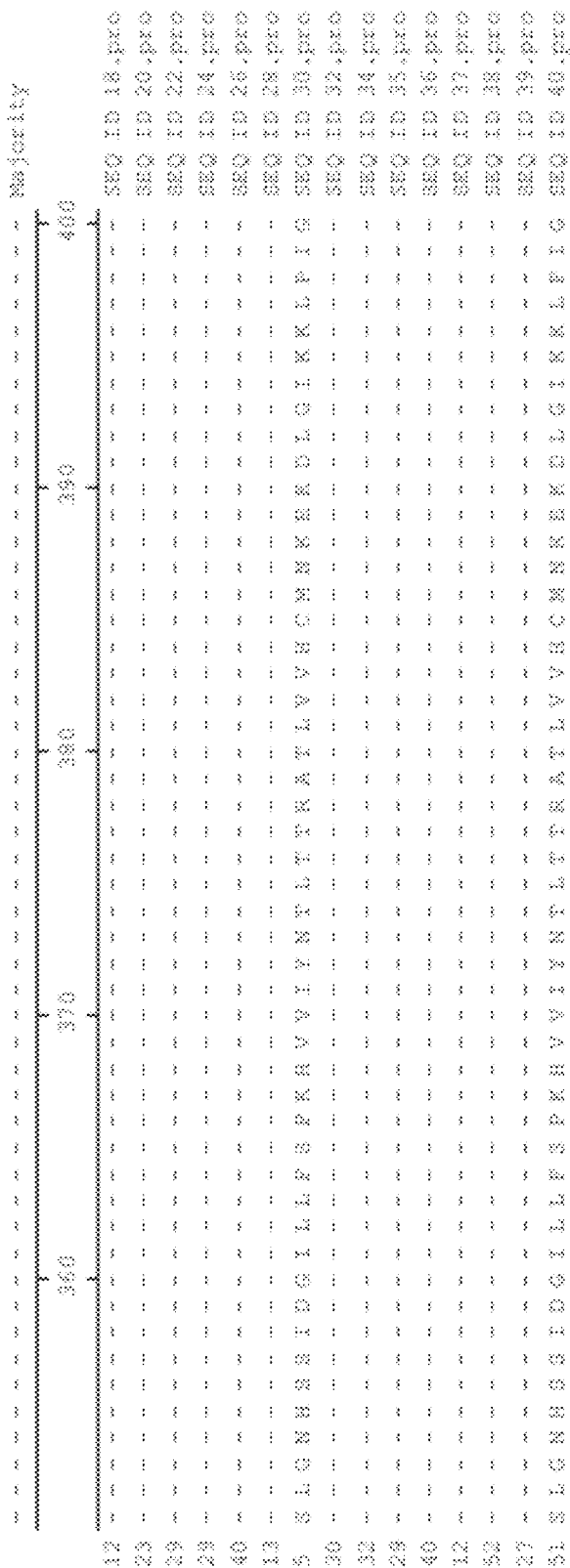
Figure 11I:
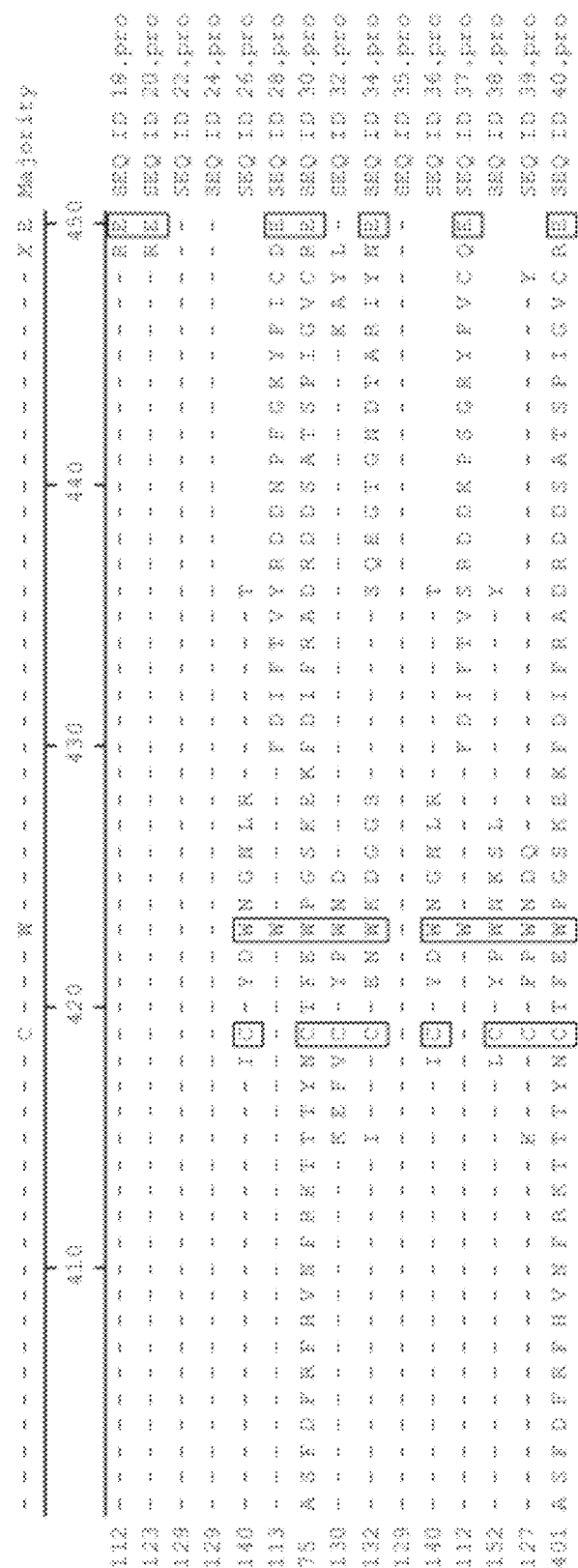
Figure 11J:
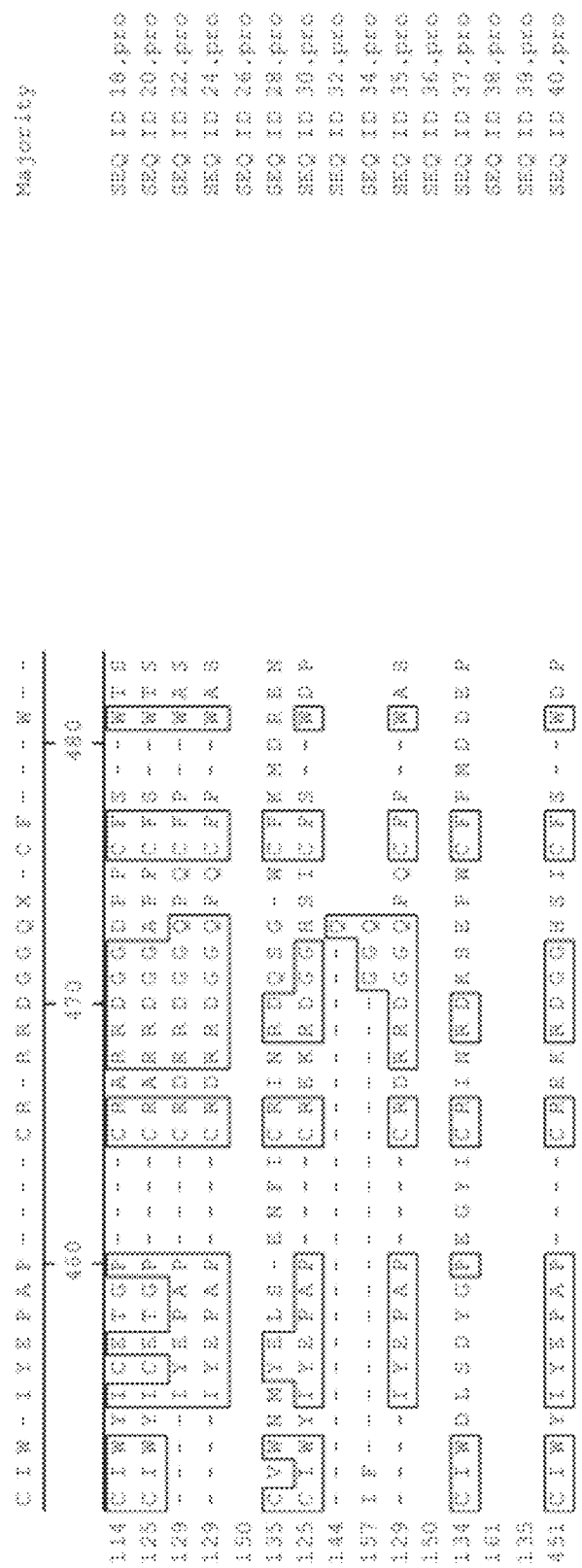

Preparation of the Destination Vector PHP23236 for Transformation Into Gaspe Flint Derived Maize Lines Destination vector PHP23236 (FIG. 6, SEQ ID NO:6) was obtained by transformation of *Agrobacterium* strain LBA4404 containing plasmid PHP10523 (FIG. 7, SEQ ID NO:7) with plasmid PHP23235 (FIG. 8, SEQ ID NO:8) and isolation of the resulting co-integration product. Destination vector PHP23236, can be used in a recombination reaction with an entry done as described in Example 16 to create a maize expression vector for transformation of Gaspe Flint-derived maize lines.

Example 16

Preparation of Plasmids for Transformation into Gaspe Flint Derived Maize Lines

Using the INVITROGEN™ GATEWAY® LR Recombination technology, the protein coding region, described in Example 5, was directionally cloned into the destination vector PHP29634 (SEQ ID NO:16) to create an expression vector, PHP33118. Destination vector PHP29634 is similar to destination vector PHP23236; however, destination vector PHP29634 has site-specific recombination sites FRT1 and FRT87 and also encodes the GAT4602 selectable marker protein for selection of transformants using glyphosate. This expression vector contains the cDNA of interest, encoding the SIPR polypeptide, under control of the UBI promoter and is a T-DNA binary vector for *Agrobacterium*-mediated transformation into corn as described, but not limited to, the examples described herein.

Example 17

Transformation of Gaspe Flint Derived Maize Lines with a Validated *Arabidopsis* Lead Gene Maize plants can be transformed to overexpress the *Arabidopsis* lead gene or the corresponding homologs from other species in order to examine the resulting phenotype.

Recipient Plants:

Recipient plant cells can be from a uniform maize line having a short life cycle ("fast cycling"), a reduced size, and high transformation potential. Typical of these plant cells for maize are plant cells from any of the publicly available Gaspe Flint (GBF) line varieties. One possible candidate plant line variety is the F1 hybrid of GBFxQ™ (Quick Turnaround Maize, a publicly available form of Gaspe Flint selected for growth under greenhouse conditions) disclosed in Tomes et al. U.S. Patent Application Publication No. 2003/0221212. Transgenic plants obtained from this line are of such a reduced size that they can be grown in four inch pots (114 the space needed for a normal sized maize plant) and mature in less than 2.5 months. (Traditionally 3.5 months is required to obtain transgenic T0 seed once the transgenic plants are acclimated to the greenhouse.) Another suitable line is a double haploid line of GS3 (a highly transformable line) X Gaspe Flint. Yet another suitable line is a transformable elite inbred line carrying a transgene which causes early flowering, reduced stature, or both.

Transformation Protocol:

Any suitable method may be used to introduce the transgenes into the maize cells, including but not limited to inoculation type procedures using *Agrobacterium* based vectors. Transformation may be performed on immature embryos of the recipient (target) plant.

Precision Growth and Plant Tracking:

The event population of transgenic (T0) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location with the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) her code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. Published Patent Application No. 200410122592, incorporated herein by reference.

Phenotypic Analysis Using Three-Dimensional Imaging:

Each greenhouse plant in the T0 event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. A digital imaging analyzer may be used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate the biomass, size and morphology of each plant.

Due to the change in size of the plants from the time the first leaf appears from the soil to the time the plants are at the end of their development, the early stages of plant development are best documented with a higher magnification from the top. This may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation:

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture and motor focus. All camera settings may be made using LemnaTec software. For example, the instrumental variance of the imaging analyzer is less than about 5% for major components and less than about 10% for minor components.

Software:

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g. Matlab, others) can be used for quantitative interpretation of the imaging data, and any of these software systems can be applied to the image data set.

Conveyor System:

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination:

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores.

Biomass Estimation Based on Three-Dimensional Imaging:

For best estimation of biomass the plant images should be taken from at least three axes, for example, the top and two side (sides 1 and 2) views. These images are then analyzed to separate the plant from the background, pot and pollen control bag (if applicable). The total area of the plant can be estimated by the calculation:

$$\text{Estimated Total Plant Area(pixels)} = \text{Top Area(pixels)} \text{ Side1 Area(pixels) Side2 Area(pixels)}$$

In the equation above the units of volume and area are 'arbitrary units'. Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification:

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen", which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis:

Transgenes which modify plant architecture parameters may also be identified using the present invention, including such parameters as maximum height and width, internodal distances, angle between leaves and stem, number of leaves starting at nodes and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date:

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g. pollination date, first silk date) can be recorded by the personnel responsible for performing plant care. To maximize data integrity and process efficiency this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants:

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition.

Example 18

Evaluation of Gaspe Flint Derived Maize Lines for Drought Tolerance

Transgenic Gaspe Flint derived maize lines containing the candidate gene can be screened for tolerance to drought stress in the following manner.

Transgenic maize plants are subjected to well-watered conditions (control) and to drought-stressed conditions. Transgenic maize plants are screened at the T1 stage or later.

For plant growth, the soil mixture consists of ⅓ TURFACE®, ⅓ SB300 and ⅓ sand. All pots are filled with the same amount of soil±10 grams. Pots are brought up to 100% field capacity ("FC") by hand watering. All plants are maintained at 60% FC using a 20-10-20 (N-P-K) 125 ppm N nutrient solution. Throughout the experiment pH is monitored at least three times weekly for each table. Starting at 13 days after planting (DAP), the experiment can be divided into two treatment groups, well watered and reduce watered. All plants comprising the reduced watered treatment are maintained at 40% FC while plants in the well watered treatment are maintained at 80% FC. Reduced watered plants are grown for 10 days under chronic drought stress conditions (40% FC). All plants are imaged daily throughout chronic stress period. Plants are sampled for metabolic profiling analyses at the end of chronic drought period, 22 DAP. At the conclusion of the chronic stress period all plants are imaged and measured for chlorophyll fluorescence. Reduced watered plants are subjected to a severe drought stress period followed by a recovery period, 23-31 DAP and 32-34 DAP respectively. During the severe drought stress, water and nutrients are withheld until the plants reached 8% FC. At the conclusion of severe stress and recovery periods all plants are again imaged and measured for chlorophyll fluorescence. The probability of a greater Student's t Test is calculated for each transgenic mean compared to the appropriate null mean (either segregant null or construct null). A minimum (P<t) of 0.1 is used as a cut off for a statistically significant result.

Example 18B

Transformation and Evaluation of Maize Lines transformed with PHP32412

The SPR polypeptide expression cassette present in co-integrate vector PHP32412 was introduced into a transformable maize line derived from an elite maize inbred line as described in Examples 14A and 14B.

Eight transformation events were screened for drought tolerance activity essentially as described in Example 2. Tables 3A-3C show the variables for each transgenic event that were significantly altered, as compared to the null segregants.

A "positive effect" was defined as statistically significant improvement in that variable for the transgenic event relative to the null control. A "negative effect" was defined as a statistically significant improvement in that variable for the null control relative to the transgenic event.

For the construct evaluated, PHP32412, the statistical value associated with each improved variable is presented in Table 3A-3C. A significant positive result had a P-value of less than or equal to 0.1 in a two-tailed test. The results for individual transformed maize lines are presented in Table 3A-3C.

Tables 3A-3C indicate that one out of eight events showed a positive effect (increase) in Fv'/Fm' (variable fluorescence difference between the maximum and minimum fluorescence/maximum fluorescence) (Table 3A) under non-stress conditions.

TABLE 3A

Evaluation of Individual Maize Lines Transformed with PHP32412* and grown under reduced water

| EVENT_NAME | Fv'/Fm' no stress | | Fv'/Fm' stress | |
| --- | --- | --- | --- | --- |
| | pvalue | % change NULL | pvalue | % change vs. NULL |
| E8266.07.5.1 | 0.38 | 2.70% | 0.42 | −9.70% |
| E8266.07.6.3 | 0.80 | 0.80% | 0.32 | −11.80% |
| E8266.07.7.1 | 0.18 | 4.00% | 0.47 | −8.30% |
| E8266.07.7.3 | 0.10 | 4.90% | 0.75 | 3.60% |

TABLE 3A-continued

Evaluation of Individual Maize Lines Transformed with
PHP32412* and grown under reduced water

| | Fv'/Fm' no stress | | Fv'/Fm' stress | |
|---|---|---|---|---|
| EVENT_NAME | pvalue | % change NULL | pvalue | % change vs. NULL |
| E8266.07.7.9 | 0.19 | 3.90% | 0.74 | −3.80% |
| E8266.07.8.3 | 0.76 | 0.90% | 0.43 | −9.00% |
| E8266.07.8.4 | 0.78 | −0.80% | 0.68 | −4.70% |
| E8266.07.8.5 | 0.41 | −2.40% | 0.93 | −1.10% |

*The P-values shown reflects the performance of the event against the reference. Significant effect has P-value less than or equal to 0.1.

TABLE 3B

Evaluation of Individual Maize Lines Transformed with
PHP32412* and grown under reduced water

| | phiPSII no stress | | phiPSII stress | |
|---|---|---|---|---|
| EVENT_NAME | Pvalue | % change vs. NULL | pvalue | % change vs. NULL |
| E8266.07.5.1 | 0.29 | 4.60% | 0.53 | −10.40% |
| E8266.07.6.3 | 0.93 | 0.40% | 0.35 | −15.00% |
| E8266.07.7.1 | 0.33 | 4.00% | 0.17 | −21.40% |
| E8266.07.7.3 | 0.12 | 6.50% | 0.92 | 1.60% |
| E8266.07.7.9 | 0.37 | 3.70% | 0.94 | −1.20% |
| E8266.07.8.3 | 0.75 | 1.30% | 0.59 | −8.30% |
| E8266.07.8.4 | 0.99 | 0.10% | 0.95 | 1.00% |
| E8266.07.8.5 | 0.40 | −3.60% | 0.90 | −1.90% |

*The P-values shown reflects the performance of the event against the reference. Significant effect has P-value less than or equal to 0.1.

TABLE 3C

Evaluation of Individual Maize Lines Transformed with
PHP32412* and grown under reduced water

| | Shoot Dwt (g) | | Shoot Fwt (g) | |
|---|---|---|---|---|
| EVENT_NAME | pvalue | % change vs. NULL | pvalue | % change vs. NULL |
| E8266.07.5.1 | 0.24 | −8.20% | 0.09 | −20.70% |
| E8266.07.6.3 | 0.07 | −12.70% | 0.11 | −19.20% |
| E8266.07.7.1 | 0.14 | −9.90% | 0.02 | −27.30% |
| E8266.07.7.3 | 0.25 | −7.70% | 0.22 | −14.40% |
| E8266.07.7.9 | 0.48 | −4.80% | 0.13 | −18.10% |
| E8266.07.8.3 | 0.30 | −7.00% | 0.10 | −19.30% |
| E8266.07.8.4 | 0.87 | −1.10% | 0.65 | −5.40% |
| E8266.07.8.5 | 0.30 | −7.10% | 0.54 | −7.30% |

*The P-values shown reflects the performance of the event against the reference. Significant effect has P-value less than or equal to 0.1.

Example 19

Yield Analysis of Maize Lines with the *Arabidopsis* Lead Gene

A recombinant DNA construct containing a validated *Arabidopsis* gene can be introduced into an elite maize inbred line either by direct transformation or introgression from a separately transformed line.

Transgenic plants, either inbred or hybrid, can undergo more vigorous field-based experiments to study yield enhancement and/or stability under well-watered and water-limiting conditions.

Subsequent yield analysis can be done to determine whether plants that contain the validated *Arabidopsis* lead gene have an improvement in yield performance under water-limiting conditions, when compared to the control plants that do not contain the validated *Arabidopsis* lead gene. Specifically, drought conditions can be imposed during the flowering and/or grain fill period for plants that contain the validated *Arabidopsis* lead gene and the control plants. Reduction in yield can be measured for both. Plants containing the validated *Arabidopsis* lead gene have less yield loss relative to the control plants, for example, at least 25% less yield loss.

The above method may be used to select transgenic plants with increased yield, under water-limiting conditions and/or well-watered conditions, when compared to a control plant not comprising said recombinant DNA construct.

Example 19B

Yield Analysis of Maize Lines transformed with PHP32412 encoding the *Arabidopsis* Lead Gene At1g26797

The Self-incompatibility related polypeptide (SIPR expression cassette present in the co-integrate vector PHP32412 was introduced into a transformable maize line derived from an elite maize inbred line as described in Examples 14A and 14B.

Ten transgenic events were field tested in 2009 at Johnston, Iowa ("JH"), York, Nebr. ("YK"), and Woodland, Calif. ("WO"). At the Woodland, Calif., location, drought conditions were imposed during flowering ("FS"; flowering stress) and during the grain fill period ("GFS"; grain fill stress). The JH location was well-watered, and the YK location did not experience drought. Yield data (bushel/acre; hu/ac) of the 10 transgenic events is shown in Table 4 together with the bulk null control (BN). Statistical significance is reported at P<0.1 for a one-tailed test. Four out of ten events had positive yield effect in the YK environment when compared to the Bulk Null (BN) control. Other locations did not show any significant yield reductions. One event E8266.07.7.3 showed positive effect (increase) in Fv'/Fm' (example 18B) under normal conditions and also showed positive yield effect in the field.

TABLE 4

2009 Field Test of Maize Transformed with PHP32412

| | Yield (bu/acre) | | | |
|---|---|---|---|---|
| Event ID | YK | JH | WO_FS | WO_GFS |
| E8266.07.5.1 | 174 | 201 | 113 | 16 |
| E8266.07.6.2 | 181 | 205 | 108 | na |
| E8266.07.6.3 | 175 | 203 | 102 | 19 |
| E8266.07.7.1 | 180 | 202 | 111 | 22 |
| E8266.07.7.3 | 187* | 205 | 105 | 21 |
| E8266.07.7.9 | 190* | 206 | 118 | 18 |
| E8266.07.8.1 | 185* | 206 | 105 | 15 |
| E8266.07.8.3 | 186* | 203 | 107 | 21 |
| E8266.07.8.4 | 178 | 204 | 113 | na |
| E8266.07.8.5 | 176 | 203 | 113 | 11 |
| BN | 177 | 202 | 115 | 23 |

*Significant gain in yield
**Significant loss in yield
na = not available

Example 20A

Preparation of Maize SIPR Polypeptide Lead Gene Expression Vector for Transformation of Maize The protein-coding region of a maize done encoding a maize SIPR polypeptide can be introduced into the INVITROGEN™ vector pENTR/D-TOPO® to create an entry done.

Using INVITROGEN's™ GATEWAY® technology, an LR Recombination Reaction can be performed with an entry clone and a destination vector to create a precursor plasmid. The precursor plasmid contains the following expression cassettes:

1. Ubiquitin promoter::moPAT::PinII terminator; cassette expressing the PAT herbicide resistance gene used for selection during the transformation process.
2. LTP2 promoter::DS-RED2::PinII terminator; cassette expressing the DS-RED color marker gene used for seed sorting.
3. Ubiquitin promoter::Zm-SIPR polypeptide::PinII terminator; cassette overexpressing the gene of interest, maize SIPR polypeptide.

Example 20B

Transformation of Maize with Maize SIPR polypeptide Lead Gene Using *Agrobacterium*

The maize SIPR polypeptide expression cassette present in the precursor plasmid described in example 20A can be introduced into a maize inbred line, or a transformable maize line derived from an elite maize inbred line, using *Agrobacterium*-mediated transformation as described in Examples 12 and 13.

The precursor plasmid can be electroporated into the LBA4404 *Agrobacterium* strain containing vector PHP10523 (FIG. 7; SEQ ID NO:7) to create a co-integrate vector. The co-integrate vector is formed by recombination of the 2 plasmids, the precursor plasmid from example 20A and PHP10523, through the COS recombination sites contained on each vector. The co-integrate vector contains the same 3 expression cassettes as above (Example 20A) in addition to other genes (TET, TET, TRFA, ORI terminator, CTL, ORI V, VIR C1, VIR C2, VIR G, VIR B) needed for the *Agrobacterium* strain and the *Agrobacterium*-mediated transformation.

Example 21

Preparation of Maize Expression Plasmids for Transformation into Gaspe Flint Derived Maize Lines A maize clone encoding a complete maize SPR homolog designated can be isolated.

Using the INVITROGEN™ GATEWAY® Recombination technology described in Example 9, the clones encoding maize SIPR polypeptide homologs can be directionally cloned into the destination vector PHP23236 (SEQ ID NO:6; FIG. 6) to create expression vectors. Each expression vector contains the cDNA of interest under control of the UBI promoter and is a T-DNA binary vector for *Agrobacterium*-mediated transformation into corn as described, but not limited to, the examples described herein.

Example 22

Transformation and Evaluation of Soybean with Soybean Homologs of Validated Lead Genes Based on homology searches, one or several candidate soybean homologs of validated *Arabidopsis* lead genes can be identified and also be assessed for their ability to enhance drought tolerance in soybean. Vector construction, plant transformation and phenotypic analysis will be similar to that in previously described Examples.

Example 23

Transformation and Evaluation of Maize with Maize Homologs of Validated Lead Genes Based on homology searches, one or several candidate maize homologs of validated *Arabidopsis* lead genes can be identified and also be assessed for their ability to enhance drought tolerance in maize. Vector construction, plant transformation and phenotypic analysis will be similar to that in previously described Examples.

Example 23

Transformation of *Arabidopsis* with Maize and Soybean Homologs of Validated Lead Genes Soybean and maize homologs to validated *Arabidopsis* lead genes can be transformed into *Arabidopsis* under control of the 35S promoter and assessed for their ability to enhance drought tolerance in *Arabidopsis*. Vector construction, plant transformation and phenotypic analysis will be similar to that in previously described Examples.

What is claimed is:

1. A plant comprising in its genome a recombinant DNA construct comprising a polynucleotide operably linked to at least one heterologous regulatory element, wherein said polynucleotide encodes a polypeptide having an amino acid sequence of at least 95% sequence identity, based on the Clustal V method of alignment, when compared to SEQ ID NOS: 18 and wherein said plant exhibits increased drought tolerance when compared to a control plant not comprising said recombinant DNA construct.

2. The plant of claim 1, wherein the plant is a maize plant or a soybean plant.

3. A method of increasing drought tolerance in a plant, comprising:
   (a) introducing into a regenerable plant cell a recombinant DNA construct comprising a polynucleotide operably linked to at least one heterologous regulatory sequence, wherein the polynucleotide encodes a polypeptide having an amino acid sequence of at least 95% sequence identity, based on the Clustal V method of alignment, when compared to SEQ ID NOS: 18; and
   (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct.

4. The method of claim 3, further comprising:
   (c) obtaining a progeny plant derived from the transgenic plant, wherein said progeny plant comprises in its genome the recombinant DNA construct and exhibits increased drought tolerance when compared to a control plant not comprising the recombinant DNA construct.

5. A method of evaluating drought tolerance in a plant, comprising:
   (a) introducing into a regenerable plant cell a recombinant DNA construct comprising a polynucleotide operably linked to at least one heterologous regulatory sequence, wherein the polynucleotide encodes a polypeptide having an amino acid sequence of at least 95% sequence identity, based on the Clustal V method of alignment, when compared to SEQ ID NOS: 18;
   (b) regenerating a transgenic plant from the regenerable plant cell after step (a), wherein the transgenic plant comprises in its genome the recombinant DNA construct; and
   (c) evaluating the transgenic plant for drought tolerance compared to a control plant not comprising the recombinant DNA construct.

6. The method of claim 5, further comprising:
   (d) obtaining a progeny plant derived from the transgenic plant, wherein the progeny plant comprises in its genome the recombinant DNA construct; and
   (e) evaluating the progeny plant for drought tolerance compared to a control plant not comprising the recombinant DNA construct.

7. A method of evaluating drought tolerance in a plant, comprising:
   (a) introducing into a regenerable plant cell a recombinant DNA construct comprising a polynucleotide operably linked to at least one heterologous regulatory sequence, wherein the polynucleotide encodes a polypeptide having an amino acid sequence of at least 95% sequence identity, based on the Clustal V method of alignment, when compared to SEQ ID NO: 18;
   (b) regenerating a transgenic plant from the regenerable plant cell after step (a), wherein the transgenic plant comprises in its genome the recombinant DNA construct;
   (c) obtaining a progeny plant derived from the transgenic plant, wherein the progeny plant comprises in its genome the recombinant DNA construct; and
   (d) evaluating the progeny plant for drought tolerance compared to a control plant not comprising the recombinant DNA construct.

8. The method of claim 3, wherein the plant is a maize plant or a soybean plant.

9. The method of claim 4, wherein the plant is a maize plant or a soybean plant.

10. The method of claim 5, wherein the plant is a maize plant or a soybean plant.

11. The method of claim 6, wherein the plant is a maize plant or a soybean plant.

12. The method of claim 7, wherein the plant is a maize plant or a soybean plant.

13. A seed of the plant of claim 1, wherein the seed comprises the recombinant DNA construct.

14. A seed of the plant of claim 2, wherein the seed comprises the recombinant DNA construct.

* * * * *

SEQUENCE LISTING

```
<160> NUMBER OF SEQ ID NOS: 40

<210> SEQ ID NO 1
<211> LENGTH: 18491
<212> TYPE: DNA
<213> ORGANISM: Artificial Sequence
<220> FEATURE:
<223> OTHER INFORMATION: pHSbarENDs2 activation tagging construct

<400> SEQUENCE: 1
catgaatcaa acaaacatac acagcgactt attcacacga gctcaaatta caacggtata      60
tatcctgccg tcgacaacca tggtctagac aggatccccg ggtaccgagc tcgaatttgc     120
aggtcgactg cgtcatccct tacgtcagtg gagatatcac atcaatccac ttgctttgaa     180
gacgtggttg gaacgtcttc tttttccacg atgctcctcg tgggtggggg tccatctttg     240
ggaccactgt cggcagaggc atcttgaacg atagcctttc ctttatcgca atgatggcat     300
```

```
ttgtaggtgc caccttcctt ttctactgtc cttttgatga agtgacagat agctgggcaa    360
tggaatccga ggaggtttcc cgatattacc ctttgttgaa aagtctcaat tgcccttttgg   420 tcttctgaga ctgttgcgtc atcccttacg tcagtggaga tatcacatca atccacttgc    480
tttgaagacg tggttggaac gtcttctttt tccacgatgc tcctcgtggg tgggggtcca    540
tctttgggac cactgtcggc agaggcatct tgaacgatag cctttccttt atcgcaatga    600
tggcatttgt aggtgccacc ttccttttct actgtccttt tgatgaagtg acagatagct    660
gggcaatgga atccgaggag gtttcccgat attaccctttt gttgaaaagt ctcagttaac    720
ccgcgatcct gcgtcatccc ttacgtcagt ggagatatca catcaatcca cttgctttga    780
agacgtggtt ggaacgtctt ctttttccac gatgctcctc gtgggtgggg gtccatcttt    840
gggaccactg tcggcagagg catcttgaac gatagccttt cctttatcgc aatgatggca    900
tttgtaggtg ccaccttcct tttctactgt ccttttgatg aagtgacaga tagctgggca    960
atggaatccg aggaggtttc ccgatattac cctttgttga aaagtctcaa ttgcccttttg   1020 gtcttctgag actgttgcgt catcccttac gtcagtggag atatcacatc aatccacttg    1080
ctttgaagac gtggttggaa cgtcttcttt tccacgatg ctcctcgtgg gtgggggtcc     1140
atctttggga ccactgtcgg cagaggcatc ttgaacgata gcctttcctt tatcgcaatg    1200
atggcatttg taggtgccac cttccttttc tactgtcctt ttgatgaagt gacagatagc    1260
tgggcaatgg aatccgagga ggtttcccga tattaccctt tgttgaaaag tctcagttaa    1320
cccgcaattc actggccgtc gttttacaac gtcgtgactg ggaaaaccct ggcgttaccc    1380
aacttaatcg ccttgcagca catccccctt tcgccagctg gcgtaatagc gaagaggccc    1440
gcaccgatcg cccttcccaa cagttgcgca gcctgaatgg cgaatggatc gatccgtcga    1500
tcgaccaaag cggccatcgt gcctcccac tcctgcagtt cgggggcatg gatgcgcgga    1560
tagccgctgc tggtttcctg gatgccgacg gatttgcact gccggtagaa ctccgcgagg    1620
tcgtccagcc tcaggcagca gctgaaccaa ctcgcgaggg gatcgagccc ctgctgagcc    1680
tcgacatgtt gtcgcaaaat tcgccctgga cccgcccaac gatttgtcgt cactgtcaag    1740
gtttgacctg cacttcattt ggggcccaca tacaccaaaa aaatgctgca taattctcgg    1800
ggcagcaagt cggttacccg gccgccgtgc tggaccgggt tgaatggtgc ccgtaacttt    1860
cggtagagcg gacggccaat actcaacttc aaggaatctc acccatgcgc gccggcgggg    1920
aaccggagtt cccttcagtg aacgttatta gttcgccgct cggtgtgtcg tagatactag    1980
cccctggggc cttttgaaat ttgaataaga tttatgtaat cagtctttta ggtttgaccg    2040
gttctgccgc ttttttttaaa attggatttg taataataaa acgcaattgt tgttattgt    2100 ggcgctctat catagatgtc gctataaacc tattcagcac aatatattgt tttcatttta    2160
atattgtaca tataagtagt agggtacaat cagtaaattg aacggagaat attattcata    2220
aaaatacgat agtaacgggt gatatattca ttagaatgaa ccgaaaccgg cggtaaggat    2280
ctgagctaca catgctcagg ttttttacaa cgtgcacaac agaattgaaa gcaaatatca    2340
tgcgatcata ggcgtctcgc atatctcatt aaagcagggg gtgggcgaag aactccagca    2400
tgagatcccc gcgctggagg atcatccagc cggcgtcccg gaaaacgatt ccgaagccca    2460
acctttcata gaaggcggcg gtggaatcga atctcgtga tggcaggttg ggcgtcgctt    2520
ggtcggtcat ttcgaacccc agagtccgc tcagaagaac tcgtcaagaa ggcgatagaa    2580
ggcgatgcgc tgcgaatcgg gagcggcgat accgtaaagc acgaggaagc ggtcagccca    2640
```

-continued

```
ttcgccgcca agctcttcag caatatcacg ggtagccaac gctatgtcct gatagcggtc      2700
cgccacaccc agccggccac agtcgatgaa tccagaaaag cggccatttt ccaccatgat      2760
attcggcaag caggcatcgc catgggtcac gacgagatcc tcgccgtcgg gcatgccccc      2820
caattcactg gccgtcgttt tacaacgtcg tgactgggaa aaccctggcg ttacccaact      2880
taatcgcctt gcagcacatc cccctttcgc cagctggcgt aatagcgaag aggcccgcac      2940
cgatcgccct tcccaacagt tgcgcagcct gaatggcgaa tggcgcctga tgcggtattt      3000
tctccttacg catctgtgcg gtatttcaca ccgcatatgg tgcactctca gtacaatctg      3060
ctctgatgcc gcatagttaa gccagccccg acacccgcca cacccgctg acgcgccctg       3120
acgggcttgt ctgctcccgg catccgctta cagacaagct gtgaccgtct ccgggagctg      3180
catgtgtcag aggttttcac cgtcatcacc gaaacgcgcg agacgaaagg cctcgtgat       3240
acgcctattt ttataggtta atgtcatgat aataatggtt tcttagacgt caggtggcac      3300
ttttcgggga atgtgcgcg gaaccccat ttgtttattt ttctaaatac attcaaatat         3360
gtatccgctc atgagacaat aaccctgata aatgcttcaa taatattgaa aaggaagag       3420
tatgagtatt caacatttcc gtgtcgccct tattccctt tttgcggcat tttgccttcc       3480
tgtttttgct cacccagaaa cgctggtgaa agtaaaagat gctgaagatc agttgggtgc      3540
acgagtgggt tacatcgaac tggatctcaa cagcggtaag atccttgaga gttttcgccc      3600
cgaagaacgt tttccaatga tgagcacttt taaagttctg ctatgtggcg cggtattatc      3660
ccgtattgac gccgggcaag agcaactcgg tcgccgcata cactattctc agaatgactt      3720
ggttgagtac tcaccagtca cagaaaagca tcttacggat ggcatgacag taagagaatt      3780
atgcagtgct gccataacca tgagtgataa cactgcggcc aacttacttc tgacaacgat      3840
cggaggaccg aaggagctaa ccgcttttt gcacaacatg gggatcatg taactcgcct        3900
tgatcgttgg gaaccggagc tgaatgaagc cataccaaac gacgagcgtg acaccacgat      3960
gcctgtagca atggcaacaa cgttgcgcaa actattaact ggcgaactac ttactctagc      4020
ttcccggcaa caattaatag actggatgga ggcggataaa gttgcaggac cacttctgcg      4080
ctcggccctt ccggctggct ggtttattgc tgataaatct ggagccggtg agcgtgggtc      4140
tcgcggtatc attgcagcac tggggccaga tggtaagccc tcccgtatcg tagttatcta     4200
cacgacgggg agtcaggcaa ctatggatga acgaaataga cagatcgctg agataggtgc      4260
ctcactgatt aagcattggt aactgtcaga ccaagtttac tcatatatac tttagattga      4320
tttaaaactt cattttaat ttaaaaggat ctaggtgaag atccttttg ataatctcat         4380
gaccaaaatc ccttaacgtg agttttcgtt ccactgagcg tcagacccg tagaaaagat       4440
caaaggatct tcttgagatc ctttttttct gcgcgtaatc tgctgcttgc aaacaaaaaa      4500
accaccgcta ccagcggtgg tttgtttgcc ggatcaagag ctaccaactc ttttccgaa       4560
ggtaactggc ttcagcagag cgcagatacc aaatactgtc cttctagtgt agccgtagtt      4620
aggccaccac ttcaagaact ctgtagcacc gcctacatac ctcgctctgc taatcctgtt      4680
accagtggct gctgccagtg gcgataagtc gtgtcttacc gggttggact caagacgata      4740
gttaccggat aaggcgcagc ggtcgggctg aacggggggt tcgtgcacac agcccagctt      4800
ggagcgaacg acctacaccg aactgagata cctacagcgt gagcattgag aaagcgccac      4860
gcttcccgaa gggagaaagg cggacaggta tccggtaagc ggcagggtcg gaacaggaga      4920
gcgcacgagg agcttccag ggggaaacgc ctggtatctt tatagtcctg tcgggtttcg       4980
ccacctctga cttgagcgtc gatttttgtg atgctcgtca ggggggcgga gcctatggaa      5040
```

-continued

```
aaacgccagc aacgcggcct ttttacggtt cctggccttt tgctggcctt ttgctcacat   5100
gttctttcct gcgttatccc ctgattctgt ggataaccgt attaccgcct ttgagtgagc   5160
tgataccgct cgccgcagcc gaacgaccga gcgcagcgag tcagtgagcg aggaagcgga   5220
agagcgccca atacgcaaac cgcctctccc cgcgcgttgg ccgattcatt aatgcagctg   5280
gcacgacagg tttcccgact ggaaagcggg cagtgagcgc aacgcaatta atgtgagtta   5340
gctcactcat taggcacccc aggctttaca ctttatgctt ccggctcgta tgttgtgtgg   5400
aattgtgagc ggataacaat ttcacacagg aaacagctat gaccatgatt acgccaagct   5460
ttctaggggg ggggtaccga tctgagatcg gtaacgaaaa cgaacgggta gggatgaaaa   5520
cggtcggtaa cggtcggtaa aatacctcta ccgttttcat tttcatattt aacttgcggg   5580
acggaaacga aaacgggata taccggtaac gaaaacgaac gggataaaata cggtaatcga   5640 aaaccgatac gatccggtcg ggttaaagtc gaaatcggac gggaaccggt attttttgttc   5700 ggtaaaatca cacatgaaaa catatattca aaacttaaaa acaaatataa aaaattgtaa   5760
acacaagtct taatgatcac tagtggcgcg cctaggagat ctcgagtagg gataacaggg   5820
taatacatag ataaaatcca tataaatctg gagcacacat agtttaatgt agcacataag   5880
tgataagtct tgggctcttg gctaacataa gaagccatat aagtctacta gcacacatga   5940
cacaatataa agtttaaaac acatattcat aatcacttgc tcacatctgg atcacttagc   6000
atgctacagc tagtgcaata ttagacactt tccaatattt ctcaaacttt tcactcattg   6060
caacggccat tctcctaatg acaaattttt catgaacaca ccattggtca atcaaatcct   6120
ttatctcaca gaaacctttg taaaataaat ttgcagtgga atattgagta ccagatagga   6180
gttcagtgag atcaaaaaac ttcttcaaac acttaaaaag agttaatgcc atcttccact   6240
cctcggcttt aggacaaatt gcatcgtacc tacaataatt gacatttgat taattgagaa   6300
tttataatga tgacatgtac aacaattgag acaaacatac ctgcgaggat cacttgtttt   6360
aagccgtgtt agtgcaggct tataatataa ggcatccctc aacatcaaat aggttgaatt   6420
ccatctagtt gagacatcat atgagatccc tttagattta tccaagtcac attcactagc   6480
acacttcatt agttcttccc actgcaaagg agaagatttt acagcaagaa caatcgcttt   6540
gattttctca attgttcctg caattacagc caagccatcc tttgcaacca agttcagtat   6600
gtgacaagca cacctcacat gaaagaaagc accatcacaa actagatttg aatcagtgtc   6660
ctgcaaatcc tcaattatat cgtgcacagc tacttcattt gcactagcat tatccaaaga   6720
caaggcaaac aatttttttct caatgttcca cttaaccatg attgcagtga aggtttgtga   6780
taacctttgg ccagtgtggc gcccttcaac atgaaaaaag ccaacaattc ttttttggag   6840
acaccaatca tcatcaatcc aatggatggt gacacacatg tatgacttat tttgacaaga   6900
tgtccacata tccatagttg tactgaagcg agactgaaca tcttttagtt ttccatacaa   6960
cttttctttt tcttccaaat acaaatccat gatatatttt ctagcagtga cacgggactt   7020
tattggaaag tgagggcgca gagacttaac aaactcaaca agtactcat gttctacaat    7080 attgaaagga tattcatgca tgattattgc caaatgaagc ttctttaggc taaccacttc   7140
atcgtactta taaggctcaa tgagatttat gtctttgcca tgatccttt cacttttag    7200 acacaactga ccttaactaa actatgtga tgttctcaag tgatttcgaa atccgcttgt    7260
tccatgatga ccctcagccc tatacttagc cttgcaatta ggaaagttgc aatgtcccca   7320
tacctgaacg tatttctttc catcgacctc cacttcaatt tccttcttgg tgaaatgctg   7380
```

```
ccatacatcc gatgtgcact tctttgccct cttctgtggt gcttcttctt cgggttcagg      7440
ttgtggctgt ggttgtggtt ctggttgtgg ttgtggttgt ggttgtggtt catgaacaat      7500
agccatatca tcttgactcg gatctgtagc tgtaccattt gcattactac tgcttacact      7560
ctgaataaaa tgcctctcgg cctcagctgt tgatgatgat ggtgatgtgc ggccacatcc      7620
atgcccacgc gcacgtgcac gtacattctg aatccgacta aagaggctt cagcttttct       7680 tttcaaccct gttataaaca gattttttcgt attattctac agtcaatatg atgcttccca     7740
atctacaacc aattagtaat gctaatgcta ttgctactgt ttttctaata tataccttga      7800
gcatatgcag agaatacgga atttgttttg cgagtagaag gcgctcttgt ggtagacatc      7860
aacttggcca atcttatggc tgagcctgag ggaggattat ttccaaccgg aggcgtcatc      7920
tgaggaatgg agtcgtagcc ggctagccga agtggagagc agagccctgg acagcaggtg     7980
ttcagcaatc agcttggtgc tgtactgctg tgacttgtga gcacctggac ggctggacag      8040
caatcagcag gtgttgcaga gccctggac agcacacaaa tgacacaaca gcttggtgca       8100
atggtgctga cgtgctgtac tgctaagtgc tgtgagcctg tgagcagccg tggagacagg      8160
gagaccgcgg atggccggat gggcgagcgc cgagcagtgg aggtctggag accgctgac       8220 cgcagatggc ggatggcgga tgggcggacc gcggatgggc gagcagtgga gtggaggtct     8280
gggcggatgg gcggaccgcg gcggatgg gcgagtcgcg agcagtggag tggagggcgg       8340
accgtggatg gcggcgtctg cgtccggcgt gccgcgtcac ggccgtcacc gcgtgtggtg      8400
cctggtgcag cccagcggcc ggccggctgg gagacaggga gagtcggaga gagcaggcga     8460
gagcgagacg cgtcgccggc gtcggcgtgc ggctggcggc gtccggactc cggcgtgggc      8520
gcgtggcggc gtgtgaatgt gtgatgctgt tactcgtgtg gtgcctggcc gcctgggaga      8580
gaggcagagc agcgttcgct aggtatttct tacatgggct gggcctcagt ggttatggat      8640
gggagttgga gctggccata ttgcagtcat cccgaattag aaaatacggt aacgaaacgg      8700
gatcatcccg attaaaaacg ggatcccggt gaaacggtcg ggaaactagc tctaccgttt      8760
ccgtttccgt ttaccgtttt gtatatcccg tttccgttcc gttttcgttt tttacctcgg      8820
gttcgaaatc gatcgggata aaactaacaa aatcggttat acgataacgg tcggtacggg      8880
attttcccat cctactttca tccctgagat tattgtcgtt tctttcgcag atcggtaccc      8940
cccccctaga gtcgacatcg atctagtaac atagatgaca ccgcgcgcga taatttatcc      9000
tagtttgcgc gctatatttt gttttctatc gcgtattaaa tgtataattg cgggactcta     9060
atcataaaaa cccatctcat aaataacgtc atgcattaca tgttaattat tacatgctta      9120
acgtaattca acagaaatta tatgataatc atcgcaagac cggcaacagg attcaatctt      9180
aagaaacttt attgccaaat gtttgaacga tctgcttcga cgcactcctt ctttaggtac     9240
ggactagatc tcggtgacgg gcaggaccgg acggggcggt accggcaggc tgaagtccag      9300
ctgccagaaa cccacgtcat gccagttccc gtgcttgaag ccggccgccc gcagcatgcc     9360 gcgggggca tatccgagcg cctcgtgcat gcgcacgctc gggtcgttgg gcagcccgat      9420
gacagcgacc acgctcttga agccctgtgc ctccagggac ttcagcaggt gggtgtagag     9480
cgtggagccc agtcccgtcc gctggtgcg ggggagacg tacacggtcg actcggccgt       9540
ccagtcgtag gcgttgcgtg ccttccaggg gcccgcgtag gcgatgccgg cgacctcgcc      9600
gtccacctcg gcgacgagcc agggatagcg ctcccgcaga cggacgaggt cgtccgtcca     9660
ctcctgcggt tcctgcggct cggtacggaa gttgaccgtg cttgtctcga tgtagtggtt     9720
gacgatggtg cagaccgccg gcatgtccgc ctcggtggca cggcggatgt cggccgggcg     9780
```

```
tcgttctggg ctcatggatc tggattgaga gtgaatatga gactctaatt ggataccgag   9840
gggaatttat ggaacgtcag tggagcattt ttgacaagaa atatttgcta gctgatagtg   9900
accttaggcg acttttgaac gcgcaataat ggtttctgac gtatgtgctt agctcattaa   9960
actccagaaa cccgcggctg agtggctcct tcaatcgttg cggttctgtc agttccaaac  10020
gtaaaacggc ttgtcccgcg tcatcggcgg gggtcataac gtgactccct taattctccg  10080
ctcatgatcc ccgggtaccg agctcgaatt gcggctgagt ggctccttca atcgttgcgg  10140
ttctgtcagt tccaaacgta aaacggcttg tcccgcgtca tcggcggggg tcataacgtg  10200
actcccttaa ttctccgctc atgatcttga tccctgcgc catcagatcc ttggcggcaa  10260
gaaagccatc cagtttactt tgcagggctt cccaacctta ccagagggcg cccagctgg   10320 caattccggt tcgcttgctg tatcgatatg gtggatttat cacaaatggg acccgccgcc  10380
gacagaggtg tgatgttagg ccaggacttt gaaaatttgc gcaactatcg tatagtggcc  10440
gacaaattga cgccgagttg acagactgcc tagcatttga gtgaattatg tgaggtaatg  10500
ggctacactg aattggtagc tcaaactgtc agtatttatg tatatgagtg tatattttcg  10560
cataatctca gaccaatctg aagatgaaat gggtatctgg gaatggcgaa atcaaggcat  10620
cgatcgtgaa gtttctcatc taagccccca tttggacgtg aatgtagaca cgtcgaaata  10680
aagatttccg aattagaata atttgtttat tgctttcgcc tataaatacg acggatcgta  10740
atttgtcgtt ttatcaaaat gtactttcat tttataataa cgctgcggac atctacattt  10800
ttgaattgaa aaaaaattgg taattactct ttctttttct ccatattgac catcatactc  10860
attgctgatc catgtagatt tcccggacat gaagccattt acaattgaat atatcctgcc  10920
gccgctgccg ctttgcaccc ggtggagctt gcatgttggt ttctacgcag aactgagccg  10980
gttaggcaga taatttccat tgagaactga gccatgtgca ccttccccccc aacacggtga  11040 gcgacgggc aacggagtga tccacatggg acttttaaac atcatccgtc ggatggcgtt  11100
gcgagagaag cagtcgatcc gtgagatcag ccgacgcacc gggcaggcgc gcaacacgat  11160
cgcaaagtat ttgaacgcag gtacaatcga gccgacgttc accgtcaccc tggatgctgt  11220
aggcataggc ttggttatgc cggtactgcc gggcctcttg cgggatatcg tccattccga  11280
cagcatcgcc agtcactatg gcgtgctgct agcgctatat gcgttgatgc aatttctatg  11340
cgcacccgtt ctcggagcac tgtccgaccg ctttggccgc cgcccagtcc tgctcgcttc  11400
gctacttgga gccactatcg actacgcgat catggcgacc acaccgtcc tgtggtccaa  11460 cccctccgct gctatagtgc agtcggcttc tgacgttcag tgcagccgtc ttctgaaaac  11520
gacatgtcgc acaagtccta agttacgcga caggctgccg ccctgccctt ttcctggcgt  11580
tttcttgtcg cgtgttttag tcgcataaag tagaatactt gcgactagaa ccggagacat  11640
tacgccatga acaagagcgc cgccgctggc ctgctgggct atgcccgcgt cagcaccgac  11700
gaccaggact tgaccaacca acgggccgaa ctgcacgcgg ccgctgcac caagctgttt  11760 tccgagaaga tcaccggcac caggcgcgac cgcccggagc tggccaggat gcttgaccac  11820
ctacgccctg gcgacgttgt gacagtgacc aggctagacc gcctggcccg cagcacccgc  11880
gacctactgg acattgccga gcgcatccag gaggccggcg cgggcctgcg tagcctggca  11940
gagccgtggg ccgacaccac cacgccggcc ggccgcatgg tgttgaccgt gttcgccggc  12000
attgccgagt tcgagcgttc cctaatcatc gaccgcaccc ggagcgggcg cgaggccgcc  12060
aaggcccgag gcgtgaagtt tggcccccgc cctaccctca ccccggcaca gatcgcgcac  12120
```

-continued

```
gcccgcgagc tgatcgacca ggaaggccgc accgtgaaag aggcggctgc actgcttggc    12180
gtgcatcgct cgaccctgta ccgcgcactt gagcgcagcg aggaagtgac gcccaccgag    12240
gccaggcggc gcggtgcctt ccgtgaggac gcattgaccg aggccgacgc cctggcggcc    12300
gccgagaatg aacgccaaga ggaacaagca tgaaaccgca ccaggacggc caggacgaac    12360 cgttttcat taccgaagag atcgaggcgg agatgatcgc ggccgggtac gtgttcgagc    12420
cgcccgcgca cgtctcaacc gtgcggctgc atgaaatcct ggccggtttg tctgatgcca    12480
agctggcggc ctggccggcc agcttggccg ctgaagaaac cgagcgccgc cgtctaaaaa    12540
ggtgatgtgt atttgagtaa acagcttgc gtcatgcggt cgctgcgtat atgatgcgat    12600
gagtaaataa acaaatacgc aagggaacgc atgaagttat cgctgtactt aaccagaaag    12660
gcgggtcagg caagacgacc atcgcaaccc atctagcccg cgccctgcaa ctcgccgggg    12720
ccgatgttct gttagtcgat tccgatcccc agggcagtgc ccgcgattgg gcggccgtgc    12780
gggaagatca accgctaacc gttgtcggca tcgaccgccc gacgattgac cgcgacgtga    12840
aggccatcgg ccgccgcgac ttcgtagtga tcgacggagc gccccaggcg gcggacttgg    12900
ctgtgtccgc gatcaaggca gccgacttcg tgctgattcc ggtgcagcca agcccttacg    12960
acatatgggc caccgccgac ctggtggagc tggttaagca gcgcattgag gtcacggatg    13020
gaaggctaca agcggccttt gtcgtgtcgc gggcgatcaa aggcacgcgc atcggcggtg    13080
aggttgccga ggcgctggcc gggtacgagc tgcccattct tgagtccgt atcacgcagc    13140 gcgtgagcta cccaggcact gccgccgccg gcacaaccgt tcttgaatca gaacccgagg    13200
gcgacgctgc ccgcgaggtc caggcgctgg ccgctgaaat taaatcaaaa ctcatttgag    13260
ttaatgaggt aaagagaaaa tgagcaaaag cacaaacacg ctaagtgccg gccgtccgag    13320
cgcacgcagc agcaaggctg caacgttggc cagcctggca gacacgccag ccatgaagcg    13380
ggtcaacttt cagttgccgg cggaggatca caccaagctg aagatgtacg cggtacgcca    13440
aggcaagacc attaccgagc tgctatctga atacatcgcg cagctaccag agtaaatgag    13500
caaatgaata aatgagtaga tgaattttag cggctaaagg aggcggcatg gaaaatcaag    13560
aacaaccagg caccgacgcc gtggaatgcc ccatgtgtgg aggaacgggc ggttggccag    13620
gcgtaagcgg ctgggttgtc tgccggccct gcaatggcac tggaaccccc aagcccgagg    13680
aatcggcgtg agcggtcgca aaccatccgg cccggtacaa atcggcgcgg cgctgggtga    13740
tgacctggtg gagaagttga aggccgcgca ggccgcccag cggcaacgca tcgaggcaga    13800
agcacgcccc ggtgaatcgt ggcaagcggc cgctgatcga atccgcaaag aatcccggca    13860
accgccggca gccggtgcgc cgtcgattag gaagccgccc aagggcgacg agcaaccaga    13920
ttttttcgtt ccgatgctct atgacgtggg cacccgcgat agtcgcagca tcatggacgt    13980
ggccgttttc cgtctgtcga agcgtgaccg acgagctggc gaggtgatcc gctacgagct    14040
tccagacggg cacgtagagg tttccgcagg gccggccggc atggccagtg tgtgggatta    14100
cgacctggta ctgatggcgg tttcccatct aaccgaatcc atgaaccgat accgggaagg    14160
gaagggagac aagcccggcc gcgtgttccg tccacacgtt gcggacgtac tcaagttctg    14220
ccggcgagcc gatggcggaa agcagaaaga cgacctggta gaaacctgca ttcggttaaa    14280
caccacgcac gttgccatgc agcgtacgaa gaaggccaag aacggccgcc tggtgacggt    14340
atccgagggt gaagccttga ttagccgcta caagatcgta aagagcgaaa ccgggcggcc    14400
ggagtacatc gagatcgagc tagctgattg gatgtaccgc gagatcacag aaggcaagaa    14460
cccggacgtg ctgacggttc accccgatta cttttgatc gatcccggca tcggccgttt    14520
```

```
tctctaccgc ctggcacgcc gcgccgcagg caaggcagaa gccagatggt tgttcaagac    14580
gatctacgaa cgcagtggca gcgccggaga gttcaagaag ttctgtttca ccgtgcgcaa    14640
gctgatcggg tcaaatgacc tgccggagta cgatttgaag gaggaggcgg ggcaggctgg    14700
cccgatccta gtcatgcgct accgcaacct gatcgagggc gaagcatccg ccggttccta    14760
atgtacggag cagatgctag ggcaaattgc cctagcaggg gaaaaaggtc gaaaaggtct    14820 cttcctgtg gatagcacgt acattgggaa cccaaagccg tacattggga accggaaccc    14880
gtacattggg aacccaaagc cgtacattgg gaaccggtca cacatgtaag tgactgatat    14940
aaaagagaaa aaaggcgatt tttccgccta aaactcttta aaacttatta aaactcttaa    15000
aacccgcctg gcctgtgcat aactgtctgg ccagcgcaca gccgaagagc tgcaaaaagc    15060
gcctacccct cggtcgctgc gctccctacg ccccgccgct tcgcgtcggc ctatcgcggc    15120
cgctggccgc tcaaaaatgg ctggcctacg gccaggcaat ctaccagggc gcggacaagc    15180
cgcgccgtcg ccactcgacc gccggcgccc acatcaaggc accctgcctc gcgcgtttcg    15240
gtgatgacgg tgaaaacctc tgacacatgc agctcccgga gacggtcaca gcttgtctgt    15300
aagcggatgc cgggagcaga caagcccgtc agggcgcgtc agcgggtgtt ggcgggtgtc    15360
ggggcgcagc catgacccag tcacgtagcg atagcggagt gtatactggc ttaactatgc    15420
ggcatcagag cagattgtac tgagagtgca ccatatgcgg tgtgaaatac cgcacagatg    15480
cgtaaggaga aaataccgca tcaggcgctc ttccgcttcc tcgctcactg actcgctgcg    15540
ctcggtcgtt cggctgcggc gagcggtatc agctcactca aaggcggtaa tacggttatc    15600
cacagaatca ggggataacg caggaaagaa catgtgagca aaaggccagc aaaaggccag    15660
gaaccgtaaa aaggccgcgt tgctggcgtt tttccatagg ctccgccccc ctgacgagca    15720
tcacaaaaat cgacgctcaa gtcagaggtg gcgaaacccg acaggactat aaagatacca    15780
ggcgtttccc cctggaagct ccctcgtgcg ctctcctgtt ccgaccctgc cgcttaccgg    15840
atacctgtcc gcctttctcc cttcgggaag cgtggcgctt tctcatagct cacgctgtag    15900
gtatctcagt tcggtgtagg tcgttcgctc caagctgggc tgtgtgcacg aaccccccgt    15960
tcagcccgac cgctgcgcct tatccggtaa ctatcgtctt gagtccaacc cggtaagaca    16020
cgacttatcg ccactggcag cagccactgg taacaggatt agcagagcga ggtatgtagg    16080
cggtgctaca gagttcttga agtggtggcc taactacggc tacactagaa ggacagtatt    16140
tggtatctgc gctctgctga agccagttac cttcggaaaa agagttggta gctcttgatc    16200
cggcaaacaa accaccgctg gtagcggtgg tttttttgtt tgcaagcagc agattacgcg    16260
cagaaaaaaa ggatctcaag aagatccttt gatcttttct acggggtctg acgctcagtg    16320
gaacgaaaac tcacgttaag ggattttggt catgagatta tcaaaaagga tcttcaccta    16380 gatccttta aattaaaaat gaagttttaa atcaatctaa agtatatatg agtaaacttg    16440
gtctgacagt taccaatgct taatcagtga ggcacctatc tcagcgatct gtctatttcg    16500
ttcatccata gttgcctgac tccccgtcgt gtagataact acgatacggg agggcttacc    16560
atctggcccc agtgctgcaa tgataccgcg agacccacgc tcaccggctc cagatttatc    16620
agcaataaac cagccagccg gaagggccga gcgcagaagt ggtcctgcaa ctttatccgc    16680
ctccatccag tctattaatt gttgccggga agctagagta agtagttcgc cagttaatag    16740
tttgcgcaac gttgttgcca ttgctacagg catcgtggtg tcacgctcgt cgtttggtat    16800
ggcttcattc agctccggtt cccaacgatc aaggcgagtt acatgatccc ccatgttgtg    16860
```

-continued

```
caaaaaagcg gttagctcct tcggtcctcc gatcgttgtc agaagtaagt tggccgcagt    16920
gttatcactc atggttatgg cagcactgca taattctctt actgtcatgc catccgtaag    16980
atgcttttct gtgactggtg agtactcaac caagtcattc tgagaatagt gtatgcggcg    17040
accgagttgc tcttgcccgg cgtcaacacg ggataatacc gcgccacata gcagaacttt    17100
aaaagtgctc atcattggaa aagacctgca ggggggggg ggaaagccac gttgtgtctc     17160
aaaatctctg atgttacatt gcacaagata aaaatatatc atcatgaaca ataaaactgt    17220
ctgcttacat aaacagtaat acaaggggtg ttatgagcca tattcaacgg gaaacgtctt    17280
gctcgaggcc gcgattaaat tccaacatgg atgctgattt atatgggtat aaatgggctc    17340
gcgataatgt cgggcaatca ggtgcgacaa tctatcgatt gtatgggaag cccgatgcgc    17400
cagagttgtt tctgaaacat ggcaaaggta gcgttgccaa tgatgttaca gatgagatgg    17460
tcagactaaa ctggctgacg gaatttatgc ctcttccgac catcaagcat tttatccgta    17520
ctcctgatga tgcatggtta ctcaccactg cgatccccgg gaaaacagca ttccaggtat    17580
tagaagaata tcctgattca ggtgaaaata ttgttgatgc gctggcagtg ttcctgcgcc    17640
ggttgcattc gattcctgtt tgtaattgtc cttttaacag cgatcgcgta tttcgtctcg    17700
ctcaggcgca atcacgaatg aataacggtt tggttgatgc gagtgatttt gatgacgagc    17760
gtaatggctg gcctgttgaa caagtctgga agaaatgca taagcttttg ccattctcac    17820
cggattcagt cgtcactcat ggtgatttct cacttgataa ccttattttt gacgagggga    17880
aattaatagg ttgtattgat gttggacgag tcggaatcgc agaccgatac caggatcttg    17940
ccatcctatg gaactgcctc ggtgagtttt ctccttcatt acagaaacgg ctttttcaaa    18000
aatatggtat tgataatcct gatatgaata aattgcagtt tcatttgatg ctcgatgagt    18060
ttttctaatc agaattggtt aattggttgt aacactggca gagcattacg ctgacttgac    18120
gggacggcgg ctttgttgaa taaatcgaac ttttgctgag ttgaaggatc agatcacgca    18180
tcttcccgac aacgcagacc gttccgtggc aaagcaaaag ttcaaaatca ccaactggtc    18240
cacctacaac aaagctctca tcaaccgtgg ctccctcact ttctggctgg atgatgggc     18300
gattcaggcc tggtatgagt cagcaacacc ttcttcacga ggcagacctc agcgcccccc    18360
ccccctgca ggtcaattcg gtcgatatgg ctattacgaa gaaggctcgt gcgcggagtc     18420
ccgtgaactt tcccacgcaa caagtgaacc gcaccgggtt gccggaggc catttcgtta     18480
aaatgcgcag c                                                        18491
```

<210> SEQ ID NO 2
<211> LENGTH: 4291
<212> TYPE: DNA
<213> ORGANISM: artificial sequence
<220> FEATURE:
<223> OTHER INFORMATION: Gateway donor vector pDONR-Zeo

<400> SEQUENCE: 2

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
```

| | | | | |
|---|---|---|---|---|
| caacagataa | aacgaaaggc | ccagtcttcc | gactgagcct | ttcgttttat ttgatgcctg | 480 |
| gcagttccct | actctcgcgt | taacgctagc | atggatgttt | tcccagtcac gacgttgtaa | 540 |
| aacgacggcc | agtcttaagc | tcgggcccca | aataatgatt | ttattttgac tgatagtgac | 600 |
| ctgttcgttg | caacacattg | atgagcaatg | cttttttata | atgccaactt tgtacaaaaa | 660 |
| agctgaacga | gaaacgtaaa | atgatataaa | tatcaatata | ttaaattaga ttttgcataa | 720 |
| aaaacagact | acataatact | gtaaaacaca | acatatccag | tcactatgaa tcaactactt | 780 |
| agatggtatt | agtgacctgt | agtcgaccga | cagccttcca | aatgttcttc gggtgatgct | 840 |
| gccaacttag | tcgaccgaca | gccttccaaa | tgttcttctc | aaacggaatc gtcgtatcca | 900 |
| gcctactcgc | tattgtcctc | aatgccgtat | taaatcataa | aaagaaataa gaaaaagagg | 960 |
| tgcgagcctc | ttttttgtgt | gacaaaataa | aaacatctac | ctattcatat acgctagtgt | 1020 |
| catagtcctg | aaaatcatct | gcatcaagaa | caatttcaca | actcttatac ttttctctta | 1080 |
| caagtcgttc | ggcttcatct | ggattttcag | cctctatact | tactaaacgt gataaagttt | 1140 |
| ctgtaatttc | tactgtatcg | acctgcagac | tggctgtgta | aagggagcc tgacatttat | 1200 |
| attccccaga | acatcaggtt | aatggcgttt | ttgatgtcat | tttcgcggtg gctgagatca | 1260 |
| gccacttctt | ccccgataac | ggagaccggc | acactggcca | tatcggtggt catcatgcgc | 1320 |
| cagctttcat | ccccgatatg | caccaccggg | taaagttcac | gggagacttt atctgacagc | 1380 |
| agacgtgcac | tggccagggg | gatcaccatc | cgtcgcccgg | gcgtgtcaat aatatcactc | 1440 |
| tgtacatcca | caaacagacg | ataacggctc | tctcttttat | aggtgtaaac cttaaactgc | 1500 |
| atttcaccag | cccctgttct | cgtcagcaaa | agagccgttc | atttcaataa accgggcgac | 1560 |
| ctcagccatc | ccttcctgat | tttccgcttt | ccagcgttcg | gcacgcagac gacgggcttc | 1620 |
| attctgcatg | gttgtgctta | ccagaccgga | gatattgaca | tcatatatgc cttgagcaac | 1680 |
| tgatagctgt | cgctgtcaac | tgtcactgta | atacgctgct | tcatagcata cctcttttg | 1740 |
| acatacttcg | ggtatacata | tcagtatata | ttcttatacc | gcaaaaatca gcgcgcaaat | 1800 |
| acgcatactg | ttatctggct | tttagtaagc | cggatccacg | cggcgtttac gccccgccct | 1860 |
| gccactcatc | gcagtactgt | tgtaattcat | taagcattct | gccgacatgg aagccatcac | 1920 |
| agacggcatg | atgaacctga | atcgccagcg | gcatcagcac | cttgtcgcct tgcgtataat | 1980 |
| atttgcccat | ggtgaaaacg | ggggcgaaga | agttgtccat | attggccacg tttaaatcaa | 2040 |
| aactggtgaa | actcacccag | ggattggctg | agacgaaaaa | catattctca ataaacccctt | 2100 |
| tagggaaata | ggccaggttt | tcaccgtaac | acgccacatc | ttgcgaatat atgtgtagaa | 2160 |
| actgccggaa | atcgtcgtgg | tattcactcc | agagcgatga | aaacgtttca gtttgctcat | 2220 |
| ggaaaacggt | gtaacaaggg | tgaacactat | cccatatcac | cagctcaccg tctttcattg | 2280 |
| ccatacggaa | ttccggatga | gcattcatca | ggcgggcaag | aatgtgaata aaggccggat | 2340 |
| aaaacttgtg | cttatttttc | tttacggtct | ttaaaaaggc | cgtaatatcc agctgaacgg | 2400 |
| tctggttata | ggtacattga | gcaactgact | gaaatgcctc | aaaatgttct tacgatgcc | 2460 |
| attgggatat | atcaacggtg | gtatatccag | tgatttttt | ctccatttta gcttccttag | 2520 |
| ctcctgaaaa | tctcgataac | tcaaaaaata | cgcccgtag | tgatcttatt tcattatggt | 2580 |
| gaaagttgga | acctcttacg | tgccgatcaa | cgtctcattt | tcgccaaaag ttggcccagg | 2640 |
| gcttcccggt | atcaacaggg | acaccaggat | ttatttattc | tgcgaagtga tcttccgtca | 2700 |
| caggtattta | ttcggcgcaa | agtgcgtcgg | gtgatgctgc | caacttagtc gactacaggt | 2760 |

-continued

| | |
|---|---|
| cactaataacc atctaagtag ttgattcata gtgactggat atgttgtgtt ttacagtatt | 2820 |
| atgtagtctg ttttttatgc aaaatctaat ttaatatatt gatatttata tcattttacg | 2880 |
| tttctcgttc agctttcttg tacaaagttg gcattataag aaagcattgc ttatcaattt | 2940 |
| gttgcaacga acaggtcact atcagtcaaa ataaaatcat tatttgccat ccagctgata | 3000 |
| tcccctatag tgagtcgtat tacatggtca tagctgtttc ctggcagctc tggcccgtgt | 3060 |
| ctcaaaatct ctgatgttac attgcacaag ataaaataat atcatcatga tcagtcctgc | 3120 |
| tcctcggcca cgaagtgcac gcagttgccg gccgggtcgc gcagggcgaa ctcccgcccc | 3180 |
| cacggctgct cgccgatctc ggtcatggcc ggcccggagg cgtcccggaa gttcgtggac | 3240 |
| acgacctccg accactcggc gtacagctcg tccaggccgc gcacccacac ccaggccagg | 3300 |
| gtgttgtccg gcaccacctg gtcctggacc gcgctgatga acagggtcac gtcgtcccgg | 3360 |
| accacaccgg cgaagtcgtc ctccacgaag tcccgggaga cccgagccg gtcggtccag | 3420 |
| aactcgaccg ctccggcgac gtcgcgcgcg gtgagcaccg gaacggcact ggtcaacttg | 3480 |
| gccatggttt agttcctcac cttgtcgtat tatactatgc cgatatacta tgccgatgat | 3540 |
| taattgtcaa cacgtgctga tcatgaccaa atcccttaa cgtgagttac gcgtcgttcc | 3600 |
| actgagcgtc agacccgta gaaaagatca aaggatcttc ttgagatcct ttttttctgc | 3660 |
| gcgtaatctg ctgcttgcaa acaaaaaaac caccgctacc agcggtggtt tgtttgccgg | 3720 |
| atcaagagct accaactctt tttccgaagg taactggctt cagcagagcg cagataccaa | 3780 |
| atactgttct tctagtgtag ccgtagttag gccaccactt caagaactct gtagcaccgc | 3840 |
| ctacatacct cgctctgcta atcctgttac cagtggctgc tgccagtggc gataagtcgt | 3900 |
| gtcttaccgg gttggactca agacgatagt taccggataa ggcgcagcgg tcgggctgaa | 3960 |
| cggggggttc gtgcacacag cccagcttgg agcgaacgac ctacaccgaa ctgagatacc | 4020 |
| tacagcgtga gctatgagaa agcgccacgc ttcccgaagg gagaaaggcg gacaggtatc | 4080 |
| cggtaagcgg cagggtcgga acaggagagc gcacgaggga gcttccaggg ggaaacgcct | 4140 |
| ggtatcttta tagtcctgtc gggtttcgcc acctctgact tgagcgtcga tttttgtgat | 4200 |
| gctcgtcagg gggcggagc ctatggaaaa acgccagcaa cgcggccttt ttacggttcc | 4260 |
| tggccttttg ctggccttt gctcacatgt t | 4291 |

<210> SEQ ID NO 3
<211> LENGTH: 4762
<212> TYPE: DNA
<213> ORGANISM: Artificial Sequence
<220> FEATURE:
<223> OTHER INFORMATION: gateway donor vector pDONR221

<400> SEQUENCE: 3

| | |
|---|---|
| ctttcctgcg ttatcccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca aatccgctcc cggcggattt gtcctactca ggagagcgtt caccgacaaa | 420 |
| caacagataa aacgaaaggc ccagtcttcc gactgagcct ttcgttttat ttgatgcctg | 480 |
| gcagttccct actctcgcgt taacgctagc atggatgttt tcccagtcac gacgttgtaa | 540 |

```
aacgacggcc agtcttaagc tcgggcccca aataatgatt ttattttgac tgatagtgac    600
ctgttcgttg caacacattg atgagcaatg cttttttata atgccaactt tgtacaaaaa    660
agctgaacga gaaacgtaaa atgatataaa tatcaatata ttaaattaga ttttgcataa    720
aaaacagact acataatact gtaaaacaca acatatccag tcactatgaa tcaactactt    780
agatggtatt agtgacctgt agtcgaccga cagccttcca aatgttcttc gggtgatgct    840
gccaacttag tcgaccgaca gccttccaaa tgttcttctc aaacggaatc gtcgtatcca    900
gcctactcgc tattgtcctc aatgccgtat aaatcataa aaagaaataa gaaaagagg     960
tgcgagcctc ttttttgtgt gacaaaataa aaacatctac ctattcatat acgctagtgt   1020
catagtcctg aaaatcatct gcatcaagaa caatttcaca actcttatac ttttctctta   1080
caagtcgttc ggcttcatct ggattttcag cctctatact tactaaacgt gataaagttt   1140
ctgtaatttc tactgtatcg acctgcagac tggctgtgta aagggagcc tgacatttat    1200
attccccaga acatcaggtt aatggcgttt tgatgtcat tttcgcggtg gctgagatca    1260
gccacttctt ccccgataac ggagaccggc acactggcca tatcggtggt catcatgcgc   1320
cagctttcat ccccgatatg caccaccggg taaagttcac gggagacttt atctgacagc   1380
agacgtgcac tggccagggg gatcaccatc cgtcgcccgg gcgtgtcaat aatatcactc   1440
tgtacatcca caaacagacg ataacggctc tctctttat aggtgtaaac cttaaactgc    1500
atttcaccag cccctgttct cgtcagcaaa agagccgttc atttcaataa accgggcgac   1560
ctcagccatc ccttcctgat tttccgcttt ccagcgttcg gcacgcagac gacgggcttc   1620
attctgcatg gttgtgctta ccagaccgga gatattgaca tcatatatgc cttgagcaac   1680
tgatagctgt cgctgtcaac tgtcactgta atacgctgct tcatagcata cctctttttg   1740
acatacttcg ggtatacata tcagtatata ttcttatacc gcaaaaatca gcgcgcaaat   1800
acgcatactg ttatctggct tttagtaagc cggatccacg cggcgtttac gccccgccct   1860
gccactcatc gcagtactgt tgtaattcat taagcattct gccgacatgg aagccatcac   1920
agacggcatg atgaacctga atcgccagcg gcatcagcac cttgtcgcct tgcgtataat   1980
atttgcccat ggtgaaaacg ggggcgaaga agttgtccat attggccacg tttaaatcaa   2040
aactggtgaa actcacccag ggattggctg agacgaaaaa catattctca ataaacccctt  2100
tagggaaata ggccaggttt tcaccgtaac acgccacatc ttgcgaatat atgtgtagaa   2160
actgccggaa atcgtcgtgg tattcactcc agagcgatga aaacgtttca gtttgctcat   2220
ggaaaacggt gtaacaaggg tgaacactat cccatatcac cagctcaccg tctttcattg   2280
ccatacggaa ttccggatga gcattcatca ggcgggcaag aatgtgaata aaggccggat   2340
aaaacttgtg cttatttttc tttacggtct taaaaaggc cgtaatatcc agctgaacgg    2400
tctggttata ggtacattga gcaactgact gaaatgcctc aaaatgttct ttacgatgcc   2460
attgggatat atcaacggtg gtatatccag tgatttttt ctccatttta gcttccttag    2520
ctcctgaaaa tctcgataac tcaaaaaata cgcccggtag tgatcttatt tcattatggt   2580
gaaagttgga acctcttacg tgccgatcaa cgtctcattt tcgccaaaag ttggcccagg   2640
gcttcccggt atcaacaggg acaccaggat ttatttattc tgcgaagtga tcttccgtca   2700
caggtattta ttcggcgcaa agtgcgtcgg gtgatgctgc caacttagtc gactacaggt   2760
cactaatacc atctaagtag ttgattcata gtgactggat atgttgtgtt ttacagtatt   2820
atgtagtctg ttttttatgc aaaatctaat ttaatatatt gatatttata tcattttacg   2880
```

```
tttctcgttc agctttcttg tacaaagttg gcattataag aaagcattgc ttatcaattt    2940
gttgcaacga acaggtcact atcagtcaaa ataaaatcat tatttgccat ccagctgata    3000
tccccctatag tgagtcgtat tacatggtca tagctgtttc ctggcagctc tggcccgtgt   3060
ctcaaaatct ctgatgttac attgcacaag ataaaataat atcatcatga acaataaaac    3120
tgtctgctta cataaacagt aatacaaggg gtgttatgag ccatattcaa cgggaaacgt    3180
cgaggccgcg attaaattcc aacatggatg ctgatttata tgggtataaa tgggctcgcg    3240
ataatgtcgg gcaatcaggt gcgacaatct atcgcttgta tgggaagccc gatgcgccag    3300
agttgtttct gaaacatggc aaaggtagcg ttgccaatga tgttacagat gagatggtca    3360
gactaaactg gctgacggaa tttatgcctc ttccgaccat caagcatttt atccgtactc    3420
ctgatgatgc atggttactc accactgcga tccccggaaa aacagcattc caggtattag    3480
aagaatatcc tgattcaggt gaaaatattg ttgatgcgct ggcagtgttc ctgcgccggt    3540
tgcattcgat tcctgtttgt aattgtcctt ttaacagcga tcgcgtattt cgtctcgctc    3600
aggcgcaatc acgaatgaat aacggtttgg ttgatgcgag tgattttgat gacgagcgta    3660
atggctggcc tgttgaacaa gtctggaaag aaatgcataa acttttgcca ttctcaccgg    3720
attcagtcgt cactcatggt gatttctcac ttgataacct tattttttgac gaggggaaat    3780
taataggttg tattgatgtt ggacgagtcg gaatcgcaga ccgataccag gatcttgcca    3840
tcctatggaa ctgcctcggt gagttttctc cttcattaca gaaacggctt ttcaaaaat    3900
atggtattga taatcctgat atgaataaat tgcagtttca tttgatgctc gatgagtttt    3960
tctaatcaga attggttaat tggttgtaac actggcagag cattacgctg acttgacggg    4020
acggcgcaag ctcatgacca aaatccctta acgtgagtta cgcgtcgttc cactgagcgt    4080
cagaccccgt agaaaagatc aaaggatctt cttgagatcc ttttttttctg cgcgtaatct    4140
gctgcttgca acaaaaaaa ccaccgctac cagcggtggt ttgtttgccg gatcaagagc    4200
taccaactct tttccgaag gtaactggct tcagcagagc gcagatacca atactgttc     4260
ttctagtgta gccgtagtta ggccaccact tcaagaactc tgtagcaccg cctacatacc    4320
tcgctctgct aatcctgtta ccagtggctg ctgccagtgg cgataagtcg tgtcttaccg    4380
ggttggactc aagacgatag ttaccggata aggcgcagcg gtcgggctga acggggggtt    4440
cgtgcacaca gcccagcttg gagcgaacga cctacaccga actgagatac ctacagcgtg    4500
agctatgaga aagcgccacg cttcccgaag ggagaaaggc ggacaggtat ccggtaagcg    4560
gcagggtcgg aacaggagag cgcacgaggg agcttccagg gggaaacgcc tggtatcttt    4620
atagtcctgt cgggtttcgc cacctctgac ttgagcgtcg atttttgtga tgctcgtcag    4680
gggggcggag cctatggaaa aacgccagca acgcggcctt tttacggttc ctggccttt    4740
gctggccttt tgctcacatg tt                                              4762

<210> SEQ ID NO 4
<211> LENGTH: 16843
<212> TYPE: DNA
<213> ORGANISM: artificial sequence
<220> FEATURE:
<223> OTHER INFORMATION: destination vector for use with arabidopsis

<400> SEQUENCE: 4
ccgggctggt tgccctcgcc gctgggctgg cggccgtcta tggccctgca acgcgccag       60
aaacgccgtc gaagccgtgt gcgagacacc gcggccgccg gcgttgtgga tacctcgcgg     120
aaaacttggc cctcactgac agatgagggg cggacgttga cacttgaggg gccgactcac    180
```

```
ccggcgcggc gttgacagat gaggggcagg ctcgatttcg gccggcgacg tggagctggc    240
cagcctcgca aatcggcgaa aacgcctgat tttacgcgag tttcccacag atgatgtgga    300
caagcctggg gataagtgcc ctgcggtatt gacacttgag gggcgcgact actgacagat    360
gaggggcgcg atccttgaca cttgaggggc agagtgctga cagatgaggg gcgcaccaat    420
tgacatttga gggctgtcc acaggcagaa atccagcat tgcaagggt tccgcccgt        480 ttttcggcca ccgctaacct gtcttttaac ctgcttttaa accaatattt ataaaccttg    540
tttttaacca gggctgcgcc ctgtgcgcgt gaccgcgcac gccgaagggg ggtgccccc     600 cttctcgaac cctcccggcc cgctaacgcg ggcctccat cccccaggg gctgcgcccc     660 tcggccgcga acggcctcac cccaaaaatg gcagcgctgg cagtccttgc cattgccggg    720
atcggggcag taacgggatg ggcgatcagc ccgagcgcga cgcccggaag cattgacgtg    780
ccgcaggtgc tggcatcgac attcagcgac caggtgccgg gcagtgaggg cggcggcctg    840
ggtggcgggc tgcccttcac ttcggccgtc ggggcattca cggacttcat ggcggggccg    900
gcaattttta ccttgggcat tcttggcata gtggtcgcgg gtgccgtgct cgtgttcggg    960
ggtgcgataa acccagcgaa ccatttgagg tgataggtaa gattataccg aggtatgaaa   1020
acgagaattg gaccttaca gaattactct atgaagcgcc atatttaaaa agctaccaag    1080
acgaagagga tgaagaggat gaggaggcag attgccttga atatattgac aatactgata   1140
agataatata tcttttatat agaagatatc gccgtatgta aggatttcag ggggcaaggc   1200
ataggcagcg cgcttatcaa tatatctata gaatgggcaa agcataaaaa cttgcatgga   1260
ctaatgcttg aaacccagga caataacctt atagcttgta aattctatca taattgggta   1320
atgactccaa cttattgata gtgttttatg ttcagataat gcccgatgac tttgtcatgc   1380
agctccaccg attttgagaa cgacagcgac ttccgtccca gccgtgccag gtgctgcctc   1440
agattcaggt tatgccgctc aattcgctgc gtatatcgct tgctgattac gtgcagcttt   1500
cccttcaggc gggattcata cagcggccag ccatccgtca tccatatcac cacgtcaaag   1560
ggtgacagca ggctcataag acgccccagc gtcgccatag tgcgttcacc gaatacgtgc   1620
gcaacaaccg tcttccggag actgtcatac gcgtaaaaca gccagcgctg gcgcgattta   1680
gccccgacat agccccactg ttcgtccatt tccgcgcaga cgatgacgtc actgcccggc   1740
tgtatgcgcg aggttaccga ctgcggcctg agttttttaa gtgacgtaaa atcgtgttga   1800
ggccaacgcc cataatgcgg gctgttgccc ggcatccaac gccattcatg gccatatcaa   1860
tgattttctg gtgcgtaccg ggttgagaag cggtgtaagt gaactgcagt tgccatgttt   1920
tacggcagtg agagcagaga tagcgctgat gtccggcggt gcttttgccg ttacgcacca   1980
ccccgtcagt agctgaacag gagggacagc tgatagacac agaagccact ggagcacctc   2040
aaaaacacca tcatacacta aatcagtaag ttggcagcat cacccataat tgtggtttca   2100
aaatcggctc cgtcgatact atgttatacg ccaactttga aaacaacttt gaaaaagctg   2160
ttttctggta tttaaggttt tagaatgcaa ggaacagtga attggagttc gtcttgttat   2220
aattagcttc ttgggggtatc tttaaatact gtagaaaaga ggaaggaaat aataaatggc   2280
taaaatgaga atatcaccgg aattgaaaaa actgatcgaa aaataccgct gcgtaaaaga   2340
tacggaagga atgtctcctg ctaaggtata taagctggtg ggagaaaatg aaaacctata   2400
tttaaaaatg acgacagcc ggtataaagg gaccacctat gatgtggaac gggaaaagga    2460
catgatgcta tggctggaag gaaagctgcc tgttccaaag gtcctgcact ttgaacggca   2520
```

-continued

```
tgatggctgg agcaatctgc tcatgagtga ggccgatggc gtcctttgct cggaagagta      2580
tgaagatgaa caaagccctg aaaagattat cgagctgtat gcggagtgca tcaggctctt      2640
tcactccatc gacatatcgg attgtcccta tacgaatagc ttagacagcc gcttagccga      2700
attggattac ttactgaata cgatctggc cgatgtggat tgcgaaaact gggaagaaga      2760
cactccattt aaagatccgc gcgagctgta tgatttttta aagacggaaa agcccgaaga      2820
ggaacttgtc ttttcccacg gcgacctggg agacagcaac atctttgtga agatggcaa      2880 agtaagtggc tttattgatc ttgggagaag cggcagggcg gacaagtggt atgacattgc      2940
cttctgcgtc cggtcgatca gggaggatat cggggaagaa cagtatgtcg agctatttt      3000 tgacttactg gggatcaagc ctgattggga gaaaataaaa tattatatt tactggatga      3060 attgttttag tacctagatg tggcgcaacg atgccggcga caagcaggag cgcaccgact      3120
tcttccgcat caagtgtttt ggctctcagg ccgaggccca cggcaagtat ttgggcaagg      3180
ggtcgctggt attcgtgcag ggcaagattc ggaataccaa gtacgagaag acggccaga      3240 cggtctacgg gaccgacttc attgccgata aggtggatta tctggacacc aaggcaccag      3300
gcgggtcaaa tcaggaataa gggcacattg ccccggcgtg agtcggggca atcccgcaag      3360
gagggtgaat gaatcggacg tttgaccgga aggcatacag gcaagaactg atcgacgcgg      3420
ggttttccgc cgaggatgcc gaaaccatcg caagccgcac cgtcatgcgt gcgccccgcg      3480
aaaccttcca gtccgtcggc tcgatggtcc agcaagctac ggccaagatc gagcgcgaca      3540
gcgtgcaact ggctcccccct gccctgcccg cgccatcggc cgccgtggag cgttcgcgtc      3600
gtctcgaaca ggaggcggca ggtttggcga agtcgatgac catcgacacg cgaggaacta      3660
tgacgaccaa gaagcgaaaa accgccggcg aggacctggc aaaacaggtc agcgaggcca      3720
agcaggccgc gttgctgaaa cacacgaagc agcagatcaa ggaaatgcag ctttccttgt      3780
tcgatattgc gccgtggccg gacacgatgc gagcgatgcc aaacgacacg gcccgctctg      3840
ccctgttcac cacgcgcaac aagaaaatcc cgcgcgaggc gctgcaaaac aaggtcattt      3900
tccacgtcaa caaggacgtg aagatcacct acaccggcgt cgagctgcgg gccgacgatg      3960
acgaactggt gtggcagcag gtgttggagt acgcgaagcg cacccctatc ggcgagccga      4020
tcaccttcac gttctacgag cttttgccagg acctgggctg gtcgatcaat ggccggtatt      4080
acacgaaggc cgaggaatgc ctgtcgcgcc tacaggcgac ggcgatgggc ttcacgtccg      4140
accgcgttgg gcacctggaa tcggtgtcgc tgctgcaccg cttccgcgtc ctggaccgtg      4200
gcaagaaaac gtcccgttgc caggtcctga tcgacgagga atcgtcgtg ctgtttgctg      4260 gcgaccacta cacgaaattc atatgggaga agtaccgcaa gctgtcgccg acggcccgac      4320
ggatgttcga ctatttcagc tcgcaccggg agccgtaccc gctcaagctg gaaaccttcc      4380
gcctcatgtg cggatcggat tccacccgcg tgaagaagtg gcgcgagcag gtcggcgaag      4440
cctgcgaaga gttgcgaggc agcggcctgg tggaacacgc ctgggtcaat gatgacctgg      4500
tgcattgcaa acgctagggc cttgtggggt cagttccggc tgggggttca gcagccagcg      4560
ctttactggc atttcaggaa caagcgggca ctgctcgacg cacttgcttc gctcagtatc      4620
gctcgggacg cacggcgcgc tctacgaact gccgataaac agaggattaa aattgacaat      4680
tgtgattaag gctcagattc gacggcttgg agcggccgac gtgcaggatt ccgcgagat      4740 ccgattgtcg gccctgaaga aagctccaga gatgttcggg tccgtttacg agcacgagga      4800 gaaaagccc atggaggcgt tcgctgaacg gttgcgagat gccgtggcat tcggcgccta      4860
catcgacggc gagatcattg ggctgtcggt cttcaaacag gaggacggcc ccaaggacgc      4920
```

```
tcacaaggcg catctgtccg gcgttttcgt ggagcccgaa cagcgaggcc gaggggtcgc    4980
cggtatgctg ctgcgggcgt tgccggcggg tttattgctc gtgatgatcg tccgacagat    5040
tccaacggga atctggtgga tgcgcatctt catcctcggc gcacttaata tttcgctatt    5100
ctggagcttg ttgtttattt cggtctaccg cctgccgggc ggggtcgcgg cgacggtagg    5160
cgctgtgcag ccgctgatgg tcgtgttcat ctctgccgct ctgctaggta gcccgatacg    5220
attgatggcg gtcctggggg ctatttgcgg aactgcgggc gtggcgctgt tggtgttgac    5280
accaaacgca gcgctagatc ctgtcggcgt cgcagcgggc ctggcggggg cggtttccat    5340
ggcgttcgga accgtgctga cccgcaagtg gcaacctccc gtgcctctgc tcacctttac    5400
cgcctggcaa ctggcggccg gaggacttct gctcgttcca gtagctttag tgtttgatcc    5460
gccaatcccg atgcctacag gaaccaatgt tctcggcctg gcgtggctcg gcctgatcgg    5520
agcgggttta acctacttcc tttggttccg ggggatctcg cgactcgaac ctacagttgt    5580
ttccttactg ggcttttctca gcccagatc tggggtcgat cagccgggga tgcatcaggc    5640
cgacagtcgg aacttcgggt ccccgacctg taccattcgg tgagcaatgg ataggggagt    5700
tgatatcgtc aacgttcact tctaaagaaa tagcgccact cagcttcctc agcggcttta    5760
tccagcgatt tcctattatg tcggcatagt tctcaagatc gacagcctgt cacggttaag    5820
cgagaaatga ataagaaggc tgataattcg gatctctgcg agggagatga tatttgatca    5880
caggcagcaa cgctctgtca tcgttacaat caacatgcta ccctcgcga gatcatccgt    5940 gtttcaaacc cggcagctta gttgccgttc ttccgaatag catcggtaac atgagcaaag    6000
tctgccgcct tacaacggct ctcccgctga cgccgtcccg gactgatggg ctgcctgtat    6060
cgagtggtga ttttgtgccg agctgccggt cggggagctg ttggctggct ggtggcagga    6120
tatattgtgg tgtaaacaaa ttgacgctta gacaacttaa taacacattg cggacgtttt    6180
taatgtactg gggtggtttt tcttttcacc agtgagacgg gcaacagctg attgcccttc    6240
accgcctggc cctgagagag ttgcagcaag cggtccacgc tggtttgccc cagcaggcga    6300
aaatcctgtt tgatggtggt tccgaaatcg gcaaaatccc ttataaatca aaagaatagc    6360
ccgagatagg gttgagtgtt gttccagttt ggaacaagag tccactatta agaacgtgg    6420 actccaacgt caaagggcga aaaccgtct atcagggcga tggcccacta cctgtatggc    6480
cgcattcgca aaacacacct agactagatt tgttttgcta acccaattga tattaattat    6540
atatgattaa tatttatatg tatatggatt tggttaatga aatgcatctg gttcatcaaa    6600
gaattataaa gacacgtgac attcatttag gataagaaat atggatgatc tctttctctt    6660
ttattcagat aactagtaat tacacataac acacaacttt gatgcccaca ttatagtgat    6720
tagcatgtca ctatgtgtgc atccttttat ttcatacatt aattaagttg gccaatccag    6780
aagatggaca agtctaggtt aaccatgtgg tacctacgcg ttcgaatatc catgggccgc    6840
ttcaggccag ggcgctgggg aaggcgatgg cgtgctcggt cagctgccac ttctggttct    6900
tggcgtcgct ccggtcctcc cgcagcagct tgtgctggat gaagtgccac tcgggcatct    6960
tgctgggcac gctcttggcc ttgtacacgg tgtcgaactg gcaccggtac cggccgccgt    7020
ccttcagcag caggtacatg ctcacgtcgc ccttcaggat gccctgctta ggcacgggca    7080
tgatcttctc gcagctggcc tcccagttgg tggtcatctt cttcatcacg ggccgtcgg    7140 cggggaagtt cacgccgttg aagatgtctc tgtggtagat gcagttctcc ttcacgctca    7200
cggtgatgtc cacgttacag atgcacacgg cgccgtcctc gaacaggaag ctccggcccc    7260
```

```
aggtgtagcc ggcggggcag ctgttcttga agtagtccac gatgtcctgg gggtactcgg    7320
tgaagatccg gtcgccgtac ttgaagccgg cgctcaggat gtcctcgctg aagggcaggg    7380
ggccgccctc gatcacgcac aggttgatgg tctgcttgcc cttgaagggg tagccgatgc    7440
cctcgccggt gatcacgaac ttgtggccgt tcacgcagcc ctccatgtgg tacttcatgg    7500
tcatctcctc cttcaggccg tgcttgctgt gggccatggt ggcgaccggt gaattcgagc    7560
tcggtacccg gggatcctga gtaaaacaga ggagggtctc actaagttta tagagagact    7620
gagagagata aagggacacg tatgaagcgt ctgttttcgt ggtgtgacgt caaagtcatt    7680
ttgctctcta cgcgtgtctg tgtcggcttg atcttttttt ttgcttttg gaactcatgt    7740 cggtagtata tcttttattt attttttctt tttttcccct ttctttcaaa ctgatgtcgg    7800
tatgatattt attccatcct aaaatgtaac ttactattat tagtagtcgg tccatgtcta    7860
ttggcccatc atgtggtcat tttacgttta cgtcgtgtgg ctgtttatta taacaaacgg    7920
cacatccttc tcattcgaat tgtatttctc cttaatcgtt ctaataggta tgatctttta    7980
ttttatacgt aaaattaaaa ttgaatgatg tcaagaacga aaattaattt gtatttacaa    8040
aggagctaaa tattgtttat tcctctactg gtagaagata aagaagtag atgaaataat    8100 gatcttacta gagaatattc ctcatttaca ctagtcaaat ggaaatcttg taaacttta    8160 caataattta tcctgaaaat atgaaaaaat agaagaaaat gtttacctcc tctctcctct    8220
taattcacct acgatcggtg cgggcctctt cgctattacg ccagctggcg aaagggggat    8280
gtgctgcaag gcgattaagt tgggtaacgc cagggttttc ccagtcacga cgttgtaaaa    8340
cgacggccag tgaattcgag ctcggtaccc ggggatcctc tagagtcgac ctgcaggcat    8400
gcaagcttgt tgaaacatcc ctgaagtgtc tcattttatt ttatttattc tttgctgata    8460
aaaaaataaa ataaaagaag ctaagcacac ggtcaaccat tgctctactg ctaaaagggt    8520
tatgtgtagt gttttactgc ataaattatg cagcaaacaa gacaactcaa attaaaaaat    8580
ttcctttgct tgtttttttg ttgtctctga cttgactttc ttgtggaagt tggttgtata    8640
aggattggga cacaccattg tccttcttaa tttaatttta tttctttgct gataaaaaaa    8700
aaaaatttca tatagtgtta aataataatt tgttaaataa ccaaaaagtc aaatatgttt    8760
actctcgttt aaataattga gagtcgtcca gcaaggctaa acgattgtat agatttatga    8820
caatatttac tttttttatag ataaatgtta tattataata aatttatata catatattat    8880
atgttattta ttatttatta ttatttttaaa tccttcaata ttttatcaaa ccaactcata    8940 atttttttt tatctgtaag aagcaataaa attaaataga cccactttaa ggatgatcca    9000 accttatac agagtaagag agttcaaata gtacccttc atatacatat caactaaaat    9060
attagaaata tcatggatca aaccttataa agacattaaa taagtggata agtataaat    9120 ataaatgggt agtatataat atataaatgg atacaaactt ctctctttat aattgttatg    9180
tctccttaac atcctaatat aatacataag tgggtaatat ataatatata aatgagaaca    9240
aacttcttcc attataattg ttatgtcttc ttaaacactta tgtctcgttc acaatgctaa    9300
agttagaatt gtttagaaag tcttatagta cacatttgtt tttgtactat ttgaagcatt    9360
ccataagccg tcacgattca gatgatttat aataataaga ggaaatttat catagaacaa    9420
taaggtgcat agatagagtg ttaatatatc ataacatcct ttgtttattc atagaagaag    9480
tgagatggag ctcagttatt atactgttac atggtcggat acaatattcc atgctctcca    9540
tgagctctta cacctacatg catttttagtt catacttcat gcacgtggcc atcacagcta    9600
gctgcagcta catatttaca ttttacaaca ccaggagaac tgccctgtta gtgcataaca    9660
```

```
atcagaagat ggccgtggct actcgagtta tcgaaccact ttgtacaaga aagctgaacg    9720
agaaacgtaa aatgatataa atatcaatat attaaattag attttgcata aaaaacagac    9780
tacataatac tgtaaaacac aacatatcca gtcactatgg tcgacctgca gactggctgt    9840
gtataaggga gcctgacatt tatattcccc agaacatcag gttaatggcg ttttttgatgt   9900 cattttcgcg gtggctgaga tcagccactt cttccccgat aacggagacc ggcacactgg   9960
ccatatcggt ggtcatcatg cgccagcttt catccccgat atgcaccacc gggtaaagtt  10020
cacgggagac tttatctgac agcagacgtg cactggccag ggggatcacc atccgtcgcc  10080
cgggcgtgtc aataatatca ctctgtacat ccacaaacag acgataacgg ctctctcttt  10140
tataggtgta aaccttaaac tgcatttcac cagtccctgt tctcgtcagc aaaagagccg  10200
ttcatttcaa taaccgggc gacctcagcc atcccttcct gattttccgc tttcagcgt    10260 tcggcacgca gacgacgggc ttcattctgc atggttgtgc ttaccagacc ggagatattg  10320
acatcatata tgccttgagc aactgatagc tgtcgctgtc aactgtcact gtaatacgct  10380
gcttcatagc acacctcttt ttgacatact tcgggtatac atatcagtat atattcttat  10440
accgcaaaaa tcagcgcgca aatacgcata ctgttatctg cttttagta agccggatcc   10500 tctagattac gccccgccct gccactcatc gcagtactgt tgtaattcat taagcattct  10560
gccgacatgg aagccatcac agacggcatg atgaacctga atcgccagcg gcatcagcac  10620
cttgtcgcct tgcgtataat atttgcccat ggtgaaaacg ggggcgaaga agttgtccat  10680
attggccacg tttaaatcaa aactggtgaa actcacccag ggattggctg agacgaaaaa  10740
catattctca ataaacccctt tagggaaata ggccaggttt tcaccgtaac acgccacatc  10800
ttgcgaatat atgtgtagaa actgccgaa atcgtcgtgg tattcactcc agagcgatga   10860
aaacgtttca gtttgctcat ggaaaacggt gtaacaaggg tgaacactat cccatatcac  10920
cagctcaccg tctttcattg ccatacgaa ttccggatga gcattcatca ggcgggcaag   10980
aatgtgaata aaggccggat aaaacttgtg cttattttc tttacggtct ttaaaaaggc   11040
cgtaatatcc agctgaacgg tctggttata ggtacattga gcaactgact gaaatgcctc  11100
aaaatgttct ttacgatgcc attgggatat atcaacggtg gtatatccag tgatttttt   11160 ctccatttta gcttccttag ctcctgaaaa tctcgccgga tcctaactca aaatccacac  11220
attatacgag ccggaagcat aaagtgtaaa gcctggggtg cctaatgcgg ccgccatagt  11280
gactggatat gttgtgtttt acagtattat gtagtctgtt ttttatgcaa aatctaattt  11340
aatatattga tatttatatc attttacgtt tctcgttcag cttttttgta caaacttgtt  11400
tgataaccgg tactagtgtg cacgtcgagc gtgtcctctc caaatgaaat gaacttcctt  11460
atatagagga agggtcttgc gaaggatagt gggattgtgc gtcatccctt acgtcagtgg  11520
agatgtcaca tcaatccact tgctttgaag acgtggttgg aacgtcttct ttttccacga  11580
tgctcctcgt gggtggggt ccatctttgg gaccactgtc ggcagaggca tcttgaatga   11640
tagcctttcc tttatcgcaa tgatggcatt tgtaggagcc accttccttt tctactgtcc  11700
tttcgatgaa gtgacagata gctgggcaat ggaatccgag gaggtttccc gaaattatcc  11760
tttgttgaaa agtctcaata gcccttggt cttctgagac tgtatctttg acattttgg    11820 agtagaccag agtgtcgtgc tccaccatgt tgacgaagat tttcttcttg tcattgagtc  11880
gtaaaagact ctgtatgaac tgttcgccag tcttcacggc gagttctgtt agatcctcga  11940
tttgaatctt agactccatg catggcctta gattcagtag gaactacctt tttagagact  12000
```

```
ccaatctcta ttacttgcct tggtttatga agcaagcctt gaatcgtcca tactggaata   12060
gtacttctga tcttgagaaa tatgtctttc tctgtgttct tgatgcaatt agtcctgaat   12120
cttttgactg catctttaac cttcttggga aggtatttga tctcctggag attgttactc   12180
gggtagatcg tcttgatgag acctgctgcg taggcctctc taaccatctg tgggtcagca   12240
ttctttctga aattgaagag gctaaccttc tcattatcag tggtgaacat agtgtcgtca   12300
ccttcacctt cgaacttcct tcctagatcg taaagataga ggaaatcgtc cattgtaatc   12360
tccggggcaa aggagatctc ttttggggct ggatcactgc tgggcttttt ggttcctagc   12420
gtgagccagt gggcttttttg ctttggtggg cttgttaggg ccttagcaaa gctcttgggc   12480
ttgagttgag cttctccttt ggggatgaag ttcaacctgt ctgtttgctg acttgttgtg   12540
tacgcgtcag ctgctgctct tgcctctgta atagtggcaa atttcttgtg tgcaactccg   12600
ggaacgccgt ttgttgccgc cttttgtacaa ccccagtcat cgtatatacc ggcatgtgga   12660
ccgttataca caacgtagta gttgatatga gggtgttgaa tacccgattc tgctctgaga   12720
ggagcaactg tgctgttaag ctcagatttt tgtgggattg gaattggatc ctctagagca   12780
aagcttggcg taatcatggt catagctgtt tcctgtgtga aattgttatc cgctcacaat   12840
tccacacaac atacgagccg gaagcataaa gtgtaaagcc tggggtgcct aatgagtgag   12900
ctaactcaca ttaattgcgt tgcgctcact gcccgctttc cagtcgggaa acctgtcgtg   12960
ccagctgcat taatgaatcg gccaacgcgc ggggagaggc ggtttgcgta ttgggccaaa   13020
gacaaagggc gacattcaa ccgattgagg gagggaaggt aaatattgac ggaaattatt   13080
cattaaaggt gaattatcac cgtcaccgac ttgagccatt tgggaattag agccagcaaa   13140
atcaccagta gcaccattac cattagcaag gccggaaacg tcaccaatga aaccatcatc   13200
tagtaacata gatgacaccg cgcgcgataa tttatcctag tttgcgcgct atattttgtt   13260
ttctatcgcg tattaaatgt ataattgcgg gactctaatc ataaaaaccc atctcataaa   13320
taacgtcatg cattacatgt taattattac atgcttaacg taattcaaca gaaattatat   13380
gataatcatc gcaagaccgg caacaggatt caatcttaag aaactttatt gccaaatgtt   13440
tgaacgatct gcttcgacgc actccttctt taggtacgga ctagatctcg gtgacgggca   13500
ggaccggacg gggcggtacc ggcaggctga agtccagctg ccagaaaccc acgtcatgcc   13560
agttcccgtg cttgaagccg gccgcccgca gcatgccgcg gggggcatat ccgagcgcct   13620
cgtgcatgcg cacgctcggg tcgttgggca gcccgatgac agcgaccacg ctcttgaagc   13680
cctgtgcctc cagggacttc agcaggtggg tgtagagcgt ggagcccagt cccgtccgct   13740
ggtggcgggg ggagacgtac acggtcgact cggccgtcca gtcgtaggcg ttgcgtgcct   13800
tccaggggcc cgcgtaggcg atgccggcga cctcgccgtc cacctcggcg acgagccagg   13860
gatagcgctc ccgcagacgg acgaggtcgt ccgtccactc ctgcggttcc tgcggctcgg   13920
tacggaagtt gaccgtgctt gtctcgatgt agtggttgac gatggtgcag accgccggca   13980
tgtccgcctc ggtggcacgg cggatgtcgg ccgggcgtcg ttctgggctc atggatctgg   14040
attgagagtg aatatgagac tctaattgga taccgagggg aatttatgga acgtcagtgg   14100
agcattttg acaagaaata tttgctagct gatagtgacc ttaggcgact tttgaacgcg   14160
caataatggt ttctgacgta tgtgcttagc tcattaaact ccagaaaccc gcggctgagt   14220
ggctccttca acgttgcggt tctgtcagtt ccaaacgtaa aacggcttgt cccgcgtcat   14280
cggcgggggt cataacgtga ctcccttaat tctccgctca tgatcagatt gtcgtttccc   14340
gccttcagtt taaactatca gtgtttgaca ggatatattg gcgggtaaac ctaagagaaa   14400
```

```
agagcgttta ttagaataat cggatattta aaagggcgtg aaaaggttta tccgttcgtc   14460
catttgtatg tgcatgccaa ccacagggtt ccccagatct ggcgccggcc agcgagacga   14520
gcaagattgg ccgccgcccg aaacgatccg acagcgcgcc cagcacaggt gcgcaggcaa   14580
attgcaccaa cgcatacagc gccagcagaa tgccatagtg ggcggtgacg tcgttcgagt   14640
gaaccagatc gcgcaggagg cccggcagca ccggcataat caggccgatg ccgacagcgt   14700
cgagcgcgac agtgctcaga attacgatca ggggtatgtt gggtttcacg tctgcctcc    14760 ggaccagcct ccgctggtcc gattgaacgc gcggattctt tatcactgat aagttggtgg   14820
acatattatg tttatcagtg ataaagtgtc aagcatgaca aagttgcagc cgaatacagt   14880
gatccgtgcc gccctggacc tgttgaacga ggtcggcgta gacggtctga cgacacgcaa   14940
actggcggaa cggttggggg ttcagcagcc ggcgctttac tggcacttca ggaacaagcg   15000
ggcgctgctc gacgcactgg ccgaagccat gctggcggag aatcatacgc attcggtgcc   15060
gagagccgac gacgactggc gctcatttct gatcgggaat gcccgcagct tcaggcaggc   15120
gctgctcgcc taccgcgatg gcgcgcgcat ccatgccggc acgcgaccgg gcgcaccgca   15180
gatggaaacg gccgacgcgc agcttcgctt cctctgcgag gcgggttttt cggccgggga   15240
cgccgtcaat gcgctgatga caatcagcta cttcactgtt ggggccgtgc ttgaggagca   15300
ggccggcgac agcgatgccg gcgagcgcgg cggcaccgtt gaacaggctc cgctctcgcc   15360
gctgttgcgg gccgcgatag acgccttcga cgaagccggt ccggacgcag cgttcgagca   15420
gggactcgcg gtgattgtcg atggattggc gaaaaggagg ctcgttgtca ggaacgttga   15480
aggaccgaga aagggtgacg attgatcagg accgctgccg gagcgcaacc cactcactac   15540
agcagagcca tgtagacaac atcccctccc cctttccacc gcgtcagacg cccgtagcag   15600
cccgctacgg gctttttcat gccctgccct agcgtccaag cctcacggcc gcgctcggcc   15660
tctctggcgg ccttctggcg ctcttccgct tcctcgctca ctgactcgct gcgctcggtc   15720
gttcggctgc ggcgagcggt atcagctcac tcaaaggcgg taatacggtt atccacagaa   15780 tcagggata acgcaggaaa gaacatgtga gcaaaaggcc agcaaaaggc caggaaccgt   15840
aaaaaggccg cgttgctggc gtttttccat aggctccgcc cccctgacga gcatcacaaa   15900
aatcgacgct caagtcagag gtggcgaaac ccgacaggac tataaagata ccaggcgttt   15960
ccccctggaa gctccctcgt gcgctctcct gttccgaccc tgccgcttac cggatacctg   16020 tccgccttc tcccttcggg aagcgtggcg ctttctccgct gcataaccct gcttcggggt    16080
cattatagcg attttttcgg tatatccatc ctttttcgca cgatatacag gattttgcca   16140
aagggttcgt gtagactttc cttggtgtat ccaacggcgt cagccgggca ggataggtga   16200
agtaggccca cccgcgagcg ggtgttcctt cttcactgtc ccttattcgc acctggcggt   16260
gctcaacggg aatcctgctc tgcgaggctg gccggctacc gccggcgtaa cagatgaggg   16320
caagcggatg ctgatgaaa ccaagccaac caggaagggc agcccaccta tcaaggtgta    16380
ctgccttcca gacgaacgaa gagcgattga ggaaaaggcg gcggcggccg gcatgagcct   16440
gtcggcctac ctgctggccg tcggccaggg ctacaaaatc acgggcgtcg tggactatga   16500
gcacgtccgc gagctggccc gcatcaatgg cgacctgggc cgcctgggcg gctgctgaa    16560 actctggctc accgacgacc cgcgcacggc gcggttcggt gatgccacga tcctcgccct   16620
gctggcgaag atcgaagaga agcaggacga gcttggcaag gtcatgatgg gcgtggtccg   16680
cccgagggca gagccatgac ttttttagcc gctaaaacgg ccggggggtg cgcgtgattg   16740
```

```
ccaagcacgt ccccatgcgc tccatcaaga agagcgactt cgcggagctg gtgaagtaca   16800
tcaccgacga gcaaggcaag accgagcgcc tttgcgacgc tca                    16843

<210> SEQ ID NO 5
<211> LENGTH: 9142
<212> TYPE: DNA
<213> ORGANISM: artificial sequence
<220> FEATURE:
<223> OTHER INFORMATION: destination vector for use with soybean

<400> SEQUENCE: 5
ctagttatct gaataaaaga gaaagagatc atccatattt cttatcctaa atgaatgtca     60
cgtgtcttta taattctttg atgaaccaga tgcatttcat taaccaaatc catatacata    120
taaatattaa tcatatataa ttaatatcaa ttgggttagc aaaacaaatc tagtctaggt    180
gtgttttgcg aattcgatat caagcttgat gggtaccggc gcgcccgatc atccggatat    240
agttcctcct ttcagcaaaa aaccccctcaa gacccgttta gaggcccccaa ggggttatgc    300 tagttattgc tcagcggtgg cagcagccaa ctcagcttcc tttcgggctt tgttagcagc    360
cggatcgatc caagctgtac ctcactattc ctttgccctc ggacgagtgc tggggcgtcg    420
gtttccacta tcggcgagta cttctacaca gccatcggtc cagacggccg cgcttctgcg    480
ggcgatttgt gtacgcccga cagtcccggc tccggatcgg acgattgcgt cgcatcgacc    540
ctgcgcccaa gctgcatcat cgaaattgcc gtcaaccaag ctctgataga gttggtcaag    600
accaatgcgg agcatatacg cccggagccg cggcgatcct gcaagctccg gatgcctccg    660
ctcgaagtag cgcgtctgct gctccataca agccaaccac ggcctccaga agaagatgtt    720
ggcgacctcg tattgggaat ccccgaacat cgcctcgctc cagtcaatga ccgctgttat    780
gcggccattg tccgtcagga cattgttgga gccgaaatcc gcgtgcacga ggtgccggac    840 ttcgggcag tcctcggccc aaagcatcag ctcatcgaga gcctgcgcga cggacgcact    900
gacggtgtcg tccatcacag tttgccagtg atacacatgg ggatcagcaa tcgcgcatat    960
gaaatcacgc catgtagtgt attgaccgat tccttgcggt ccgaatgggc cgaacccgct   1020
cgtctggcta agatcggccg cagcgatcgc atccatagcc tccgcgaccg gctgcagaac   1080
agcgggcagt tcggtttcag gcaggtcttg caacgtgaca ccctgtgcac ggcgggagat   1140
gcaataggtc aggctctcgc tgaattcccc aatgtcaagc acttccggaa tcgggagcgc   1200
ggccgatgca aagtgccgat aaacataacg atctttgtag aaaccatcgg cgcagctatt   1260
tacccgcagg acatatccac gccctcctac atcgaagctg aaagcacgag attcttcgcc   1320
ctccgagagc tgcatcaggt cggagacgct gtcgaacttt tcgatcagaa acttctcgac   1380
agacgtcgcg gtgagttcag cttttccat gggtatatct ccttcttaaa gttaaacaaa   1440
attatttcta gagggaaacc gttgtggtct ccctatagtg agtcgtatta atttcgcggg   1500
atcgagatct gatcaacctg cattaatgaa tcggccaacg cgcggggaga ggcggtttgc   1560
gtattgggcg ctcttccgct tcctcgctca ctgactcgct gcgctcggtc gttcggctgc   1620
ggcgagcggt atcagctcac tcaaaggcgg taatacggtt atccacagaa tcaggggata   1680
acgcaggaaa gaacatgtga gcaaaaggcc agcaaaggc caggaaccgt aaaaaggccg   1740
cgttgctggc gtttttccat aggctccgcc ccctgacga gcatcacaaa aatcgacgct   1800
caagtcagag gtggcgaaac ccgacaggac tataaagata ccaggcgttt ccccctggaa   1860
gctccctcgt gcgctctcct gttccgaccc tgccgcttac cggatacctg tccgcctttc   1920
tcccttcggg aagcgtggcg ctttctcaat gctcacgctg taggtatctc agttcggtgt   1980
```

```
aggtcgttcg ctccaagctg ggctgtgtgc acgaaccccc cgttcagccc gaccgctgcg     2040
ccttatccgg taactatcgt cttgagtcca acccggtaag acacgactta tcgccactgg     2100
cagcagccac tggtaacagg attagcagag cgaggtatgt aggcggtgct acagagttct     2160
tgaagtggtg gcctaactac ggctacacta gaaggacagt atttggtatc tgcgctctgc     2220
tgaagccagt taccttcgga aaaagagttg gtagctcttg atccggcaaa caaaccaccg     2280
ctggtagcgg tggttttttt gtttgcaagc agcagattac gcgcagaaaa aaggatctc      2340 aagaagatcc tttgatcttt tctacggggt ctgacgctca gtggaacgaa aactcacgtt     2400
aagggatttt ggtcatgaca ttaacctata aaaataggcg tatcacgagg ccctttcgtc     2460
tcgcgcgttt cggtgatgac ggtgaaaacc tctgacacat gcagctcccg gagacggtca     2520
cagcttgtct gtaagcggat gccgggagca gacaagcccg tcagggcgcg tcagcgggtg     2580
ttggcgggtg tcgggctgg  cttaactatg cggcatcaga gcagattgta ctgagagtgc     2640
accatatgga catattgtcg ttagaacgcg gctacaatta atacataacc ttatgtatca     2700
tacacatacg atttaggtga cactatagaa cggcgcgcca agctgggtct agaactagaa     2760
acgtgatgcc acttgttatt gaagtcgatt acagcatcta ttctgtttta ctatttataa     2820
ctttgccatt tctgactttt gaaaactatc tctggatttc ggtatcgctt tgtgaagatc     2880
gagcaaaaga gacgttttgt ggacgcaatg gtccaaatcc gttctacatg aacaaattgg     2940
tcacaatttc cactaaaagt aaataaatgg caagttaaaa aaggaatatg catttt actg    3000 attgcctagg tgagctccaa gagaagttga atctacacgt ctaccaaccg ctaaaaaaag     3060
aaaaacattg aatatgtaac ctgattccat tagcttttga cttcttcaac agattctcta     3120
cttagatttc taacagaaat attattacta gcacatcatt ttcagtctca ctacagcaaa     3180
aaatccaacg gcacaataca gacaacagga gatatcagac tacagagata gatagatgct     3240
actgcatgta gtaagttaaa taaaaggaaa ataaaatgtc ttgctaccaa aactactaca     3300
gactatgatg ctcaccacag gccaaatcct gcaactagga cagcattatc ttatatatat     3360
tgtacaaaac aagcatcaag gaacatttgg tctaggcaat cagtacctcg ttctaccatc     3420
accctcagtt atcacatcct tgaaggatcc attactggga atcatcggca acacatgctc     3480
ctgatggggc acaatgacat caagaaggta ggggccaggg gtgtccaaca ttctctgaat     3540
tgccgctcta agctcttcct tcttcgtcac tcgcgctgcc ggtatccac  aagcatcagc     3600 aaacttgagc atgtttggga atatctcgct ctcgctagac ggatctccaa gataggtgtg     3660
agctctattg gacttgtaga acctatcctc caactgaacc accatacccca aatgctgatt     3720 gttcaacaac aatatcttaa ctgggagatt ctccactctt atagtggcca actcctgaac     3780
attcatgatg aaactaccat ccccatcaat gtcaaccaca acagcccag  ggttagcaac     3840 agcagcacca atagccgcag gcaatccaaa acccatggct ccaagacccc ctgaggtcaa     3900
ccactgcctc ggtctcttgt acttgtaaaa ctgcgcagcc cacatttgat gctgcccaac     3960
cccagtacta acaatagcat ctccattagt caactcatca agaacctcga tagcatgctg     4020
cggagaaatc gcgtcctgga atgtcttgta acccaatgga aacttgtgtt tctgcacatt     4080
aatctcttct ctccaacctc caagatcaaa cttaccctcc actcctttct cctccaaaat     4140
catattaatt cccttcaagg ccaacttcaa atccgcgcaa accgacacgt gcgcctgctt     4200
gttcttccca atctcggcag aatcaatatc aatgtgaaca atcttagccc tactagcaaa     4260
agcctcaagc ttcccagtaa cacggtcatc aaaccttacc ccaaaggcaa gcaacaaatc     4320
```

```
actattgtca acagcatagt tagcataaac agtaccatgc atacccagca tctgaaggga    4380
atattcatca ccaataggaa aagttccaag acccattaaa gtgctagcaa cgggaatacc    4440
agtgagttca acaaagcgcc tcaattcagc actggaattc aaactgccac cgccgacgta    4500
gagaacgggc ttttgggcct ccatgatgag tctgacaatg tgttccaatt gggcctcggc    4560
ggggggcctg ggcagcctgg cgaggtaacc ggggaggtta acgggctcgt cccaattagg    4620
cacggcgagt tgctgctgaa cgtctttggg aatgtcgatg aggaccggac cggggcggcc    4680
ggaggtggcg acgaagaaag cctcggcgac gacgcggggg atgtcgtcga cgtcgaggat    4740
gaggtagttg tgcttcgtga tggatctgct cacctccacg atcggggttt cttggaaggc    4800
gtcggtgccg atcatccggc gggcgacctg gccggtgatg gcgacgactg ggacgctgtc    4860
cattaaagcg tcggcgaggc cgctcacgag gttggtggcg ccggggccgg aggtggcaat    4920
gcagacgccg gggaggccgg aggaacgcgc gtagccttcg gcggcgaaga cgccgccctg    4980
ctcgtggcgc gggagcacgt tgcggatggc ggcggagcgc gtgagcgcct ggtggatctc    5040
catcgacgca ccgccggggt acgcgaacac cgtcgtcacg ccctgcctct ccagcgcctc    5100
cacaaggatg tccgcgccct tgcgaggttc gccggaggcg aaccgtgaca cgaagggctc    5160
cgtggtcggc gcttccttgg tgaagggcgc cgccgtgggg ggtttggaga tggaacattt    5220
gattttgaga gcgtggttgg gtttggtgag ggtttgatga gagagaggga gggtggatct    5280
agtaatgcgt ttggggaagg tggggtgtga agaggaagaa gagaatcggg tggttctgga    5340
agcggtggcc gccattgtgt tgtgtggcat ggttatactt caaaaactgc acaacaagcc    5400
tagagttagt acctaaacag taaatttaca acagagagca aagacacatg caaaaatttc    5460
agccataaaa aaagttataa tagaatttaa agcaaaagtt tcattttta aacatatata    5520 caaacaaact ggatttgaag gaagggatta attcccctgc tcaaagtttg aattcctatt    5580
gtgacctata ctcgaataaa attgaagcct aaggaatgta tgagaaacaa gaaaacaaaa    5640
caaaactaca gacaaacaag tacaattaca aaattcgcta aaattctgta atcaccaaac    5700
cccatctcag tcagcacaag gcccaaggtt tattttgaaa taaaaaaaaa gtgattttat    5760
ttctcataag ctaaaagaaa gaaaggcaat tatgaaatga tttcgactag atctgaaagt    5820
caaacgcgta ttccgcagat attaaagaaa gagtagagtt tcacatggat cctagatgga    5880
cccagttgag gaaaaagcaa ggcaaagcaa accagaagtg caagatccga aattgaacca    5940
cggaatctag gatttggtag agggagaaga aaagtacctt gagaggtaga agagaagaga    6000
agagcagaga gatatatgaa cgagtgtgtc ttggtctcaa ctctgaagcg atacgagttt    6060
agaggggagc attgagttcc aatttatagg gaaaccgggt ggcagggtg agttaatgac    6120 ggaaaagccc ctaagtaacg agattggatt gtgggttaga ttcaaccgtt tgcatccgcg    6180
gcttagattg gggaagtcag agtgaatctc aaccgttgac tgagttgaaa attgaatgta    6240
gcaaccaatt gagccaaccc cagccttttgc cctttgattt tgatttgttt gttgcatact    6300
ttttatttgt cttctggttc tgactctctt tctctcgttt caatgccagg ttgcctactc    6360
ccacaccact cacaagaaga ttctactgtt agtattaaat atttttttaat gtattaaatg    6420 atgaatgctt ttgtaaacag aacaagacta tgtctaataa gtgtcttgca acatttttta    6480
agaaattaaa aaaaatatat ttattatcaa aatcaaatgt atgaaaaatc atgaataata    6540 taatttttata catttttta aaaaatcttt taatttctta attaatatct taaaaataat    6600
gattaatatt taacccaaaa taattagtat gattggtaag gaagatatcc atgttatgtt    6660
tggatgtgag tttgatctag agcaaagctt actagagtcg acctgcagcc cctccaccgc    6720
```

-continued

| | | | | | |
|---|---|---|---|---|---|
| ggtggcggcc | gctctagaga | tccgtcaaca | tggtggagca | cgacactctc | gtctactcca | 6780 |
| agaatatcaa | agatacagtc | tcagaagacc | aaagggctat | tgagactttt | caacaaaggg | 6840 |
| taatatcggg | aaacctcctc | ggattccatt | gcccagctat | ctgtcacttc | atcaaaagga | 6900 |
| cagtagaaaa | ggaaggtggc | acctacaaat | gccatcattg | cgataaagga | aaggctatcg | 6960 |
| ttcaagatgc | ctctgccgac | agtggtccca | aagatggacc | cccacccacg | aggagcatcg | 7020 |
| tggaaaaaga | agacgttcca | accacgtctt | caaagcaagt | ggattgatgt | gatgatccta | 7080 |
| tgcgtatggt | atgacgtgtg | ttcaagatga | tgacttcaaa | cctacctatg | acgtatggta | 7140 |
| tgacgtgtgt | cgactgatga | cttagatcca | ctcgagcggc | tataaatacg | tacctacgca | 7200 |
| ccctgcgcta | ccatccctag | agctgcagct | tattttttaca | acaattacca | acaacaacaa | 7260 |
| acaacaaaca | acattacaat | tactatttac | aattacagtc | gacccatcaa | caagtttgta | 7320 |
| caaaaaagct | gaacgagaaa | cgtaaaatga | tataaatatc | aatatattaa | attagatttt | 7380 |
| gcataaaaaa | cagactacat | aatactgtaa | aacacaacat | atccagtcat | attggcggcc | 7440 |
| gcattaggca | ccccaggctt | tacactttat | gcttccggct | cgtataatgt | gtggattttg | 7500 |
| agttaggatc | cgtcgagatt | ttcaggagct | aaggaagcta | aaatggagaa | aaaaatcact | 7560 |
| ggatatacca | ccgttgatat | atcccaatgg | catcgtaaag | aacattttga | ggcatttcag | 7620 |
| tcagttgctc | aatgtaccta | taaccagacc | gttcagctgg | atattacggc | ctttttaaag | 7680 |
| accgtaaaga | aaaataagca | caagttttat | ccggccttta | ttcacattct | tgcccgcctg | 7740 |
| atgaatgctc | atccggaatt | ccgtatggca | atgaaagacg | gtgagctggt | gatatgggat | 7800 |
| agtgttcacc | cttgttacac | cgttttccat | gagcaaactg | aaacgttttc | atcgctctgg | 7860 |
| agtgaatacc | acgacgattt | ccggcagttt | ctacacatat | attcgcaaga | tgtggcgtgt | 7920 |
| tacggtgaaa | acctggccta | tttccctaaa | gggtttattg | agaatatgtt | tttcgtctca | 7980 |
| gccaatccct | gggtgagttt | caccagtttt | gatttaaacg | tggccaatat | ggacaacttc | 8040 |
| ttcgccccg | ttttcaccat | gggcaaatat | tatacgcaag | cgacaaggt | gctgatgccg | 8100 |
| ctggcgattc | aggttcatca | tgccgtttgt | gatggcttcc | atgtcggcag | aatgcttaat | 8160 |
| gaattacaac | agtactgcga | tgagtggcag | ggcggggcgt | aaagatctgg | atccggctta | 8220 |
| ctaaaagcca | gataacagta | tgcgtatttg | cgcgctgatt | tttgcggtat | aagaatatat | 8280 |
| actgatatgt | atacccgaag | tatgtcaaaa | agaggtatgc | tatgaagcag | cgtattacag | 8340 |
| tgacagttga | cagcgacagc | tatcagttgc | tcaaggcata | tatgatgtca | atatctccgg | 8400 |
| tctggtaagc | acaaccatgc | agaatgaagc | ccgtcgtctg | cgtgccgaac | gctggaaagc | 8460 |
| ggaaaatcag | aagggatgg | ctgaggtcgc | ccggtttatt | gaaatgaacg | gctcttttgc | 8520 |
| tgacgagaac | aggggctggt | gaaatgcagt | ttaaggttta | cacctataaa | agagagagcc | 8580 |
| gttatcgtct | gtttgtggat | gtacagagtg | atattattga | cacgcccggg | cgacggatgg | 8640 |
| tgatccccct | ggccagtgca | cgtctgctgt | cagataaagt | ctcccgtgaa | ctttacccgg | 8700 |
| tggtgcatat | cggggatgaa | agctggcgca | tgatgaccac | cgatatggcc | agtgtgccgg | 8760 |
| tctccgttat | cggggaagaa | gtggctgatc | tcagccaccg | cgaaaatgac | atcaaaaacg | 8820 |
| ccattaacct | gatgttctgg | ggaatataaa | tgtcaggctc | ccttatacac | agccagtctg | 8880 |
| caggtcgacc | atagtgactg | gatatgttgt | gttttacagt | attatgtagt | ctgttttta | 8940 |
| tgcaaaatct | aatttaatat | attgatattt | atatcatttt | acgtttctcg | ttcagctttc | 9000 |
| ttgtacaaag | tggttgataa | cctagacttg | tccatcttct | ggattggcca | acttaattaa | 9060 |

```
tgtatgaaat aaaaggatgc acacatagtg acatgctaat cactataatg tgggcatcaa      9120
agttgtgtgt tatgtgtaat ta                                               9142

<210> SEQ ID NO 6
<211> LENGTH: 49911
<212> TYPE: DNA
<213> ORGANISM: artificial sequence
<220> FEATURE:
<223> OTHER INFORMATION: destination vector for use with Gaspe-Flint
      derived maize lines

<400> SEQUENCE: 6
gtgcagcgtg acccggtcgt gcccctctct agagataatg agcattgcat gtctaagtta        60
taaaaaatta ccacatattt tttttgtcac acttgtttga agtgcagttt atctatcttt       120
atacatatat ttaaactttta ctctacgaat aatataatct atagtactac aataatatca      180
gtgttttaga gaatcatata aatgaacagt tagacatggt ctaaaggaca attgagtatt       240
ttgacaacag gactctacag ttttatcttt ttagtgtgca tgtgttctcc tttttttttg       300
caaatagctt cacctatata atacttcatc cattttatta gtacatccat ttagggttta      360
gggttaatgg tttttataga ctaattttttt tagtacatct atttttattct atttttagcct    420 ctaaattaag aaaactaaaa ctctatttta gttttttttat ttaataatttt agatataaaa    480 tagaataaaa taaagtgact aaaaattaaa caaatacct ttaagaaatt aaaaaaacta       540
aggaaacatt tttcttgttt cgagtagata atgccagcct gttaaacgcc gtcgacgagt       600
ctaacggaca ccaaccagcg aaccagcagc gtcgcgtcgg gccaagcgaa gcagacggca       660
cggcatctct gtcgctgcct ctggacccct ctcgagagtt ccgctccacc gttggacttg       720
ctccgctgtc ggcatccaga aattgcgtgg cggagcggca gacgtgagcc ggcacggcag       780
gcggcctcct cctcctctca cggcacggca gctacggggg attccttttcc caccgctcct     840 tcgcttttccc ttcctcgccc gccgtaataa atagacaccc cctccacacc ctcttttcccc    900 aacctcgtgt tgttcggagc gcacacacac acaaccagat ctcccccaaa tccaccccgtc     960 ggcacctccg cttcaaggta cgccgctcgt cctccccccc cccccctctc taccttctct    1020
agatcggcgt tccggtccat ggttagggcc cggtagttct acttctgttc atgtttgtgt     1080
tagatccgtg tttgtgttag atccgtgctg ctagcgttcg tacacggatg cgacctgtac      1140
gtcagacacg ttctgattgc taacttgcca gtgtttctct tggggaatc ctgggatggc      1200 tctagccgtt ccgcagacgg gatcgatttc atgatttttt ttgtttcgtt gcatagggtt    1260
tggtttgccc ttttccttta tttcaatata tgccgtgcac ttgtttgtcg ggtcatcttt    1320
tcatgctttt ttttgtcttg gttgtgatga tgtggtctgg ttgggcggtc gttctagatc     1380
ggagtagaat tctgtttcaa actacctggt ggatttatta attttggatc tgtatgtgtg    1440
tgccatacat attcatagtt acgaattgaa gatgatggat ggaaatatcg atctaggata     1500
ggtatacatg ttgatgcggg ttttactgat gcatatacag agatgctttt tgttcgcttg    1560
gttgtgatga tgtggtgtgg ttgggcggtc gttcattcgt tctagatcgg agtagaatac    1620
tgtttcaaac tacctggtgt atttattaat tttggaactg tatgtgtgtg tcatacatct     1680
tcatagttac gagtttaaga tggatggaaa tatcgatcta ggataggtat acatgttgat    1740
gtgggtttta ctgatgcata tacatgatgg catatgcagc atcgatgcat atgctctaac    1800
cttgagtacc tatctattat aataaacaag tatgttttat aattattttg atcttgatat    1860
acttggatga tggcatatgc agcagctata tgtggatttt tttagccctg ccttcatacg     1920
```

```
ctatttattt gcttggtact gtttcttttg tcgatgctca ccctgttgtt tggtgttact   1980
tctgcaggtc gactctagag gatccacaag tttgtacaaa aaagctgaac gagaaacgta   2040
aaatgatata aatatcaata tattaaatta gattttgcat aaaaaacaga ctacataata   2100
ctgtaaaaca caacatatcc agtcactatg gcggccgcat taggcacccc aggctttaca   2160
ctttatgctt ccggctcgta taatgtgtgg attttgagtt aggatttaaa tacgcgttga   2220
tccggcttac taaaagccag ataacagtat gcgtatttgc gcgctgattt ttgcggtata   2280
agaatatata ctgatatgta tacccgaagt atgtcaaaaa gaggtatgct atgaagcagc   2340
gtattacagt gacagttgac agcgacagct atcagttgct caaggcatat atgatgtcaa   2400
tatctccggt ctggtaagca caaccatgca gaatgaagcc cgtcgtctgc gtgccgaacg   2460
ctggaaagcg gaaaatcagg aagggatggc tgaggtcgcc cggtttattg aaatgaacgg   2520
ctcttttgct gacgagaaca ggggctggtg aaatgcagtt taaggtttac acctataaaa   2580
gagagagccg ttatcgtctg tttgtggatg tacagagtga tatcattgac acgcccggtc   2640
gacggatggt gatcccctg gccagtgcac gtctgctgtc agataaagtc tcccgtgaac   2700
tttacccggt ggtgcatatc ggggatgaaa gctggcgcat gatgaccacc gatatggcca   2760
gtgtgccggt ctccgttatc ggggaagaag tggctgatct cagccaccgc gaaaatgaca   2820
tcaaaaacgc cattaacctg atgttctggg aatataaat gtcaggctcc cttatacaca   2880
gccagtctgc aggtcgacca tagtgactgg atatgttgtg ttttacagta ttatgtagtc   2940
tgttttttat gcaaaatcta atttaatata ttgatattta tatcatttta cgtttctcgt   3000
tcagctttct tgtacaaagt ggtgttaacc tagacttgtc catcttctgg attggccaac   3060
ttaattaatg tatgaaataa aaggatgcac acatagtgac atgctaatca ctataatgtg   3120
ggcatcaaag ttgtgtgtta tgtgtaatta ctagttatct gaataaaaga gaagagatc   3180 atccatattt cttatcctaa atgaatgtca cgtgtcttta taattctttg atgaaccaga   3240
tgcatttcat taaccaaatc catatacata taaatattaa tcatatataa ttaatatcaa   3300
ttgggttagc aaaacaaatc tagtctaggt gtgttttgcg aattgcggcc gccaccgcgg   3360
tggagctcga attccggtcc gggtcacctt tgtccaccaa gatggaactg cggccgctca   3420
ttaattaagt caggcgcgcc tctagttgaa gacacgttca tgtcttcatc gtaagaagac   3480
actcagtagt cttcggccag aatggccatc tggattcagc aggcctagaa ggccatttaa   3540
atcctgagga tctggtcttc ctaaggaccc gggatatcgg accgattaaa ctttaattcg   3600
gtccgaagct tgcatgcctg cagtgcagcg tgacccggtc gtgcccctct ctagagataa   3660
tgagcattgc atgtctaagt tataaaaaat taccacatat ttttttgtc acacttgttt   3720 gaagtgcagt ttatctatct ttatacatat atttaaactt tactctacga ataatataat   3780
ctatagtact acaataatat cagtgtttta gagaatcata taaatgaaca gttagacatg   3840
gtctaaagga caattgagta ttttgacaac aggactctac agttttatct ttttagtgtg   3900
catgtgttct ccttttttt tgcaaatagc ttcacctata taatacttca tccattttat   3960
tagtacatcc atttagggtt tagggttaat ggtttttata gactaatttt tttagtacat   4020 ctatttatt ctattttagc ctctaaatta agaaaactaa aactctatt tagtttttt   4080 atttaataat ttagatataa aatagaataa aataaagtga ctaaaaatta aacaaatacc   4140
ctttaagaaa ttaaaaaaac taaggaaaca ttttttcttgt ttcgagtaga taatgccagc   4200
ctgttaaacg ccgtcgacga gtctaacgga caccaaccag cgaaccagca gcgtcgcgtc   4260
gggccaagcg aagcagacgg cacggcatct ctgtcgctgc ctctggaccc ctctcgagag   4320
```

```
ttccgctcca ccgttggact tgctccgctg tcggcatcca gaaattgcgt ggcggagcgg    4380
cagacgtgag ccggcacggc aggcggcctc ctcctcctct cacggcaccg gcagctacgg    4440
gggattcctt tcccaccgct ccttcgcttt cccttcctcg cccgccgtaa taaatagaca    4500 cccccctccac accctctttc cccaacctcg tgttgttcgg agcgcacaca cacacaacca    4560
gatctccccc aaatccaccc gtcggcacct ccgcttcaag gtacgccgct cgtcctcccc    4620
cccccccctc tctaccttct ctagatcggc gttccggtcc atgcatggtt agggcccggt    4680
agttctactt ctgttcatgt ttgtgttaga tccgtgtttg tgttagatcc gtgctgctag    4740
cgttcgtaca cggatgcgac ctgtacgtca gacacgttct gattgctaac ttgccagtgt    4800
ttctctttgg ggaatcctgg gatggctcta gccgttccgc agacgggatc gatttcatga    4860 tttttttgt ttcgttgcat agggtttggt ttgccctttt cctttatttc aatatatgcc    4920
gtgcacttgt ttgtcgggtc atcttttcat gcttttttt gtcttggttg tgatgatgtg    4980
gtctggttgg gcggtcgttc tagatcggag tagaattctg tttcaaacta cctggtggat    5040
ttattaattt tggatctgta tgtgtgtgcc atacatattc atagttacga attgaagatg    5100
atggatggaa atatcgatct aggataggta tacatgttga tgcgggtttt actgatgcat    5160
atacagagat gcttttttgtt cgcttggttg tgatgatgtg gtgtggttgg gcggtcgttc    5220
attcgttcta gatcggagta gaatactgtt tcaaactacc tggtgtattt attaattttg    5280
gaactgtatg tgtgtgtcat acatcttcat agttacgagt ttaagatgga tggaaatatc    5340
gatctaggat aggtatacat gttgatgtgg gttttactga tgcatataca tgatggcata    5400
tgcagcatct attcatatgc tctaaccttg agtacctatc tattataata aacaagtatg    5460
ttttataatt atttttgatct tgatatactt ggatgatggc atatgcagca gctatatgtg    5520 gatttttta gccctgcctt catacgctat ttatttgctt ggtactgttt cttttgtcga    5580
tgctcaccct gttgtttggt gttacttctg caggtcgact ttaacttagc ctaggatcca    5640
cacgacacca tgtcccccga gcgccgcccc gtcgagatcc gcccggccac cgccgccgac    5700
atggccgccg tgtgcgacat cgtgaaccac tacatcgaga cctccaccgt gaacttccgc    5760
accgagccgc agacccgca ggagtggatc gacgacctgg agcgcctcca ggaccgctac    5820
ccgtggctcg tggccgaggt ggagggcgtg gtggccggca tcgcctacgc cggcccgtgg    5880
aaggcccgca acgcctacga ctggaccgtg gagtccaccg tgtacgtgtc ccaccgccac    5940
cagcgcctcg gcctcggctc caccctctac acccacctcc tcaagagcat ggaggcccag    6000
ggcttcaagt ccgtggtggc cgtgatcggc ctcccgaacg accgtccgt gcgcctccac    6060 gaggccctcg gctacaccgc ccgcggcacc ctccgcgccg ccggctacaa gcacggcggc    6120
tggcacgacg tcggcttctg gcagcgcgac ttcgagctgc cggccccgcc gcgcccggtg    6180
cgcccggtga cgcagatctg agtcgaaacc tagacttgtc catcttctgg attggccaac    6240
ttaattaatg tatgaaataa aaggatgcac acatagtgac atgctaatca ctataatgtg    6300
ggcatcaaag ttgtgtgtta tgtgtaatta ctagttatct gaataaaaga gaaagagatc    6360
atccatattt cttatcctaa atgaatgtca cgtgtcttta taattctttg atgaaccaga    6420
tgcatttcat taaccaaatc catatacata taaatattaa tcatatataa ttaatatcaa    6480
ttgggttagc aaaacaaatc tagtctaggt gtgttttgcg aattgcggcc gccaccgcgg    6540
tggagctcga attcattccg attaatcgtg gcctcttgct cttcaggatg aagagctatg    6600
tttaaacgtg caagcgctac tagacaattc agtacattaa aaacgtccgc aatgtgttat    6660
```

-continued

```
taagttgtct aagcgtcaat ttggtttaca ccacaatata tcctgccacc agccagccaa   6720
cagctccccg accggcagct cggcacaaaa tcaccactcg atacaggcag cccatcagtc   6780
cgggacggcg tcagcgggag agccgttgta aggcggcaga ctttgctcat gttaccgatg   6840
ctattcggaa gaacgcaac taagctgccg ggtttgaaac acggatgatc tcgcggaggg    6900
tagcatgttg attgtaacga tgacagagcg ttgctgcctg tgatcaaata tcatctccct   6960
cgcagagatc cgaattatca gccttcttat tcatttctcg cttaaccgtg acaggctgtc   7020
gatcttgaga actatgccga cataatagga aatcgctgga taaagccgct gaggaagctg   7080
agtggcgcta tttctttaga agtgaacgtt gaccgatcgtc gaccgtaccc cgatgaatta  7140
attcggacgt acgttctgaa cacagctgga tacttacttg ggcgattgtc atacatgaca   7200
tcaacaatgt acccgtttgt gtaaccgtct cttggaggtt cgtatgacac tagtggttcc   7260
cctcagcttg cgactagatg ttgaggccta acattttatt agagagcagg ctagttgctt   7320
agatacatga tcttcaggcc gttatctgtc agggcaagcg aaaattggcc atttatgacg   7380
accaatgccc cgcagaagct cccatctttg ccgccataga cgccgcgccc ccttttggg    7440
gtgtagaaca tccttttgcc agatgtggaa aagaagttcg ttgtcccatt gttggcaatg   7500
acgtagtagc cggcgaaagt gcgagaccca tttgcgctat atataagcct acgatttccg   7560
ttgcgactat tgtcgtaatt ggatgaacta ttatcgtagt tgctctcaga gttgtcgtaa   7620
tttgatggac tattgtcgta attgcttatg gagttgtcgt agttgcttgg agaaatgtcg   7680
tagttggatg gggagtagtc atagggaaga cgagcttcat ccactaaaac aattggcagg   7740
tcagcaagtg cctgccccga tgccatcgca agtacgaggc ttagaaccac cttcaacaga   7800
tcgcgcatag tcttccccag ctctctaacg cttgagttaa gccgcgccgc gaagcggcgt   7860
cggcttgaac gaattgttag acattatttg ccgactacct tggtgatctc gcctttcacg   7920
tagtgaacaa attcttccaa ctgatctgcg cgcgaggcca agcgatcttc ttgtccaaga   7980
taagcctgcc tagcttcaag tatgacgggc tgatactggg ccggcaggcg ctccattgcc   8040
cagtcggcag cgacatcctt cggcgcgatt ttgccggtta ctgcgctgta ccaaatgcgg   8100
gacaacgtaa gcactacatt tcgctcatcg ccagcccagt cgggcggcga gttccatagc   8160
gttaaggttt catttagcgc ctcaaataga tcctgttcag gaaccggatc aaagagttcc   8220
tccgccgctg gacctaccaa ggcaacgcta tgttctcttg cttttgtcag caagatagcc   8280
agatcaatgt cgatcgtggc tggctcgaag ataccgtgcaa gaatgtcatt gcgctgccat   8340
tctccaaatt gcagttcgcg cttagctgga taacgccacg gaatgatgtc gtcgtgcaca   8400
acaatggtga cttctacagc gcggagaatc tcgctctctc caggggaagc cgaagtttcc   8460
aaaaggtcgt tgatcaaagc tcgccgcgtt gtttcatcaa gccttacagt caccgtaacc   8520
agcaaatcaa tatcactgtg tggcttcagg ccgccatcca ctgcggagcc gtacaaatgt   8580
acggccagca acgtcggttc gagatggcgc tcgatgacgc caactacctc tgatagttga   8640
gtcgatactt cggcgatcac cgcttccctc atgatgttta actcctgaat taagccgcgc   8700
cgcgaagcgg tgtcggcttg aatgaattgt taggcgtcat cctgtgctcc cgagaaccag   8760
taccagtaca tcgctgtttc gttcgagact tgaggtctag ttttatacgt gaacaggtca   8820
atgccgccga gagtaaagcc acattttgcg tacaaattgc aggcaggtac attgttcgtt   8880
tgtgtctcta atcgtatgcc aaggagctgt ctgcttagtg cccactttt cgcaaattcg    8940
atgagactgt gcgcgactcc tttgcctcgg tgcgtgtgcg acacaacaat gtgttcgata   9000
gaggctagat cgttccatgt tgagttgagt tcaatcttcc cgacaagctc ttggtcgatg   9060
```

```
aatgcgccat agcaagcaga gtcttcatca gagtcatcat ccgagatgta atccttccgg    9120
tagggctca cacttctggt agatagttca aagccttggt cggataggtg cacatcgaac    9180
acttcacgaa caatgaaatg gttctcagca tccaatgttt ccgccacctg ctcagggatc    9240
accgaaatct tcatatgacg cctaacgcct ggcacagcgg atcgcaaacc tggcgcggct    9300
tttggcacaa aaggcgtgac aggtttgcga atccgttgct gccacttgtt aaccctttg    9360
ccagatttgg taactataat ttatgttaga ggcgaagtct tgggtaaaaa ctggcctaaa    9420
attgctgggg atttcaggaa agtaaacatc accttccggc tcgatgtcta ttgtagatat    9480
atgtagtgta tctacttgat cgggggatct gctgcctcgc gcgtttcggt gatgacggtg    9540
aaaacctctg acacatgcag ctcccggaga cggtcacagc ttgtctgtaa gcggatgccg    9600
ggagcagaca gcccgtcag ggcgcgtcag cgggtgttgg cgggtgtcgg ggcgcagcca    9660
tgacccagtc acgtagcgat agcggagtgt atactggctt aactatgcgg catcagagca    9720
gattgtactg agagtgcacc atatgcggtg tgaaataccg cacagatgcg taaggagaaa    9780
ataccgcatc aggcgctctt ccgcttcctc gctcactgac tcgctgcgct cggtcgttcg    9840
gctgcggcga gcggtatcag ctcactcaaa ggcggtaata cggttatcca cagaatcagg    9900
ggataacgca ggaaagaaca tgtgagcaaa aggccagcaa aaggccagga accgtaaaaa    9960
ggccgcgttg ctggcgtttt tccataggct ccgcccccct gacgagcatc acaaaaatcg   10020
acgctcaagt cagaggtggc gaaacccgac aggactataa agataccagg cgtttccccc   10080
tggaagctcc ctcgtgcgct ctcctgttcc gaccctgccg cttaccggat acctgtccgc   10140
cttctccct tcgggaagcg tggcgctttc tcatagctca cgctgtaggt atctcagttc   10200
ggtgtaggtc gttcgctcca agctgggctg tgtgcacgaa ccccccgttc agcccgaccg   10260
ctgcgcctta tccggtaact atcgtcttga gtccaacccg gtaagacacg acttatcgcc   10320
actggcagca gccactggta acaggattag cagagcgagg tatgtaggcg gtgctacaga   10380
gttcttgaag tggtggccta actacggcta cactagaagg acagtatttg gtatctgcgc   10440
tctgctgaag ccagttacct tcggaaaaag agttggtagc tcttgatccg gcaaacaaac   10500
caccgctggt agcggtggtt ttttgtttg caagcagcag attacgcgca gaaaaaaagg   10560
atctcaagaa gatcctttga tcttttctac ggggtctgac gctcagtgga acgaaaactc   10620
acgttaaggg attttggtca tgagattatc aaaaaggatc ttcacctaga tccttttaaa   10680
ttaaaaatga agttttaaat caatctaaag tatatatgag taaacttggt ctgacagtta   10740
ccaatgctta atcagtgagg cacctatctc agcgatctgt ctatttcgtt catccatagt   10800
tgcctgactc cccgtcgtgt agataactac gatacgggag ggcttaccat ctggccccag   10860
tgctgcaatg ataccgcgag acccacgctc accggctcca gatttatcag caataaacca   10920
gccagccgga agggccgagc gcagaagtgg tcctgcaact ttatccgcct ccatccagtc   10980
tattaattgt tgccgggaag ctagagtaag tagttcgcca gttaatagtt tgcgcaacgt   11040
tgttgccatt gctgcagggg gggggggggg ggggacttc cattgttcat tccacggaca   11100
aaaacagaga aaggaaacga cagaggccaa aaagcctcgc tttcagcacc tgtcgtttcc   11160
tttcttttca gagggtattt taaataaaaa cattaagtta tgacgaagaa gaacggaaac   11220
gccttaaacc ggaaaatttt cataaatagc gaaaacccgc gaggtcgccg ccccgtaacc   11280
tacctgtcgg atcaccggaa aggacccgta aagtgataat gattatcatc tacatatcac   11340
aacgtgcgtg gaggccatca aaccacgtca aataatcaat tatgacgcag gtatcgtatt   11400
```

```
aattgatctg catcaactta acgtaaaaac aacttcagac aatacaaatc agcgacactg    11460 aatacgggc  aacctcatgt ccccccccc  cccccccctg caggcatcgt ggtgtcacgc    11520
tcgtcgtttg gtatggcttc attcagctcc ggttcccaac gatcaaggcg agttacatga    11580
tcccccatgt tgtgcaaaaa agcggttagc tccttcggtc ctccgatcgt tgtcagaagt    11640
aagttggccg cagtgttatc actcatggtt atggcagcac tgcataattc tcttactgtc    11700
atgccatccg taagatgctt ttctgtgact ggtgagtact caaccaagtc attctgagaa    11760
tagtgtatgc ggcgaccgag ttgctcttgc ccggcgtcaa cacgggataa taccgcgcca    11820
catagcagaa ctttaaaagt gctcatcatt ggaaaacgtt cttcggggcg aaaactctca    11880
aggatcttac cgctgttgag atccagttcg atgtaaccca ctcgtgcacc caactgatct    11940
tcagcatctt ttactttcac cagcgtttct gggtgagcaa aaacaggaag gcaaaatgcc    12000
gcaaaaaagg gaataagggc gacacggaaa tgttgaatac tcatactctt ccttttttcaa   12060 tattattgaa gcatttatca gggttattgt ctcatgagcg gatacatatt tgaatgtatt    12120
tagaaaaata aacaaatagg ggttccgcgc acatttcccc gaaaagtgcc acctgacgtc    12180
taagaaacca ttattatcat gacattaacc tataaaaata ggcgtatcac gaggcccttt    12240
cgtcttcaag aattcggagc ttttgccatt ctcaccggat tcagtcgtca ctcatggtga    12300
tttctcactt gataaccta  tttttgacga ggggaaatta ataggttgta ttgatgttgg    12360
acgagtcgga atcgcagacc gataccagga tcttgccatc ctatggaact gcctcggtga    12420
gttttctcct tcattacaga aacggctttt tcaaaaatat ggtattgata atcctgatat    12480
gaataaattg cagtttcatt tgatgctcga tgagttttc  taatcagaat tggttaattg    12540
gttgtaacac tggcagagca ttacgctgac ttgacgggac ggcggctttg ttgaataaat    12600
cgaacttttg ctgagttgaa ggatcagatc acgcatcttc ccgacaacgc agaccgttcc    12660
gtggcaaagc aaaagttcaa aatcaccaac tggtccacct acaacaaagc tctcatcaac    12720
cgtggctccc tcactttctg gctggatgat ggggcgattc aggcctggta tgagtcagca    12780
acaccttctt cacgaggcag acctcagcgc cagaaggccg ccagagaggc cgagcgcggc    12840
cgtgaggctt ggacgctagg gcagggcatg aaaaagcccg tagcgggctg ctacgggcgt    12900
ctgacgcggt ggaaaggggg aggggatgtt gtctacatgg ctctgctgta gtgagtgggt    12960
tgcgctccgg cagcggtcct gatcaatcgt caccctttct cggtccttca acgttcctga    13020
caacgagcct ccttttcgcc aatccatcga caatcaccgc gagtccctgc tcgaacgctg    13080
cgtccggacc ggcttcgtcg aaggcgtcta tcgcggcccg caacagcggc gagagcgag    13140 cctgttcaac ggtgccgccg cgctcgccgg catcgctgtc gccggcctgc tcctcaagca    13200 cggcccaac  agtgaagtag ctgattgtca tcagcgcatt gacggcgtcc ccggccgaaa    13260
aacccgcctc gcagaggaag cgaagctgcg cgtcggccgt ttccatctgc ggtgcgcccg    13320
gtcgcgtgcc ggcatggatg cgcgcgccat cgcggtaggc gagcagcgcc tgcctgaagc    13380
tgcgggcatt cccgatcaga aatgagcgcc agtcgtcgtc ggctctcggc accgaatgcg    13440
tatgattctc cgccagcatg gcttcggcca gtgcgtcgag cagcgcccgc ttgttcctga    13500
agtgccagta aagcgccggc tgctgaaccc ccaaccgttc cgccagtttg cgtgtcgtca    13560
gaccgtctac gccgacctcg ttcaacaggt ccagggcggc acggatcact gtattcggct    13620
gcaactttgt catgcttgac actttatcac tgataaacat aatatgtcca ccaacttatc    13680
agtgataaag aatccgcgcg ttcaatcgga ccagcggagg ctggtccgga ggccagacgt    13740
gaaacccaac ataccccctga tcgtaattct gagcactgtc gcgctcgacg ctgtcggcat    13800
```

-continued

```
cggcctgatt atgccggtgc tgccgggcct cctgcgcgat ctggttcact cgaacgacgt   13860
caccgcccac tatggcattc tgctggcgct gtatgcgttg gtgcaatttg cctgcgcacc   13920
tgtgctgggc gcgctgtcgg atcgtttcgg gcggcggcca atcttgctcg tctcgctggc   13980
cggcgccact gtcgactacg ccatcatggc gacagcgcct ttcctttggg ttctctatat   14040
cgggcggatc gtggccggca tcaccggggc gactggggcg gtagccggcg cttatattgc   14100
cgatatcact gatggcgatg agcgcgcgcg gcacttcggc ttcatgagcg cctgtttcgg   14160
gttcgggatg gtcgcgggac ctgtgctcgg tgggctgatg ggcggtttct cccccacgc   14220
tccgttcttc gccgcggcag ccttgaacgg cctcaatttc ctgacgggct gtttcctttt   14280
gccggagtcg cacaaaggcg aacgccggcc gttacgccgg gaggctctca acccgctcgc   14340
ttcgttccgg tgggcccggg gcatgaccgt cgtcgccgcc ctgatggcgg tcttcttcat   14400
catgcaactt gtcggacagg tgccggccgc gctttgggtc attttcggcg aggatcgctt   14460
tcactgggac gcgaccacga tcggcatttc gcttgccgca tttggcattc tgcattcact   14520
cgcccaggca atgatcaccg ccctgtagc cgccggctc ggcgaaaggc gggcactcat   14580
gctcggaatg attgccgacg gcacaggcta catcctgctt gccttcgcga cacggggatg   14640
gatggcgttc ccgatcatgg tcctgcttgc ttcgggtggc atcggaatgc cggcgctgca   14700
agcaatgttg tccaggcagg tggatgagga acgtcagggg cagctgcaag gctcactggc   14760
ggcgctcacc agcctgacct cgatcgtcgg accctcctc ttcacggcga tctatgcggc   14820
ttctataaca acgtggaacg ggtgggcatg gattgcaggc gctgccctct acttgctctg   14880
cctgccggcg ctgcgtcgcg ggctttggag cggcgcaggg caacgagccg atcgctgatc   14940
gtggaaacga taggcctatg ccatgcgggt caaggcgact tccggcaagc tatacgcgcc   15000
ctaggagtgc ggttggaacg ttggcccagc cagatactcc cgatcacgag caggacgccg   15060
atgatttgaa gcgcactcag cgtctgatcc aagaacaacc atcctagcaa cacggcggtc   15120
cccgggctga gaaagcccag taaggaaaca actgtaggtt cgagtcgcga gatccccgg   15180
aaccaaagga agtaggttaa acccgctccg atcaggccga gccacgccag gccgagaaca   15240
ttggttcctg taggcatcgg gattggcgga tcaaacacta aagctactgg aacgagcaga   15300
agtcctccgg ccgccagttg ccaggcggta aaggtgagca gaggcacggg aggttgccac   15360
ttgcgggtca gcacggttcc gaacgccatg gaaaccgccc ccgccaggcc cgctgcgacg   15420
ccgacaggat ctagcgctgc gtttggtgtc aacaccaaca gcgccacgcc cgcagttccg   15480
caaatagccc ccaggaccgc catcaatcgt atcgggctac ctagcagagc ggcagagatg   15540
aacacgacca tcagcggctg cacagcgcct accgtcgccg cgaccccgcc cggcaggcgg   15600
tagaccgaaa taaacaacaa gctccagaat agcgaaatat taagtgcgcc gaggatgaag   15660
atgcgcatcc accagattcc cgttggaatc tgtcggacga tcatcacgag caataaaccc   15720
gccggcaacg cccgcagcag catacggcg acccctcggc ctcgctgttc gggctccacg   15780
aaaacgccgg acagatgcgc cttgtgagcg tccttgggc cgtcctcctg tttgaagacc   15840
gacagcccaa tgatctcgcc gtcgatgtag gcgccgaatg ccacggcatc tcgcaaccgt   15900
tcagcgaacg cctccatggg cttttctcc tcgtgctcgt aaacggaccc gaacatctct   15960
ggagctttct tcagggccga caatcggatc tcgcggaaat cctgcacgtc ggccgctcca   16020
agccgtcgaa tctgagcctt aatcacaatt gtcaattta atcctctgtt tatcggcagt   16080
tcgtagagcg cgccgtgcgt cccgagcgat actgagcgaa gcaagtgcgt cgagcagtgc   16140
```

```
ccgcttgttc ctgaaatgcc agtaaagcgc tggctgctga accccagcc ggaactgacc    16200 ccacaaggcc ctagcgtttg caatgcacca ggtcatcatt gacccaggcg tgttccacca    16260
ggccgctgcc tcgcaactct tcgcaggctt cgccgacctg ctcgcgccac ttcttcacgc    16320
gggtggaatc cgatccgcac atgaggcgga aggtttccag cttgagcggg tacggctccc    16380
ggtgcgagct gaaatagtcg aacatccgtc gggccgtcgg cgacagcttg cggtacttct    16440
cccatatgaa tttcgtgtag tggtcgccag caaacagcac gacgatttcc tcgtcgatca    16500
ggacctggca acgggacgtt ttcttgccac ggtccaggac gcggaagcgg tgcagcagcg    16560
acaccgattc caggtgccca acgcggtcgg acgtgaagcc catcgccgtc gcctgtaggc    16620
gcgacaggca ttcctcggcc ttcgtgtaat accggccatt gatcgaccag cccaggtcct    16680
ggcaaagctc gtagaacgtg aaggtgatcg gctcgccgat aggggtgcgc ttcgcgtact    16740
ccaacacctg ctgccacacc agttcgtcat cgtcggcccg cagctcgacg ccggtgtagg    16800
tgatcttcac gtccttgttg acgtggaaaa tgaccttgtt ttgcagcgcc tcgcgcggga    16860
ttttcttgtt gcgcgtggtg aacagggcag agcgggccgt gtcgtttggc atcgctcgca    16920
tcgtgtccgg ccacggcgca atatcgaaca aggaaagctg catttccttg atctgctgct    16980
tcgtgtgttt cagcaacgcg gcctgcttgg cctcgctgac ctgttttgcc aggtcctcgc    17040
cggcggtttt tcgcttcttg gtcgtcatag ttcctcgcgt gtcgatggtc atcgacttcg    17100
ccaaacctgc cgcctcctgt tcgagacgac gcgaacgctc cacggcggcc gatggcgcgg    17160
gcagggcagg gggagccagt tgcacgctgt cgcgctcgat cttggccgta gcttgctgga    17220
ccatcgagcc gacggactgg aaggtttcgc ggggcgcacg catgacggtg cggcttgcga    17280
tggtttcggc atcctcggcg gaaaaccccg cgtcgatcag ttcttgcctg tatgccttcc    17340
ggtcaaacgt ccgattcatt caccctcctt gcgggattgc cccgactcac gccggggcaa    17400
tgtgccctta ttcctgattt gacccgcctg gtgccttggt gtccagataa tccaccttat    17460
cggcaatgaa gtcggtcccg tagaccgtct ggccgtcctt tcgtacttg gtattccgaa     17520 tcttgccctg cacgaatacc agcgaccct tgcccaaata cttgccgtgg gcctcggcct     17580
gagagccaaa acacttgatg cggaagaagt cggtgcgctc ctgcttgtcg ccggcatcgt    17640
tgcgccactc ttcattaacc gctatatcga aaattgcttg cggcttgtta gaattgccat    17700
gacgtacctc ggtgtcacgg gtaagattac cgataaactg gaactgatta tggctcatat    17760
cgaaagtctc cttgagaaag gagactctag tttagctaaa cattggttcc gctgtcaaga    17820
actttagcgg ctaaaatttt gcgggccgcg accaaaggtg cgaggggcgg cttccgctgt    17880
gtacaaccag atattttca ccaacatcct tcgtctgctc gatgagcggg gcatgacgaa      17940
acatgagctg tcgagaggg cagggggttc aatttcgttt ttatcagact taaccaacgg     18000
taaggccaac ccctcgttga aggtgatgga ggccattgcc gacgccctgg aaactcccct    18060
acctcttctc ctggagtcca ccgaccttga ccgcgaggca ctcgcggaga ttgcgggtca    18120
tcctttcaag agcagcgtgc cgcccggata cgaacgcatc agtgtggttt tgccgtcaca    18180
taaggcgttt atcgtaaaga aatggggcga cgacacccga aaaaagctgc gtggaaggct    18240
ctgacgccaa gggttagggc ttgcacttcc ttctttagcc gctaaaacgg ccccttctct    18300
gcgggccgtc ggctcgcgca tcatatcgac atcctcaacg gaagccgtgc cgcgaatggc    18360
atcgggcggg tgcgctttga cagttgtttt ctatcagaac ccctacgtcg tgcggttcga    18420
ttagctgttt gtcttgcagg ctaaacactt tcggtatatc gtttgcctgt gcgataatgt    18480
tgctaatgat ttgttgcgta ggggttactg aaaagtgagc gggaaagaag agtttcagac    18540
```

```
catcaaggag cgggccaagc gcaagctgga acgcgacatg ggtgcggacc tgttggccgc   18600
gctcaacgac ccgaaaaccg ttgaagtcat gctcaacgcg gacggcaagg tgtggcacga   18660
acgccttggc gagccgatgc ggtacatctg cgacatgcgg cccagccagt cgcaggcgat   18720
tatagaaacg gtggccggat tccacggcaa agaggtcacg cggcattcgc ccatcctgga   18780
aggcgagttc cccttggatg gcagccgctt tgccggccaa ttgccgccgg tcgtggccgc   18840
gccaaccttt gcgatccgca agcgcgcggt cgccatcttc acgctggaac agtacgtcga   18900
ggcgggcatc atgacccgcg agcaatacga ggtcattaaa agcgccgtcg cggcgcatcg   18960
aaacatcctc gtcattggcg gtactggctc gggcaagacc acgctcgtca acgcgatcat   19020
caatgaaatg gtcgccttca acccgtctga gcgcgtcgtc atcatcgagg acaccggcga   19080
aatccagtgc gccgcagaga acgccgtcca ataccacacc agcatcgacg tctcgatgac   19140
gctgctgctc aagacaacgc tgcgtatgcg ccccgaccgc atcctggtcg gtgaggtacg   19200
tggccccgaa gcccttgatc tgttgatggc ctggaacacc gggcatgaag gaggtgccgc   19260
caccctgcac gcaaacaacc ccaaagcggg cctgagccgg ctcgccatgc ttatcagcat   19320
gcacccggat tcaccgaaac ccattgagcc gctgattggc gaggcggttc atgtggtcgt   19380
ccatatcgcc aggaccccta gcggccgtcg agtgcaagaa attctcgaag ttcttggtta   19440
cgagaacggc cagtacatca ccaaaaccct gtaaggagta tttccaatga caacggctgt   19500
tccgttccgt ctgaccatga atcgcggcat tttgttctac cttgccgtgt tcttcgttct   19560
cgctctcgcg ttatccgcgc atccggcgat ggcctcggaa ggcaccggcg gcagcttgcc   19620
atatgagagc tggctgacga acctgcgcaa ctccgtaacc ggcccggtgg ccttcgcgct   19680
gtccatcatc ggcatcgtcg tcgcggcgg cgtgctgatc ttcggcgcg aactcaacgc   19740
cttcttccga accctgatct tcctggttct ggtgatggcg ctgctggtcg gcgcgcagaa   19800
cgtgatgagc accttcttcg gtcgtggtgc cgaaatcgcg gccctcggca acggggcgct   19860
gcaccaggtg caagtcgcgg cggcggatgc cgtgcgtgcg gtagcggctg gacggctcgc   19920
ctaatcatgg ctctgcgcac gatccccatc cgtcgcgcag gcaaccgaga aaacctgttc   19980
atgggtggta tcgtgaact ggtgatgttc tcgggcctga tggcgtttgc gctgattttc   20040
agcgcccaag agctgcgggc caccgtggtc ggtctgatcc tgtggttcgg ggcgctctat   20100
gcgttccgaa tcatggcgaa ggccgatccg aagatgcggt tcgtgtacct gcgtcaccgc   20160
cggtacaagc cgtattaccc ggcccgctcg accccgttcc gcgagaacac caatagccaa   20220
gggaagcaat accgatgatc caagcaattg cgattgcaat cgcgggcctc ggcgcgcttc   20280
tgttgttcat cctctttgcc cgcatccgcg cggtcgatgc cgaactgaaa ctgaaaaagc   20340
atcgttccaa ggacgccggc ctggccgatc tgctcaacta cgccgctgtc gtcgatgacg   20400
gcgtaatcgt gggcaagaac ggcagcttta tggctgcctg gctgtacaag ggcgatgaca   20460
acgcaagcag caccgaccag cagcgcgaag tagtgtccgc ccgcatcaac caggccctcg   20520
cgggcctggg aagtgggtgg atgatccatg tggacgccgt gcggcgtcct gctccgaact   20580
acgcggagcg gggcctgtcg gcgttccctg accgtctgac ggcagcgatt gaagaagagc   20640
gctcggtctt gccttgctcg tcggtgatgt acttcaccag ctccgcgaag tcgctcttct   20700
tgatggagcg catggggacg tgcttggcaa tcacgcgcac ccccggccg ttttagcggc   20760
taaaaaagtc atggctctgc cctcgggcgg accacgccca tcatgacctt gccaagctcg   20820
tcctgcttct cttcgatctt cgccagcagg gcgaggatcg tggcatcacc gaaccgcgcc   20880
```

```
gtgcgcgggt cgtcggtgag ccagagtttc agcaggccgc ccaggcggcc caggtcgcca   20940
ttgatgcggg ccagctcgcg gacgtgctca tagtccacga cgcccgtgat tttgtagccc   21000
tggccgacgg ccagcaggta ggccgacagg ctcatgccgg ccgccgccgc cttttcctca   21060
atcgctcttc gttcgtctgg aaggcagtac accttgatag gtgggctgcc cttcctggtt   21120
ggcttggttt catcagccat ccgcttgccc tcatctgtta cgccggcggt agccggccag   21180
cctcgcagag caggattccc gttgagcacc gccaggtgcg aataagggac agtgaagaag   21240
gaacacccgc tcgcgggtgg gcctacttca cctatcctgc ccggctgacg ccgttggata   21300
caccaaggaa agtctacacg aacccttggg caaaatcctg tatatcgtgc gaaaaaggat   21360
ggatataccg aaaaaatcgc tataatgacc ccgaagcagg gttatgcagc ggaaaagcgc   21420
tgcttccctg ctgttttgtg aatatctac cgactggaaa caggcaaatg caggaaatta    21480
ctgaactgag gggacaggcg agagacgatg ccaaagagct acaccgacga gctggccgag   21540
tgggttgaat cccgcgcggc caagaagcgc cggcgtgatg aggctgcggt tgcgttcctg   21600
gcggtgaggg cggatgtcga ggcggcgtta gcgtccggct atgcgctcgt caccatttgg   21660
gagcacatgc gggaaacggg gaaggtcaag ttctcctacg agacgttccg ctcgcacgcc   21720
aggcggcaca tcaaggccaa gcccgccgat gtgcccgcac cgcaggccaa ggctgcggaa   21780
cccgcgccgg cacccaagac gccggagcca cggcggccga agcagggggg caaggctgaa   21840
aagccggccc ccgctgcggc cccgaccggc ttcaccttca acccaacacc ggacaaaaag   21900
gatctactgt aatggcgaaa attcacatgg ttttgcaggg caagggcggg gtcggcaagt   21960
cggccatcgc cgcgatcatt gcgcagtaca agatggacaa ggggcagaca cccttgtgca   22020
tcgacaccga cccggtgaac gcgacgttcg agggctacaa ggccctgaac gtccgccggc   22080
tgaacatcat ggccggcgac gaaattaact cgcgcaactt cgacaccctg gtcgagctga   22140
ttgcgccgac caaggatgac gtggtgatcg acaacggtgc cagctcgttc gtgcctctgt   22200
cgcattacct catcagcaac caggtgccgg ctctgctgca agaaatgggg catgagctgg   22260
tcatccatac cgtcgtcacc ggcggccagg ctctcctgga cacggtgagc ggcttcgccc   22320
agctcgccag ccagttcccg gccgaagcgc ttttcgtggt ctggctgaac ccgtattggg   22380
ggcctatcga gcatgagggc aagagctttg agcagatgaa ggcgtacacg ccaacaagg    22440 cccgcgtgtc gtccatcatc cagattccgg ccctcaagga agaaacctac ggccgcgatt   22500
tcagcgacat gctgcaagag cggctgacgt tcgaccaggc gctggccgat gaatcgctca   22560
cgatcatgac gcggcaacgc ctcaagatcg tgcggcgcgg cctgtttgaa cagctcgacg   22620
cggcggccgt gctatgagcg accagattga agagctgatc cgggagattg cggccaagca   22680
cggcatcgcc gtcggccgcg acgacccggt gctgatcctg cataccatca cgcccggct    22740 catggccgac agtgcggcca agcaagagga aatccttgcc gcgttcaagg aagagctgga   22800
agggatcgcc catcgttggg gcgaggacgc caaggccaaa gcggagcgga tgctgaacgc   22860
ggccctggcg gccagcaagg acgcaatggc gaaggtaatg aaggacagcg ccgcgcaggc   22920
ggccgaagcg atccgcaggg aaatcgacga cggccttggc cgccagctcg cggccaaggt   22980
cgcggacgcg cggcgcgtgg cgatgatgaa catgatcgcc ggcggcatgg tgttgttcgc   23040
ggccgccctg gtggtgtggg cctcgttatg aatcgcagag gcgcagatga aaaagcccgg   23100
cgttgccggg ctttgttttt gcgttagctg ggcttgtttg acaggcccaa gctctgactg   23160
cgcccgcgct cgcgctcctg ggcctgtttc ttctcctgct cctgcttgcg catcagggcc   23220
tggtgccgtc gggctgcttc acgcatcgaa tcccagtcgc cggccagctc gggatgctcc   23280
```

```
gcgcgcatct tgcgcgtcgc cagttcctcg atcttgggcg cgtgaatgcc catgccttcc    23340
ttgatttcgc gcaccatgtc cagccgcgtg tgcagggtct gcaagcgggc ttgctgttgg    23400
gcctgctgct gctgccaggc ggcctttgta cgcggcaggg acagcaagcc ggggcattg     23460 gactgtagct gctgcaaacg cgcctgctga cggtctacga gctgttctag gcggtcctcg    23520
atgcgctcca cctggtcatg ctttgcctgc acgtagagcg caagggtctg ctggtaggtc    23580
tgctcgatgg gcgcggattc taagagggcc tgctgttccg tctcggcctc ctgggccgcc    23640
tgtagcaaat cctcgccgct gttgccgctg gactgcttta ctgccgggga ctgctgttgc    23700
cctgctcgcg ccgtcgtcgc agttcggctt gcccccactc gattgactgc ttcatttcga    23760
gccgcagcga tgcgatctcg gattgcgtca acggacgggg cagcgcggag gtgtccggct    23820
tctccttggg tgagtcggtc gatgccatag ccaaaggttt ccttccaaaa tgcgtccatt    23880
gctggaccgt gtttctcatt gatgcccgca agcatcttcg gcttgaccgc caggtcaagc    23940
gcgccttcat gggcggtcat gacgacgcc gccatgacct tgccgccgtt gttctcgatg     24000
tagccgcgta atgaggcaat ggtgccgccc atcgtcagcg tgtcatcgac aacgatgtac    24060
ttctggccgg ggatcacctc cccctcgaaa gtcgggttga acgccaggcg atgatctgaa    24120
ccggctccgg ttcgggcgac cttctcccgc tgcacaatgt ccgtttcgac ctcaaggcca    24180
aggcggtcgg ccagaacgac cgccatcatg gccggaatct tgttgttccc cgccgcctcg    24240
acggcgagga ctggaacgat gcggggcttg tcgtcgccga tcagcgtctt gagctgggca    24300
acagtgtcgt ccgaaatcag gcgctcgacc aaattaagcg ccgcttccgc gtcgccctgc    24360
ttcgcagcct ggtattcagg ctcgttggtc aaagaaccaa ggtcgccgtt gcgaaccacc    24420
ttcgggaagt ctccccacgg tgcgcgctcg gctctgctgt agctgctcaa gacgcctccc    24480
tttttagccg ctaaaactct aacgagtgcg cccgcgactc aacttgacgc tttcggcact    24540
tacctgtgcc ttgccacttg cgtcataggt gatgcttttc gcactcccga tttcaggtac    24600
tttatcgaaa tctgaccggg cgtgcattac aaagttcttc cccacctgtt ggtaaatgct    24660
gccgctatct gcgtggacga tgctgccgtc gtggcgctgc gacttatcgg ccttttgggc    24720
catatagatg ttgtaaatgc caggtttcag ggccccggct ttatctacct tctggttcgt    24780
ccatgcgcct tggttctcgg tctggacaat tctttgccca ttcatgacca ggaggcggtg    24840
tttcattggg tgactcctga cggttgcctc tggtgttaaa cgtgtcctgg tcgcttgccg    24900
gctaaaaaaa agccgacctc ggcagttcga ggccggcttt ccctagagcc gggcgcgtca    24960
aggttgttcc atctatttta gtgaactgcg ttcgatttat cagttacttt cctcccgctt    25020
tgtgtttcct cccactcgtt tccgcgtcta gccgacccct caacatagcg gcctcttctt    25080
gggctgcctt tgcctcttgc cgcgcttcgt cacgctcggc ttgcaccgtc gtaaagcgct    25140
cggcctgcct ggccgcctct tgcgccgcca acttcctttg ctcctggtgg gcctcggcgt    25200
cggcctgcgc cttcgctttc accgctgcca actccgtgcg caaactctcc gcttcgcgcc    25260
tggtggcgtc gcgctcgccg cgaagcgcct gcatttcctg gttggccgcg tccagggtct    25320
tgcggctctc ttctttgaat gcgcgggcgt cctggtgagc gtagtccagc tcggcgcgca    25380
gctcctgcgc tcgacgctcc acctcgtcgg cccgctgcgt cgccagcgcg gccgctgct    25440 cggctcctgc cagggcggtg cgtgcttcgg ccagggcttg ccgctggcgt gcggccagct    25500
cggccgcctc ggcggcctgc tgctctagca atgtaacgcg cgcctgggct tcttccagct    25560 cgcggggcctg cgcctcgaag gcgtcggcca gctccccgcg cacggcttcc aactcgttgc    25620
```

```
gctcacgatc ccagccggct tgcgctgcct gcaacgattc attggcaagg gcctgggcgg    25680
cttgccagag ggcggccacg gcctggttgc cggcctgctg caccgcgtcc ggcacctgga    25740
ctgccagcgg ggcggcctgc gccgtgcgct ggcgtcgcca ttcgcgcatg ccggcgctgg    25800
cgtcgttcat gttgacgcgg gcggccttac gcactgcatc cacggtcggg aagttctccc    25860
ggtcgccttg ctcgaacagc tcgtccgcag ccgcaaaaat gcggtcgcgc gtctctttgt    25920
tcagttccat gttggctccg gtaattggta agaataataa tactcttacc taccttatca    25980
gcgcaagagt ttagctgaac agttctcgac ttaacggcag gttttttagc ggctgaaggg    26040
caggcaaaaa aagccccgca cggtcggcgg gggcaaaggg tcagcgggaa ggggattagc    26100
gggcgtcggg cttcttcatg cgtcggggcc gcgcttcttg ggatggagca cgacgaagcg    26160
cgcacgcgca tcgtcctcgg ccctatcggc ccgcgtcgcg gtcaggaact tgtcgcgcgc    26220
taggtcctcc ctggtgggca ccaggggcat gaactcggcc tgctcgatgt aggtccactc    26280
catgaccgca tcgcagtcga ggccgcgttc cttcaccgtc tcttgcaggt cgcggtacgc    26340
ccgctcgttg agcggctggt aacgggccaa ttggtcgtaa atggctgtcg gccatgagcg    26400 gccttcctg ttgagccagc agccgacgac gaagccggca atgcaggccc ctggcacaac    26460
caggccgacg ccggggcag gggatggcag cagctcgcca accaggaacc ccgccgcgat    26520
gatgccgatg ccggtcaacc agccttgaa actatccggc cccgaaacac ccctgcgcat    26580
tgcctggatg ctgcgccgga tagcttgcaa catcaggagc cgtttctttt gttcgtcagt    26640
catggtccgc cctcaccagt tgttcgtatc ggtgtcggac gaactgaaat cgcaagagct    26700
gccggtatcg gtccagccgc tgtccgtgtc gctgctgccg aagcacggcg aggggtccgc    26760
gaacgccgca gacggcgtat ccggccgcag cgcatcgccc agcatggccc cggtcagcga    26820
gccgccggcc aggtagccca gcatggtgct gttggtcgcc ccggccacca gggccgacgt    26880
gacgaaatcg ccgtcattcc ctctggattg ttcgctgctc ggcggggcag tgcgccgcgc    26940
cggcggcgtc gtggatggct cgggttggct ggcctgcgac ggccggcgaa aggtgcgcag    27000
cagctcgtta tcgaccggct gcggcgtcgg ggccgccgcc ttgcgctgcg gtcggtgttc    27060
cttcttcggc tcgcgcagct tgaacagcat gatcgcggaa accagcagca acgccgcgcc    27120
tacgcctccc gcgatgtaga acagcatcgg attcattctt cggtcctcct tgtagcggaa    27180
ccgttgtctg tgcggcgcgg gtggcccgcg ccgctgtctt tggggatcag ccctcgatga    27240
gcgcgaccag tttcacgtcg gcaaggttcg cctcgaactc ctggccgtcg tcctcgtact    27300
tcaaccaggc atagccttcc gccggcggcc gacggttgag gataaggcgg gcagggcgct    27360
cgtcgtgctc gacctggacg atggccttt tcagcttgtc cgggtccggc tccttcgcgc    27420
ccttttcctt ggcgtcctta ccgtcctggt cgccgtcctc gccgtcctgg ccgtcgccgg    27480
cctccgcgtc acgctcggca tcagtctggc cgttgaaggc atcgacggtg ttgggatcgc    27540
ggcccttctc gtccaggaac tcgcgcagca gcttgaccgt gccgcgcgtg atttcctggg    27600
tgtcgtcgtc aagccacgcc tcgacttcct ccgggcgctt cttgaaggcc gtcaccagct    27660
cgttcaccac ggtcacgtcg cgcacgcggc cggtgttgaa cgcatcggcg atcttctccg    27720
gcaggtccag cagcgtgacg tgctgggtga tgaacgccgg cgacttgccg atttccttgg    27780
cgatatcgcc tttcttcttg cccttcgcca gctcgcggcc aatgaagtcg gcaatttcgc    27840
gcggggtcag ctcgttgcgt tgcaggttct cgataacctg gtcggcttcg ttgtagtcgt    27900
tgtcgatgaa cgccgggatg gacttcttgc cggcccactt cgagccacgg tagcggcggg    27960
cgccgtgatt gatgatatag cggcccggct gctcctggtt ctcgcgcacc gaaatgggtg    28020
```

```
acttcacccc gcgctctttg atcgtggcac cgatttccgc gatgctctcc ggggaaaagc   28080
cggggttgtc ggccgtccgc ggctgatgcg gatcttcgtc gatcaggtcc aggtccagct   28140
cgatagggcc ggaaccgccc tgagacgccg caggagcgtc caggaggctc gacaggtcgc   28200
cgatgctatc caaccccagg ccggacggct gcgccgcgcc tgcggcttcc tgagcggccg   28260
cagcggtgtt tttcttggtg gtcttggctt gagccgcagt cattgggaaa tctccatctt   28320
cgtgaacacg taatcagcca gggcgcgaac ctctttcgat gccttgcgcg cggccgtttt   28380
cttgatcttc cagaccggca caccggatgc gagggcatcg gcgatgctgc tgcgcaggcc   28440
aacggtggcc ggaatcatca tcttggggta cgcggccagc agctcggctt ggtggcgcgc   28500
gtggcgcgga ttccgcgcat cgaccttgct gggcaccatg ccaaggaatt gcagcttggc   28560
gttcttctgg cgcacgttcg caatggtcgt gaccatcttc ttgatgccct ggatgctgta   28620
cgcctcaagc tcgatggggg acagcacata gtcggccgcg aagagggcgg ccgccaggcc   28680
gacgccaagg gtcggggccg tgtcgatcag gcacacgtcg aagccttggt tcgcagggc    28740
cttgatgttc gccccgaaca gctcgcgggc gtcgtccagc gacagccgtt cggcgttcgc   28800
cagtaccggg ttggactcga tgagggcgag gcgcgcggcc tggccgtcgc cggctgcggg   28860
tgcggtttcg gtccagccgc cggcagggac agcgccgaac agcttgcttg catgcaggcc   28920
ggtagcaaag tccttgagcg tgtaggacgc attgccctgg gggtccaggt cgatcacggc   28980
aacccgcaag ccgcgctcga aaagtcgaa ggcaagatgc acaagggtcg aagtcttgcc    29040
gacgccgcct ttctggttgg ccgtgaccaa agttttcatc gtttggtttc ctgtttttc    29100
ttggcgtccg cttcccactt ccggacgatg tacgcctgat gttccggcag aaccgccgtt   29160
acccgcgcgt acccctcggg caagttcttg tcctcgaacg cggcccacac gcgatgcacc   29220
gcttgcgaca ctgcgcccct ggtcagtccc agcgacgttg cgaacgtcgc ctgtggcttc   29280
ccatcgacta agacgccccg cgctatctcg atggtctgct gccccacttc cagcccctgg   29340
atcgcctcct ggaactggct ttcggtaagc cgtttcttca tggataacac ccataatttg   29400
ctccgcgcct tggttgaaca tagcggtgac agccgccagc acatgagaga agtttagcta   29460
aacatttctc gcacgtcaac acctttagcc gctaaaactc gtccttggcg taacaaaaca   29520
aaagcccgga aaccgggctt tcgtctcttg ccgcttatgg ctctgcaccc ggctccatca   29580
ccaacaggtc gcgcacgcgc ttcactcggt tgcggatcga cactgccagc caacaaagc    29640
cggttgccgc cgccgccagg atcgcgccga tgatgccggc cacaccggcc atcgcccacc   29700
aggtcgccgc cttccggttc cattcctgct ggtactgctt cgcaatgctg gacctcggct   29760
caccataggc tgaccgctcg atggcgtatg ccgcttctcc ccttggcgta aaacccagcg   29820
ccgcaggcgg cattgccatg ctgccgccg ctttcccgac cacgacgcgc gcaccaggct    29880
tgcggtccag accttcggcc acggcgagct gcgcaaggac ataatcagcc gccgacttgg   29940
ctccacgcgc ctcgatcagc tcttgcactc gcgcgaaatc cttggcctcc acggccgcca   30000
tgaatcgcgc acgcggcgaa ggctccgcag ggccggcgtc gtgatcgccg ccgagaatgc   30060
ccttcaccaa gttcgacgac acgaaaatca tgctgacggc tatcaccatc atgcagacgg   30120
atcgcacgaa cccgctgaat tgaacacgag cacggcaccc gcgaccacta tgccaagaat   30180
gcccaaggta aaaattgccg gccccgccat gaagtccgtg aatgccccga cggccgaagt   30240
gaagggcagg ccgccaccca ggccgccgcc ctcactgccc ggcacctggt cgctgaatgt   30300
cgatgccagc acctgcggca cgtcaatgct tccgggcgtc gcgctcgggc tgatcgccca   30360
```

```
tcccgttact gccccgatcc cggcaatggc aaggactgcc agcgctgcca tttttggggt    30420
gaggccgttc gcggccgagg ggcgcagccc ctgggggat gggaggcccg cgttagcggg    30480
ccgggagggt tcgagaaggg ggggcacccc ccttcggcgt gcgcggtcac gcgcacaggg    30540
cgcagccctg gttaaaaaca aggtttataa atattggttt aaaagcaggt taaaagacag    30600
gttagcggtg gccgaaaaac gggcggaaac ccttgcaaat gctggatttt ctgcctgtgg    30660
acagcccctc aaatgtcaat aggtgcgccc ctcatctgtc agcactctgc ccctcaagtg    30720
tcaaggatcg cgcccctcat ctgtcagtag tcgcgcccct caagtgtcaa taccgcaggg    30780
cacttatccc caggcttgtc cacatcatct gtgggaaact cgcgtaaaat caggcgtttt    30840
cgccgatttg cgaggctggc cagctccacg tcgccggccg aaatcgagcc tgcccctcat    30900
ctgtcaacgc cgcgccgggt gagtcggccc ctcaagtgtc aacgtccgcc cctcatctgt    30960
cagtgagggc caagttttcc gcgaggtatc cacaacgccg gcggccgcgg tgtctcgcac    31020
acggcttcga cggcgtttct ggcgcgtttt cagggccata acggccgcc agcccagcgg    31080 cgagggcaac cagcccggtg agcgtcggaa aggcgctgga agccccgtag cgacgcggag    31140
aggggcgaga caagccaagg gcgcaggctc gatgcgcagc acgacatagc cggttctcgc    31200
aaggacgaga atttccctgc ggtgcccctc aagtgtcaat gaaagtttcc aacgcgagcc    31260
attcgcgaga gccttgagtc cacgctagat gagagctttg ttgtaggtgg accagttggt    31320
gattttgaac ttttgctttg ccacggaacg gtctgcgttg tcgggaagat gcgtgatctg    31380
atccttcaac tcagcaaaag ttcgatttat tcaacaaagc cacgttgtgt ctcaaaatct    31440
ctgatgttac attgcacaag ataaaaatat atcatcatga acaataaaac tgtctgctta    31500
cataaacagt aatacaaggg gtgttatgag ccatattcaa cgggaaacgt cttgctcgac    31560
tctagagctc gttcctcgag gaacggtacc tgcggggaag cttacaataa tgtgtgttgt    31620
taagtcttgt tgcctgtcat cgtctgactg actttcgtca taaatcccgg cctccgtaac    31680 ccagcttttgg gcaagctcac ggatttgatc cggcggaacg ggaatatcga gatgccggc    31740 tgaacgctgc agttccagct ttccctttcg ggacaggtac tccagctgat tgattatctg    31800
ctgaagggtc ttggttccac ctcctggcac aatgcgaatg attacttgag gcgatcggg    31860 catccaattt tctcccgtca ggtgcgtggt caagtgctac aaggcacctt tcagtaacga    31920
gcgaccgtcg atccgtcgcc gggatacgga caaaatggag cgcagtagtc catcgagggc    31980
ggcgaaagcc tcgccaaaag caatacgttc atctcgcaca gcctccagat ccgatcgagg    32040
gtcttcggcg taggcagata gaagcatgga tacattgctt gagagtattc cgatggactg    32100
aagtatggct tccatctttt ctcgtgtgtc tgcatctatt tcgagaaagc ccccgatgcg    32160
gcgcaccgca acgcgaattg ccatactatc cgaaagtccc agcaggcgcg cttgatagga    32220
aaaggtttca tactcggccg atcgcagacg ggcactcacg accttgaacc cttcaacttt    32280
cagggatcga tgctggttga tggtagtctc actcgacgtg gctctggtgt gttttgacat    32340
agcttcctcc aaagaaagcg gaaggtctgg atactccagc acgaaatgtg cccgggtaga    32400
cggatggaag tctagccctg ctcaatatga aatcaacagt acatttacag tcaatactga    32460
atatacttgc tacatttgca attgtcttat aacgaatgtg aaataaaaat agtgtaacaa    32520
cgcttttact catcgataat cacaaaaaca tttatacgaa caaaaataca aatgcactcc    32580
ggtttcacag gataggcggg atcagaatat gcaacttttg acgttttgtt ctttcaaagg    32640
gggtgctggc aaaaccaccg cactcatggg cctttgcgct gctttggcaa atgacggtaa    32700
acgagtggcc ctctttgatg ccgacgaaaa ccggcctctg acgcgatgga gagaaaacgc    32760
```

```
cttacaaagc agtactggga tcctcgctgt gaagtctatt ccgccgacga aatgcccctt    32820
cttgaagcag cctatgaaaa tgccgagctc gaaggatttg attatgcgtt ggccgatacg    32880
cgtggcggct cgagcgagct caacaacaca atcatcgcta gctcaaacct gcttctgatc    32940
cccaccatgc taacgccgct cgacatcgat gaggcactat ctacctaccg ctacgtcatc    33000
gagctgctgt tgagtgaaaa tttggcaatt cctacagctg ttttgcgcca acgcgtcccg    33060
gtcggccgat tgacaacatc gcaacgcagg atgtcagaga cgctagagag ccttccagtt    33120
gtaccgtctc ccatgcatga aagagatgca tttgccgcga tgaaagaacg cggcatgttg    33180
catcttacat tactaaacac gggaactgat ccgacgatgc gcctcataga gaggaatctt    33240
cggattgcga tggaggaagt cgtggtcatt tcgaaactga tcagcaaaat cttggaggct    33300
tgaagatggc aattcgcaag cccgcattgt cggtcggcga agcacggcgg cttgctggtg    33360
ctcgacccga gatccaccat cccaaccccga cacttgttcc ccagaagctg gacctccagc    33420
acttgcctga aaaagccgac gagaaagacc agcaacgtga gcctctcgtc gccgatcaca    33480
tttacagtcc cgatcgacaa cttaagctaa ctgtggatgc ccttagtcca cctccgtccc    33540
cgaaaaagct ccaggttttt cttttcagcgc gaccgcccgc gcctcaagtg tcgaaaacat    33600
atgacaacct cgttcggcaa tacagtccct cgaagtcgct acaaatgatt ttaaggcgcg    33660
cgttggacga tttcgaaagc atgctggcag atggatcatt tcgcgtggcc ccgaaaagtt    33720
atccgatccc ttcaactaca gaaaaatccg ttctcgttca gacctcacgc atgttcccgg    33780
ttgcgttgct cgaggtcgct cgaagtcatt ttgatccgtt ggggttggag accgctcgag    33840
ctttcggcca caagctggct accgccgcgc tcgcgtcatt ctttgctgga gagaagccat    33900
cgagcaattg gtgaagaggg acctatcgga accccctcacc aaatattgag tgtaggtttg    33960
aggccgctgg ccgcgtcctc agtcacctttt tgagccagat aattaagagc caaatgcaat    34020
tggctcaggc tgccatcgtc cccccgtgcg aaacctgcac gtccgcgtca agaaaataac    34080
cggcacctct tgctgttttt atcagttgag ggcttgacgg atccgcctca gtttgcggc    34140
gcagccgcaa aatgagaaca tctatactcc tgtcgtaaac ctcctcgtcg cgtactcgac    34200
tggcaatgag aagttgctcg cgcgatagaa cgtcgcgggg tttctctaaa aacgcgagga    34260
gaagattgaa ctcacctgcc gtaagtttca cctcaccgcc agcttcggac atcaagcgac    34320
gttgcctgag attaagtgtc cagtcagtaa aacaaaaaga ccgtcggtct ttggagcgga    34380
caacgttggg gcgcacgcgc aaggcaaccc gaatgcgtgc aagaaactct ctcgtactaa    34440
acggcttagc gataaaatca cttgctccta gctcgagtgc aacaacttta tccgtctcct    34500
caaggcggtc gccactgata attatgattg gaatatcaga cttttgccgcc agatttcgaa    34560
cgatctcaag cccatcttca cgacctaaat ttagatcaac aaccacgaca tcgaccgtcg    34620
cggaagagag tactctagtg aactgggtgc tgtcggctac cgcggtcact ttgaaggcgt    34680
ggatcgtaag gtattcgata taagatgcc gcatagcgac atcgtcatcg ataagaagaa    34740
cgtgtttcaa cggctcacct ttcaatctaa aatctgaacc cttgttcaca gcgcttgaga    34800
aattttcacg tgaaggatgt acaatcatct ccagctaaat gggcagttcg tcagaattgc    34860
ggctgaccgc ggatgacgaa aatgcgaacc aagtatttca atttatgac aaaagttctc    34920
aatcgttgtt acaagtgaaa cgcttcgagg ttacagctac tattgattaa ggagatcgcc    34980
tatggtctcg ccccggcgtc gtgcgtccgc cgcgagccag atctcgccta cttcataaac    35040
gtcctcatag gcacggaatg gaatgatgac atcgatcgcc gtagagagca tgtcaatcag    35100
```

```
tgtgcgatct tccaagctag caccttgggc gctacttttg acaagggaaa acagtttctt   35160
gaatccttgg attggattcg cgccgtgtat tgttgaaatc gatcccggat gtcccgagac   35220
gacttcactc agataagccc atgctgcatc gtcgcgcatc tcgccaagca atatccggtc   35280
cggccgcata cgcagacttg cttggagcaa gtgctcggcg ctcacagcac ccagcccagc   35340
accgttcttg gagtagagta gtctaacatg attatcgtgt ggaatgacga gttcgagcgt   35400
atcttctatg gtgattagcc tttcctgggg ggggatggcg ctgatcaagg tcttgctcat   35460
tgttgtcttg ccgcttccgg tagggccaca tagcaacatc gtcagtcggc tgacgacgca   35520
tgcgtgcaga aacgcttcca aatccccgtt gtcaaaatgc tgaaggatag cttcatcatc   35580
ctgattttgg cgtttccttc gtgtctgcca ctggttccac ctcgaagcat cataacggga   35640
ggagacttct ttaagaccag aaacacgcga gcttggccgt cgaatggtca agctgacggt   35700
gcccgaggga acggtcggcg gcagacagat ttgtagtcgt tcaccaccag gaagttcagt   35760
ggcgcagagg gggttacgtg gtccgacatc ctgctttctc agcgcgcccg ctaaaatagc   35820
gatatcttca agatcatcat aagagacggg caaaggcatt ttggtaaaaa tgccggcttg   35880
gcgcacaaat gcctctccag gtcgattgat cgcaatttct tcagtcttcg ggtcatcgag   35940
ccattccaaa atcggcttca gaagaaagcg tagttgcgga tccacttcca tttacaatgt   36000
atcctatctc taagcggaaa tttgaattca ttaagagcgg cggttcctcc cccgcgtggc   36060
gccgccagtc aggcggagct ggtaaacacc aaagaaatcg aggtcccgtg ctacgaaaat   36120
ggaaacggtg tcaccctgat tcttcttcag ggttggcggt atgttgatgg ttgccttaag   36180
ggctgtctca gttgtctgct caccgttatt ttgaaagctg ttgaagctca tcccgccacc   36240
cgagctgccg gcgtaggtgc tagctgcctg gaaggcgcct tgaacaacac tcaagagcat   36300
agctccgcta aaacgctgcc agaagtggct gtcgaccgag cccggcaatc ctgagcgacc   36360
gagttcgtcc gcgcttggcg atgttaacga gatcatcgca tggtcaggtg tctcggcgcg   36420
atcccacaac acaaaaacgc gcccatctcc ctgttgcaag ccacgctgta tttcgccaac   36480
aacggtggtg ccacgatcaa gaagcacgat attgttcgtt gttccacgaa tatcctgagg   36540
caagacacac tttacatagc ctgccaaatt tgtgtcgatt gcggttttgca agatgcacgg   36600
aattattgtc ccttgcgtta ccataaaatc ggggtgcggc aagagcgtgg cgctgctggg   36660
ctgcagctcg gtgggtttca tacgtatcga caaatcgttc tcgccggaca cttcgccatt   36720
cggcaaggag ttgtcgtcac gcttgccttc ttgtcttcgg cccgtgtcgc cctgaatggc   36780
gcgtttgctg acccccttgat cgccgctgct atatgcaaaa atcggtgttt cttccggccg   36840
tggctcatgc cgctccggtt cgcccctcgg cggtagagga gcagcaggct gaacagcctc   36900
ttgaaccgct ggaggatccg gcggcacctc aatcggagct ggatgaaatg gcttggtgtt   36960
tgttgcgatc aaagttgacg gcgatgcgtt ctcattcacc ttcttttggc gcccacctag   37020
ccaaatgagg cttaatgata acgcgagaac gacacctccg acgatcaatt tctgagaccc   37080
cgaaagacgc cggcgatgtt tgtcggagac cagggatcca gatgcatcaa cctcatgtgc   37140
cgcttgctga ctatcgttat tcatcccttc gcccccttca ggacgcgttt cacatcgggc   37200
ctcaccgtgc ccgtttgcgg cctttggcca acgggatcgt aagcggtgtt ccagatacat   37260
agtactgtgt ggccatccct cagacgccaa cctcgggaaa ccgaagaaat ctcgacatcg   37320
ctcccttttaa ctgaatagtt ggcaacagct tccttgccat caggattgat ggtgtagatg   37380
gagggtatgc gtacattgcc cggaaagtgg aataccgtcg taaatccatt gtcgaagact   37440
tcgagtggca acagcgaacg atcgccttgg gcgacgtagt gccaattact gtccgccgca   37500
```

```
ccaagggctg tgacaggctg atccaataaa ttctcagctt tccgttgata ttgtgcttcc   37560
gcgtgtagtc tgtccacaac agccttctgt tgtgcctccc ttcgccgagc cgccgcatcg   37620 tcggcgggt aggcgaattg gacgctgtaa tagagatcgg gctgctcttt atcgaggtgg    37680
gacagagtct tggaacttat actgaaaaca taacggcgca tcccggagtc gcttgcggtt   37740
agcacgatta ctggctgagg cgtgaggacc tggcttgcct tgaaaaatag ataatttccc   37800
cgcggtaggg ctgctagatc tttgctattt gaaacggcaa ccgctgtcac cgtttcgttc   37860
gtggcgaatg ttacgaccaa agtagctcca accgccgtcg agaggcgcac cacttgatcg   37920
ggattgtaag ccaaataacg catgcgcgga tctagcttgc ccgccattgg agtgtcttca   37980
gcctccgcac cagtcgcagc ggcaaataaa catgctaaaa tgaaaagtgc ttttctgatc   38040
atggttcgct gtggcctacg tttgaaacgg tatcttccga tgtctgatag gaggtgacaa   38100
ccagacctgc cgggttggtt agtctcaatc tgccgggcaa gctggtcacc ttttcgtagc   38160
gaactgtcgc ggtccacgta ctcaccacag gcattttgcc gtcaacgacg agggtccttt   38220
tatagcgaat ttgctgcgtg cttggagtta catcatttga agcgatgtgc tcgacctcca   38280
ccctgccgcg tttgccaaga atgacttgag gcgaactggg attgggatag ttgaagaatt   38340
gctggtaatc ctggcgcact gttggggcac tgaagttcga taccaggtcg taggcgtact   38400
gagcggtgtc ggcatcataa ctctcgcgca ggcgaacgta ctcccacaat gaggcgttaa   38460
cgacggcctc ctcttgagtt gcaggcaatc gcgagacaga cacctcgctg tcaacggtgc   38520
cgtccggccg tatccataga tatacgggca caagcctgct caacggcacc attgtggcta   38580
tagcgaacgc ttgagcaaca tttcccaaaa tcgcgatagc tgcgacagct gcaatgagtt   38640
tggagagacg tcgcgccgat ttcgctcgcg cggtttgaaa ggcttctact tccttatagt   38700
gctcggcaag gctttcgcgc gccactagca tggcatattc aggccccgtc atagcgtcca   38760
cccgaattgc cgagctgaag atctgacgga gtaggctgcc atcgcccac attcagcggg    38820 aagatcgggc ctttgcagct cgctaatgtg tcgtttgtct ggcagccgct caaagcgaca   38880
actaggcaca gcaggcaata cttcatagaa ttctccattg aggcgaattt ttgcgcgacc   38940
tagcctcgct caacctgagc gaagcgacgg tacaagctgc tggcagattg ggttgcgccg   39000
ctccagtaac tgcctccaat gttgccggcg atcgccggca aagcgacaat gagcgcatcc   39060
cctgtcagaa aaaacatatc gagttcgtaa agaccaatga tcttggccgc ggtcgtaccg   39120
gcgaaggtga ttacaccaag cataagggtg agcgcagtcg cttcggttag gatgacgatc   39180
gttgccacga ggtttaagag gagaagcaag agaccgtagg tgataagttg cccgatccac   39240
ttagctgcga tgtcccgcgt gcgatcaaaa atatatccga cgaggatcag aggcccgatc   39300
gcgagaagca ctttcgtgag aattccaacg gcgtcgtaaa ctccgaaggc agaccagagc   39360
gtgccgtaaa ggacccactg tgccccttgg aaagcaagga tgtcctggtc gttcatcgga   39420
ccgatttcgg atgcgatttt ctgaaaaacg gcctgggtca cggcgaacat tgtatccaac   39480
tgtgccggaa cagtctgcag aggcaagccg gttacactaa actgctgaac aaagtttggg   39540
accgtctttt cgaagatgga aaccacatag tcttggtagt tagcctgccc aacaattaga   39600
gcaacaacga tggtgaccgt gatcacccga gtgataccgc tacgggtatc gacttcgccg   39660
cgtatgacta aaatacccctg aacaataatc caaagagtga cacaggcgat caatggcgca  39720
ctcaccgcct cctggatagt ctcaagcatc gagtccaagc ctgtcgtgaa ggctacatcg   39780
aagatcgtat gaatggccgt aaacggcgcc ggaatcgtga aattcatcga ttggacctga   39840
```

```
acttgactgg tttgtcgcat aatgttggat aaaatgagct cgcattcggc gaggatgcgg    39900
gcggatgaac aaatcgccca gcctaggggg agggcaccaa agatgacagc ggtcttttga    39960
tgctccttgc gttgagcggc cgcctcttcc gcctcgtgaa ggccggcctg cgcggtagtc    40020
atcgttaata ggcttgtcgc ctgtacattt tgaatcattg cgtcatggat ctgcttgaga    40080
agcaaaccat tggtcacggt tgcctgcatg atattgcgag atcgggaaag ctgagcagac    40140
gtatcagcat tcgccgtcaa gcgtttgtcc atcgtttcca gattgtcagc cgcaatgcca    40200
gcgctgtttg cggaaccggt gatctgcgat cgcaacaggt ccgcttcagc atcactaccc    40260
acgactgcac gatctgtatc gctggtgatc gcacgtgccg tggtcgacat tggcattcgc    40320
ggcgaaaaca tttcattgtc taggtccttc gtcgaaggat actgattttt ctggttgagc    40380
gaagtcagta gtccagtaac gccgtaggcc gacgtcaaca tcgtaaccat cgctatagtc    40440
tgagtgagat tctccgcagt cgcgagcgca gtcgcgagcg tctcagcctc cgttgccggg    40500
tcgctaacaa caaactgcgc ccgcgcgggc tgaatatata gaaagctgca ggtcaaaact    40560
gttgcaataa gttgcgtcgt cttcatcgtt tcctacctta tcaatcttct gcctcgtggt    40620
gacgggccat gaattcgctg agccagccag atgagttgcc ttcttgtgcc tcgcgtagtc    40680
gagttgcaaa gcgcaccgtg ttggcacgcc ccgaaagcac ggcgacatat tcacgcatat    40740
cccgcagatc aaattcgcag atgacgcttc cactttctcg tttaagaaga aacttacggc    40800
tgccgaccgt catgtcttca cggatcgcct gaaattcctt tcggtacat ttcagtccat    40860
cgacataagc cgatcgatct gcggttggtg atggatagaa aatcttcgtc atacattgcg    40920
caaccaagct ggctcctagc ggcgattcca gaacatgctc tggttgctgc gttgccagta    40980
ttagcatccc gttgttttt cgaacggtca ggaggaattt gtcgacgaca gtcgaaaatt    41040
tagggtttaa caaataggcg cgaaactcat cgcagctcat cacaaaacgg cggccgtcga    41100
tcatggctcc aatccgatgc aggagatatg ctgcagcggg agcgcatact tcctcgtatt    41160
cgagaagatg cgtcatgtcg aagccggtaa tcgacggatc taactttact tcgtcaactt    41220
cgccgtcaaa tgcccagcca agcgcatggc cccggcacca gcgttggagc cgcgctcctg    41280
cgccttcggc gggcccatgc aacaaaaatt cacgtaaccc cgcgattgaa cgcatttgtg    41340
gatcaaacga gagctgacga tggataccac ggaccagacg gcggttctct tccggagaaa    41400
tcccaccccg accatcactc tcgatgagag ccacgatcca ttcgcgcaga aaatcgtgtg    41460
aggctgctgt gttttctagg ccacgcaacg gcgccaaccc gctgggtgtg cctctgtgaa    41520
gtgccaaata tgttcctcct gtggcgcgaa ccagcaattc gccacccggg tccttgtcaa    41580
agaacacgac cgtacctgca cggtcgacca tgctctgttc gagcatggct agaacaaaca    41640
tcatgagcgt cgtcttaccc ctcccgatag gcccgaatat tgccgtcatg ccaacatcgt    41700
gctcatgcgg gatatagtcg aaaggcgttc cgccattggt acgaaatcgg gcaatcgcgt    41760
tgccccagtg gcctgagctg gcgccctctg gaaagttttc gaaagagaca aaccctgcga    41820
aattgcgtga agtgattgcg ccagggcgtg tgcgccactt aaaattcccc ggcaattggg    41880
accaataggc gcttccata ccaatacctt cttggacaac cacggcacct gcatccgcca    41940
ttcgtgtccg agcccgcgcg cccctgtccc caagactatt gagatcgtct gcatagacgc    42000
aaaggctcaa atgatgtgag cccataacga attcgttgct cgcaagtgcg tcctcagcct    42060
cggataattt gccgatttga gtcacggctt tatcgccgga actcagcatc tggctcgatt    42120
tgaggctaag tttcgcgtgc gcttgcgggc gagtcaggaa cgaaaaactc tgcgtgagaa    42180
caagtggaaa atcgagggat agcagcgcgt tgagcatgcc cggccgtgtt tttgcagggt    42240
```

```
attcgcgaaa cgaatagatg gatccaacgt aactgtctttt tggcgttctg atctcgagtc   42300
ctcgcttgcc gcaaatgact ctgtcggtat aaatcgaagc gccgagtgag ccgctgacga   42360
ccggaaccgg tgtgaaccga ccagtcatga tcaaccgtag cgcttcgcca atttcggtga   42420
agagcacacc ctgcttctcg cggatgccaa gacgatgcag gccatacgct ttaagagagc   42480
cagcgacaac atgccaaaga tcttccatgt tcctgatctg gcccgtgaga tcgttttccc   42540
tttttccgct tagcttggtg aacctcctct ttaccttccc taaagccgcc tgtgggtaga   42600
caatcaacgt aaggaagtgt tcattgcgga ggagttggcc ggagagcacg cgctgttcaa   42660
aagcttcgtt caggctagcg gcgaaaacac tacggaagtg tcgcggcgcc gatgatggca   42720
cgtcggcatg acgtacgagg tgagcatata ttgacacatg atcatcagcg atattgcgca   42780
acagcgtgtt gaacgcacga caacgcgcat tgcgcatttc agtttcctca agctcgaatg   42840
caacgccatc aattctcgca atggtcatga tcgatccgtc ttcaagaagg acgatatggt   42900
cgctgaggtg gccaatataa gggagataga tctcaccgga tctttcggtc gttccactcg   42960
cgccgagcat cacaccattc ctctccctcg tgggggaacc ctaattggat ttgggctaac   43020
agtagcgccc ccccaaactg cactatcaat gcttcttccc gcggtccgca aaaatagcag   43080
gacgacgctc gccgcattgt agtctcgctc cacgatgagc cgggctgcaa accataacgg   43140
cacgagaacg acttcgtaga gcgggttctg aacgataacg atgacaaagc cggcgaacat   43200
catgaataac cctgccaatg tcagtggcac cccaagaaac aatgcgggcc gtgtggctgc   43260
gaggtaaagg gtcgattctt ccaaacgatc agccatcaac taccgccagt gagcgtttgg   43320
ccgaggaagc tcgccccaaa catgataaca atgccgccga cgacgccggc aaccagccca   43380
agcgaagccc gcccgaacat ccaggagatc ccgatagcga caatgccgag aacagcgagt   43440
gactggccga acggaccaag gataaacgtg catatattgt taaccattgt ggcggggtca   43500
gtgccgccac ccgcagattg cgctgcggcg ggtccggatg aggaaatgct ccatgcaatt   43560
gcaccgcaca agcttggggc gcagctcgat atcacgcgca tcatcgcatt cgagagcgag   43620
aggcgattta gatgtaaacg gtatctctca aagcatcgca tcaatgcgca cctccttagt   43680
ataagtcgaa taagacttga ttgtcgtctg cggatttgcc gttgtcctgg tgtggcggtg   43740
gcggagcgat taaaccgcca gcgccatcct cctgcgagcg gcgctgatat gaccccaaa    43800
catcccacgt ctcttcggat tttagcgcct cgtgatcgtc ttttggaggc tcgattaacg   43860
cgggcaccag cgattgagca gctgtttcaa cttttcgcac gtagccgttt gcaaaaccgc   43920
cgatgaaatt accggtgttg taagcggaga tcgcccgacg aagcgcaaat tgcttctcgt   43980
caatcgtttc gccgcctgca taacgacttt tcagcatgtt tgcagcggca gataatgatg   44040
tgcacgcctg gagcgcaccg tcaggtgtca gaccgagcat agaaaaattt cgagagttta   44100
tttgcatgag gccaacatcc agcgaatgcc gtgcatcgag acggtgcctg acgacttggg   44160
ttgcttggct gtgatcttgc cagtgaagcg tttcgccggt cgtgttgtca tgaatcgcta   44220
aaggatcaaa gcgactctcc accttagcta tcgccgcaag cgtagatgtc gcaactgatg   44280
gggcacactt gcgagcaaca tggtcaaact cagcagatga gagtggcgtg gcaaggctcg   44340
acgaacagaa ggagaccatc aaggcaagag aaagcgaccc cgatctctta agcatacctt   44400
atctccttag ctcgcaacta acaccgcctc tcccgttgga agaagtgcgt tgtttatgt    44460
tgaagattat cgggagggtc ggttactcga aaattttcaa ttgcttcttt atgatttcaa   44520
ttgaagcgag aaacctcgcc cggcgtcttg gaacgcaaca tggaccgaga accgcgcatc   44580
```

```
catgactaag caaccggatc gacctattca ggccgcagtt ggtcaggtca ggctcagaac   44640
gaaaatgctc ggcgaggtta cgctgtctgt aaacccattc gatgaacggg aagcttcctt   44700
ccgattgctc ttggcaggaa tattggccca tgcctgcttg cgctttgcaa atgctcttat   44760
cgcgttggta tcatatgcct tgtccgccag cagaaacgca ctctaagcga ttatttgtaa   44820
aaatgtttcg gtcatgcggc ggtcatgggc ttgacccgct gtcagcgcaa gacggatcgg   44880
tcaaccgtcg gcatcgacaa cagcgtgaat cttggtggtc aaaccgccac gggaacgtcc   44940
catacagcca tcgtcttgat cccgctgttt cccgtcgccg catgttggtg gacgcggaca   45000
caggaactgt caatcatgac gacattctat cgaaagcctt ggaaatcaca ctcagaatat   45060
gatcccagac gtctgcctca cgccatcgta caaagcgatt gtagcaggtt gtacaggaac   45120
cgtatcgatc aggaacgtct gcccagggcg ggccgtccg gaagcgccac aagatgacat   45180
tgatcacccg cgtcaacgcg cggcacgcga cgcggcttat ttgggaacaa aggactgaac   45240
aacagtccat tcgaaatcgg tgacatcaaa gcggggacgg gttatcagtg gcctccaagt   45300
caagcctcaa tgaatcaaaa tcagaccgat ttgcaaacct gatttatgag tgtgcggcct   45360
aaatgatgaa atcgtccttc tagatcgcct ccgtggtgta gcaacacctc gcagtatcgc   45420
cgtgctgacc ttggccaggg aattgactgg caagggtgct ttcacatgac cgctcttttg   45480
gccgcgatag atgatttcgt tgctgctttg ggcacgtaga aggagagaag tcatatcgga   45540
gaaattcctc ctggcgcgag agcctgctct atcgcgacgg catcccactg tcgggaacag   45600
accggatcat tcacgaggcg aaagtcgtca acacatgcgt tataggcatc ttcccttgaa   45660
ggatgatctt gttgctgcca atctggaggt gcggcagccg caggcagatg cgatctcagc   45720
gcaacttgcg gcaaaacatc tcactcacct gaaaaccact agcgagtctc gcgatcagac   45780
gaaggccttt tacttaacga cacaatatcc gatgtctgca tcacaggcgt cgctatccca   45840
gtcaatacta aagcggtgca ggaactaaag attactgatg acttaggcgt gccacgaggc   45900
ctgagacgac gcgcgtagac agttttttga aatcattatc aaagtgatgg cctccgctga   45960
agcctatcac ctctgcgccg gtctgtcgga gagatgggca agcattatta cggtcttcgc   46020
gcccgtacat gcattggacg attgcagggt caatggatct gagatcatcc agaggattgc   46080
cgcccttacc ttccgtttcg agttggagcc agcccctaaa tgagacgaca tagtcgactt   46140
gatgtgacaa tgccaagaga gagatttgct taacccgatt ttttttgctca agcgtaagcc   46200 tattgaagct tgccggcatg acgtccgcgc cgaaagaata tcctacaagt aaaacattct   46260
gcacaccgaa atgcttggtg tagacatcga ttatgtgacc aagatcctta gcagtttcgc   46320
ttggggaccg ctccgaccag aaataccgaa gtgaactgac gccaatgaca ggaatccctt   46380
ccgtctgcag ataggtacca tcgatagatc tgctgcctcg cgcgtttcgg tgatgacggt   46440
gaaaacctct gacacatgca gctcccggag acggtcacag cttgtctgta agcggatgcc   46500
gggagcagac aagcccgtca gggcgcgtca gcgggtgttg gcgggtgtcg gggcgcagcc   46560
atgacccagt cacgtagcga tagcggagtg tatactggct taactatgcg gcatcagagc   46620
agattgtact gagagtgcac catatgcggt gtgaaatacc gcacagatgc gtaaggagaa   46680
aataccgcat caggcgctct tccgcttcct cgctcactga ctcgctgcgc tcggtcgttc   46740
ggctgcggcg agcggtatca gctcactcaa aggcggtaat acgttatcc acagaatcag   46800 gggataacgc aggaaagaac atgtgagcaa aaggccagca aaaggccagg aaccgtaaaa   46860
aggccgcgtt gctggcgttt ttccataggc tccgcccccc tgacgagcat cacaaaaatc   46920
gacgctcaag tcagaggtgg cgaaacccga caggactata aagataccag gcgtttcccc   46980
```

```
ctggaagctc cctcgtgcgc tctcctgttc cgaccctgcc gcttaccgga tacctgtccg   47040
cctttctccc ttcgggaagc gtggcgcttt ctcatagctc acgctgtagg tatctcagtt   47100
cggtgtaggt cgttcgctcc aagctgggct gtgtgcacga acccccgtt cagcccgacc    47160
gctgcgcctt atccggtaac tatcgtcttg agtccaaccc ggtaagacac gacttatcgc   47220
cactggcagc agccactggt aacaggatta gcagagcgag gtatgtaggc ggtgctacag   47280
agttcttgaa gtggtggcct aactacggct acactagaag gacagtattt ggtatctgcg   47340
ctctgctgaa gccagttacc ttcggaaaaa gagttggtag ctcttgatcc ggcaaacaaa   47400
ccaccgctgg tagcggtggt ttttttgttt gcaagcagca gattacgcgc agaaaaaaag   47460
gatctcaaga agatcctttg atcttttcta cggggtctga cgctcagtgg aacgaaaact   47520
cacgttaagg gattttggtc atgagattat caaaaaggat cttcacctag atccttttaa   47580
attaaaaatg aagttttaaa tcaatctaaa gtatatatga gtaaacttgg tctgacagtt   47640
accaatgctt aatcagtgag gcacctatct cagcgatctg tctatttcgt tcatccatag   47700
ttgcctgact ccccgtcgtg tagataacta cgatacggga gggcttacca tctggcccca   47760
gtgctgcaat gataccgcga gacccacgct caccggctcc agatttatca gcaataaacc   47820
agccagccgg aagggccgag cgcagaagtg gtcctgcaac tttatccgcc tccatccagt   47880
ctattaattg ttgccgggaa gctagagtaa gtagttcgcc agttaatagt ttgcgcaacg   47940
ttgttgccat tgctgcaggg gggggggggg gggggacttc cattgttca ttccacggac     48000
aaaaacagag aaaggaaacg acagaggcca aaaagcctcg cttttcagcac ctgtcgtttc   48060
cttttctttc agagggtatt ttaaataaaa acattaagtt atgacgaaga agaacggaaa   48120
cgccttaaac cggaaaattt tcataaatag cgaaaacccg cgaggtcgcc gccccgtagt    48180
cggatcaccg gaaaggaccc gtaaagtgat aatgattatc atctacatat cacaacgtgc   48240
gtggaggcca tcaaaccacg tcaaataatc aattatgacg caggtatcgt attaattgat    48300
ctgcatcaac ttaacgtaaa aacaacttca gacaatacaa atcagcgaca ctgaatacgg   48360
ggcaacctca tgtcccccccc cccccccccc ctgcaggcat cgtggtgtca cgctcgtcgt   48420
ttggtatggc ttcattcagc tccggttccc aacgatcaag gcgagttaca tgatccccca   48480
tgttgtgcaa aaaagcggtt agctccttcg gtcctccgat cgttgtcaga agtaagttgg   48540
ccgcagtgtt atcactcatg gttatggcag cactgcataa ttctcttact gtcatgccat   48600
ccgtaagatg cttttctgtg actggtgagt actcaaccaa gtcattctga aatagtgta    48660
tgcggcgacc gagttgctct tgcccggcgt caacacggga taataccgcg ccacatagca   48720
gaactttaaa agtgctcatc attggaaaac gttcttcggg gcgaaaactc tcaaggatct   48780
taccgctgtt gagatccagt tcgatgtaac ccactcgtgc acccaactga tcttcagcat   48840
cttttacttt caccagcgtt tctgggtgag caaaaacagg aaggcaaaat gccgcaaaaa   48900
agggaataag ggcgacacgg aaatgttgaa tactcatact cttccttttt caatattatt   48960
gaagcattta tcagggttat tgtctcatga gcggatacat atttgaatgt atttagaaaa   49020
ataaacaaat aggggttccg cgcacatttc cccgaaaagt gccacctgac gtctaagaaa   49080
ccattattat catgacatta acctataaaa ataggcgtat cacgaggccc tttcgtcttc   49140
aagaattggt cgacgatctt gctgcgttcg gatattttcg tggagttccc gccacagacc   49200
cggattgaag gcgagatcca gcaactcgcg ccagatcatc ctgtgacgga actttggcgc   49260
gtgatgactg gccaggacgt cggccgaaag agcgacaagc agatcacgct tttcgacagc   49320
```

-continued

| | |
|---|---|
| gtcggatttg cgatcgagga tttttcggcg ctgcgctacg tccgcgaccg cgttgaggga | 49380 |
| tcaagccaca gcagcccact cgaccttcta gccgacccag acgagccaag ggatcttttt | 49440 |
| ggaatgctgc tccgtcgtca ggctttccga cgtttgggtg gttgaacaga agtcattatc | 49500 |
| gtacggaatg ccaagcactc ccgaggggaa ccctgtggtt ggcatgcaca tacaaatgga | 49560 |
| cgaacggata aaccttttca cgccctttta aatatccgtt attctaataa acgctctttt | 49620 |
| ctcttaggtt tacccgccaa tatatcctgt caaacactga tagtttaaac tgaaggcggg | 49680 |
| aaacgacaat ctgatcatga gcggagaatt aagggagtca cgttatgacc cccgccgatg | 49740 |
| acgcgggaca agccgtttta cgtttggaac tgacagaacc gcaacgttga aggagccact | 49800 |
| cagcaagctg gtacgattgt aatacgactc actatagggc gaattgagcg ctgtttaaac | 49860 |
| gctcttcaac tggaagagcg gttacccgga ccgaagcttg catgcctgca g | 49911 |

<210> SEQ ID NO 7
<211> LENGTH: 36909
<212> TYPE: DNA
<213> ORGANISM: artificial sequence
<220> FEATURE:
<223> OTHER INFORMATION: NCBI General Identifier No. 59797027

<400> SEQUENCE: 7

| | |
|---|---|
| tctagagctc gttcctcgag gcctcgaggc ctcgaggaac ggtacctgcg gggaagctta | 60 |
| caataatgtg tgttgttaag tcttgttgcc tgtcatcgtc tgactgactt tcgtcataaa | 120 |
| tcccggcctc cgtaacccag ctttgggcaa gctcacggat ttgatccggc ggaacgggaa | 180 |
| tatcgagatg ccgggctgaa cgctgcagtt ccagctttcc ctttcgggac aggtactcca | 240 |
| gctgattgat tatctgctga agggtcttgg ttccacctcc tggcacaatg cgaatgatta | 300 |
| cttgagcgcg atcgggcatc caattttctc ccgtcaggtg cgtggtcaag tgctacaagg | 360 |
| cacctttcag taacgagcga ccgtcgatcc gtcgccggga tacggacaaa atggagcgca | 420 |
| gtagtccatc gagggcggcg aaagcctcgc caaaagcaat acgttcatct cgcacagcct | 480 |
| ccagatccga tcgagggtct tcggcgtagg cagatagaag catggataca ttgcttgaga | 540 |
| gtattccgat ggactgaagt atggcttcca tcttttctcg tgtgtctgca tctatttcga | 600 |
| gaaagccccc gatgcggcgc accgcaacgc gaattgccat actatccgaa agtcccagca | 660 |
| ggcgcgcttg ataggaaaag gtttcatact cggccgatcg cagacgggca ctcacgacct | 720 |
| tgaacccttc aactttcagg gatcgatgct ggttgatggt agtctcactc gacgtggctc | 780 |
| tggtgtgttt tgacatagct tcctccaaag aaagcggaag gtctggatac tccagcacga | 840 |
| aatgtgcccg ggtagacgga tggaagtcta gccctgctca atatgaaatc aacagtacat | 900 |
| ttacagtcaa tactgaatat acttgctaca tttgcaattg tcttataacg aatgtgaaat | 960 |
| aaaaatagtg taacaacgct tttactcatc gataatcaca aaaacattta tacgaacaaa | 1020 |
| aatacaaatg cactccggtt tcacaggata ggcgggatca gaatatgcaa cttttgacgt | 1080 |
| tttgttcttt caaggggggt gctggcaaaa ccaccgcact catgggcctt tgcgctgctt | 1140 |
| tggcaaatga cggtaaacga gtggccctct ttgatgccga cgaaaccgg cctctgacgc | 1200 |
| gatggagaga aaacgcctta caaagcagta ctgggatcct cgctgtgaag tctattccgc | 1260 |
| cgacgaaatg ccccttcttg aagcagccta tgaaaatgcc gagctcgaag gatttgatta | 1320 |
| tgcgttggcc gatacgcgtg gcggctcgag cgagctcaac aacacaatca tcgctagctc | 1380 |
| aaacctgctt ctgatcccca ccatgctaac gccgctcgac atcgatgagg cactatctac | 1440 |
| ctaccgctac gtcatcgagc tgctgttgag tgaaaatttg gcaattccta cagctgtttt | 1500 |

-continued

```
gcgccaacgc gtcccggtcg gccgattgac aacatcgcaa cgcaggatgt cagagacgct    1560
agagagcctt ccagttgtac cgtctcccat gcatgaaaga gatgcatttg ccgcgatgaa    1620
agaacgcggc atgttgcatc ttacattact aaacacggga actgatccga cgatgcgcct    1680
catagagagg aatcttcgga ttgcgatgga ggaagtcgtg gtcatttcga aactgatcag    1740
caaaatcttg gaggcttgaa gatggcaatt cgcaagcccg cattgtcggt cggcgaagca    1800
cggcggcttg ctggtgctcg acccgagatc caccatccca acccgacact tgttccccag    1860
aagctggacc tccagcactt gcctgaaaaa gccgacgaga agaccagca acgtgagcct    1920 ctcgtcgccg atcacattta cagtcccgat cgacaactta agctaactgt ggatgccctt    1980
agtccacctc cgtccccgaa aaagctccag ttttttcttt cagcgcgacc gcccgcgcct    2040
caagtgtcga aaacatatga caacctcgtt cggcaataca gtccctcgaa gtcgctacaa    2100
atgattttaa ggcgcgcgtt ggacgatttc gaaagcatgc tggcagatgg atcatttcgc    2160
gtggccccga aaagttatcc gatcccttca actacagaaa aatccgttct cgttcagacc    2220
tcacgcatgt tcccggttgc gttgctcgag gtcgctcgaa gtcattttga tccgttgggg    2280
ttggagaccg ctcgagcttt cggccacaag ctggctaccg ccgcgctcgc gtcattcttt    2340
gctggagaga agccatcgag caattggtga agagggacct atcggaaccc ctcaccaaat    2400
attgagtgta ggtttgaggc cgctggccgc gtcctcagtc acctttgag ccagataatt     2460 aagagccaaa tgcaattggc tcaggctgcc atcgtcccc cgtgcgaaac ctgcacgtcc     2520
gcgtcaaaga aataaccggc acctcttgct gtttttatca gttgagggct tgacggatcc    2580
gcctcaagtt tgcggcgcag ccgcaaaatg agaacatcta tactcctgtc gtaaacctcc    2640
tcgtcgcgta ctcgactggc aatgagaagt tgctcgcgcg atagaacgtc gcggggtttc    2700
tctaaaaacg cgaggagaag attgaactca cctgccgtaa gtttcacctc accgccagct    2760
tcggacatca agcgacgttg cctgagatta agtgtccagt cagtaaaaca aaaagaccgt    2820
cggtctttgg agcggacaac gttggggcgc acgcgcaagg caacccgaat gcgtgcaaga    2880
aactctctcg tactaaacgg cttagcgata aaatcacttg ctcctagctc gagtgcaaca    2940
actttatccg tctcctcaag gcggtcgcca ctgataatta tgattggaat atcagactt     3000 gccgccagat ttcgaacgat ctcaagccca tcttcacgac ctaaatttag atcaacaacc    3060
acgacatcga ccgtcgcgga agagagtact ctagtgaact gggtgctgtc ggctaccgcg    3120
gtcactttga aggcgtggat cgtaaggtat tcgataataa gatgccgcat agcgacatcg    3180
tcatcgataa gaagaacgtg tttcaacggc tcacctttca atctaaaatc tgaacccttg    3240
ttcacagcgc ttgagaaatt ttcacgtgaa ggatgtacaa tcatctccag ctaaatgggc    3300
agttcgtcag aattgcggct gaccgcggat gacgaaaatg cgaaccaagt atttcaattt    3360
tatgacaaaa gttctcaatc gttgttacaa gtgaaacgct tcgaggttac agctactatt    3420
gattaaggag atcgcctatg gtctcgcccc ggcgtcgtgc gtccgccgcg agccagatct    3480
cgcctacttc ataaacgtcc tcataggcac ggaatggaat gatgacatcg atcgccgtag    3540
agagcatgtc aatcagtgtg cgatcttcca agctagcacc ttgggcgcta cttttgacaa    3600
gggaaaacag tttcttgaat ccttggattg gattcgcgcc gtgtattgtt gaaatcgatc    3660
ccggatgtcc cgagacgact tcactcagat aagcccatgc tgcatcgtcg cgcatctcgc    3720
caagcaatat ccggtccggc cgcatacgca gacttgcttg gagcaagtgc tcggcgctca    3780
cagcacccag cccagcaccg ttcttggagt agagtagtct aacatgatta tcgtgtggaa    3840
```

-continued

```
tgacgagttc gagcgtatct tctatggtga ttagcctttc ctgggggggg atggcgctga    3900
tcaaggtctt gctcattgtt gtcttgccgc ttccggtagg gccacatagc aacatcgtca    3960
gtcggctgac gacgcatgcg tgcagaaacg cttccaaatc cccgttgtca aaatgctgaa    4020
ggatagcttc atcatcctga ttttggcgtt tccttcgtgt ctgccactgg ttccacctcg    4080
aagcatcata acgggaggag acttctttaa gaccagaaac acgcgagctt ggccgtcgaa    4140
tggtcaagct gacggtgccc gagggaacgg tcggcggcag acagatttgt agtcgttcac    4200
caccaggaag ttcagtggcg cagaggtggtgtacgtggtcc gacatcctgc tttctcagcg    4260
cgcccgctaa aatagcgata tcttcaagat catcataaga gacgggcaaa ggcatcttgg    4320
taaaaatgcc ggcttggcgc acaaatgcct ctccaggtcg attgatcgca atttcttcag    4380
tcttcgggtc atcgagccat tccaaaatcg gcttcagaag aaagcgtagt tgcggatcca    4440
cttccattta caatgtatcc tatctctaag cggaaatttg aattcattaa gagcggcggt    4500
tcctcccccg cgtggcgccg ccagtcaggc ggagctggta acaccaaag aaatcgaggt     4560
cccgtgctac gaaaatggaa acggtgtcac cctgattctt cttcagggtt ggcggtatgt    4620
tgatggttgc cttaagggct gtctcagttg tctgctcacc gttattttga aagctgttga    4680
agctcatccc gccacccgag ctgccggcgt aggtgctagc tgcctggaag gcgccttgaa    4740
caacactcaa gagcatagct ccgctaaaac gctgccagaa gtggctgtcg accgagcccg    4800
gcaatcctga gcgaccgagt tcgtccgcgc ttggcgatgt taacgagatc atcgcatggt    4860
caggtgtctc ggcgcgatcc cacaacacaa aaacgcgccc atctccctgt tgcaagccac    4920
gctgtatttc gccaacaacg gtggtgccac gatcaagaag cacgatattg ttcgttgttc    4980
cacgaatatc ctgaggcaag acacacttta catagcctgc caaatttgtg tcgattgcgg    5040
tttgcaagat gcacggaatt attgtcccttgcgttaccat aaaatcgggg tgcggcaaga    5100
gcgtggcgct gctgggctgc agctcggtgg gtttcatacg tatcgacaaa tcgttctcgc    5160
cggacacttc gccattcggc aaggagttgt cgtcacgctt gccttcttgt cttcggcccg    5220
tgtcgccctg aatggcgcgt ttgctgaccc cttgatcgcc gctgctatat gcaaaaatcg    5280
gtgtttcttc cggccgtggc tcatgccgct ccggttcgcc cctcggcggt agaggagcag    5340
caggctgaac agcctcttga accgctggag gatccggcgg cacctcaatc ggagctggat    5400
gaaatggctt ggtgtttgtt gcgatcaaag ttgacggcga tgcgttctca ttcaccttct    5460
tttggcgccc acctagccaa atgaggctta atgataacgc gagaacgaca cctccgacga    5520
tcaatttctg agaccccgaa agacgccggc gatgtttgtc ggagaccagg gatccagatg    5580
catcaacctc atgtgccgct tgctgactat cgttattcat cccttcgccc ccttcaggac    5640
gcgtttcaca tcgggcctca ccgtgccgt ttgcggcctt tggccaacgg gatcgtaagc     5700
ggtgttccag atacatagta ctgtgtggcc atccctcaga cgccaacctc gggaaaccga    5760
agaaatctcg acatcgctcc ctttaactga atagttggca acagcttcct tgccatcagg    5820
attgatggtg tagatggagg gtatgcgtac attgcccgga agtggaata ccgtcgtaaa     5880
tccattgtcg aagacttcga gtggcaacag cgaacgatcg ccttgggcga cgtagtgcca    5940
attactgtcc gccgcaccaa gggctgtgac aggctgatca aataaattct cagctttccg    6000
ttgatattgt gcttccgcgt gtagtctgtc cacaacagcc ttctgttgtg cctcccttcg    6060
ccgagccgcc gcatcgtcgg cggggtaggc gaattggacg ctgtaataga gatcgggctg    6120
ctctttatcg aggtgggaca gagtcttgga acttatactg aaaacataac ggcgcatccc    6180
ggagtcgctt gcggttagca cgattactgg ctgaggcgtg aggacctggc ttgccttgaa    6240
```

```
aaatagataa tttccccgcg gtagggctgc tagatctttg ctatttgaaa cggcaaccgc   6300
tgtcaccgtt tcgttcgtgg cgaatgttac gaccaaagta gctccaaccg ccgtcgagag   6360
gcgcaccact tgatcgggat tgtaagccaa ataacgcatg cgcggatcta gcttgcccgc   6420
cattggagtg tcttcagcct ccgcaccagt cgcagcggca aataaacatg ctaaaatgaa   6480
aagtgctttt ctgatcatgg ttcgctgtgg cctacgtttg aaacggtatc ttccgatgtc   6540
tgataggagg tgacaaccag acctgccggg ttggttagtc tcaatctgcc gggcaagctg   6600 gtcaccttt cgtagcgaac tgtcgcggtc cacgtactca ccacaggcat tttgccgtca   6660
acgacgaggg tccttttata gcgaatttgc tgcgtgcttg gagttacatc atttgaagcg   6720
atgtgctcga cctccaccct gccgcgtttg ccaagaatga cttgaggcga actgggattg   6780
ggatagttga agaattgctg gtaatcctgg cgcactgttg gggcactgaa gttcgatacc   6840
aggtcgtagg cgtactgagc ggtgtcggca tcataactct cgcgcaggcg aacgtactcc   6900
cacaatgagg cgttaacgac ggcctcctct tgagttgcag gcaatcgcga gacagacacc   6960
tcgctgtcaa cggtgccgtc cggccgtatc catagatata cgggcacaag cctgctcaac   7020
ggcaccattg tggctatagc gaacgcttga gcaacatttc ccaaaatcgc gatagctgcg   7080
acagctgcaa tgagtttgga gagacgtcgc gccgatttcg ctcgcgcggt ttgaaaggct   7140
tctacttcct tatagtgctc ggcaaggctt tcgcgcgcca ctagcatggc atattcaggc   7200
cccgtcatag cgtccacccg aattgccgag ctgaagatct gacggagtag gctgccatcg   7260
ccccacattc agcgggaaga tcgggccttt gcagctcgct aatgtgtcgt ttgtctggca   7320
gccgctcaaa gcgacaacta ggcacagcag gcaatacttc atagaattct ccattgaggc   7380 gaattttgc gcgacctagc ctcgctcaac ctgagcgaag cgacggtaca agctgctggc   7440
agattgggtt gcgccgctcc agtaactgcc tccaatgttg ccggcgatcg ccggcaaagc   7500
gacaatgagc gcatcccctg tcagaaaaaa catatcgagt tcgtaaagac caatgatctt   7560
ggccgcggtc gtaccggcga aggtgattac accaagcata agggtgagcg cagtcgcttc   7620
ggttaggatg acgatcgttg ccacgaggtt taagaggaga agcaagagac cgtaggtgat   7680
aagttgcccg atccacttag ctgcgatgtc ccgcgtgcga tcaaaatat atccgacgag   7740 gatcagaggc ccgatcgcga gaagcacttt cgtgagaatt ccaacggcgt cgtaaactcc   7800
gaaggcagac cagagcgtgc cgtaaaggac ccactgtgcc ccttggaaag caaggatgtc   7860
ctggtcgttc atcggaccga tttcggatgc gattttctga aaaacggcct gggtcacggc   7920
gaacattgta tccaactgtg ccggaacagt ctgcagaggc aagccggtta cactaaactg   7980
ctgaacaaag tttgggaccg tctttcgaa gatggaaacc acatagtctt ggtagttagc   8040
ctgcccaaca attagagcaa caacgatggt gaccgtgatc acccgagtga taccgctacg   8100
ggtatcgact tcgccgcgta tgactaaaat accctgaaca ataatccaaa gagtgacaca   8160
ggcgatcaat ggcgcactca ccgcctcctg gatagtctca agcatcgagt ccaagcctgt   8220
cgtgaaggct acatcgaaga tcgtatgaat ggccgtaaac ggcgccggaa tcgtgaaatt   8280
catcgattgg acctgaactt gactggtttg tcgcataatg ttggataaaa tgagctcgca   8340
ttcggcgagg atgcgggcgg atgaacaaat cgcccagcct taggggaggg caccaaagat   8400
gacagcggtc ttttgatgct ccttgcgttg agcggccgcc tcttccgcct cgtgaaggcc   8460
ggcctgcgcg gtagtcatcg ttaataggct tgtcgcctgt acattttgaa tcattgcgtc   8520
atggatctgc ttgagaagca aaccattggt cacggttgcc tgcatgatat tgcgagatcg   8580
```

```
ggaaagctga gcagacgtat cagcattcgc cgtcaagcgt tgtccatcg tttccagatt    8640
gtcagccgca atgccagcgc tgtttgcgga accggtgatc tgcgatcgca acaggtccgc    8700
ttcagcatca ctacccacga ctgcacgatc tgtatcgctg gtgatcgcac gtgccgtggt    8760
cgacattggc attcgcggcg aaaacatttc attgtctagg tccttcgtcg aaggatactg    8820
atttttctgg ttgagcgaag tcagtagtcc agtaacgccg taggccgacg tcaacatcgt    8880
aaccatcgct atagtctgag tgagattctc cgcagtcgcg agcgcagtcg cgagcgtctc    8940
agcctccgtt gccgggtcgc taacaacaaa ctgcgcccgc gcgggctgaa tatatagaaa    9000
gctgcaggtc aaaactgttg caataagttg cgtcgtcttc atcgtttcct accttatcaa    9060
tcttctgcct cgtggtgacg ggccatgaat tcgctgagcc agccagatga gttgccttct    9120
tgtgcctcgc gtagtcgagt tgcaaagcgc accgtgttgg cacgcccga aagcacggcg    9180
acatattcac gcatatcccg cagatcaaat tcgcagatga cgcttccact ttctcgttta    9240
agaagaaact tacggctgcc gaccgtcatg tcttcacgga tcgcctgaaa ttccttttcg    9300
gtacatttca gtccatcgac ataagccgat cgatctgcgg ttggtgatgg atagaaaatc    9360
ttcgtcatac attgcgcaac caagctggct cctagcggcg attccagaac atgtctggt     9420
tgctgcgttg ccagtattag catcccgttg ttttttcgaa cggtcaggag gaatttgtcg    9480
acgacagtcg aaaatttagg gtttaacaaa taggcgcgaa actcatcgca gctcatcaca    9540
aaacggcggc cgtcgatcat ggctccaatc cgatgcagga gatatgctgc agcgggagcg    9600
catacttcct cgtattcgag aagatgcgtc atgtcgaagc cggtaatcga cggatctaac    9660
tttacttcgt caacttcgcc gtcaaatgcc cagccaagcg catggccccg gcaccagcgt    9720
tggagccgcg ctcctgcgcc ttcggcgggc ccatgcaaca aaaattcacg taaccccgcg    9780
attgaacgca tttgtggatc aaacgagagc tgacgatgga taccacggac cagacggcgg    9840
ttctcttccg gagaaatccc accccgacca tcactctcga tgagagccac gatccattcg    9900
cgcagaaaat cgtgtgaggc tgctgtgttt tctaggccac gcaacggcgc caacccgctg    9960
ggtgtgcctc tgtgaagtgc caaatatgtt cctcctgtgg cgcgaaccag caattcgcca   10020
ccccggtcct tgtcaaagaa cacgaccgta cctgcacggt cgaccatgct ctgttcgagc   10080
atggctagaa caaacatcat gagcgtcgtc ttaccctcc cgataggccc gaatattgcc     10140
gtcatgccaa catcgtgctc atgcgggata tagtcgaaag gcgttccgcc attggtacga   10200
aatcgggcaa tcgcgttgcc ccagtggcct gagctggcgc cctctggaaa gttttcgaaa   10260
gagacaaacc ctgcgaaatt gcgtgaagtg attgcgccag ggcgtgtgcg ccacttaaaa   10320
ttccccggca attgggacca ataggccgct tccataccaa taccttcttg gacaaccacg   10380
gcacctgcat ccgccattcg tgtccgagcc cgcgcgcccc tgtccccaag actattgaga   10440
tcgtctgcat agacgcaaag gctcaaatga tgtgagccca taacgaattc gttgctcgca   10500
agtgcgtcct cagcctcgga taatttgccg atttgagtca cggctttatc gccggaactc   10560
agcatctggc tcgatttgag gctaagtttc gcgtgcgctt gcgggcgagt caggaacgaa   10620
aaactctgcg tgagaacaag tggaaaatcg agggatagca gcgcgttgag catgcccggc   10680
cgtgttttg cagggtattc gcgaaacgaa tagatggatc caacgtaact gtcttttggc    10740
gttctgatct cgagtcctcg cttgccgcaa atgactctgt cggtataaat cgaagcgccg   10800
agtgagccgc tgacgaccgg aaccggtgtg aaccgaccag tcatgatcaa ccgtagcgct   10860
tcgccaattt cggtgaagag cacaccctgc ttctcgcgca tgccaagacg atgcaggcca   10920
tacgctttaa gagagccagc gacaacatgc caaagatctt ccatgttcct gatctggccc   10980
```

```
gtgagatcgt tttcccttt tccgcttagc ttggtgaacc tcctctttac cttccctaaa    11040
gccgcctgtg ggtagacaat caacgtaagg aagtgttcat tgcggaggag ttggccggag    11100
agcacgcgct gttcaaaagc ttcgttcagg ctagcggcga aaacactacg gaagtgtcgc    11160
ggcgccgatg atggcacgtc ggcatgacgt acgaggtgag catatattga cacatgatca    11220
tcagcgatat tgcgcaacag cgtgttgaac gcacgacaac gcgcattgcg catttcagtt    11280
tcctcaagct cgaatgcaac gccatcaatt ctcgcaatgg tcatgatcga tccgtcttca    11340
agaaggacga tatggtcgct gaggtggcca atataaggga gatagatctc accggatctt    11400
tcggtcgttc cactcgcgcc gagcatcaca ccattcctct ccctcgtggg ggaaccctaa    11460
ttggatttgg gctaacagta gcgcccccc aaactgcact atcaatgctt cttcccgcgg    11520
tccgcaaaaa tagcaggacg acgctcgccg cattgtagtc tcgctccacg atgagccggg    11580
ctgcaaacca taacggcacg agaacgactt cgtagagcgg gttctgaacg ataacgatga    11640
caaagccggc gaacatcatg aataaccctg ccaatgtcag tggcaccccca agaaacaatg    11700
cgggccgtgt ggctgcgagg taaagggtcg attcttccaa acgatcagcc atcaactacc    11760
gccagtgagc gtttggccga ggaagctcgc cccaaacatg ataacaatgc cgccgacgac    11820
gccggcaacc agcccaagcg aagcccgccc gaacatccag gagatcccga tagcgacaat    11880
gccgagaaca gcgagtgact ggccgaacgg accaaggata aacgtgcata tattgttaac    11940
cattgtggcg gggtcagtgc cgccacccgc agattgcgct gcggcgggtc cggatgagga    12000
aatgctccat gcaattgcac cgcacaagct tggggcgcag ctcgatatca cgcgcatcat    12060
cgcattcgag agcgagaggc gatttagatg taaacggtat ctctcaaagc atcgcatcaa    12120
tgcgcacctc cttagtataa gtcgaataag acttgattgt cgtctgcgga tttgccgttg    12180
tcctggtgtg gcggtggcgg agcgattaaa ccgccagcgc catcctcctg cgagcggcgc    12240
tgatatgacc cccaaacatc ccacgtctct tcggattta gcgcctcgtg atcgtctttt    12300
ggaggctcga ttaacgcggg caccagcgat tgagcagctg tttcaacttt tcgcacgtag    12360
ccgtttgcaa aaccgccgat gaaattaccg gtgttgtaag cggagatcgc ccgacgaagc    12420
gcaaattgct tctcgtcaat cgtttcgccg cctgcataac gacttttcag catgtttgca    12480
gcggcagata atgatgtgca cgcctggagc gcaccgtcag gtgtcagacc gagcatagaa    12540
aaatttcgag agtttatttg catgaggcca acatccagcg aatgccgtgc atcgagacgg    12600
tgcctgacga cttgggttgc ttggctgtga tcttgccagt gaagcgtttc gccggtcgtg    12660
ttgtcatgaa tcgctaaagg atcaaagcga ctctccacct tagctatcgc cgcaagcgta    12720
gatgtcgcaa ctgatggggc acacttgcga gcaacatggt caaactcagc agatgagagt    12780
ggcgtggcaa ggctcgacga acagaaggag accatcaagg caagagaaag cgaccccgat    12840
ctcttaagca taccttatct ccttagctcg caactaacac cgcctctccc gttggaagaa    12900
gtgcgttgtt ttatgttgaa gattatcggg agggtcggtt actcgaaaat tttcaattgc    12960
ttctttatga tttcaattga agcgagaaac ctcgcccggc gtcttggaac gcaacatgga    13020
ccgagaaccg cgcatccatg actaagcaac cggatcgacc tattcaggcc gcagttggtc    13080
aggtcaggct cagaacgaaa atgctcggcg aggttacgct gtctgtaaac ccattcgatg    13140
aacgggaagc ttccttccga ttgctcttgg caggaatatt ggcccatgcc tgcttgcgct    13200
ttgcaaatgc tcttatcgcg ttggtatcat atgccttgtc cgccagcaga aacgcactct    13260
aagcgattat ttgtaaaaat gtttcggtca tgcggcggtc atgggcttga cccgctgtca    13320
```

```
gcgcaagacg gatcggtcaa ccgtcggcat cgacaacagc gtgaatcttg gtggtcaaac   13380
cgccacggga acgtcccata cagccatcgt cttgatcccg ctgtttcccg tcgccgcatg   13440
ttggtggacg cggacacagg aactgtcaat catgacgaca ttctatcgaa agccttggaa   13500
atcacactca gaatatgatc ccagacgtct gcctcacgcc atcgtacaaa gcgattgtag   13560
caggttgtac aggaaccgta tcgatcagga acgtctgccc agggcgggcc cgtccggaag   13620
cgccacaaga tgacattgat cacccgcgtc aacgcgcggc acgcgacgcg cttatttgg    13680 gaacaaagga ctgaacaaca gtccattcga aatcggtgac atcaaagcgg ggacgggtta   13740
tcagtggcct ccaagtcaag cctcaatgaa tcaaaatcag accgatttgc aaacctgatt   13800
tatgagtgtg cggcctaaat gatgaaatcg tccttctaga tcgcctccgt ggtgtagcaa   13860
cacctcgcag tatcgccgtg ctgaccttgg ccagggaatt gactggcaag ggtgcttca   13920 catgaccgct cttttggccg cgatagatga tttcgttgct gctttgggca cgtagaagga   13980
gagaagtcat atcggagaaa ttcctcctgg cgcgagagcc tgctctatcg cgacggcatc   14040
ccactgtcgg gaacagaccg gatcattcac gaggcgaaag tcgtcaacac atgcgttata   14100
ggcatcttcc cttgaaggat gatcttgttg ctgccaatct ggaggtgcgg cagccgcagg   14160
cagatgcgat ctcagcgcaa cttgcggcaa acatctcac tcacctgaaa accactagcg    14220
agtctcgcga tcagacgaag gccttttact taacgacaca atatccgatg tctgcatcac   14280
aggcgtcgct atcccagtca atactaaagc ggtgcaggaa ctaaagatta ctgatgactt   14340
aggcgtgcca cgaggcctga cgacgcgcgc gtagacagtt ttttgaaatc attatcaaag   14400
tgatggcctc cgctgaagcc tatcacctct gcgccggtct gtcggagaga tgggcaagca   14460
ttattacggt cttcgcgccc gtacatgcat tggacgattg cagggtcaat ggatctgaga   14520
tcatccagag gattgccgcc cttaccttcc gtttcgagtt ggagccagcc ctaaatgag    14580 acgacatagt cgacttgatg tgacaatgcc aagagagaga tttgcttaac ccgatttttt   14640
tgctcaagcg taagcctatt gaagcttgcc ggcatgacgt ccgcgccgaa agaatatcct   14700
acaagtaaaa cattctgcac accgaaatgc ttggtgtaga catcgattat gtgaccaaga   14760
tccttagcag tttcgcttgg ggaccgctcc gaccagaaat accgaagtga actgacgcca   14820
atgacaggaa tcccttccgt ctgcagatag gtaccatcga tagatctgct gcctcgcgcg   14880
tttcggtgat gacggtgaaa acctctgaca catgcagctc ccggagacgg tcacagcttg   14940
tctgtaagcg gatgccggga gcagacaagc ccgtcagggc gcgtcagcgg tgttggcgg    15000 gtgtcggggc gcagccatga cccagtcacg tagcgatagc ggagtgtata ctggcttaac   15060
tatgcggcat cagagcagat tgtactgaga gtgcaccata tgcggtgtga aataccgcac   15120
agatgcgtaa ggagaaaata ccgcatcagg cgctcttccg cttcctcgct cactgactcg   15180
ctgcgctcgg tcgttcggct gcggcgagcg gtatcagctc actcaaaggc ggtaatacgg   15240
ttatccacag aatcagggga taacgcagga agaacatgt gagcaaaagg ccagcaaaag    15300
gccaggaacc gtaaaaaggc cgcgttgctg gcgtttttcc ataggctccg ccccctgac    15360 gagcatcaca aaaatcgacg ctcaagtcag aggtggcgaa acccgacagg actataaaga   15420
taccaggcgt ttccccctgg aagctccctc gtgcgctctc ctgttccgac cctgccgctt   15480
accggatacc tgtccgcctt tctcccttcg ggaagcgtgg cgctttctca tagctcacgc   15540
tgtaggtatc tcagttcggt gtaggtcgtt cgctccaagc tgggctgtgt gcacgaaccc   15600
cccgttcagc ccgaccgctg cgccttatcc ggtaactatc gtcttgagtc caacccggta   15660
agacacgact tatcgccact ggcagcagcc actggtaaca ggattagcag agcgaggtat   15720
```

```
gtaggcggtg ctacagagtt cttgaagtgg tggcctaact acggctacac tagaaggaca   15780
gtatttggta tctgcgctct gctgaagcca gttaccttcg gaaaaagagt tggtagctct   15840
tgatccggca aacaaaccac cgctggtagc ggtggttttt ttgtttgcaa gcagcagatt   15900
acgcgcagaa aaaaggatc tcaagaagat cctttgatct tttctacggg gtctgacgct    15960
cagtggaacg aaaactcacg ttaagggatt ttggtcatga gattatcaaa aaggatcttc   16020
acctagatcc ttttaaatta aaaatgaagt tttaaatcaa tctaaagtat atatgagtaa   16080
acttggtctg acagttacca atgcttaatc agtgaggcac ctatctcagc gatctgtcta   16140
tttcgttcat ccatagttgc ctgactcccc gtcgtgtaga taactacgat acgggagggc   16200
ttaccatctg gccccagtgc tgcaatgata ccgcgagacc cacgctcacc ggctccagat   16260
ttatcagcaa taaaccagcc agccggaagg gccgagcgca gaagtggtcc tgcaacttta   16320
tccgcctcca tccagtctat taattgttgc cgggaagcta gagtaagtag ttcgccagtt   16380
aatagtttgc gcaacgttgt tgccattgct gcagggggg gggggggggg gttccattgt    16440
tcattccacg gacaaaaaca gagaaaggaa acgacagagg ccaaaaagct cgctttcagc   16500
acctgtcgtt tcctttcttt tcagagggta ttttaaataa aaacattaag ttatgacgaa   16560
gaagaacgga aacgccttaa accggaaaat tttcataaat agcgaaaacc cgcgaggtcg   16620 ccgcccgta acctgtcgga tcaccggaaa ggacccgtaa agtgataatg attatcatct     16680
acatatcaca acgtgcgtgg aggccatcaa accacgtcaa ataatcaatt atgacgcagg    16740
tatcgtatta attgatctgc atcaacttaa cgtaaaaaca acttcagaca atacaaatca    16800
gcgacactga atacggggca acctcatgtc cccccccccc cccccctgc aggcatcgtg     16860 gtgtcacgct cgtcgtttgg tatggcttca ttcagctccg gttcccaacg atcaaggcga   16920
gttacatgat cccccatgtt gtgcaaaaaa gcggttagct ccttcggtcc tccgatcgtt   16980
gtcagaagta agttggccgc agtgttatca ctcatggtta tggcagcact gcataattct    17040
cttactgtca tgccatccgt aagatgcttt tctgtgactg gtgagtactc aaccaagtca    17100
ttctgagaat agtgtatgcg gcgaccgagt tgctcttgcc cggcgtcaac acgggataat    17160
accgcgccac atagcagaac tttaaaagtg ctcatcattg gaaaacgttc ttcggggcga   17220
aaactctcaa ggatcttacc gctgttgaga tccagttcga tgtaacccac tcgtgcaccc   17280
aactgatctt cagcatcttt tactttcacc agcgtttctg ggtgagcaaa aacaggaagg   17340
caaaatgccg caaaaaaggg aataagggcg acacggaaat gttgaatact catactcttc   17400 cttttcaat attattgaag catttatcag ggttattgtc tcatgagcgg atacatattt     17460
gaatgtattt agaaaaataa acaataggg gttccgcgca catttccccg aaaagtgcca    17520
cctgacgtct aagaaaccat tattatcatg acattaacct ataaaaatag gcgtatcacg   17580
aggccctttc gtcttcaaga attcggagct tttgccattc tcaccggatt cagtcgtcac   17640
tcatggtgat ttctcacttg ataaccttat ttttgacgag gggaaattaa taggttgtat   17700
tgatgttgga cgagtcggaa tcgcagaccg ataccaggat cttgccatcc tatggaactg   17760
cctcggtgag ttttctcctt cattacagaa acggcttttt caaaaatatg gtattgataa   17820
tcctgatatg aataaattgc agtttcattt gatgctcgat gagttttttct aatcagaatt   17880 ggttaattgg ttgtaacact ggcagagcat tacgctgact tgacgggacg cggctttgt     17940 tgaataaatc gaacttttgc tgagttgaag gatcagatca cgcatcttcc cgacaacgca   18000
gaccgttccg tggcaaagca aaagttcaaa atcaccaact ggtccaccta caacaaagct   18060
```

```
ctcatcaacc gtggctccct cactttctgg ctggatgatg gggcgattca ggcctggtat    18120
gagtcagcaa caccttcttc acgaggcaga cctcagcgcc agaaggccgc cagagaggcc    18180
gagcgcggcc gtgaggcttg gacgctaggg cagggcatga aaaagcccgt agcgggctgc    18240
tacgggcgtc tgacgcggtg gaaaggggga ggggatgttg tctacatggc tctgctgtag    18300
tgagtgggtt gcgctccggc agcggtcctg atcaatcgtc accctttctc ggtccttcaa    18360
cgttcctgac aacgagcctc cttttcgcca atccatcgac aatcaccgcg agtccctgct    18420
cgaacgctgc gtccggaccg gcttcgtcga aggcgtctat cgcggcccgc aacagcggcg    18480
agagcggagc ctgttcaacg gtgccgccgc gctccgccgg atcgctgtcg ccggcctgct    18540
cctcaagcac ggccccaaca gtgaagtagc tgattgtcat cagcgcattg acggcgtccc    18600
cggccgaaaa acccgcctcg cagaggaagc gaagctgcgc gtcggccgtt ccatctgcg    18660
gtgcgcccgg tcgcgtgccg gcatggatgc gcgcgccatc gcgtaggcg agcagcgcct    18720
gcctgaagct gcgggcattc ccgatcagaa atgagcgcca gtcgtcgtcg gctctcggca    18780
ccgaatgcgt atgattctcc gccagcatgg cttcggccag tgcgtcgagc agcgcccgct    18840
tgttcctgaa gtgccagtaa agcgccggct gctgaacccc caaccgttcc gccagtttgc    18900
gtgtcgtcag accgtctacg ccgacctcgt tcaacaggtc cagggcggca cggatcactg    18960
tattcggctg caactttgtc atgcttgaca ctttatcact gataaacata atatgtccac    19020
caacttatca gtgataaaga atccgcgcgt tcaatcggac cagcggaggc tggtccggag    19080
gccagacgtg aaacccaaca taccctgat cgtaattctg agcactgtcg cgctcgacgc    19140
tgtcggcatc ggcctgatta tgccggtgct gccgggcctc ctgcgcgatc tggttcactc    19200
gaacgacgtc accgcccact atggcattct gctggcgctg tatgcgttgg tgcaatttgc    19260
ctgcgcacct gtgctgggcg cgctgtcgga tcgtttcggg cggcggccaa tcttgctcgt    19320
ctcgctggcc ggcgccactg tcgactacgc catcatggcg acagcgcctt cctttgggt    19380
tctctatatc gggcggatcg tggccggcat caccggggcg actggggcgg tagccggcgc    19440
ttatattgcc gatatcactg atggcgatga gcgcgcgcgg cacttcggct tcatgagcgc    19500
ctgtttcggt ttcgggatgg tcgcgggacc tgtgctcggt gggctgatgg gcggtttctc    19560
cccccacgct ccgttcttcg ccgcggcagc cttgaacggc ctcaatttcc tgacgggctg    19620
tttccttttg ccggagtcgc acaaaggcga acgccggccg ttacgccggg aggctctcaa    19680
cccgctcgct tcgttccggt gggcccgggg catgaccgtc gtcgccgccc tgatggcggt    19740
cttcttcatc atgcaacttg tcggacaggt gccggccgcg cttggggtca ttttcggcga    19800
ggatcgcttt cactgggacg cgaccacgat cggcatttcg cttgccgcat ttggcattct    19860
gcattcactc gcccaggcaa tgatcaccgg ccctgtagcc gccggctcg gcgaaaggcg    19920
ggcactcatg ctcggaatga ttgccgacgg cacaggctac atcctgcttg ccttcgcgac    19980
acggggatgg atggcgttcc cgatcatggt cctgcttgct cgggtggca tcggaatgcc    20040
ggcgctgcaa gcaatgttgt ccaggcaggt ggatgaggaa cgtcaggggc agctgcaagg    20100
ctcactggcg gcgctcacca gcctgacctc gatcgtcgga cccctcctct tcacggcgat    20160
ctatgcggct tctataacaa cgtggaacgg gtgggcatgg attgcaggcg ctgccctcta    20220
cttgctctgc ctgccggcgc tgcgtcgcgg gctttggagc ggcgcagggc aacgagccga    20280
tcgctgatcg tggaaacgat aggcctatgc catgcgggtc aaggcgactt ccggcaagct    20340
atacgcgccc taggagtgcg gttggaacgt tgcccagcc agatactccc gatcacgagc    20400
aggacgccga tgatttgaag cgcactcagc gtctgatcca agaacaacca tcctagcaac    20460
```

```
acggcggtcc ccgggctgag aaagcccagt aaggaaacaa ctgtaggttc gagtcgcgag   20520
atcccccgga accaaaggaa gtaggttaaa cccgctccga tcaggccgag ccacgccagg   20580
ccgagaacat tggttcctgt aggcatcggg attggcggat caaacactaa agctactgga   20640
acgagcagaa gtcctccggc cgccagttgc caggcggtaa aggtgagcag aggcacggga   20700
ggttgccact tgcgggtcag cacggttccg aacgccatgg aaaccgcccc cgccaggccc   20760
gctgcgacgc cgacaggatc tagcgctgcg tttggtgtca acaccaacag cgccacgccc   20820
gcagttccgc aaatagcccc caggaccgcc atcaatcgta tcgggctacc tagcagagcg   20880
gcagagatga acacgaccat cagcggctgc acagcgccta ccgtcgccgc gaccccgccc   20940
ggcaggcggt agaccgaaat aaacaacaag ctccagaata gcgaaatatt aagtgcgccg   21000
aggatgaaga tgcgcatcca ccagattccc gttggaatct gtcggacgat catcacgagc   21060
aataaacccg ccggcaacgc ccgcagcagc ataccggcga cccctcggcc tcgctgttcg   21120
ggctccacga aaacgccgga cagatgcgcc ttgtgagcgt ccttggggcc gtcctcctgt   21180
ttgaagaccg acagcccaat gatctcgccg tcgatgtagg cgccgaatgc cacggcatct   21240
cgcaaccgtt cagcgaacgc ctccatgggc ttttttctcct cgtgctcgta aacggacccg   21300
aacatctctg gagctttctt cagggccgac aatcggatct cgcggaaatc ctgcacgtcg   21360
gccgctccaa gccgtcgaat ctgagcctta atcacaattg tcaattttaa tcctctgttt   21420
atcggcagtt cgtagagcgc gccgtgcgtc ccgagcgata ctgagcgaag caagtgcgtc   21480
gagcagtgcc cgcttgttcc tgaaatgcca gtaaagcgct ggctgctgaa cccccagccg   21540
gaactgaccc cacaaggccc tagcgtttgc aatgcaccag gtcatcattg acccaggcgt   21600
gttccaccag gccgctgcct cgcaactctt cgcaggcttc gccgacctgc tcgcgccact   21660
tcttcacgcg ggtggaatcc gatccgcaca tgaggcggaa ggtttccagc ttgagcgggt   21720
acggctcccg gtgcgagctg aaatagtcga acatccgtcg ggccgtcggc gacagcttgc   21780
ggtacttctc ccatatgaat ttcgtgtagt ggtcgccagc aaacagcacg acgatttcct   21840
cgtcgatcag gacctggcaa cgggacgttt tcttgccacg gtccaggacg cggaagcggt   21900
gcagcagcga caccgattcc aggtgcccaa cgcggtcgga cgtgaagccc atcgccgtcg   21960
cctgtaggcg cgacaggcat tcctcggcct tcgtgtaata ccggccattg atcgaccagc   22020
ccaggtcctg gcaaagctcg tagaacgtga aggtgatcgg ctcgccgata ggggtgcgct   22080
tcgcgtactc caacacctgc tgccacacca gttcgtcatc gtcggcccgc agctcgacgc   22140
cggtgtaggt gatcttcacg tccttgttga cgtggaaaat gaccttgttt tgcagcgcct   22200
cgcgcgggat tttcttgttg cgcgtggtga acagggcaga gcgggccgtg tcgtttggca   22260
tcgctcgcat cgtgtccggc cacggcgcaa tatcgaacaa ggaaagctgc atttccttga   22320
tctgctgctt cgtgtgtttc agcaacgcgg cctgcttggc ctcgctgacc tgttttgcca   22380
ggtcctcgcc ggcggttttt cgcttcttgg tcgtcatagt tcctcgcgtg tcgatggtca   22440
tcgacttcgc caaacctgcc gcctcctgtt cgagacgacg cgaacgctcc acggcggccg   22500
atggcgcggg cagggcaggg ggagccagtt gcacgctgtc gcgctcgatc ttggccgtag   22560
cttgctggac catcgagccg acggactgga aggtttcgcg gggcgcacgc atgacggtgc   22620
ggcttgcgat ggtttcggca tcctcggcgg aaaaccccgc gtcgatcagt tcttgcctgt   22680
atgccttccg gtcaaacgtc cgattcattc acccctccttg cgggattgcc ccgactcacg   22740
ccggggcaat gtgcccttat tcctgatttg acccgcctgg tgccttggtg tccagataat   22800
```

```
ccaccttatc ggcaatgaag tcggtcccgt agaccgtctg gccgtccttc tcgtacttgg   22860
tattccgaat cttgccctgc acgaatacca gcgacccctt gcccaaatac ttgccgtggg   22920
cctcggcctg agagccaaaa cacttgatgc ggaagaagtc ggtgcgctcc tgcttgtcgc   22980
cggcatcgtt gcgccactct tcattaaccg ctatatcgaa aattgcttgc ggcttgttag   23040
aattgccatg acgtacctcg gtgtcacggg taagattacc gataaactgg aactgattat   23100
ggctcatatc gaaagtctcc ttgagaaagg agactctagt ttagctaaac attggttccg   23160
ctgtcaagaa ctttagcggc taaaattttg cgggccgcga ccaaaggtgc gaggggcggc   23220
ttccgctgtg tacaaccaga tatttttcac caacatcctt cgtctgctcg atgagcgggg   23280
catgacgaaa catgagctgt cggagagggc aggggtttca atttcgtttt tatcagactt   23340
aaccaacggt aaggccaacc cctcgttgaa ggtgatggag gccattgccg acgccctgga   23400
aactccccta cctcttctcc tggagtccac cgaccttgac cgcgaggcac tcgcggagat   23460
tgcgggtcat cctttcaaga gcagcgtgcc gcccggatac gaacgcatca gtgtggtttt   23520
gccgtcacat aaggcgttta tcgtaaagaa atggggcgac gacacccgaa aaagctgcg    23580
tggaaggctc tgacgccaag ggttagggct tgcacttcct tctttagccg ctaaaacggc   23640
cccttctctg cgggccgtcg gctcgcgcat catatcgaca tcctcaacgg aagccgtgcc   23700
gcgaatggca tcgggcgggt gcgctttgac agttgttttc tatcagaacc cctacgtcgt   23760
gcggttcgat tagctgtttg tcttgcaggc taaacacttt cggtatatcg tttgcctgtg   23820
cgataatgtt gctaatgatt tgttgcgtag gggttactga aaagtgagcg ggaaagaaga   23880
gtttcagacc atcaaggagc gggccaagcg caagctggaa cgcgacatgg gtgcggacct   23940
gttggccgcg ctcaacgacc cgaaaaccgt tgaagtcatg ctcaacgcgg acggcaaggt   24000
gtggcacgaa cgccttggcg agccgatgcg gtacatctgc gacatgcggc ccagccagtc   24060
gcaggcgatt atagaaacgg tggccggatt ccacggcaaa gaggtcacgc ggcattcgcc   24120
catcctggaa ggcgagttcc ccttggatgg cagccgcttt gccggccaat tgccgccggt   24180
cgtggccgcg ccaacctttg cgatccgcaa gcgcgcggtc gccatcttca cgctggaaca   24240
gtacgtcgag gcgggcatca tgacccgcga gcaatacgag gtcattaaaa gcgccgtcgc   24300
ggcgcatcga acatcctcg tcattggcgg tactggctcg gcaagacca cgctcgtcaa    24360
cgcgatcatc aatgaaatgg tcgccttcaa cccgtctgag cgcgtcgtca tcatcgagga   24420
caccggcgaa atccagtgcg ccgcagagaa cgccgtccaa taccacacca gcatcgacgt   24480
ctcgatgacg ctgctgctca agacaacgct gcgtatgcgc cccgaccgca tcctggtcgg   24540
tgaggtacgt ggccccgaag cccttgatct gttgatggcc tggaacaccg gcatgaagg    24600
aggtgccgcc accctgcacg caaacaaccc caaagcgggc ctgagccggc tcgccatgct   24660
tatcagcatg caccggatt caccgaaacc cattgagccg ctgattggcg aggcggttca    24720
tgtggtcgtc catatcgcca ggaccccag cggccgtcga gtgcaagaaa ttctcgaagt   24780
tcttggttac gagaacggcc agtacatcac caaaaccctg taaggagtat ttccaatgac   24840
aacggctgtt ccgttccgtc tgaccatgaa tcgcggcatt tgttctacc ttgccgtgtt    24900
cttcgttctc gctctcgcgt tatccgcgca tccggcgatg gcctcggaag caccggcgg    24960
cagcttgcca tatgagagct ggctgacgaa cctgcgcaac tccgtaaccg gcccggtggc   25020
cttcgcgctg tccatcatcg gcatcgtcgt cgccggcggc gtgctgatct tcggcggcga   25080
actcaacgcc ttcttccgaa ccctgatctt cctggttctg gtgatggcgc tgctggtcgg   25140
cgcgcagaac gtgatgagca ccttcttcgg tcgtggtgcc gaaatcgcgg ccctcggcaa   25200
```

```
cggggcgctg caccaggtgc aagtcgcggc ggcggatgcc gtgcgtgcgg tagcggctgg   25260
acggctcgcc taatcatggc tctgcgcacg atccccatcc gtcgcgcagg caaccgagaa   25320
aacctgttca tgggtggtga tcgtgaactg gtgatgttct cgggcctgat ggcgtttgcg   25380
ctgattttca gcgcccaaga gctgcgggcc accgtggtcg gtctgatcct gtggttcggg   25440
gcgctctatg cgttccgaat catggcgaag gccgatccga agatgcggtt cgtgtacctg   25500
cgtcaccgcc ggtacaagcc gtattacccg gcccgctcga ccccgttccg cgagaacacc   25560
aatagccaag ggaagcaata ccgatgatcc aagcaattgc gattgcaatc gcgggcctcg   25620
gcgcgcttct gttgttcatc ctcttttgcc gcatccgcgc ggtcgatgcc gaactgaaac   25680
tgaaaaagca tcgttccaag gacgccggcc tggccgatct gctcaactac gccgctgtcg   25740
tcgatgacgg cgtaatcgtg ggcaagaacg gcagctttat ggctgcctgg ctgtacaagg   25800
gcgatgacaa cgcaagcagc accgaccagc agcgcgaagt agtgtccgcc cgcatcaacc   25860
aggccctcgc gggcctggga agtgggtgga tgatccatgt ggacgccgtg cggcgtcctg   25920
ctccgaacta cgcggagcgg ggcctgtcgg cgttccctga ccgtctgacg gcagcgattg   25980
aagaagagcg ctcggtcttg ccttgctcgt cggtgatgta cttcaccagc tccgcgaagt   26040
cgctcttctt gatggagcgc atggggacgt gcttggcaat cacgcgcacc ccccggccgt   26100
tttagcggct aaaaaagtca tggctctgcc ctcgggcgga ccacgcccat catgaccttg   26160
ccaagctcgt cctgcttctc ttcgatcttc gccagcaggg cgaggatcgt ggcatcaccg   26220
aaccgcgccg tgcgcgggtc gtcggtgagc cagagtttca gcaggccgcc caggcggccc   26280
aggtcgccat tgatgcgggc cagctcgcgg acgtgctcat agtccacgac gcccgtgatt   26340
ttgtagccct ggccgacggc cagcaggtag gccgacaggc tcatgccggc cgccgccgcc   26400
ttttcctcaa tcgctcttcg ttcgtctgga aggcagtaca ccttgatagg tgggctgccc   26460
ttcctggttg gcttggtttc atcagccatc cgcttgccct catctgttac gccggcggta   26520
gccggccagc ctcgcagagc aggattcccg ttgagcaccg ccaggtgcga ataagggaca   26580
gtgaagaagg aacacccgct cgcgggtggg cctacttcac ctatcctgcc cggctgacgc   26640
cgttggatac accaaggaaa gtctacacga acccctttggc aaaatcctgt atatcgtgcg   26700
aaaaaggatg gatataccga aaaaatcgct ataatgaccc cgaagcaggg ttatgcagcg   26760
gaaaagcgct gcttccctgc tgttttgtgg aatatctacc gactgaaaac aggcaaatgc   26820
aggaaattac tgaactgagg ggacaggcga gagacgatgc caaagagcta caccgacgag   26880
ctggccgagt gggttgaatc ccgcgcggcc aagaagcgcc ggcgtgatga ggctgcggtt   26940
gcgttcctgg cggtgagggc ggatgtcgag gcggcgttag cgtccggcta tgcgctcgtc   27000
accatttggg agcacatgcg ggaaacgggg aaggtcaagt tctcctacga gacgttccgc   27060
tcgcacgcca ggcggcacat caaggccaag cccgccgatg tgcccgcacc gcaggccaag   27120
gctgcggaac ccgcgccggc acccaagacg ccggagccac ggcggccgaa gcaggggggc   27180
aaggctgaaa agccggcccc cgctgcggcc ccgaccggct tcaccttcaa cccaacaccg   27240
gacaaaaagg atctactgta atggcgaaaa ttcacatggt tttgcagggc aagggcgggg   27300
tcggcaagtc ggccatcgcc gcgatcattg cgcagtacaa gatggacaag gggcagacac   27360
ccttgtgcat cgacaccgac ccggtgaacg cgacgttcga gggctacaag gccctgaacg   27420
tccgccggct gaacatcatg gccggcgacg aaattaactc gcgcaacttc gacaccctgg   27480
tcgagctgat tgcgccgacc aaggatgacg tggtgatcga caacggtgcc agctcgttcg   27540
```

```
tgcctctgtc gcattacctc atcagcaacc aggtgccggc tctgctgcaa gaaatggggc   27600
atgagctggt catccatacc gtcgtcaccg gcggccaggc tctcctggac acggtgagcg   27660
gcttcgccca gctcgccagc cagttcccgg ccgaagcgct tttcgtggtc tggctgaacc   27720
cgtattgggg gcctatcgag catgagggca agagctttga gcagatgaag gcgtacacgg   27780
ccaacaaggc ccgcgtgtcg tccatcatcc agattccggc cctcaaggaa gaaacctacg   27840
gccgcgattt cagcgacatg ctgcaagagc ggctgacgtt cgaccaggcg ctggccgatg   27900
aatcgctcac gatcatgacg cggcaacgcc tcaagatcgt gcggcgcggc ctgtttgaac   27960
agctcgacgc ggcggccgtg ctatgagcga ccagattgaa gagctgatcc gggagattgc   28020
ggccaagcac ggcatcgccg tcggccgcga cgacccggtg ctgatcctgc ataccatcaa   28080
cgcccggctc atggccgaca gtgcggccaa gcaagaggaa atccttgccg cgttcaagga   28140
agagctggaa gggatcgccc atcgttgggg cgaggacgcc aaggccaaag cggagcggat   28200
gctgaacgcg gccctggcgg ccagcaagga cgcaatggcg aaggtaatga aggacagcgc   28260
cgcgcaggcg gccgaagcga tccgcaggga aatcgacgac ggccttggcc gccagctcgc   28320
ggccaaggtc gcggacgcgc ggcgcgtggc gatgatgaac atgatcgccg gcggcatggt   28380
gttgttcgcg gccgccctgg tggtgtgggc ctcgttatga atcgcagagg cgcagatgaa   28440
aaagcccggc gttgccgggc tttgtttttg cgttagctgg gcttgtttga caggcccaag   28500
ctctgactgc gcccgcgctc gcgctcctgg gcctgtttct tctcctgctc ctgcttgcgc   28560
atcagggcct ggtgccgtcg ggctgcttca cgcatcgaat cccagtcgcc ggccagctcg   28620
ggatgctccg cgcgcatctt gcgcgtcgcc agttcctcga tcttgggcgc gtgaatgccc   28680
atgccttcct tgatttcgcg caccatgtcc agccgcgtgt gcagggtctg caagcgggct   28740
tgctgttggg cctgctgctg ctgccaggcg gcctttgtac gcggcaggga cagcaagccg   28800
ggggcattgg actgtagctg ctgcaaacgc gcctgctgac ggtctacgag ctgttctagg   28860
cggtcctcga tgcgctccac ctggtcatgc tttgcctgca cgtagagcgc aagggtctgc   28920
tggtaggtct gctcgatggg cgcggattct aagagggcct gctgttccgt ctcggcctcc   28980
tgggccgcct gtagcaaatc ctcgccgctg ttgccgctgg actgctttac tgccggggac   29040
tgctgttgcc ctgctcgcgc cgtcgtcgca gttcggcttg cccccactcg attgactgct   29100
tcatttcgag ccgcagcgat gcgatctcgg attgcgtcaa cggacggggc agcgcggagg   29160
tgtccggctt ctccttgggt gagtcggtcg atgccatagc caaaggtttc cttccaaaat   29220
gcgtccattg ctggaccgtg tttctcattg atgcccgcaa gcatcttcgg cttgaccgcc   29280
aggtcaagcg cgccttcatg ggcggtcatg acggacgccg ccatgacctt gccgccgttg   29340
ttctcgatgt agccgcgtaa tgaggcaatg gtgccgccca tcgtcagcgt gtcatcgaca   29400
acgatgtact tctggccggg gatcacctcc ccctcgaaag tcgggttgaa cgccaggcga   29460
tgatctgaac cggctccggt tcgggcgacc ttctcccgct gcacaatgtc cgttcgacc   29520 tcaaggccaa ggcggtcggc cagaacgacc gccatcatgg ccggaatctt gttgttcccc   29580
gccgcctcga cggcgaggac tggaacgatg cggggcttgt cgtcgccgat cagcgtcttg   29640
agctgggcaa cagtgtcgtc cgaaatcagg cgctcgacca aattaagcgc gcttccgcg    29700 tcgccctgct tcgcagcctg gtattcaggc tcgttggtca agaaccaag gtcgccgttg    29760 cgaaccacct tcgggaagtc tccccacggt gcgcgctcgg ctctgctgta gctgctcaag   29820 acgcctcct tttttagccgc taaaactcta acgagtcgcc ccgcgactca acttgacgct   29880
ttcggcactt acctgtgcct tgccacttgc gtcataggtg atgcttttcg cactcccgat   29940
```

```
ttcaggtact ttatcgaaat ctgaccgggc gtgcattaca aagttcttcc ccacctgttg    30000
gtaaatgctg ccgctatctg cgtggacgat gctgccgtcg tggcgctgcg acttatcggc    30060
cttttgggcc atatagatgt tgtaaatgcc aggtttcagg gccccggctt tatctacctt    30120
ctggttcgtc catgcgcctt ggttctcggt ctggacaatt ctttgcccat tcatgaccag    30180
gaggcggtgt ttcattgggt gactcctgac ggttgcctct ggtgttaaac gtgtcctggt    30240
cgcttgccgg ctaaaaaaaa gccgacctcg gcagttcgag gccggctttc cctagagccg    30300
ggcgcgtcaa ggttgttcca tctattttag tgaactgcgt tcgatttatc agttactttc    30360
ctcccgcttt gtgtttcctc ccactcgttt ccgcgtctag ccgaccccte aacatagcgg    30420
cctcttcttg ggctgccttt gcctcttgcc gcgcttcgtc acgctcggct tgcaccgtcg    30480
taaagcgctc ggcctgcctg gccgcctctt gcgccgccaa cttcctttgc tcctggtggg    30540
cctcggcgtc ggcctgcgcc ttcgctttca ccgctgccaa ctccgtgcgc aaactctccg    30600
cttcgcgcct ggtggcgtcg cgctcgccgc gaagcgcctg catttcctgg ttggccgcgt    30660
ccagggtctt gcggctctct tctttgaatg cgcgggcgtc ctggtgagcg tagtccagct    30720
cggcgcgcag ctcctgcgct cgacgctcca cctcgtcggc ccgctgcgtc gccagcgcgg    30780
cccgctgctc ggctcctgcc agggcggtgc gtgcttcggc cagggcttgc cgctggcgtg    30840
cggccagctc ggccgcctcg gcggcctgct gctctagcaa tgtaacgcgc gcctgggctt    30900
cttccagctc gcgggcctgc gcctcgaagg cgtcggccag ctccccgcgc acggcttcca    30960
actcgttgcg ctcacgatcc cagccggctt gcgctgcctg caacgattca ttggcaaggg    31020
cctgggcggc ttgccagagg gcggccacgg cctggttgcc ggcctgctgc accgcgtccg    31080
gcacctggac tgccagcggg gcggcctgcg ccgtgcgctg gcgtcgccat tcgcgcatgc    31140
cggcgctggc gtcgttcatg ttgacgcggg cggccttacg cactgcatcc acggtcggga    31200
agttctcccg gtcgccttgc tcgaacagct cgtccgcagc cgcaaaaatg cggtcgcgcg    31260
tctctttgtt cagttccatg ttggctccgg taattggtaa gaataataat actcttacct    31320
accttatcag cgcaagagtt tagctgaaca gttctcgact taacggcagg ttttttagcg    31380
gctgaagggc aggcaaaaaa agccccgcac ggtcggcggg ggcaaagggt cagcgggaag    31440
gggattagcg ggcgtcgggc ttcttcatgc gtcggggccg cgcttcttgg gatggagcac    31500
gacgaagcgc gcacgcgcat cgtcctcggc cctatcggcc cgcgtcgcgg tcaggaactt    31560
gtcgcgcgct aggtcctccc tggtgggcac caggggcatg aactcggcct gctcgatgta    31620
ggtccactcc atgaccgcat cgcagtcgag gccgcgttcc ttcaccgtct cttgcaggtc    31680
gcggtacgcc cgctcgttga gcggctggta acgggccaat tggtcgtaaa tggctgtcgg    31740
ccatgagcgg cctttcctgt tgagccagca gccgacgacg aagccggcaa tgcaggcccc    31800
tggcacaacc aggccgacgc cgggggcagg ggatggcagc agctcgccaa ccaggaaccc    31860
cgccgcgatg atgccgatgc cggtcaacca gcccttgaaa ctatccggcc ccgaaacacc    31920
cctgcgcatt gcctggatgc tgcgccggat agcttgcaac atcaggagcc gtttctttttg    31980
ttcgtcagtc atggtccgcc ctcaccagtt gttcgtatcg gtgtcggacg aactgaaatc    32040
gcaagagctg ccggtatcgg tccagccgct gtccgtgtcg ctgctgccga agcacggcga    32100
ggggtccgcg aacgccgcag acggcgtatc cggccgcagc gcatcgccca gcatggcccc    32160
ggtcagcgag ccgccggcca ggtagcccag catggtgctg ttggtcgccc cggccaccag    32220
ggccgacgtg acgaaatcgc cgtcattccc tctggattgt tcgctgctcg gcggggcagt    32280
```

```
gcgccgcgcc ggcggcgtcg tggatggctc gggttggctg gcctgcgacg gccggcgaaa   32340
ggtgcgcagc agctcgttat cgaccggctg cggcgtcggg gccgccgcct tgcgctgcgg   32400
tcggtgttcc ttcttcggct cgcgcagctt gaacagcatg atcgcggaaa ccagcagcaa   32460
cgccgcgcct acgcctcccg cgatgtagaa cagcatcgga ttcattcttc ggtcctcctt   32520
gtagcggaac cgttgtctgt gcggcgcggg tggcccgcgc cgctgtcttt ggggatcagc   32580
cctcgatgag cgcgaccagt ttcacgtcgg caaggttcgc ctcgaactcc tggccgtcgt   32640
cctcgtactt caaccaggca tagccttccg ccggcggccg acggttgagg ataaggcggg   32700
cagggcgctc gtcgtgctcg acctggacga tggcctttt cagcttgtcc gggtccggct    32760
ccttcgcgcc cttttccttg gcgtccttac cgtcctggtc gccgtcctcg ccgtcctggc   32820
cgtcgccggc ctccgcgtca cgctcggcat cagtctggcc gttgaaggca tcgacggtgt   32880
tgggatcgcg gcccttctcg tccaggaact cgcgcagcag cttgaccgtg ccgcgcgtga   32940
tttcctgggt gtcgtcgtca agccacgcct cgacttcctc cgggcgcttc ttgaaggccg   33000
tcaccagctc gttcaccacg gtcacgtcgc gcacgcggcc ggtgttgaac gcatcggcga   33060
tcttctccgg caggtccagc agcgtgacgt gctgggtgat gaacgccggc gacttgccga   33120
tttccttggc gatatcgcct tcttcttgc ccttcgccag ctcgcggcca atgaagtcgg    33180
caatttcgcg cggggtcagc tcgttgcgtt gcaggttctc gataacctgg tcggcttcgt   33240
tgtagtcgtt gtcgatgaac gccgggatgg acttcttgcc ggcccacttc gagccacggt   33300
agcggcgggc gccgtgattg atgatatagc ggcccggctg ctcctggttc tcgcgcaccg   33360
aaatgggtga cttcaccccg cgctctttga tcgtggcacc gatttccgcg atgctctccg   33420
gggaaaagcc ggggttgtcg gccgtccgcg gctgatgcgg atcttcgtcg atcaggtcca   33480
ggtccagctc gatagggccg gaaccgcccct gagacgccgc aggagcgtcc aggaggctcg   33540
acaggtcgcc gatgctatcc aaccccaggc cggacggctg cgccgcgcct gcggcttcct   33600
gagcggccgc agcggtgttt ttcttggtgg tcttggcttg agccgcagtc attgggaaat   33660
ctccatcttc gtgaacacgt aatcagccag ggcgcgaacc tctttcgatg ccttgcgcgc   33720
ggccgttttc ttgatcttcc agaccggcac accggatgcg agggcatcgg cgatgctgct   33780
gcgcaggcca acggtggccg gaatcatcat cttggggtac gcggccagca gctcggcttg   33840
gtggcgcgcg tggcgcggat tccgcgcatc gaccttgctg gcaccatgc caaggaattg    33900
cagcttggcg ttcttctggc gcacgttcgc aatggtcgtg accatcttct tgatgccctg   33960
gatgctgtac gcctcaagct cgatggggga cagcacatag tcggccgcga agagggcggc   34020
cgccaggccg acgccaaggg tcggggccgt gtcgatcagg cacacgtcga agccttggtt   34080
cgccaggggc ttgatgttcg ccccgaacag ctcgcgggcg tcgtccagcg acagccgttc   34140
ggcgttcgcc agtaccgggt tggactcgat gagggcgagg cgcgcggcct ggccgtcgcc   34200
ggctgcgggt gcggtttcgg tccagccgcc ggcaggaca gcgccgaaca gcttgcttgc    34260
atgcaggccg gtagcaaagt ccttgagcgt gtaggacgca ttgccctggg ggtccaggtc   34320
gatcacggca acccgcaagc cgcgctcgaa aaagtcgaag gcaagatgca caagggtcga   34380
agtcttgccg acgccgcctt tctgttggc cgtgaccaaa gttttcatcg tttggtttcc    34440
tgtttttct tggcgtccgc ttcccacttc cggacgatgt acgcctgatg ttccggcaga    34500
accgccgtta ccccgcgcta cccctcgggc aagttcttgt cctcgaacgc ggcccacacg   34560
cgatgcaccg cttgcgacac tgcgcccctg gtcagtccca gcgacgttgc gaacgtcgcc   34620
tgtggcttcc catcgactaa gacgccccgc gctatctcga tggtctgctg ccccacttcc   34680
```

```
agcccctgga tcgcctcctg gaactggctt tcggtaagcc gtttcttcat ggataacacc   34740
cataatttgc tccgcgcctt ggttgaacat agcggtgaca gccgccagca catgagagaa   34800
gtttagctaa acatttctcg cacgtcaaca cctttagccg ctaaaactcg tccttggcgt   34860
aacaaaacaa aagcccggaa accgggcttt cgtctcttgc cgcttatggc tctgcacccg   34920
gctccatcac caacaggtcg cgcacgcgct tcactcggtt gcggatcgac actgccagcc   34980
caacaaagcc ggttgccgcc gccgccagga tcgcgccgat gatgccggcc acaccggcca   35040
tcgcccacca ggtcgccgcc ttccggttcc attcctgctg gtactgcttc gcaatgctgg   35100
acctcggctc accataggct gaccgctcga tggcgtatgc cgcttctccc cttggcgtaa   35160
aacccagcgc cgcaggcggc attgccatgc tgcccgccgc tttcccgacc acgacgcgcg   35220
caccaggctt gcggtccaga ccttcggcca cggcgagctg cgcaaggaca taatcagccg   35280
ccgacttggc tccacgcgcc tcgatcagct cttgcactcg cgcgaaatcc ttggcctcca   35340
cggccgccat gaatcgcgca cgcggcgaag gctccgcagg gccggcgtcg tgatcgccgc   35400
cgagaatgcc cttcaccaag ttcgacgaca cgaaaatcat gctgacggct atcaccatca   35460
tgcagacgga tcgcacgaac ccgctgaatt gaacacgagc acggcacccg cgaccactat   35520
gccaagaatg cccaaggtaa aaattgccgg ccccgccatg aagtccgtga atgccccgac   35580
ggccgaagtg aagggcaggc cgccacccag gccgccgccc tcactgcccg gcacctggtc   35640
gctgaatgtc gatgccagca cctgcggcac gtcaatgctt ccgggcgtcg cgctcgggct   35700
gatcgcccat cccgttactg ccccgatccc ggcaatggca aggactgcca gcgctgccat   35760 tttttggggtg aggccgttcg cggccgaggg gcgcagcccc tggggggatg ggaggcccgc   35820
gttagcgggc cggagggtt cgagaagggg gggcaccccc cttcggcgtg cgcggtcacg   35880
cgcacagggc gcagccctgg ttaaaaacaa ggtttataaa tattggttta aaagcaggtt   35940
aaaagacagg ttagcggtgg ccgaaaaacg ggcggaaacc cttgcaaatg ctggattttc   36000
tgcctgtgga cagcccctca aatgtcaata ggtgcgcccc tcatctgtca gcactctgcc   36060
cctcaagtgt caaggatcgc gcccctcatc tgtcagtagt cgcgcccctc aagtgtcaat   36120
accgcagggc acttatcccc aggcttgtcc acatcatctg tgggaaactc gcgtaaaatc   36180
aggcgttttc gccgatttgc gaggctggcc agctccacgt cgccggccga atcgagcct   36240 gcccctcatc tgtcaacgcc gcgccgggtg agtcggcccc tcaagtgtca acgtccgccc   36300
ctcatctgtc agtgagggcc aagttttccg cgaggtatcc acaacgccgg cggccgcggt   36360
gtctcgcaca cggcttcgac ggcgtttctg gcgcgtttgc agggccatag acggccgcca   36420
gcccagcggc gagggcaacc agcccggtga gcgtcggaaa ggcgctggaa gccccgtagc   36480
gacgcggaga gggcgagac aagccaaggg cgcaggctcg atgcgcagca cgacatagcc   36540
ggttctcgca aggacgagaa tttccctgcg gtgcccctca gtgtcaatg aaagtttcca   36600 acgcgagcca ttcgcgagag ccttgagtcc acgctagatg agagctttgt tgtaggtgga   36660
ccagttggtg attttgaact tttgctttgc cacggaacgg tctgcgttgt cgggaagatg   36720
cgtgatctga tccttcaact cagcaaaagt tcgatttatt caacaaagcc acgttgtgtc   36780
tcaaaatctc tgatgttaca ttgcacaaga taaaaatata tcatcatgaa caataaaact   36840
gtctgcttac ataaacagta ataccaagggg tgttatgagc catattcaac gggaaacgtc   36900
ttgctcgac                                                          36909
```

<210> SEQ ID NO 8

<211> LENGTH: 13019
<212> TYPE: DNA
<213> ORGANISM: artificial sequence
<220> FEATURE:
<223> OTHER INFORMATION: vector used to construct PHP23236

<400> SEQUENCE: 8

| | |
|---|---|
| gttacccgga ccgaagctta gcccgggcat gcctgcagtg cagcgtgacc cggtcgtgcc | 60 |
| cctctctaga gataatgagc attgcatgtc taagttataa aaaattacca catattttt | 120 |
| ttgtcacact tgtttgaagt gcagtttatc tatctttata catatattta aactttactc | 180 |
| tacgaataat ataatctata gtactacaat aatatcagtg ttttagagaa tcatataaat | 240 |
| gaacagttag acatggtcta aaggacaatt gagtattttg acaacaggac tctacagttt | 300 |
| tatcttttta gtgtgcatgt gttctccttt ttttttgcaa atagcttcac ctatataata | 360 |
| cttcatccat tttattagta catccattta gggtttaggg ttaatggttt ttatagacta | 420 |
| atttttttag tacatctatt ttattctatt ttagcctcta aattaagaaa actaaaactc | 480 |
| tatttagtt ttttattta ataatttaga tataaaatag aataaaataa agtgactaaa | 540 |
| aattaaacaa ataccttta agaaattaaa aaaactaagg aaacatttt cttgtttcga | 600 |
| gtagataatg ccagcctgtt aaacgccgtc gacgagtcta acggacacca accagcgaac | 660 |
| cagcagcgtc gcgtcgggcc aagcgaagca gacggcacgg catctctgtc gctgcctctg | 720 |
| gaccctctc gagagttccg ctccaccgtt ggacttgctc cgctgtcggc atccagaaat | 780 |
| tgcgtggcgg agcggcagac gtgagccggc acggcaggcg gcctcctcct cctctcacgg | 840 |
| cacggcagct acgggggatt cctttcccac cgctccttcg cttccctttc ctcgcccgcc | 900 |
| gtaataaata gacacccct ccacaccctc tttccccaac ctcgtgttgt tcggagcgca | 960 |
| cacacacaca accagatctc ccccaaatcc acccgtcggc acctccgctt caaggtacgc | 1020 |
| cgctcgtcct ccccccccc ccctctctac cttctctaga tcggcgttcc ggtccatggt | 1080 |
| tagggcccgg tagttctact tctgttcatg tttgtgttag atccgtgttt gtgttagatc | 1140 |
| cgtgctgcta gcgttcgtac acggatgcga cctgtacgtc agacacgttc tgattgctaa | 1200 |
| cttgccagtg tttctctttg gggaatcctg ggatggctct agccgttccg cagacgggat | 1260 |
| cgatttcatg atttttttg tttcgttgca tagggtttgg tttgcccttt tccttatt | 1320 |
| caatatatgc cgtgcacttg tttgtcgggt catcttttca tgcttttttt tgtcttggtt | 1380 |
| gtgatgatgt ggtctggttg ggcggtcgtt ctagatcgga gtagaattct gtttcaaact | 1440 |
| acctggtgga tttattaatt ttggatctgt atgtgtgtgc catacatatt catagttacg | 1500 |
| aattgaagat gatggatgga aatatcgatc taggataggt atacatgttg atgcgggttt | 1560 |
| tactgatgca tatacagaga tgcttttgt tcgcttggtt gtgatgatgt ggtgtggttg | 1620 |
| ggcggtcgtt cattcgttct agatcggagt agaatactgt ttcaaactac ctggtgtatt | 1680 |
| tattaatttt ggaactgtat gtgtgtgtca tacatcttca tagttacgag tttaagatgg | 1740 |
| atggaaatat cgatctagga taggtataca tgttgatgtg ggtttactg atgcatatac | 1800 |
| atgatggcat atgcagcatc tattcatatg ctctaacctt gagtacctat ctattataat | 1860 |
| aaacaagtat gttttataat tattttgatc ttgatatact tggatgatgg catatgcagc | 1920 |
| agctatatgt ggattttttt agccctgcct tcatacgcta tttatttgct tggtactgtt | 1980 |
| tcttttgtcg atgctcaccc tgttgtttgg tgttacttct gcaggtcgac tctagaggat | 2040 |
| ccacaagttt gtacaaaaaa gctgaacgag aaacgtaaaa tgatataaat atcaatatat | 2100 |
| taaattagat tttgcataaa aaacagacta cataatactg taaaacacaa catatccagt | 2160 |

```
cactatggcg gccgcattag gcacccagg ctttacactt tatgcttccg gctcgtataa    2220
tgtgtggatt ttgagttagg atttaaatac gcgttgatcc ggcttactaa aagccagata    2280
acagtatgcg tatttgcgcg ctgattttg cggtataaga atatatactg atatgtatac     2340
ccgaagtatg tcaaaaagag gtatgctatg aagcagcgta ttacagtgac agttgacagc    2400
gacagctatc agttgctcaa ggcatatatg atgtcaatat ctccggtctg gtaagcacaa    2460
ccatgcagaa tgaagcccgt cgtctgcgtg ccgaacgctg gaaagcggaa aatcaggaag    2520
ggatggctga ggtcgcccgg tttattgaaa tgaacggctc ttttgctgac gagaacaggg    2580
gctggtgaaa tgcagtttaa ggtttacacc tataaaagag agagccgtta tcgtctgttt    2640
gtggatgtac agagtgatat cattgacacg cccggtcgac ggatggtgat cccctggcc     2700 agtgcacgtc tgctgtcaga taaagtctcc cgtgaacttt acccggtggt gcatatcggg    2760
gatgaaagct ggcgcatgat gaccaccgat atggccagtg tgccggtctc cgttatcggg    2820
gaagaagtgg ctgatctcag ccaccgcgaa aatgacatca aaaacgccat taacctgatg    2880
ttctggggaa tataaatgtc aggctccctt atacacagcc agtctgcagg tcgaccatag    2940
tgactggata tgttgtgttt tacagtatta tgtagtctgt tttttatgca aaatctaatt    3000
taatatattg atatttatat cattttacgt ttctcgttca gctttcttgt acaaagtggt    3060
gttaacctag acttgtccat cttctggatt ggccaactta attaatgtat gaaataaaag    3120
gatgcacaca tagtgacatg ctaatcacta taatgtgggc atcaaagttg tgtgttatgt    3180
gtaattacta gttatctgaa taaaagagaa agagatcatc catatttctt atcctaaatg    3240
aatgtcacgt gtcttttataa ttctttgatg aaccagatgc atttcattaa ccaaatccat    3300
atacatataa atattaatca tatataatta atatcaattg ggttagcaaa acaaatctag    3360
tctaggtgtg ttttgcgaat tgcggccgcc accgcggtgg agctcgaatt ccggtccggg    3420
tcacctttgt ccaccaagat ggaactgcgg ccgctcatta attaagtcag gcgcgcctct    3480
agttgaagac acgttcatgt cttcatcgta agaagacact cagtagtctt cggccagaat    3540
ggccatctgg attcagcagg cctagaaggc catttaaatc ctgaggatct ggtcttccta    3600
aggacccggg atatcggacc gattaaactt taattcggtc cgaagcttgc atgcctgcag    3660
tgcagcgtga cccggtcgtg cccctctcta gagataatga gcattgcatg tctaagttat    3720
aaaaaattac cacatatttt ttttgtcaca cttgtttgaa gtgcagttta tctatcttta    3780
tacatatatt taaactttac tctacgaata atataatcta tagtactaca ataatatcag    3840
tgttttagag aatcatataa atgaacagtt agacatggtc taaaggacaa ttgagtattt    3900
tgacaacagg actctacagt tttatctttt tagtgtgcat gtgttctcct ttttttttgc    3960 aaaatagcttc acctatataa tacttcatcc attttattag tacatccatt tagggtttag    4020
ggttaatggt ttttatagac taattttttt agtacatcta ttttattcta ttttagcctc    4080
taaattaaga aaactaaaac tctattttag tttttttatt taataattta gatataaaat    4140
agaataaaat aaagtgacta aaaattaaac aaatacccct taagaaatta aaaaaactaa    4200
ggaaacattt ttcttgtttc gagtagataa tgccagcctg ttaaacgccg tcgacgagtc    4260
taacggacac caaccagcga accagcagcg tcgcgtcggg ccaagcgaag cagacggcac    4320
ggcatctctg tcgctgcctc tggaccctc tcgagagttc cgctccaccg ttggacttgc    4380
tccgctgtcg gcatccagaa attgcgtggc ggagcggcag acgtgagccg gcacggcagg    4440
cggcctcctc ctcctctcac ggcaccggca gctacggggg attcctttcc caccgctcct    4500
```

-continued

```
tcgctttccc ttcctcgccc gccgtaataa atagacaccc cctccacacc ctctttcccc    4560
aacctcgtgt tgttcggagc gcacacacac acaaccagat ctcccccaaa tccacccgtc    4620
ggcacctccg cttcaaggta cgccgctcgt cctcccccc ccccctctct accttctcta    4680
gatcggcgtt ccggtccatg catggttagg gcccggtagt tctacttctg ttcatgtttg    4740
tgttagatcc gtgtttgtgt tagatccgtg ctgctagcgt tcgtacacgg atgcgacctg    4800
tacgtcagac acgttctgat tgctaacttg ccagtgtttc tctttgggga atcctgggat    4860
ggctctagcc gttccgcaga cgggatcgat ttcatgattt tttttgtttc gttgcatagg    4920
gtttggtttg ccctttctcct ttatttcaat atatgccgtg cacttgtttg tcgggtcatc    4980
ttttcatgct ttttttgtc ttggttgtga tgatgtggtc tggttgggcg gtcgttctag    5040
atcggagtag aattctgttt caaactacct ggtggattta ttaattttgg atctgtatgt    5100
gtgtgccata catattcata gttacgaatt gaagatgatg gatggaaata tcgatctagg    5160
ataggtatac atgttgatgc gggttttact gatgcatata cagagatgct ttttgttcgc    5220
ttggttgtga tgatgtggtg tggttgggcg gtcgttcatt cgttctagat cggagtagaa    5280
tactgtttca aactacctgg tgtatttatt aattttggaa ctgtatgtgt gtgtcataca    5340
tcttcatagt tacgagttta agatggatgg aaatatcgat ctaggatagg tatacatgtt    5400
gatgtgggtt ttactgatgc atatacatga tggcatatgc agcatctatt catatgctct    5460
aaccttgagt acctatctat tataataaac aagtatgttt tataattatt ttgatcttga    5520
tatacttgga tgatggcata tgcagcagct atatgtggat tttttagcc ctgccttcat    5580 acgctattta tttgcttggt actgttttctt ttgtcgatgc tcaccctgtt gtttggtgtt    5640
acttctgcag gtcgacttta acttagccta ggatccacac gacaccatgt cccccgagcg    5700
ccgccccgtc gagatccgcc cggccaccgc cgccgacatg gccgccgtgt gcgacatcgt    5760
gaaccactac atcgagacct ccaccgtgaa cttccgcacc gagccgcaga ccccgcagga    5820
gtggatcgac gacctggagc gcctccagga ccgctacccg tggctcgtgg ccgaggtgga    5880
gggcgtggtg gccggcatcg cctacgccgg cccgtggaag gcccgcaacg cctacgactg    5940
gaccgtggag tccaccgtgt acgtgtccca ccgccaccag cgcctcggcc tcggctccac    6000
cctctacacc cacctcctca agagcatgga ggcccagggc ttcaagtccg tggtggccgt    6060
gatcggcctc ccgaacgacc cgtccgtgcg cctccacgag gccctcggct acaccgcccg    6120 cggcacccte cgcgccgccg gctacaagca cggcggctgg cacgacgtcg gcttctggca    6180
gcgcgacttc gagctgccgg ccccgccgcg ccggtgcgc ccggtgacgc agatctgagt    6240
cgaaacctag acttgtccat cttctggatt ggccaactta attaatgtat gaaataaaag    6300
gatgcacaca tagtgacatg ctaatcacta taatgtgggc atcaaagttg tgtgttatgt    6360
gtaattacta gttatctgaa taaaagagaa agagatcatc catatttctt atcctaaatg    6420
aatgtcacgt gtctttataa ttcttttgatg aaccagatgc atttcattaa ccaaatccat    6480
atacatataa atattaatca tatataatta atatcaattg ggttagcaaa acaaatctag    6540
tctaggtgtg ttttgcgaat tgcggccgcc accgcggtgg agctcgaatt cattccgatt    6600
aatcgtggcc tcttgctctt caggatgaag agctatgttt aaacgtgcaa gcgctactag    6660
acaattcagt acattaaaaa cgtccgcaat gtgttattaa gttgtctaag cgtcaatttg    6720
tttacaccac aatatatcct gccaccagcc agccaacagc tccccgaccg gcagctcggc    6780
acaaaatcac cactcgatac aggcagccca tcagtccggg acggcgtcag cgggagagcc    6840
gttgtaaggc ggcagacttt gctcatgtta ccgatgctat tcggaagaac ggcaactaag    6900
```

```
ctgccgggtt tgaaacacgg atgatctcgc ggagggtagc atgttgattg taacgatgac    6960
agagcgttgc tgcctgtgat caaatatcat ctccctcgca gagatccgaa ttatcagcct    7020
tcttattcat ttctcgctta accgtgacag gctgtcgatc ttgagaacta tgccgacata    7080
ataggaaatc gctggataaa gccgctgagg aagctgagtg gcgctatttc tttagaagtg    7140
aacgttgacg atcgtcgacc gtaccccgat gaattaattc ggacgtacgt tctgaacaca    7200
gctggatact tacttgggcg attgtcatac atgacatcaa caatgtaccc gtttgtgtaa    7260
ccgtctcttg gaggttcgta tgacactagt ggttcccctc agcttgcgac tagatgttga    7320
ggcctaacat tttattagag agcaggctag ttgcttagat acatgatctt caggccgtta    7380
tctgtcaggg caagcgaaaa ttggccattt atgacgacca atgccccgca gaagctccca    7440
tctttgccgc catagacgcc gcgccccccct tttggggtgt agaacatcct tttgccagat    7500
gtggaaaaga agttcgttgt cccattgttg gcaatgacgt agtagccggc gaaagtgcga    7560
gacccatttg cgctatatat aagcctacga tttccgttgc gactattgtc gtaattggat    7620
gaactattat cgtagttgct ctcagagttg tcgtaatttg atggactatt gtcgtaattg    7680
cttatggagt tgtcgtagtt gcttggagaa atgtcgtagt tggatgggga gtagtcatag    7740
ggaagacgag cttcatccac taaaacaatt ggcaggtcag caagtgcctg ccccgatgcc    7800
atcgcaagta cgaggcttag aaccaccttc aacagatcgc gcatagtctt ccccagctct    7860
ctaacgcttg agttaagccg cgccgcgaag cggcgtcggc ttgaacgaat tgttagacat    7920
tatttgccga ctaccttggt gatctcgcct ttcacgtagt gaacaaattc ttccaactga    7980
tctgcgcgcg aggccaagcg atcttcttgt ccaagataag cctgcctagc ttcaagtatg    8040
acgggctgat actgggccgg caggcgctcc attgcccagt cggcagcgac atccttcggc    8100
gcgattttgc cggttactgc gctgtaccaa atgcgggaca acgtaagcac tacatttcgc    8160
tcatcgccag cccagtcggg cggcgagttc catagcgtta aggtttcatt tagcgcctca    8220
aatagatcct gttcaggaac cggatcaaag agttcctccg ccgctggacc taccaaggca    8280
acgctatgtt ctcttgcttt tgtcagcaag atagccagat caatgtcgat cgtggctggc    8340
tcgaagatac ctgcaagaat gtcattgcgc tgccattctc caaattgcag ttcgcgctta    8400
gctggataac gccacggaat gatgtcgtcg tgcacaacaa tggtgacttc tacagcgcgg    8460
agaatctcgc tctctccagg ggaagccgaa gtttccaaaa ggtcgttgat caaagctcgc    8520
cgcgttgttt catcaagcct tacagtcacc gtaaccagca aatcaatatc actgtgtggc    8580
ttcaggccgc catccactgc ggagccgtac aaatgtacgg ccagcaacgt cggttcgaga    8640
tggcgctcga tgacgccaac tacctctgat agttgagtcg atacttcggc gatcaccgct    8700
tccctcatga tgtttaactc ctgaattaag ccgcgccgcg aagcggtgtc ggcttgaatg    8760
aattgttagg cgtcatcctg tgctcccgag aaccagtacc agtacatcgc tgtttcgttc    8820
gagacttgag gtctagtttt atacgtgaac aggtcaatgc cgccgagagt aaagccacat    8880
tttgcgtaca aattgcaggc aggtacattg ttcgtttgtg tctctaatcg tatgccaagg    8940
agctgtctgc ttagtgccca ctttttcgca aattcgatga gactgtgcgc gactcctttg    9000
cctcggtgcg tgtgcgacac aacaatgtgt tcgatagagg ctagatcgtt ccatgttgag    9060
ttgagttcaa tcttcccgac aagctcttgg tcgatgaatg cgccatagca agcagagtct    9120
tcatcagagt catcatccga gatgtaatcc ttccggtagg ggctcacact tctggtagat    9180
agttcaaagc cttggtcgga taggtgcaca tcgaacactt cacgaacaat gaaatggttc    9240
```

```
tcagcatcca atgtttccgc cacctgctca gggatcaccg aaatcttcat atgacgccta    9300
acgcctggca cagcggatcg caaacctggc gcggcttttg cacaaaagg cgtgacaggt     9360 ttgcgaatcc gttgctgcca cttgttaacc cttttgccag atttggtaac tataatttat    9420
gttagaggcg aagtcttggg taaaaactgg cctaaaattg ctggggattt caggaaagta    9480
aacatcacct tccggctcga tgtctattgt agatatatgt agtgtatcta cttgatcggg    9540
ggatctgctg cctcgcgcgt ttcggtgatg acggtgaaaa cctctgacac atgcagctcc    9600
cggagacggt cacagcttgt ctgtaagcgg atgccgggag cagacaagcc cgtcagggcg    9660
cgtcagcggg tgttggcggg tgtcggggcg cagccatgac ccagtcacgt agcgatagcg    9720
gagtgtatac tggcttaact atgcggcatc agagcagatt gtactgagag tgcaccatat    9780
gcggtgtgaa ataccgcaca gatgcgtaag gagaaaatac cgcatcaggc gctcttccgc    9840
ttcctcgctc actgactcgc tgcgctcggt cgttcggctg cggcgagcgg tatcagctca    9900
ctcaaaggcg gtaatacggt tatccacaga atcaggggat aacgcaggaa agaacatgtg    9960
agcaaaaggc cagcaaaagg ccaggaaccg taaaaaggcc gcgttgctgg cgtttttcca   10020
taggctccgc cccctgacg agcatcacaa aaatcgacgc tcaagtcaga ggtggcgaaa    10080
cccgacagga ctataaagat accaggcgtt tccccctgga agctccctcg tgcgctctcc    10140
tgttccgacc ctgccgctta ccggatacct gtccgccttt ctcccttcgg aagcgtggc    10200 gctttctcat agctcacgct gtaggtatct cagttcggtg taggtcgttc gctccaagct    10260
gggctgtgtg cacgaacccc ccgttcagcc cgaccgctgc gccttatccg gtaactatcg    10320
tcttgagtcc aacccggtaa gacacgactt atcgccactg gcagcagcca ctggtaacag    10380
gattagcaga gcgaggtatg taggcggtgc tacagagttc ttgaagtggt ggcctaacta    10440
cggctacact agaaggacag tatttggtat ctgcgctctg ctgaagccag ttaccttcgg    10500
aaaaagagtt ggtagctctt gatccggcaa acaaaccacc gctggtagcg gtggtttttt    10560
tgtttgcaag cagcagatta cgcgcagaaa aaaaggatct caagaagatc ctttgatctt    10620
ttctacgggg tctgacgctc agtggaacga aaactcacgt taagggattt tggtcatgag    10680
attatcaaaa aggatcttca cctagatcct tttaaattaa aaatgaagtt ttaaatcaat    10740
ctaaagtata tatgagtaaa cttggtctga cagttaccaa tgcttaatca gtgaggcacc    10800
tatctcagcg atctgtctat ttcgttcatc catagttgcc tgactccccg tcgtgtagat    10860
aactacgata cgggagggct taccatctgg ccccagtgct gcaatgatac cgcgagaccc    10920
acgctcaccg gctccagatt tatcagcaat aaaccagcca gccggaaggg ccgagcgcag    10980
aagtggtcct gcaactttat ccgcctccat ccagtctatt aattgttgcc gggaagctag    11040
agtaagtagt tcgccagtta atagtttgcg caacgttgtt gccattgctg cagggggggg    11100 ggggggggg gacttccatt gttcattcca cggacaaaaa cagagaaagg aaacgacaga    11160
ggccaaaaag cctcgctttc agcacctgtc gtttcctttc ttttcagagg gtatttaaa     11220 taaaaacatt aagttatgac gaagaagaac ggaaacgcct aaaccggaa aattttcata    11280 aatagcgaaa acccgcgagg tcgccgcccc gtaacctgtc ggatcaccgg aaaggacccg    11340
taaagtgata atgattatca tctacatatc acaacgtgcg tggaggccat caaaccacgt    11400
caaataatca attatgacgc aggtatcgta ttaattgatc tgcatcaact taacgtaaaa    11460
acaacttcag acaatacaaa tcagcgacac tgaatacggg gcaacctcat gtcccccccc    11520
cccccccccc tgcaggcatc gtggtgtcac gctcgtcgtt tggtatggct tcattcagct    11580
ccggttccca acgatcaagg cgagttacat gatcccccat gttgtgcaaa aaagcggtta    11640
```

```
gctccttcgg tcctccgatc gttgtcagaa gtaagttggc cgcagtgtta tcactcatgg   11700
ttatggcagc actgcataat tctcttactg tcatgccatc cgtaagatgc ttttctgtga   11760
ctggtgagta ctcaaccaag tcattctgag aatagtgtat gcggcgaccg agttgctctt   11820
gcccggcgtc aacacgggat aataccgcgc cacatagcag aactttaaaa gtgctcatca   11880
ttggaaaacg ttcttcgggg cgaaaactct caaggatctt accgctgttg agatccagtt   11940
cgatgtaacc cactcgtgca cccaactgat cttcagcatc ttttactttc accagcgttt   12000
ctgggtgagc aaaaacagga aggcaaaatg ccgcaaaaaa gggaataagg gcgacacgga   12060
aatgttgaat actcatactc ttcctttttc aatattattg aagcatttat cagggttatt   12120
gtctcatgag cggatacata tttgaatgta tttagaaaaa taaacaaata ggggttccgc   12180
gcacatttcc ccgaaaagtg ccacctgacg tctaagaaac cattattatc atgacattaa   12240
cctataaaaa taggcgtatc acgaggccct ttcgtcttca agaattggtc gacgatcttg   12300
ctgcgttcgg atattttcgt ggagttcccg ccacagaccc ggattgaagg cgagatccag   12360
caactcgcgc cagatcatcc tgtgacggaa ctttggcgcg tgatgactgg ccaggacgtc   12420
ggccgaaaga gcgacaagca gatcacgctt ttcgacagcg tcggatttgc gatcgaggat   12480
ttttcggcgc tgcgctacgt ccgcgaccgc gttgagggat caagccacag cagcccactc   12540
gaccttctag ccgacccaga cgagccaagg gatcttttg gaatgctgct ccgtcgtcag   12600
gctttccgac gtttgggtgg ttgaacagaa gtcattatcg tacggaatgc caagcactcc   12660 cgagggaac cctgtggttg gcatgcacat acaaatggac gaacggataa acctttcac    12720 gcccttttaa atatccgtta ttctaataaa cgctctttc tcttaggttt acccgccaat    12780
atatcctgtc aaacactgat agtttaaact gaaggcggga acgacaatc tgatcatgag    12840 cggagaatta agggagtcac gttatgaccc ccgccgatga cgcgggacaa gccgttttac    12900
gtttggaact gacagaaccg caacgttgaa ggagccactc agcaagctgg tacgattgta    12960
atacgactca ctataggcgc aattgagcgc tgtttaaacg ctcttcaact ggaagagcg     13019
```

<210> SEQ ID NO 9
<211> LENGTH: 15663
<212> TYPE: DNA
<213> ORGANISM: Artificial Sequence
<220> FEATURE:
<223> OTHER INFORMATION: PHP28647 destination vector for use with maize
      inbred-derived lines

<400> SEQUENCE: 9

```
gtttacccgc caatatatcc tgtcaaacac tgatagttta aactgaaggc gggaaacgac    60
aatctgatca tgagcggaga attaagggag tcacgttatg accccgccg atgacgcggg   120 acaagccgtt ttacgtttgg aactgacaga accgcaacgt tgaaggagcc actcagcaag   180
ctggtacgat tgtaatacga ctcactatag ggcgaattga gcgctgttta aacgctcttc   240
aactggaaga gcggttaccc ggaccgaagc ttgcatgcct gcagtgcagc gtgacccggt   300 cgtgccctc tctagagata atgagcattg catgtctaag ttataaaaaa ttaccacata   360
ttttttttgt cacacttgtt tgaagtgcag tttatctatc tttatacata tatttaaact   420
ttactctacg aataatataa tctatagtac tacaataata tcagtgtttt agagaatcat   480
ataaatgaac agttagacat ggtctaaagg acaattgagt attttgacaa caggactcta   540
cagttttatc tttttagtgt gcatgtgttc tccttttttt ttgcaaatag cttcacctat   600
ataatacttc atccatttta ttagtacatc catttagggt ttagggttaa tggtttttat   660
```

```
agactaattt ttttagtaca tctattttat tctattttag cctctaaatt aagaaaacta      720
aaactctatt ttagttttt tatttaataa tttagatata aaatagaata aaataaagtg       780
actaaaaatt aaacaaatac cctttaagaa attaaaaaaa ctaaggaaac atttttcttg      840
tttcgagtag ataatgccag cctgttaaac gccgtcgacg agtctaacgg acaccaacca      900
gcgaaccagc agcgtcgcgt cgggccaagc gaagcagacg gcacggcatc tctgtcgctg      960
cctctggacc cctctcgaga gttccgctcc accgttggac ttgctccgct gtcggcatcc     1020
agaaattgcg tggcggagcg gcagacgtga gccggcacgg caggcggcct cctcctcctc     1080
tcacggcacg gcagctacgg gggattcctt tcccaccgct ccttcgcttt cccttcctcg     1140
cccgccgtaa taaatagaca cccctccac accctctttc cccaacctcg tgttgttcgg      1200
agcgcacaca cacacaacca gatctccccc aaatccaccc gtcggcacct ccgcttcaag     1260
gtacgccgct cgtcctcccc ccccccccct ctctaccttc tctagatcgg cgttccggtc     1320
catggttagg gcccggtagt tctacttctg ttcatgtttg tgttagatcc gtgtttgtgt     1380
tagatccgtg ctgctagcgt tcgtacacgg atgcgacctg tacgtcagac acgttctgat     1440
tgctaacttg ccagtgtttc tctttgggga atcctgggat ggctctagcc gttccgcaga     1500
cgggatcgat ttcatgattt ttttgtttc gttgcatagg gtttggtttg ccttttcct      1560 ttatttcaat atatgccgtg cacttgtttg tcggtcatc ttttcatgct ttttttgtc      1620 ttggttgtga tgatgtggtc tggttgggcg gtcgttctag atcggagtag aattctgttt     1680
caaactacct ggtggattta ttaattttgg atctgtatgt gtgtgccata catattcata     1740
gttacgaatt gaagatgatg gatggaaata tcgatctagg ataggtatac atgttgatgc     1800
gggttttact gatgcatata cagagatgct ttttgttcgc ttggttgtga tgatgtggtg     1860
tggttgggcg gtcgttcatt cgttctagat cggagtagaa tactgtttca aactacctgg     1920
tgtatttatt aattttggaa ctgtatgtgt gtgtcataca tcttcatagt tacgagttta     1980
agatggatgg aaatatcgat ctaggatagg tatacatgtt gatgtgggtt ttactgatgc     2040
atatacatga tggcatatgc agcatctatt catatgctct aaccttgagt acctatctat     2100
tataataaac aagtatgttt tataattatt ttgatcttga tatacttgga tgatggcata     2160
tgcagcagct atatgtggat ttttttagcc ctgccttcat acgctattta tttgcttggt     2220
actgtttctt ttgtcgatgc tcaccctgtt gtttggtgtt acttctgcag gtcgactcta     2280
gaggatctac aagtttgtac aaaaaagctg aacgagaaac gtaaaatgat ataaatatca     2340
atatattaaa ttagattttg cataaaaaac agactacata atactgtaaa acacaacata     2400
tccagtcact atggcggccg cattaggcac cccaggcttt acactttatg cttccggctc     2460
gtataatgtg tggattttga gttaggatcc ggcgagattt tcaggagcta aggaagctaa     2520
aatggagaaa aaaatcactg gatataccac cgttgatata tcccaatggc atcgtaaaga     2580
acattttgag gcatttcagt cagttgctca atgtacctat aaccagaccg ttcagctgga     2640
tattacggcc ttttttaaga ccgtaaagaa aaataagcac aagttttatc cggcctttat     2700
tcacattctt gcccgcctga tgaatgctca tccggaattc cgtatggcaa tgaaagacgg     2760
tgagctggtg atatgggata gtgttcaccc ttgttacacc gttttccatg agcaaactga     2820
aacgttttca tcgctctgga gtgaatacca cgacgatttc cggcagtttc tacacatata     2880
ttcgcaagat gtggcgtgtt acggtgaaaa cctggcctat ttccctaaag ggtttattga     2940
gaatatgttt ttcgtctcag ccaatccctg ggtgagtttc accagttttg atttaaacgt     3000
```

```
ggccaatatg gacaacttct tcgcccccgt tttccaccatg gcaaatatt atacgcaagg    3060
cgacaaggtg ctgatgccgc tggcgattca ggttcatcat gccgtctgtg atggcttcca    3120
tgtcggcaga atgcttaatg aattacaaca gtactgcgat gagtggcagg cgggggcgta    3180
aacgcgtgga tccggcttac taaaagccag ataacagtat gcgtatttgc gcgctgattt    3240
ttgcggtata agaatatata ctgatatgta tacccgaagt atgtcaaaaa gaggtatgct    3300
atgaagcagc gtattacagt gacagttgac agcgacagct atcagttgct caaggcatat    3360
atgatgtcaa tatctccggt ctggtaagca caaccatgca gaatgaagcc cgtcgtctgc    3420
gtgccgaacg ctggaaagcg gaaaatcagg aagggatggc tgaggtcgcc cggtttattg    3480
aaatgaacgg ctcttttgct gacgagaaca ggggctggtg aaatgcagtt taaggtttac    3540
acctataaaa gagagagccg ttatcgtctg tttgtggatg tacagagtga tattattgac    3600
acgcccgggc gacggatggt gatcccctg gccagtgcac gtctgctgtc agataaagtc    3660
tcccgtgaac tttacccggt ggtgcatatc ggggatgaaa gctggcgcat gatgaccacc    3720
gatatgccca gtgtgccggt ctccgttatc ggggaagaag tggctgatct cagccaccgc    3780
gaaaatgaca tcaaaaacgc cattaacctg atgttctggg aatataaat gtcaggctcc    3840
cttatacaca gccagtctgc aggtcgacca tagtgactgg atatgttgtg ttttacagta    3900
ttatgtagtc tgttttttat gcaaaatcta atttaatata ttgatattta tcatttta    3960
cgtttctcgt tcagctttct tgtacaaagt ggtgttaacc tagacttgtc catcttctgg    4020
attggccaac ttaattaatg tatgaaataa aaggatgcac acatagtgac atgctaatca    4080
ctataatgtg ggcatcaaag ttgtgtgtta tgtgtaatta ctagttatct gaataaaaga    4140
gaaagagatc atccatattt cttatcctaa atgaatgtca cgtgtcttta taattctttg    4200
atgaaccaga tgcatttcat taaccaaatc catatacata taaatattaa tcatatataa    4260
ttaatatcaa ttgggttagc aaaacaaatc tagtctaggt gtgttttgcg aattgcggcc    4320
gccaccgcgg tggagctcga attccggtcc gggtcaccttt tgtccaccaa gatgaactg    4380
cggccgctca ttaattaagt caggcgcgcc tctagttgaa gacacgttca tgtcttcatc    4440
gtaagaagac actcagtagt cttccggccag aatggccatc tggattcagc aggcctagaa    4500
ggccatttaa atcctgagga tctggtcttc ctaaggaccc gggatatcgg accgaagctg    4560
gccgctctag aactagtgga tctcgatgtg tagtctacga gaagggttaa ccgtctcttc    4620
gtgagaataa ccgtggccta aaaataagcc gatgaggata aataaaatgt ggtggtacag    4680
tacttcaaga ggtttactca tcaagaggat gcttttccga tgagctctag tagtacatcg    4740
gacctcacat acctccattg tggtgaaata ttttgtgctc atttagtgat gggtaaattt    4800
tgtttatgtc actctaggtt ttgacatttc agttttgcca ctcttaggtt ttgacaaata    4860
atttccattc cgcggcaaaa gcaaacaat tttatttac ttttaccact cttagctttc    4920
acaatgtatc acaaatgcca ctctagaaat tctgtttatg ccacagaatg tgaaaaaaaa    4980
cactcactta tttgaagcca aggtgttcat ggcatgaaa tgtgacataa agtaacgttc    5040
gtgtataaga aaaaattgta ctcctcgtaa caagagacgg aaacatcatg agacaatcgc    5100
gtttggaagg ctttgcatca cctttggatg atgcgcatga atggagtcgt ctgcttgcta    5160
gccttcgcct accgcccact gagtccgggc ggcaactacc atcggcgaac gacccagctg    5220
acctctaccg accggacttg aatgcgctac cttcgtcagc gacgatggcc gcgtacgctg    5280
gcgacgtgcc cccgcatgca tggcggcaca tggcgagctc agaccgtgcg tggctggcta    5340
caaatacgta ccccgtgagt gccctagcta gaaacttaca cctgcaactg cgagagcgag    5400
```

```
cgtgtgagtg tagccgagta gatccccegg gctgcaggtc gactctagag gatccaccgg    5460
tcgccaccat ggcctcctcc gagaacgtca tcaccgagtt catgcgcttc aaggtgcgca    5520
tggagggcac cgtgaacggc cacgagttcg agatcgaggg cgagggcgag ggccgcccct    5580
acgagggcca caacaccgtg aagctgaagg tgaccaaggg cggccccctg cccttcgcct    5640
gggacatcct gtccccccag ttccagtacg gctccaaggt gtacgtgaag caccccgccg    5700
acatccccga ctacaagaag ctgtccttcc ccgagggctt caagtgggag cgcgtgatga    5760
acttcgagga cggcggcgtg gcgaccgtga cccaggactc ctccctgcag gacggctgct    5820
tcatctacaa ggtgaagttc atcggcgtga acttcccctc cgacggcccc gtgatgcaga    5880
agaagaccat gggctgggag gcctccaccg agcgcctgta ccccgcgac ggcgtgctga    5940
agggcgagac ccacaaggcc ctgaagctga aggacggcgg ccactacctg gtggagttca    6000
agtccatcta catggccaag aagcccgtgc agctgcccgg ctactactac gtggacgcca    6060
agctggacat cacctcccac aacgaggact acaccatcgt ggagcagtac gagcgcaccg    6120
agggccgcca ccacctgttc ctgtagcggc ccatggatat tcgaacgcgt aggtaccaca    6180
tggttaacct agacttgtcc atcttctgga ttggccaact taattaatgt atgaaataaa    6240
aggatgcaca catagtgaca tgctaatcac tataatgtgg gcatcaaagt tgtgtgttat    6300
gtgtaattac tagttatctg aataaaagag aaagagatca tccatatttc ttatcctaaa    6360
tgaatgtcac gtgtctttat aattctttga tgaaccagat gcatttcatt aaccaaatcc    6420
atatacatat aaatattaat catatataat taatatcaat tgggttagca aaacaaatct    6480
agtctaggtg tgttttgcga atgcggccgc caccgcggtg gagctcgaat tccggtccga    6540
agcttgcatg cctgcagtgc agcgtgaccc ggtcgtgccc ctctctagag ataatgagca    6600
ttgcatgtct aagttatata aaattaccac atattttttt tgtcacactt gtttgaagtg    6660
cagtttatct atctttatac atatatttaa actttactct acgaataata taatctatag    6720
tactacaata atatcagtgt tttagagaat catataaatg aacagttaga catggtctaa    6780
aggacaattg agtatttga caacaggact ctacagtttt atcttttag tgtgcatgtg    6840
ttctcctttt tttttgcaaa tagcttcacc tatataaatac ttcatccatt ttattagtac    6900
atccatttag ggtttagggt taatggtttt tatagactaa ttttttttagt acatctattt    6960
tattctattt tagcctctaa attaagaaaa ctaaaactct attttagttt ttttatttaa    7020
taatttagat ataaaataga ataaaataaa gtgactaaaa attaaacaaa taccctttaa    7080
gaaattaaaa aaactaagga aacattttc ttgtttcgag tagataatgc cagcctgtta    7140
aacgccgtcg acgagtctaa cggacaccaa ccagcgaacc agcagcgtcg cgtcgggcca    7200
agcgaagcag acggcacggc atctctgtcg ctgcctctgg acccctctcg agagttccgc    7260
tccaccgttg gacttgctcc gctgtcggca tccagaaatt gcgtggcgga gcggcagacg    7320
tgagccggca cggcaggcgg cctcctcctc ctctcacggc accggcagct acggggatt    7380
cctttcccac cgctccttcg ctttcccttc ctcgcccgcc gtaataaata gacacccct    7440
ccacaccctc tttccccaac ctcgtgttgt tcggagcgca cacacacaca accagatctc    7500
ccccaaatcc acccgtcggc acctccgctt caaggtacgc cgctcgtcct ccccccccc    7560
cctctctacc ttctctagat cggcgttccg gtccatgcat ggttagggcc cggtagttct    7620
acttctgttc atgtttgtgt tagatccgtg tttgtgttag atccgtgctg ctagcgttcg    7680
tacacggatg cgacctgtac gtcagacacg ttctgattgc taacttgcca gtgtttctct    7740
```

```
ttggggaatc ctgggatggc tctagccgtt ccgcagacgg gatcgatttc atgattttt     7800 ttgtttcgtt gcatagggtt tggtttgccc ttttccttta tttcaatata tgccgtgcac    7860
ttgtttgtcg ggtcatcttt tcatgctttt ttttgtcttg gttgtgatga tgtggtctgg    7920
ttgggcggtc gttctagatc ggagtagaat tctgtttcaa actacctggt ggatttatta    7980
attttggatc tgtatgtgtg tgccatacat attcatagtt acgaattgaa gatgatggat    8040
ggaaatatcg atctaggata ggtatacatg ttgatgcggg ttttactgat gcatatacag    8100
agatgctttt tgttcgcttg gttgtgatga tgtggtgtgg ttgggcggtc gttcattcgt    8160
tctagatcgg agtagaatac tgtttcaaac tacctggtgt attattaat tttggaactg     8220 tatgtgtgtg tcatacatct tcatagttac gagtttaaga tggatggaaa tatcgatcta    8280
ggataggtat acatgttgat gtgggtttta ctgatgcata tacatgatgg catatgcagc    8340
atctattcat atgctctaac cttgagtacc tatctattat aataaacaag tatgttttat    8400
aattattttg atcttgatat acttggatga tggcatatgc agcagctata tgtggatttt    8460
tttagccctg ccttcatacg ctatttattt gcttggtact gtttcttttg tcgatgctca    8520
ccctgttgtt tggtgttact tctgcaggtc gactttaact tagcctagga tccacacgac    8580
accatgtccc ccgagcgccg ccccgtcgag atccgcccgg ccaccgccgc cgacatggcc    8640
gccgtgtgcg acatcgtgaa ccactacatc gagacctcca ccgtgaactt ccgcaccgag    8700
ccgcagaccc cgcaggagtg gatcgacgac ctggagcgcc tccaggaccg ctacccgtgg    8760
ctcgtggccg aggtggaggg cgtggtggcc ggcatcgcct acgccggccc gtggaaggcc    8820
cgcaacgcct acgactggac cgtggagtcc accgtgtacg tgtcccaccg ccaccagcgc    8880
ctcggcctcg gctccaccct ctacacccac ctcctcaaga gcatggaggc ccagggcttc    8940
aagtccgtgg tggccgtgat cggcctcccg aacgacccgt ccgtgcgcct ccacgaggcc    9000
ctcggctaca ccgcccgcgg cacccttccgc gccgcggct acaagcacgg cggctggcac    9060
gacgtcggct tctggcagcg cgacttcgag ctgccggccc cgccgcgccc ggtgcgcccg    9120
gtgacgcaga tctgagtcga aacctagact tgtccatctt ctggattggc caacttaatt    9180
aatgtatgaa ataaaaggat gcacacatag tgacatgcta atcactataa tgtgggcatc    9240
aaagttgtgt gttatgtgta attactagtt atctgaataa aagagaaaga gatcatccat    9300
atttcttatc ctaaatgaat gtcacgtgtc tttataattc tttgatgaac cagatgcatt    9360
tcattaacca aatccatata catataaata ttaatcatat ataattaata tcaattgggt    9420
tagcaaaaca aatctagtct aggtgtgttt tgcgaattgc ggccgccacc gcggtggagc    9480
tcgaattcat tccgattaat cgtggcctct tgctcttcag gatgaagagc tatgtttaaa    9540
cgtgcaagcg ctactagaca attcagtaca ttaaaaacgt ccgcaatgtg ttattaagtt    9600
gtctaagcgt caatttgttt acaccacaat atatcctgcc accagccagc caacagctcc    9660
ccgaccggca gctcggcaca aaatcaccac tcgatacagg cagcccatca gtccgggacg    9720
gcgtcagcgg gagagccgtt gtaaggcggc agactttgct catgttaccg atgctattcg    9780
gaagaacggc aactaagctg ccgggtttga aacacggatg atctcgcgga gggtagcatg    9840
ttgattgtaa cgatgacaga gcgttgctgc ctgtgatcaa atatcatctc cctcgcagag    9900
atccgaatta tcagccttct tattcatttc tcgcttaacc gtgacaggct gtcgatcttg    9960
agaactatgc cgacataata ggaaatcgct ggataaagcc gctgaggaag ctgagtggcg   10020
ctatttcttt agaagtgaac gttgacgatc gtcgaccgta ccccgatgaa ttaattcgga   10080
cgtacgttct gaacacagct ggatacttac ttgggcgatt gtcatacatg acatcaacaa   10140
```

```
tgtacccgtt tgtgtaaccg tctcttggag gttcgtatga cactagtggt tcccctcagc   10200
ttgcgactag atgttgaggc ctaacatttt attagagagc aggctagttg cttagataca   10260
tgatcttcag gccgttatct gtcagggcaa gcgaaaattg gccatttatg acgaccaatg   10320
ccccgcagaa gctcccatct tgccgcgcat agacgccgcg cccccctttt ggggtgtaga   10380 acatccttt  gccagatgtg gaaaagaagt tcgttgtccc attgttggca atgacgtagt   10440
agccggcgaa agtgcgagac ccatttgcgc tatatataag cctacgattt ccgttgcgac   10500
tattgtcgta attggatgaa ctattatcgt agttgctctc agagttgtcg taatttgatg   10560
gactattgtc gtaattgctt atggagttgt cgtagttgct tggagaaatg tcgtagttgg   10620
atggggagta gtcataggga agacgagctt catccactaa acaattggc  aggtcagcaa   10680 gtgcctgccc cgatgccatc gcaagtacga ggcttagaac caccttcaac agatcgcgca   10740
tagtcttccc cagctctcta acgcttgagt taagccgcgc cgcgaagcgg cgtcggcttg   10800
aacgaattgt tagacattat ttgccgacta ccttggtgat ctcgcctttc acgtagtgaa   10860
caaattcttc caactgatct gcgcgcgagg ccaagcgatc ttcttgtcca agataagcct   10920
gcctagcttc aagtatgacg ggctgatact gggccggcag gcgctccatt gcccagtcgg   10980
cagcgacatc cttcggcgcg atttttgccgg ttactgcgct gtaccaaatg cgggacaacg   11040
taagcactac atttcgctca tcgccagccc agtcgggcgg cgagttccat agcgttaagg   11100
tttcatttag cgcctcaaat agatcctgtt caggaaccgg atcaaagagt tcctccgccg   11160
ctggacctac caaggcaacg ctatgttctc ttgcttttgt cagcaagata gccagatcaa   11220
tgtcgatcgt ggctggctcg aagatacctg caagaatgtc attgcgctgc cattctccaa   11280
attgcagttc gcgcttagct ggataacgcc acggaatgat gtcgtcgtgc acaacaatgg   11340
tgacttctac agcgcggaga atctcgctct ctccagggga agccgaagtt tccaaaaggt   11400
cgttgatcaa agctcgccgc gttgtttcat caagccttac agtcaccgta accagcaaat   11460
caatatcact gtgtggcttc aggccgccat ccactgcgga gccgtacaaa tgtacggcca   11520
gcaacgtcgg ttcgagatgg cgctcgatga cgccaactac ctctgatagt tgagtcgata   11580
cttcggcgat caccgcttcc ctcatgatgt ttaactcctg aattaagccg cgccgcgaag   11640
cggtgtcggc ttgaatgaat tgttaggcgt catcctgtgc tcccgagaac cagtaccagt   11700
acatcgctgt ttcgttcgag acttgaggtc tagttttata cgtgaacagg tcaatgccgc   11760
cgagagtaaa gccacatttt gcgtacaaat tgcaggcagg tacattgttc gtttgtgtct   11820
ctaatcgtat gccaaggagc tgtctgctta gtgcccactt tttcgcaaat tcgatgagac   11880
tgtgcgcgac tccttttgcct cggtgcgtgt gcgacacaac aatgtgttcg atagaggcta   11940
gatcgttcca tgttgagttg agttcaatct tcccgacaag ctcttggtcg atgaatgcgc   12000
catagcaagc agagtcttca tcagagtcat catccgagat gtaatccttc cggtaggggc   12060
tcacacttct ggtagatagt tcaaagcctt ggtcggatag gtgcacatcg aacacttcac   12120
gaacaatgaa atggttctca gcatccaatg tttccgccac ctgctcaggg atcaccgaaa   12180
tcttcatatg acgcctaacg cctggcacag cggatcgcaa acctggcgcg gcttttggca   12240
caaaaggcgt gacaggtttg cgaatccgtt gctgccactt gttaaccctt ttgccagatt   12300
tggtaactat aatttatgtt agaggcgaag tcttgggtaa aaactggcct aaaattgctg   12360
gggatttcag gaaagtaaac atcaccttcc ggctcgatgt ctattgtaga tatatgtagt   12420
gtatctactt gatcggggga tctgctgcct cgcgcgtttc ggtgatgacg gtgaaaacct   12480
```

```
ctgacacatg cagctcccgg agacggtcac agcttgtctg taagcggatg ccgggagcag   12540
acaagcccgt cagggcgcgt cagcgggtgt tggcgggtgt cggggcgcag ccatgaccca   12600
gtcacgtagc gatagcggag tgtatactgg cttaactatg cggcatcaga gcagattgta   12660
ctgagagtgc accatatgcg gtgtgaaata ccgcacagat gcgtaaggag aaaataccgc   12720
atcaggcgct cttccgcttc ctcgctcact gactcgctgc gctcggtcgt tcggctgcgg   12780
cgagcggtat cagctcactc aaaggcggta atacggttat ccacagaatc agggggataac   12840 gcaggaaaga acatgtgagc aaaaggccag caaaaggcca ggaaccgtaa aaaggccgcg   12900
ttgctggcgt ttttccatag gctccgcccc cctgacgagc atcacaaaaa tcgacgctca   12960
agtcagaggt ggcgaaaccc gacaggacta taaagatacc aggcgtttcc ccctggaagc   13020
tccctcgtgc gctctcctgt tccgaccctg ccgcttaccg gatacctgtc cgcctttctc   13080
ccttcgggaa gcgtggcgct ttctcatagc tcacgctgta ggtatctcag ttcggtgtag   13140
gtcgttcgct ccaagctggg ctgtgtgcac gaaccccccg ttcagcccga ccgctgcgcc   13200
ttatccggta actatcgtct tgagtccaac ccggtaagac acgacttatc gccactggca   13260
gcagccactg gtaacaggat tagcagagcg aggtatgtag gcggtgctac agagttcttg   13320
aagtggtggc ctaactacgg ctacactaga aggacagtat ttggtatctg cgctctgctg   13380
aagccagtta ccttcggaaa aagagttggt agctcttgat ccggcaaaca aaccaccgct   13440
ggtagcggtg gtttttttgt ttgcaagcag cagattacgc gcagaaaaaa aggatctcaa   13500
gaagatcctt tgatcttttc tacggggtct gacgctcagt ggaacgaaaa ctcacgttaa   13560
gggattttgg tcatgagatt atcaaaaagg atcttcacct agatcctttt aaattaaaaa   13620
tgaagtttta aatcaatcta agtatatat gagtaaactt ggtctgacag ttaccaatgc   13680
ttaatcagtg aggcacctat ctcagcgatc tgtctatttc gttcatccat agttgcctga   13740
ctccccgtcg tgtagataac tacgatacgg gagggcttac catctggccc cagtgctgca   13800
atgataccgc gagacccacg ctcaccggct ccagatttat cagcaataaa ccagccagcc   13860
ggaagggccg agcgcagaag tggtcctgca actttatccg cctccatcca gtctattaat   13920
tgttgccggg aagctagagt aagtagttcg ccagttaata gtttgcgcaa cgttgttgcc   13980
attgctgcag ggggggggg ggggggggac ttccattgtt cattccacgg acaaaaacag   14040
agaaaggaaa cgacagaggc caaaaagcct cgctttcagc acctgtcgtt cctttctttt   14100
tcagagggta ttttaaataa aaacattaag ttatgacgaa gaagaacgga aacgccttaa   14160
accggaaaat tttcataaat agcgaaaacc cgcgaggtcg ccgccccgta acctgtcgga   14220
tcaccggaaa ggacccgtaa agtgataatg attatcatct acatatcaca acgtgcgtgg   14280
aggccatcaa accacgtcaa ataatcaatt atgacgcagg tatcgtatta attgatctgc   14340
atcaacttaa cgtaaaaaca acttcagaca atacaaatca gcgacactga atacggggca   14400
acctcatgtc ccccccccc ccccccctgc aggcatcgtg gtgtcacgct cgtcgtttgg   14460
tatggcttca ttcagctccg gttcccaacg atcaaggcga gttacatgat cccccatgtt   14520
gtgcaaaaaa gcggttagct ccttcggtcc tccgatcgtt gtcagaagta agttggccgc   14580
agtgttatca ctcatggtta tggcagcact gcataattct cttactgtca tgccatccgt   14640
aagatgcttt tctgtgactg gtgagtactc aaccaagtca ttctgagaat agtgtatgcg   14700
gcgaccgagt tgctcttgcc cggcgtcaac acgggataat accgcgccac atagcagaac   14760
tttaaaagtg ctcatcattg gaaaacgttc ttcggggcga aaactctcaa ggatcttacc   14820
gctgttgaga tccagttcga tgtaacccac tcgtgcaccc aactgatctt cagcatcttt   14880
```

-continued

```
tactttcacc agcgtttctg ggtgagcaaa aacaggaagg caaaatgccg caaaaagggg    14940
aataagggcg acacggaaat gttgaatact catactcttc cttttttcaat attattgaag   15000 catttatcag ggttattgtc tcatgagcgg atacatattt gaatgtattt agaaaaataa    15060
acaaataggg gttccgcgca catttccccg aaaagtgcca cctgacgtct aagaaaccat    15120
tattatcatg acattaacct ataaaaatag gcgtatcacg aggccctttc gtcttcaaga    15180
attggtcgac gatcttgctg cgttcggata ttttcgtgga gttcccgcca cagacccgga    15240
ttgaaggcga gatccagcaa ctcgcgccag atcatcctgt gacggaactt ggcgcgtga    15300 tgactggcca ggacgtcggc cgaaagagcg acaagcagat cacgcttttc gacagcgtcg    15360
gatttgcgat cgaggatttt tcggcgctgc gctacgtccg cgaccgcgtt gagggatcaa    15420
gccacagcag cccactcgac cttctagccg acccagacga gccaagggat cttttttggaa  15480 tgctgctccg tcgtcaggct ttccgacgtt tgggtggttg aacagaagtc attatcgtac    15540
ggaatgccaa gcactcccga ggggaaccct gtggttggca tgcacataca aatggacgaa    15600
cggataaacc ttttcacgcc cttttaaata tccgttattc taataaacgc tcttttctct    15660
tag                                                                   15663
```

<210> SEQ ID NO 10
<211> LENGTH: 25
<212> TYPE: DNA
<213> ORGANISM: Artificial Sequence
<220> FEATURE:
<223> OTHER INFORMATION: attB1 site

<400> SEQUENCE: 10
acaagtttgt acaaaaaagc aggct                                25

<210> SEQ ID NO 11
<211> LENGTH: 25
<212> TYPE: DNA
<213> ORGANISM: Artificial Sequence
<220> FEATURE:
<223> OTHER INFORMATION: attB2 site

<400> SEQUENCE: 11
accactttgt acaagaaagc tgggt                                25

<210> SEQ ID NO 12
<211> LENGTH: 50
<212> TYPE: DNA
<213> ORGANISM: Artificial Sequence
<220> FEATURE:
<223> OTHER INFORMATION: At1g26797 5'attB forward primer

<400> SEQUENCE: 12
ggggacaagt ttgtacaaaa aagcaggctc catgctaatc acagttctag             50

<210> SEQ ID NO 13
<211> LENGTH: 50
<212> TYPE: DNA
<213> ORGANISM: Artificial Sequence
<220> FEATURE:
<223> OTHER INFORMATION: At1g26797 3'attB reverse primer

<400> SEQUENCE: 13
ggggaccact ttgtacaaga aagctgggtc agtcaatctc taagatgtcc             50

<210> SEQ ID NO 14

```
<211> LENGTH: 54
<212> TYPE: DNA
<213> ORGANISM: Artificial Sequence
<220> FEATURE:
<223> OTHER INFORMATION: VC062 primer

<400> SEQUENCE: 14
ttaaacaagt tgtacaaaa aagcaggctg caattaaccc tcactaaagg gaac         54

<210> SEQ ID NO 15
<211> LENGTH: 53
<212> TYPE: DNA
<213> ORGANISM: Artificial Sequence
<220> FEATURE:
<223> OTHER INFORMATION: VC063 primer

<400> SEQUENCE: 15
ttaaaccact tgtacaaga aagctgggtg cgtaatacga ctcactatag ggc          53

<210> SEQ ID NO 16
<211> LENGTH: 50905
<212> TYPE: DNA
<213> ORGANISM: Artificial Sequence
<220> FEATURE:
<223> OTHER INFORMATION: destination vector for use with Gaspe-flint
      derived maize lines

<400> SEQUENCE: 16
gggggggggg ggggggggtt ccattgttca ttccacggac aaaaacagag aaaggaaacg    60
acagaggcca aaaagctcgc tttcagcacc tgtcgtttcc tttcttttca gagggtattt   120
taaataaaaa cattaagtta tgacgaagaa gaacggaaac gccttaaacc ggaaaatttt   180
cataaatagc gaaaacccgc gaggtcgccg cccgtaacc tgtcggatca ccggaaagga    240
cccgtaaagt gataatgatt atcatctaca tatcacaacg tgcgtggagg ccatcaaacc   300
acgtcaaata atcaattatg acgcaggtat cgtattaatt gatctgcatc aacttaacgt   360
aaaaacaact tcagacaata caaatcagcg acactgaata cggggcaacc tcatgtcccc   420 ccccccccc cccctgcagg catcgtggtg tcacgctcgt cgtttggtat ggcttcattc    480
agctccggtt cccaacgatc aaggcgagtt acatgatccc ccatgttgtg caaaaaagcg   540
gttagctcct tcggtcctcc gatcgttgtc agaagtaagt tggccgcagt gttatcactc   600
atggttatgg cagcactgca taattctctt actgtcatgc catccgtaag atgcttttct   660
gtgactggtg agtactcaac caagtcattc tgagaatagt gtatgcggcg accgagttgc   720
tcttgcccgg cgtcaacacg gataataccg cgccacata gcagaacttt aaaagtgctc    780
atcattggaa aacgttcttc ggggcgaaaa ctctcaagga tcttaccgct gttgagatcc   840
agttcgatgt aacccactcg tgcacccaac tgatcttcag catcttttac tttcaccagc   900
gtttctgggt gagcaaaaac aggaaggcaa aatgccgcaa aaagggaat aagggcgaca    960 cggaaatgtt gaatactcat actcttcctt tttcaatatt attgaagcat ttatcagggt  1020
tattgtctca tgagcggata catatttgaa tgtatttaga aaataaaca ataggggtt    1080 ccgcgcacat ttccccgaaa agtgccacct gacgtctaag aaaccattat tatcatgaca  1140
ttaacctata aaaataggcg tatcacgagg cccttttcgtc ttcaagaatt cggagctttt  1200
gccattctca ccggattcag tcgtcactca tggtgatttc tcacttgata accttatttt  1260
tgacgagggg aaattaatag gttgtattga tgttggacga gtcggaatcg cagaccgata  1320
ccaggatctt gccatcctat ggaactgcct cggtgagttt tctccttcat tacagaaacg  1380
```

```
gcttttttcaa aaatatggta ttgataatcc tgatatgaat aaattgcagt ttcatttgat      1440
gctcgatgag tttttctaat cagaattggt taattggttg taacactggc agagcattac      1500
gctgacttga cgggacggcg gctttgttga ataaatcgaa cttttgctga gttgaaggat      1560
cagatcacgc atcttcccga caacgcagac cgttccgtgg caaagcaaaa gttcaaaatc      1620
accaactggt ccacctacaa caaagctctc atcaaccgtg gctccctcac tttctggctg      1680
gatgatgggg cgattcaggc ctggtatgag tcagcaacac cttcttcacg aggcagacct      1740
cagcgccaga aggccgccag agaggccgag cgcggccgtg aggcttggac gctagggcag      1800
ggcatgaaaa agcccgtagc gggctgctac gggcgtctga cgcggtggaa aggggagggg      1860
gatgttgtct acatggctct gctgtagtga gtgggttgcg ctccggcagc ggtcctgatc      1920
aatcgtcacc ctttctcggt ccttcaacgt tcctgacaac gagcctcctt ttcgccaatc      1980
catcgacaat caccgcgagt ccctgctcga acgctgcgtc cggaccggct tcgtcgaagg      2040
cgtctatcgc ggcccgcaac agcggcgaga cggagcctg ttcaacggtg ccgccgcgct       2100
cgccggcatc gctgtcgccg gcctgctcct caagcacggc cccaacagtg aagtagctga      2160
ttgtcatcag cgcattgacg gcgtccccgg ccgaaaaacc cgcctcgcag aggaagcgaa      2220
gctgcgcgtc ggccgtttcc atctgcggtg cgcccggtcg cgtgccggca tggatgcgcg      2280
cgccatcgcg gtaggcgagc agcgcctgcc tgaagctgcg ggcattcccg atcagaaatg      2340
agcgccagtc gtcgtcggct ctcggcaccg aatgcgtatg attctccgcc agcatggctt      2400
cggccagtgc gtcgagcagc gcccgcttgt tcctgaagtg ccagtaaagc gccggctgct      2460 gaaccccaa ccgttccgcc agtttgcgtg tcgtcagacc gtctacgccg acctcgttca       2520
acaggtccag ggcggcacgg atcactgtat tcggctgcaa cttttgtcatg cttgacactt     2580 tatcactgat aaacataata tgtccaccaa cttatcagtg ataaagaatc cgcgcgttca      2640
atcggaccag cggaggctgg tccggaggcc agacgtgaaa cccaacatac ccctgatcgt      2700
aattctgagc actgtcgcgc tcgacgctgt cggcatcggc ctgattatgc cggtgctgcc      2760
gggcctcctg cgcgatctgg ttcactcgaa cgacgtcacc gcccactatg gcattctgct      2820
ggcgctgtat gcgttggtgc aatttgcctg cgcacctgtg ctgggcgcgc tgtcggatcg      2880
tttcgggcgg cggccaatct tgctcgtctc gctggccggc gccactgtcg actacgccat      2940
catggcgaca gcgcctttcc tttgggttct ctatatcggg cggatcgtgg ccggcatcac      3000
cggggcgact ggggcggtag ccggcgctta tattgccgat atcactgatg gcgatgagcg      3060
cgcgcggcac ttcggcttca tgagcgcctg tttcgggttc gggatggtcg cgggacctgt      3120
gctcggtggg ctgatgggcg gtttctcccc ccacgctccg ttcttcgccg cggcagcctt      3180
gaacggcctc aatttcctga cgggctgttt ccttttgccg gagtcgcaca aaggcgaacg      3240
ccggccgtta cgccgggagg ctctcaaccc gctcgcttcg ttccggtggg cccggggcat      3300
gaccgtcgtc gccgccctga tggcggtctt cttcatcatg caacttgtcg gacaggtgcc      3360
ggccgcgctt tgggtcattt tcggcgagga tcgctttcac tgggacgcga ccacgatcgg      3420
catttcgctt gccgcatttg gcattctgca ttcactcgcc caggcaatga tcaccggccc      3480
tgtagccgcc cggctcggcg aaaggcgggc actcatgctc ggaatgattg ccgacggcac      3540
aggctacatc ctgcttgcct tcgcgacacg gggatggatg gcgttcccga tcatggtcct      3600
gcttgcttcg ggtggcatcg gaatgccggc gctgcaagca atgttgtcca ggcaggtgga      3660
tgaggaacgt caggggcagc tgcaaggctc actggcggcg ctcaccagcc tgacctcgat      3720
cgtcggaccc ctcctcttca cggcgatcta tgcggcttct ataacaacgt ggaacgggtg      3780
```

```
ggcatggatt gcaggcgctg ccctctactt gctctgcctg ccggcgctgc gtcgcgggct    3840
ttggagcggc gcagggcaac gagccgatcg ctgatcgtgg aaacgatagg cctatgccat    3900
gcgggtcaag gcgacttccg gcaagctata cgcgccctag gagtgcggtt ggaacgttgg    3960
cccagccaga tactcccgat cacgagcagg acgccgatga tttgaagcgc actcagcgtc    4020
tgatccaaga caaccatcc tagcaacacg gcggtccccg ggctgagaaa gcccagtaag     4080
gaaacaactg taggttcgag tcgcgagatc ccccggaacc aaaggaagta ggttaaaccc    4140
gctccgatca ggccgagcca cgccaggccg agaacattgg ttcctgtagg catcgggatt    4200
ggcggatcaa acactaaagc tactggaacg agcagaagtc ctccggccgc cagttgccag    4260
gcggtaaagg tgagcagagg cacgggaggt tgccacttgc gggtcagcac ggttccgaac    4320
gccatggaaa ccgccccgc caggcccgct gcgacgccga caggatctag cgctgcgttt     4380
ggtgtcaaca ccaacagcgc cacgcccgca gttccgcaaa tagcccccag gaccgccatc    4440
aatcgtatcg ggctacctag cagagcgca gagatgaaca cgaccatcag cggctgcaca     4500
gcgcctaccg tcgccgcgac cccgcccggc aggcggtaga ccgaaataaa caacaagctc    4560
cagaatagcg aaatattaag tgcgccgagg atgaagatgc gcatccacca gattcccgtt    4620
ggaatctgtc ggacgatcat cacgagcaat aaacccgccg gcaacgcccg cagcagcata    4680
ccggcgaccc ctcggcctcg ctgttcgggc tccacgaaaa cgccgacag atgcgccttg     4740 tgagcgtcct tggggccgtc ctcctgtttg aagaccgaca gcccaatgat ctcgccgtcg    4800
atgtaggcgc cgaatgccac ggcatctcgc aaccgttcag cgaacgcctc catgggcttt    4860
ttctcctcgt gctcgtaaac ggacccgaac atctctggag cttttcttcag ggccgacaat   4920 cggatctcgc ggaaatcctg cacgtcggcc gctccaagcc gtcgaatctg agccttaatc    4980
acaattgtca attttaatcc tctgtttatc ggcagttcgt agagcgcgcc gtgcgtcccg    5040
agcgatactg agcgaagcaa gtgcgtcgag cagtgcccgc ttgttcctga aatgccagta    5100
aagcgctggc tgctgaaccc ccagccggaa ctgaccccac aaggccctag cgtttgcaat    5160
gcaccaggtc atcattgacc caggcgtgtt ccaccaggcc gctgcctcgc aactcttcgc    5220
aggcttcgcc gacctgctcg cgccacttct tcacgcgggt ggaatccgat ccgcacatga    5280
ggcggaaggt ttccagcttg agcgggtacg gctcccggtg cgagctgaaa tagtcgaaca    5340
tccgtcgggc cgtcggcgac agcttgcggt acttctccca tatgaatttc gtgtagtggt    5400
cgccagcaaa cagcacgacg atttcctcgt cgatcaggac ctggcaacgg gacgttttct    5460
tgccacggtc caggacgcgg aagcggtgca gcagcgacac cgattccagg tgcccaacgc    5520
ggtcggacgt gaagcccatc gccgtcgcct gtaggcgcga caggcattcc tcggccttcg    5580
tgtaataccg gccattgatc gaccagccca ggtcctggca aagctcgtag aacgtgaagg    5640
tgatcggctc gccgataggg gtgcgcttcg cgtactccaa cacctgctgc cacaccagtt    5700
cgtcatcgtc ggcccgcagc tcgacgccgg tgtaggtgat cttcacgtcc ttgttgacgt    5760
ggaaaatgac cttgttttgc agcgcctcgc gcgggatttt cttgttgcgc gtggtgaaca    5820
gggcagagcg ggccgtgtcg tttggcatcg ctcgcatcgt gtccggccac ggcgcaatat    5880
cgaacaagga aagctgcatt tccttgatct gctgcttcgt gtgtttcagc aacgcggcct    5940
gcttggcctc gctgacctgt tttgccaggt cctcgccggc ggtttttcgc ttcttggtcg    6000
tcatagttcc tcgcgtgtcg atggtcatcg acttcgccaa acctgccgcc tcctgttcga    6060
gacgacgcga acgctccacg gcggccgatg gcgcgggcag ggcaggggga gccagttgca    6120
```

```
cgctgtcgcg ctcgatcttg gccgtagctt gctggaccat cgagccgacg gactggaagg    6180
tttcgcgggg cgcacgcatg acggtgcggc ttgcgatggt ttcggcatcc tcggcggaaa    6240
accccgcgtc gatcagttct tgcctgtatg ccttccggtc aaacgtccga ttcattcacc    6300
ctccttgcgg gattgccccg actcacgccg gggcaatgtg cccttattcc tgatttgacc    6360
cgcctggtgc cttggtgtcc agataatcca ccttatcggc aatgaagtcg gtcccgtaga    6420
ccgtctggcc gtccttctcg tacttggtat tccgaatctt gccctgcacg aataccagcg    6480
accccttgcc caaatacttg ccgtgggcct cggcctgaga gccaaaacac ttgatgcgga    6540
agaagtcggt gcgctcctgc ttgtcgccgg catcgttgcg ccactcttca ttaaccgcta    6600
tatcgaaaat tgcttgcggc ttgttagaat tgccatgacg tacctcggtg tcacgggtaa    6660
gattaccgat aaactggaac tgattatggc tcatatcgaa agtctccttg agaaaggaga    6720
ctctagttta gctaaacatt ggttccgctg tcaagaactt tagcggctaa aattttgcgg    6780
gccgcgacca aggtgcgag gggcggcttc cgctgtgtac aaccagatat ttttcaccaa     6840
catccttcgt ctgctcgatg agcggggcat gacgaaacat gagctgtcgg agagggcagg    6900
ggtttcaatt tcgttttat cagacttaac caacggtaag gccaacccct cgttgaaggt      6960
gatggaggcc attgccgacg ccctggaaac tcccctacct cttctcctgg agtccaccga    7020
ccttgaccgc gaggcactcg cggagattgc gggtcatcct ttcaagagca gcgtgccgcc    7080
cggatacgaa cgcatcagtg tggttttgcc gtcacataag gcgtttatcg taaagaaatg    7140
gggcgacgac acccgaaaaa agctgcgtgg aaggctctga cgccaagggt tagggcttgc    7200
acttccttct ttagccgcta aaacggcccc ttctctgcgg gccgtcggct cgcgcatcat    7260
atcgacatcc tcaacggaag ccgtgccgcg aatggcatcg ggcgggtgcg ctttgacagt    7320
tgttttctat cagaacccct acgtcgtgcg gttcgattag ctgtttgtct tgcaggctaa    7380
acactttcgg tatatcgttt gcctgtgcga taatgttgct aatgatttgt tgcgtagggg    7440
ttactgaaaa gtgagcggga aagaagagtt tcagaccatc aaggagcggg ccaagcgcaa    7500
gctggaacgc gacatgggtg cggacctgtt ggccgcgctc aacgacccga aaaccgttga    7560
agtcatgctc aacgcggacg gcaaggtgtg cacgaacgc cttggcgagc cgatgcggta     7620
catctgcgac atgcggccca gccagtcgca ggcgattata gaaacggtgg ccggattcca    7680
cggcaaagag gtcacgcggc attcgcccat cctggaaggc gagttcccct tggatggcag    7740
ccgctttgcc ggccaattgc cgccggtcgt ggccgcgcca acctttgcga tccgcaagcg    7800
cgcggtcgcg atcttcacgc tggaacagta cgtcgaggcg ggcatcatga cccgcgagca    7860
atacgaggtc attaaaagcg ccgtcgcggc gcatcgaaac atcctcgtca ttggcggtac    7920
tggctcgggc aagaccacgc tcgtcaacgc gatcatcaat gaaatggtcg ccttcaaccc    7980
gtctgagcgc gtcgtcatca tcgaggacac cggcgaaatc cagtgcgccg cagagaacgc    8040
cgtccaatac cacaccagca tcgacgtctc gatgacgctg ctgctcaaga caacgctgcg    8100
tatgcgcccc gaccgcatcc tggtcggtga ggtacgtggc cccgaagccc ttgatctgtt    8160
gatggcctgg aacaccgggc atgaaggagg tgccgccacc ctgcacgcaa caaccccaa    8220 agcgggcctg agccggctcg ccatgcttat cagcatgcac ccggattcac cgaaacccat    8280
tgagccgctg attggcgagg cggttcatgt ggtcgtccat atcgccagga ccctagcgg    8340 ccgtcgagtg caagaaattc tcgaagttct tggttacgag aacggccagt acatcaccaa    8400
aaccctgtaa ggagtatttc caatgacaac ggctgttccg ttccgtctga ccatgaatcg    8460
cggcattttg ttctaccttg ccgtgttctt cgttctcgct ctcgcgttat ccgcgcatcc    8520
```

```
ggcgatggcc tcggaaggca ccggcggcag cttgccatat gagagctggc tgacgaacct   8580
gcgcaactcc gtaaccggcc cggtggcctt cgcgctgtcc atcatcggca tcgtcgtcgc   8640
cggcggcgtg ctgatcttcg gcggcgaact caacgccttc ttccgaaccc tgatcttcct   8700
ggttctggta tggcgctgc tggtcggcgc gcagaacgtg atgagcacct cttcggtcg    8760
tggtgccgaa atcgcggccc tcggcaacgg ggcgctgcac caggtgcaag tcgcggcggc   8820
ggatgccgtg cgtgcggtag cggctggacg gctcgcctaa tcatggctct gcgcacgatc   8880
cccatccgtc gcgcaggcaa ccgagaaaac ctgttcatgg gtggtgatcg tgaactggtg   8940
atgttctcgg gcctgatggc gtttgcgctg attttcagcg cccaagagct gcgggccacc   9000
gtggtcggtc tgatcctgtg gttcggggcg ctctatgcgt tccgaatcat ggcgaaggcc   9060
gatccgaaga tgcggttcgt gtacctgcgt caccgccggt acaagccgta ttacccggcc   9120
cgctcgaccc cgttccgcga gaacaccaat agccaaggga agcaataccg atgatccaag   9180
caattgcgat tgcaatcgcg ggcctcggcg cgcttctgtt gttcatcctc tttgcccgca   9240
tccgcgcggt cgatgccgaa ctgaaactga aaaagcatcg ttccaaggac gccggcctgg   9300
ccgatctgct caactacgcc gctgtcgtcg atgacgcgct aatcgtgggc aagaacggca   9360
gcttatggc tgcctggctg tacaagggcg atgacaacgc aagcagcacc gaccagcagc   9420
gcgaagtagt gtccgcccgc atcaaccagg ccctcgcggg cctggaagt gggtggatga    9480
tccatgtgga cgccgtgcgg cgtcctgctc cgaactacgc ggagcggggc ctgtcggcgt   9540
tccctgaccg tctgacggca gcgattgaag aagagcgctc ggtcttgcct tgctcgtcgg   9600
tgatgtactt caccagctcc gcgaagtcgc tcttcttgat ggagcgcatg gggacgtgct   9660
tggcaatcac gcgcaccccc cggccgtttt agcggctaaa aaagtcatgg ctctgccctc   9720
gggcggacca cgcccatcat gaccttgcca agctcgtcct gcttctcttc gatcttcgcc   9780
agcagggcga ggatcgtggc atcaccgaac cgcgccgtgc gcgggtcgtc ggtgagccag   9840
agtttcagca ggccgcccag gcggcccagg tcgccattga tgcgggccag ctcgcggacg   9900
tgctcatagt ccacgacgcc cgtgattttg tagcccctggc cgacggccag caggtaggcc   9960
gacaggctca tgccggccgc cgccgccttt tcctcaatcg ctcttcgttc gtctggaagg  10020
cagtacacct tgataggtgg gctgcccttc ctggttggct tggtttcatc agccatccgc  10080
ttgccctcat ctgttacgcc ggcggtagcc ggccagcctc gcagagcagg attcccgttg  10140
agcaccgcca ggtgcgaata agggacagtg aagaaggaac accgctcgc gggtgggcct   10200
acttcaccta tcctgcccgg ctgacgccgt tggatacacc aaggaaagtc tacacgaacc  10260
ctttggcaaa atcctgtata tcgtgcgaaa aaggatggat ataccgaaaa aatcgctata  10320
atgaccccga agcagggtta tgcagcgaa aagcgctgct tccctgctgt tttgtggaat    10380
atctaccgac tggaaacagg caaatgcagg aaattactga actgagggga caggcgagag  10440
acgatgccaa agagctacac cgacgagctg gccgagtggg ttgaatcccg cgcggccaag  10500
aagcgccggc gtgatgaggc tgcggttgcg ttcctggcgg tgagggcgga tgtcgaggcg  10560
gcgttagcgt ccggctatgc gctcgtcacc atttgggagc acatgcggga aacggggaag  10620
gtcaagttct cctacgagac gttccgctcg cacgccaggc ggcacatcaa ggccaagccc  10680
gccgatgtgc ccgcaccgca ggccaaggct gcggaacccg cgccggcacc caagacgccg  10740
gagccacggc ggccgaagca gggggggcaag gctgaaaagc cggcccccgc tgcggccccg  10800
accggcttca ccttcaaccc aacaccggac aaaaaggatc tactgtaatg gcgaaaattc  10860
```

```
acatggtttt gcagggcaag ggcggggtcg gcaagtcggc catcgccgcg atcattgcgc    10920
agtacaagat ggacaagggg cagacaccct tgtgcatcga caccgacccg gtgaacgcga    10980
cgttcgaggg ctacaaggcc ctgaacgtcc gccggctgaa catcatggcc ggcgacgaaa    11040
ttaactcgcg caacttcgac accctggtcg agctgattgc gccgaccaag gatgacgtgg    11100
tgatcgacaa cggtgccagc tcgttcgtgc ctctgtcgca ttacctcatc agcaaccagg    11160
tgccggctct gctgcaagaa atggggcatg agctggtcat ccataccgtc gtcaccggcg    11220
gccaggctct cctggacacg gtgagcggct tcgcccagct cgccagccag ttcccggccg    11280
aagcgctttt cgtggtctgg ctgaacccgt attgggggcc tatcgagcat gagggcaaga    11340
gctttgagca gatgaaggcg tacacggcca acaaggcccg cgtgtcgtcc atcatccaga    11400
ttccggccct caaggaagaa acctacggcc gcgatttcag cgacatgctg caagagcggc    11460
tgacgttcga ccaggcgctg gccgatgaat cgctcacgat catgacgcgg caacgcctca    11520
agatcgtgcg gcgcggcctg tttgaacagc tcgacgcggc ggccgtgcta tgagcgacca    11580
gattgaagag ctgatccggg agattgcggc caagcacgga atcgccgtcg gccgcgacga    11640
cccggtgctg atcctgcata ccatcaacgc ccggctcatg gccgacagtg cggccaagca    11700
agaggaaatc cttgccgcgt tcaaggaaga gctggaaggg atcgcccatc gttggggcga    11760
ggacgccaag gccaaagcgg agcggatgct gaacgcggcc ctggcggcca gcaaggacgc    11820
aatggcgaag gtaatgaagg acagcgccgc gcaggcggcc gaagcgatcc gcaggaaat    11880
cgacgacggc cttggccgcc agctcgcggc caaggtcgcg gacgcgcggc gcgtggcgat    11940
gatgaacatg atcgccggcg gcatggtgtt gttcgcggcc gccctggtgg tgtgggcctc    12000
gttatgaatc gcagaggcgc agatgaaaaa gcccggcgtt gccgggcttt gtttttgcgt    12060
tagctgggct tgtttgacag gcccaagctc tgactgcgcc cgcgctcgcg ctcctgggcc    12120
tgtttcttct cctgctcctg cttgcgcatc agggcctggt gccgtcgggc tgcttcacgc    12180
atcgaatccc agtcgccggc cagctcggga tgctccgcgc gcatcttgcg cgtcgccagt    12240
tcctcgatct tgggcgcgtg aatgcccatg ccttccttga tttcgcgcac catgtccagc    12300
cgcgtgtgca gggtctgcaa gcgggcttgc tgtttgggcct gctgctgctg ccaggcggcc    12360
tttgtacgcg gcagggacag caagccgggg gcattggact gtagctgctg caaacgcgcc    12420
tgctgacggt ctacgagctg ttctaggcgg tcctcgatgc gctccacctg gtcatgcttt    12480
gcctgcacgt agagcgcaag ggtctgctgg taggtctgct cgatgggcgc ggattctaag    12540
agggcctgct gttccgtctc ggcctcctgg gccgcctgta gcaaatcctc gccgctgttg    12600
ccgctggact gctttactgc cggggactgc tgttgccctg ctcgcgccgt cgtcgcagtt    12660
cggcttgccc ccactcgatt gactgcttca tttcgagccg cagcgatgcg atctcggatt    12720
gcgtcaacgg acggggcagc gcggaggtgt ccggcttctc cttgggtgag tcggtcgatg    12780
ccatagccaa aggtttcctt ccaaaatgcg tccattgctg gaccgtgttt ctcattgatg    12840
cccgcaagca tcttcggctt gaccgccagg tcaagcgcgc cttcatgggc ggtcatgacg    12900
gacgccgcca tgaccttgcc gccgttgttc tcgatgtagc cgcgtaatga ggcaatggtg    12960
ccgcccatcg tcagcgtgtc atcgacaacg atgtacttct ggccggggat caccteccec    13020
tcgaaagtcg ggttgaacgc caggcgatga tctgaaccgg ctccggttcg ggcgaccttc    13080
tcccgctgca caatgtccgt ttcgacctca aggccaaggc ggtcggccag aacgaccgcc    13140
atcatggccg gaatcttgtt gttccccgcc gcctcgacgg cgaggactgg aacgatgcgg    13200
ggcttgtcgt cgccgatcag cgtcttgagc tgggcaacag tgtcgtccga aatcaggcgc    13260
```

```
tcgaccaaat taagcgccgc ttccgcgtcg ccctgcttcg cagcctggta ttcaggctcg   13320
ttggtcaaag aaccaaggtc gccgttgcga accaccttcg ggaagtctcc ccacggtgcg   13380
cgctcggctc tgctgtagct gctcaagacg cctcccttt tagccgctaa aactctaacg   13440
agtgcgcccg cgactcaact tgacgctttc ggcacttacc tgtgccttgc cacttgcgtc   13500
ataggtgatg cttttcgcac tcccgatttc aggtacttta tcgaaatctg accgggcgtg   13560
cattacaaag ttcttcccca cctgttggta aatgctgccg ctatctgcgt ggacgatgct   13620
gccgtcgtgg cgctgcgact tatcggcctt ttgggccata tagatgttgt aaatgccagg   13680
tttcagggcc ccggctttat ctaccttctg gttcgtccat gcgccttggt tctcggtctg   13740
gacaattctt tgcccattca tgaccaggag gcggtgtttc attgggtgac tcctgacggt   13800
tgcctctggt gttaaacgtg tcctggtcgc ttgccggcta aaaaaaagcc gacctcggca   13860
gttcgaggcc ggctttccct agagccgggc gcgtcaaggt tgttccatct attttagtga   13920
actgcgttcg atttatcagt tactttcctc ccgctttgtg tttcctccca ctcgtttccg   13980
cgtctagccg accctcaac atagcggcct cttcttgggc tgcctttgcc tcttgccgcg   14040
cttcgtcacg ctcggcttgc accgtcgtaa agcgctcggc ctgcctggcc gcctcttgcg   14100
ccgccaactt cctttgctcc tggtgggcct cggcgtcggc ctgcgccttc gctttcaccg   14160
ctgccaactc cgtgcgcaaa ctctccggctt cgcgcctggt ggcgtcgcgc tcgccgcgaa   14220
gcgcctgcat ttcctggttg gccgcgtcca gggtcttgcg gctctcttct ttgaatgcgc   14280
gggcgtcctg gtgagcgtag tccagctcgg cgcgcagctc ctgcgctcga cgctccacct   14340
cgtcggcccg ctgcgtcgcc agcgcggccc gctgctcggc tcctgccagg gcggtgcgtg   14400
cttcggccag ggcttgccgc tggcgtgcgg ccagctcggc cgcctcggcg gcctgctgct   14460
ctagcaatgt aacgcgcgcc tgggcttctt ccagctcgcg ggcctgcgcc tcgaaggcgt   14520
cggccagctc ccccgcgcacg gcttccaact cgttgcgctc acgatcccag ccggcttgcg   14580
ctgcctgcaa cgattcattg gcaagggcct gggcggcttg ccagagggcg ccacggcct   14640 ggttgccggc ctgctgcacc gcgtccggca cctggactgc cagcggggcg gcctgcgccg   14700
tgcgctggcg tcgccattcg cgcatgccgg cgctggcgtc gttcatgttg acgcgggcgg   14760
ccttacgcac tgcatccacg gtcgggaagt tctcccggtc gccttgctcg aacagctcgt   14820
ccgcagccgc aaaaatgcgg tcgcgcgtct ctttgttcag ttccatgttg gctccggtaa   14880
ttggtaagaa taataatact cttacctacc ttatcagcgc aagagtttag ctgaacagtt   14940
ctcgacttaa cggcaggttt tttagcggct gaagggcagg caaaaaaagc cccgcacggt   15000 cggcggggc aaagggtcag cgggaagggg attagcgggc gtcggcttc ttcatgcgtc   15060 ggggccgcgc ttcttgggat ggagcacgac gaagcgcgca cgcgcatcgt cctcggccct   15120
atcggcccgc gtcgcggtca ggaacttgtc gcgcgctagg tcctccctgg tgggcaccag   15180
gggcatgaac tcggcctgct cgatgtaggt ccactccatg accgcatcgc agtcgaggcc   15240
gcgttccttc accgtctctt gcaggtcgcg gtacgcccgc tcgttgagcg gctggtaacg   15300
ggccaattgg tcgtaaatgg ctgtcggcca tgagcggcct ttcctgttga gccagcagcc   15360
gacgacgaag ccgcaatgc aggccctgg cacaaccagg ccgacgccgg gggcagggga   15420
tggcagcagc tcgccaacca ggaaccccgc cgcgatgatg ccgatgccgg tcaaccagcc   15480
cttgaaacta tccggccccg aaacacccct gcgcattgcc tggatgctgc gccggatagc   15540
ttgcaacatc aggagccgtt tcttttgttc gtcagtcatg gtccgccctc accagttgtt   15600
```

```
cgtatcggtg tcggacgaac tgaaatcgca agagctgccg gtatcggtcc agccgctgtc    15660
cgtgtcgctg ctgccgaagc acggcgaggg gtccgcgaac gccgcagacg gcgtatccgg    15720
ccgcagcgca tcgcccagca tggccccggt cagcgagccg ccggccaggt agcccagcat    15780
ggtgctgttg gtcgcccggg ccaccagggc cgacgtgacg aaatcgccgt cattccctct    15840
ggattgttcg ctgctcggcg gggcagtgcg ccgcgccggc ggcgtcgtgg atggctcggg    15900
ttggctggcc tgcgacggcc ggcgaaaggt gcgcagcagc tcgttatcga ccggctgcgg    15960
cgtcggggcc gccgccttgc gctgcggtcg gtgttccttc ttcggctcgc gcagcttgaa    16020
cagcatgatc gcggaaaacca gcagcaacgc cgcgcctacg cctcccgcga tgtagaacag    16080
catcggattc attcttcggt cctccttgta gcggaaccgt tgtctgtgcg gcgcgggtgg    16140
cccgcgccgc tgtctttggg gatcagccct cgatgagcgc gaccagtttc acgtcggcaa    16200
ggttcgcctc gaactcctgg ccgtcgtcct cgtacttcaa ccaggcatag ccttccgccg    16260
gcggccgacg gttgaggata aggcgggcag ggcgctcgtc gtgctcgacc tggacgatgg    16320 ccttttttcag cttgtccggg tccggctcct tcgcgccctt ttccttggcg tccttaccgt    16380
cctggtcgcc gtcctcgccg tcctggccgt cgccggcctc cgcgtcacgc tcggcatcag    16440
tctggccgtt gaaggcatcg acggtgttgg gatcgcggcc cttctcgtcc aggaactcgc    16500
gcagcagctt gaccgtgccg cgcgtgattt cctgggtgtc gtcgtcaagc cacgcctcga    16560
cttcctccgg gcgcttcttg aaggccgtca ccagctcgtt caccacggtc acgtcgcgca    16620
cgcggccggt gttgaacgca tcggcgatct tctccggcag gtccagcagc gtgacgtgct    16680
gggtgatgaa cgccggcgac ttgccgattt ccttggcgat atcgcctttc ttcttgccct    16740
tcgccagctc gcggccaatg aagtcggcaa tttcgcgcgg ggtcagctcg ttgcgttgca    16800
ggttctcgat aacctggtcg gcttcgttgt agtcgttgtc gatgaacgcc gggatggact    16860
tcttgccggc ccacttcgag ccacggtagc ggcgggcgcc gtgattgatg atatagcggc    16920
ccggctgctc ctggttctcg cgcaccgaaa tgggtgactt cacccgcgc tctttgatcg    16980 tggcaccgat ttccgcgatg ctctccgggg aaaagccggg gttgtcggcc gtccgcggct    17040
gatgcggatc ttcgtcgatc aggtccaggt ccagctcgat agggccggaa ccgccctgag    17100
acgccgcagg agcgtccagg aggctcgaca ggtcgccgat gctatccaac cccaggccgg    17160
acggctgcgc cgcgcctgcg gcttcctgag cggccgcagc ggtgttttc ttggtggtct    17220 tggcttgagc cgcagtcatt gggaaatctc catcttcgtg aacacgtaat cagccagggc    17280
gcgaacctct ttcgatgcct tgcgcgcggc cgttttcttg atcttccaga ccggcacacc    17340
ggatgcgagg gcatcggcga tgctgctgcg caggccaacg gtggccggaa tcatcatctt    17400
ggggtacgcg gccagcagct cggcttggtg gcgcgcgtgg cgcggattcc gcgcatcgac    17460
cttgctgggc accatgccaa ggaattgcag cttggcgttc ttctggcgca cgttcgcaat    17520
ggtcgtgacc atcttcttga tgccctggat gctgtacgcc tcaagctcga tggggggacag    17580 cacatagtcg gccgcgaaga gggcggccgc caggccgacg ccaagggtcg gggccgtgtc    17640
gatcaggcac acgtcgaagc cttggttcgc cagggccttg atgttcgccc cgaacagctc    17700
gcgggcgtcg tccagcgaca gccgttcggc gttcgcagt accgggttgg actcgatgag    17760
ggcgaggcgc gcggcctggc cgtcgccggc tgcgggtgcg gtttcggtcc agccgccggc    17820
agggacagcg ccgaacagct tgcttgcatg caggccggta gcaaagtcct tgagcgtgta    17880
ggacgcattg ccctggggg ccaggtcgat cacggcaacc cgcaagccgc gctcgaaaaa    17940
gtcgaaggca agatgcacaa gggtcgaagt cttgccgacg ccgcctttct ggttggccgt    18000
```

```
gaccaaagtt tcatcgttt ggtttcctgt tttttcttgg cgtccgcttc ccacttccgg    18060
acgatgtacg cctgatgttc cggcagaacc gccgttaccc gcgcgtaccc ctcgggcaag   18120
ttcttgtcct cgaacgcggc ccacacgcga tgcaccgctt gcgacactgc gccctggtc    18180 agtcccagcg acgttgcgaa cgtcgcctgt ggcttccat  cgactaagac gccccgcgct   18240
atctcgatgg tctgctgccc cacttccagc ccctggatcg cctcctggaa ctggctttcg   18300
gtaagccgtt tcttcatgga taacacccat aatttgctcc gcgccttggt tgaacatagc   18360
ggtgacagcc gccagcacat gagagaagtt tagctaaaca tttctcgcac gtcaacacct   18420
ttagccgcta aaactcgtcc ttggcgtaac aaaacaaaag cccggaaacc gggctttcgt   18480
ctcttgccgc ttatggctct gcacccggct ccatcaccaa caggtcgcgc acgcgcttca   18540
ctcggttgcg gatcgacact gccagcccaa caaagccggt tgccgccgcc gccaggatcg   18600
cgccgatgat gccggccaca ccggccatcg cccaccaggt cgccgccttc cggttccatt   18660
cctgctggta ctgcttcgca atgctggacc tcggctcacc ataggctgac cgctcgatgg   18720
cgtatgccgc ttctcccctt ggcgtaaaac ccagcgccgc aggcggcatt gccatgctgc   18780
ccgccgcttt cccgaccacg acgcgcgcac caggcttgcg gtccagacct tcggccacgg   18840
cgagctgcgc aaggacataa tcagccgccg acttggctcc acgcgcctcg atcagctctt   18900
gcactcgcgc gaaatccttg gcctccacgg ccgccatgaa tcgcgcacgc ggcgaaggct   18960
ccgcagggcc ggcgtcgtga tcgccgccga gaatgcccct accaagttc  gacgacacga   19020 aaatcatgct gacggctatc accatcatgc agacggatcg cacgaacccg ctgaattgaa   19080
cacgagcacg gcaccgcga  ccactatgcc aagaatgccc aaggtaaaaa ttgccggccc   19140
cgccatgaag tccgtgaatg ccccgacggc cgaagtgaag ggcaggccgc cacccaggcc   19200
gccgccctca ctgccggca  cctggtcgct gaatgtcgat gccagcacct gcggcacgtc   19260
aatgcttccg ggcgtcgcgc tcgggctgat cgcccatccc gttactgccc cgatcccggc   19320
aatggcaagg actgccagcg ctgccatttt tgggtgagg  ccgttcgcgg ccgaggggcg   19380
cagcccctgg ggggatggga ggcccgcgtt agcgggccgg gagggttcga aaggggggg   19440 caccccctt  cggcgtgcgc ggtcacgcgc acagggcgca gccctggtta aaaacaaggt   19500
ttataaatat tggtttaaaa gcaggttaaa agacaggtta gcggtggccg aaaaacgggc   19560
ggaaaccctt gcaaatgctg gattttctgc ctgtggacag ccctcaaat  gtcaataggt   19620 gcgcccctca tctgtcagca ctctgccct  caagtgtcaa ggatcgcgcc cctcatctgt   19680
cagtagtcgc gcccctcaag tgtcaatacc gcagggcact tatccccagg cttgtccaca   19740
tcatctgtgg gaaactcgcg taaaatcagg cgttttcgcc gatttgcgag gctggccagc   19800
tccacgtcgc cggccgaaat cgagcctgcc cctcatctgt caacgccgcg ccgggtgagt   19860
cggcccctca gtgtcaacg  tccgcccctc atctgtcagt gagggccaag ttttccgcga   19920
ggtatccaca acgccggcgg ccgcggtgtc tcgcacacgg cttcgacggc gtttctggcg   19980
cgtttgcagg gccatagacg gccgccagcc cagcggcgag ggcaaccagc ccggtgagcg   20040
tcggaaaggc gctggaagcc ccgtagcgac gcggagaggg gcgagacaag ccaagggcgc   20100
aggctcgatg cgcagcacga catagccggt tctcgcaagg acgagaattt ccctgcggtg   20160
cccctcaagt gtcaatgaaa gtttccaacg cgagccattc gcgagagcct tgagtccacg   20220
ctagatgaga gctttgttgt aggtggacca gttggtgatt ttgaacttt  gctttgccac   20280 ggaacggtct gcgttgtcgg gaagatgcgt gatctgatcc ttcaactcag caaaagttcg   20340
```

```
atttattcaa caaagccacg ttgtgtctca aaatctctga tgttacattg cacaagataa   20400
aaatatatca tcatgaacaa taaaactgtc tgcttacata aacagtaata caagggtgt    20460 tatgagccat attcaacggg aaacgtcttg ctcgactcta gagctcgttc ctcgaggcct   20520
cgaggcctcg aggaacggta cctgcgggga agcttacaat aatgtgtgtt gttaagtctt   20580
gttgcctgtc atcgtctgac tgactttcgt cataaatccc ggcctccgta acccagcttt   20640
gggcaagctc acggatttga tccggcgaaa cgggaatatc gagatgccgg gctgaacgct   20700
gcagttccag ctttcccttt cgggacaggt actccagctg attgattatc tgctgaaggg   20760
tcttggttcc acctcctggc acaatgcgaa tgattacttg agcgcgatcg ggcatccaat   20820
tttctcccgt caggtgcgtg gtcaagtgct acaaggcacc tttcagtaac gagcgaccgt   20880
cgatccgtcg ccgggatacg gacaaaatgg agcgcagtag tccatcgagg gcggcgaaag   20940
cctcgccaaa agcaatacgt tcatctcgca cagcctccag atccgatcga gggtcttcgg   21000
cgtaggcaga tagaagcatg gatacattgc ttgagagtat tccgatggac tgaagtatgg   21060
cttccatctt ttctcgtgtg tctgcatcta tttcgagaaa gccccgatg cggcgcaccg    21120 caacgcgaat tgccatacta tccgaaagtc ccagcaggcg cgcttgatag gaaaaggttt   21180
catactcggc cgatcgcaga cgggcactca cgaccttgaa cccttcaact ttcagggatc   21240
gatgctggtt gatggtagtc tcactcgacg tggctctggt gtgttttgac atagcttcct   21300
ccaaagaaag cggaaggtct ggatactcca gcacgaaatg tgcccgggta gacggatgga   21360
agtctagccc tgctcaatat gaaatcaaca gtacatttac agtcaatact gaatatactt   21420
gctacatttg caattgtctt ataacgaatg tgaaataaaa atagtgtaac aacgctttta   21480
ctcatcgata atcacaaaaa catttatacg aacaaaaata caaatgcact ccggtttcac   21540
aggataggcg ggatcagaat atgcaacttt tgacgttttg ttctttcaaa gggggtgctg   21600
gcaaaaccac cgcactcatg ggcctttgcg ctgctttggc aaatgacggt aaacgagtgg   21660
ccctctttga tgccgacgaa aaccggcctc tgacgcgatg gagagaaaac gccttacaaa   21720
gcagtactgg gatcctcgct gtgaagtcta ttccgccgac gaaatgcccc ttcttgaagc   21780
agcctatgaa aatgccgagc tcgaaggatt tgattatgcg ttggccgata cgcgtggcgg   21840
ctcgagcgag ctcaacaaca caatcatcgc tagctcaaac ctgcttctga tccccaccat   21900
gctaacgccg ctcgacatcg atgaggcact atctacctac cgctacgtca tcgagctgct   21960
gttgagtgaa aatttggcaa ttcctacagc tgttttgcgc caacgcgtcc cggtcggccg   22020
attgacaaca tcgcaacgca ggatgtcaga gacgctagag agccttccag ttgtaccgtc   22080
tcccatgcat gaaagagatg catttgccgc gatgaaagaa cgcggcatgt tgcatcttac   22140
attactaaac acgggaactg atccgacgat gcgcctcata gagaggaatc ttcggattgc   22200
gatggaggaa gtcgtggtca tttcgaaact gatcagcaaa atcttggagg cttgaagatg   22260
gcaattcgca agcccgcatt gtcggtcggc gaagcacggc ggcttgctgg tgctcgaccc   22320
gagatccacc atcccaaccc gacacttgtt ccccagaagc tggacctcca gcacttgcct   22380
gaaaaagccg acgagaaaga ccagcaacgt gagcctctcg tcgccgatca catttacagt   22440
cccgatcgac aacttaagct aactgtggat gcccttagtc cacctccgtc cccgaaaaag   22500
ctccaggttt ttctttcagc gcgaccgccc gcgcctcaag tgtcgaaaac atatgacaac   22560
ctcgttcggc aatacagtcc ctcgaagtcg ctacaaatga ttttaaggcg cgcgttggac   22620
gatttcgaaa gcatgctggc agatggatca tttcgcgtgg ccccgaaaag ttatccgatc   22680
ccttcaacta cagaaaaatc cgttctcgtt cagacctcac gcatgttccc ggttgcgttg   22740
```

```
ctcgaggtcg ctcgaagtca tttgatccg ttggggttgg agaccgctcg agctttcggc    22800
cacaagctgg ctaccgccgc gctcgcgtca ttctttgctg gagagaagcc atcgagcaat    22860
tggtgaagag ggacctatcg gaaccctca ccaaatattg agtgtaggtt tgaggccgct    22920
ggccgcgtcc tcagtcacct tttgagccag ataattaaga gccaaatgca attggctcag    22980
gctgccatcg tcccccgtg cgaaacctgc acgtccgcgt caaagaaata accggcacct    23040
cttgctgttt ttatcagttg agggcttgac ggatccgcct caagtttgcg gcgcagccgc    23100
aaaatgagaa catctatact cctgtcgtaa acctcctcgt cgcgtactcg actggcaatg    23160
agaagttgct cgcgcgatag aacgtcgcgg ggtttctcta aaaacgcgag gagaagattg    23220
aactcacctg ccgtaagttt caccctcaccg ccagcttcgg acatcaagcg acgttgcctg    23280
agattaagtg tccagtcagt aaaacaaaaa gaccgtcggt cttgagcg acaacgttg    23340 gggcgcacgc gcaaggcaac ccgaatgcgt gcaagaaact ctctcgtact aaacggctta    23400
gcgataaaat cacttgctcc tagctcgagt gcaacaactt tatccgtctc ctcaaggcgg    23460
tcgccactga taattatgat tggaatatca gactttgccg ccagatttcg aacgatctca    23520
agcccatctt cacgacctaa atttagatca acaaccacga catcgaccgt cgcggaagag    23580
agtactctag tgaactgggt gctgtcggct accgcggtca ctttgaaggc gtggatcgta    23640
aggtattcga taataagatg ccgcatacg acatcgtcat cgataagaag aacgtgtttc    23700
aacggctcac ctttcaatct aaaatctgaa cccttgttca cagcgcttga gaaattttca    23760
cgtgaaggat gtacaatcat ctccagctaa atgggcagtt cgtcagaatt gcggctgacc    23820
gcggatgacg aaaatgcgaa ccaagtattt caattttatg acaaaagttc tcaatcgttg    23880
ttacaagtga aacgcttcga ggttacagct actattgatt aaggagatcg cctatggtct    23940
cgccccggcg tcgtgcgtcc gccgcgagcc agatctcgcc tacttcataa acgtcctcat    24000
aggcacggaa tggaatgatg acatcgatcg ccgtagagag catgtcaatc agtgtgcgat    24060
cttccaagct agcaccttgg gcgctacttt tgacaaggga aaacagtttc ttgaatcctt    24120
ggattggatt cgcgccgtgt attgttgaaa tcgatcccgg atgtcccgag acgacttcac    24180
tcagataagc ccatgctgca tcgtcgcgca tctcgccaag caatatccgg tccggccgca    24240
tacgcagact tgcttggagc aagtgctcgg cgctcacagc acccagccca gcaccgttct    24300
tggagtagag tagtctaaca tgattatcgt gtggaatgac gagttcgagc gtatcttcta    24360
tggtgattag cctttcctgg gggggatgg cgctgatcaa ggtcttgctc attgttgtct    24420
tgccgcttcc ggtagggcca catagcaaca tcgtcagtcg gctgacgacg catgcgtgca    24480
gaaacgcttc caaatccccg ttgtcaaaat gctgaaggat agcttcatca tcctgatttt    24540
ggcgtttcct tcgtgtctgc cactggttcc acctcgaagc atcataacgg gaggagactt    24600
ctttaagacc agaaacacgc gagcttggcc gtcgaatggt caagctgacg gtgcccgagg    24660
gaacggtcgg cggcagacag atttgtagtc gttcaccacc aggaagttca gtggcgcaga    24720
gggggttacg tggtccgaca tcctgctttc tcagcgcgcc cgctaaaata gcgatatctt    24780
caagatcatc ataagagacg ggcaaaggca tcttggtaaa aatgccggct tggcgcacaa    24840
atgcctctcc aggtcgattg atcgcaattt cttcagtctt cgggtcatcg agccattcca    24900
aaatcggctt cagaagaaag cgtagttgcg gatccactttc catttacaat gtatcctatc    24960
tctaagcgga aatttgaatt cattaagagc ggcggttcct ccccccgcgtg gcgccgccag    25020 tcaggcggag ctggtaaaca ccaaagaaat cgaggtcccg tgctacgaaa atggaaacgg    25080
```

```
tgtcaccctg attcttcttc agggttggcg gtatgttgat ggttgcctta agggctgtct   25140
cagttgtctg ctcaccgtta tttttgaaagc tgttgaagct catcccgcca cccgagctgc   25200
cggcgtaggt gctagctgcc tggaaggcgc cttgaacaac actcaagagc atagctccgc   25260
taaaacgctg ccagaagtgg ctgtcgaccg agcccggcaa tcctgagcga ccagttcgt    25320
ccgcgcttgg cgatgttaac gagatcatcg catggtcagg tgtctcggcg cgatcccaca   25380
acacaaaaac gcgcccatct ccctgttgca agccacgctg tatttcgcca caacggtgg    25440
tgccacgatc aagaagcacg atattgttcg ttgttccacg aatatcctga ggcaagacac   25500
actttacata gcctgccaaa tttgtgtcga ttgcggtttg caagatgcac ggaattattg   25560
tcccttgcgt taccataaaa tcggggtgcg gcaagagcgt ggcgctgctg ggctgcagct   25620
cggtgggttt catacgtatc gacaaatcgt tctcgccgga cacttcgcca ttcggcaagg   25680
agttgtcgtc acgcttgcct tcttgtcttc ggcccgtgtc gccctgaatg gcgcgtttgc   25740
tgacccttg atcgccgctg ctatatgcaa aaatcggtgt ttcttccggc cgtggctcat    25800
gccgctccgg ttcgcccctc ggcggtagag gagcagcagg ctgaacagcc tcttgaaccg   25860
ctggaggatc cggcggcacc tcaatcggag ctggatgaaa tggcttggtg tttgttgcga   25920
tcaaagttga cggcgatgcg ttctcattca ccttctttttg cgcccacct agccaaatga   25980
ggcttaatga taacgcgaga acgacacctc cgacgatcaa tttctgagac cccgaaagac   26040
gccggcgatg tttgtcggag accagggatc cagatgcatc aacctcatgt gccgcttgct   26100
gactatcgtt attcatccct tcgcccccctt caggacgcgt ttcacatcgg gcctcaccgt   26160
gcccgtttgc ggccttttggc caacgggatc gtaagcggtg ttccagatac atagtactgt   26220
gtggccatcc ctcagacgcc aacctcggga aaccgaagaa atctcgacat cgctccctttt  26280
aactgaatag ttggcaacag cttccttgcc atcaggattg atggtgtaga tggagggtat   26340
gcgtacattg cccggaaagt ggaataccgt cgtaaatcca ttgtcgaaga cttcgagtgg   26400
caacagcgaa cgatcgcctt gggcgacgta gtgccaatta ctgtccgccg caccaagggc   26460
tgtgacaggc tgatccaata aattctcagc tttccgttga tattgtgctt ccgcgtgtag   26520
tctgtccaca acagccttct gttgtgcctc ccttcgccga gccgccgcat cgtcggcggg   26580
gtaggcgaat tggacgctgt aatagagatc gggctgctct ttatcgaggt gggacagagt   26640
cttgaacttt atactgaaaa cataacggcg catcccggag tcgcttgcgg ttagcacgat   26700
tactggctga ggcgtgagga cctggcttgc cttgaaaaat agataatttc cccgcggtag   26760
ggctgctaga tctttgctat ttgaaacggc aaccgctgtc accgtttcgt tcgtggcgaa   26820
tgttacgacc aaagtagctc caaccgccgt cgagaggcgc accacttgat cgggattgta   26880
agccaaataa cgcatgcgcg gatctagctt gcccgccatt ggagtgtctt cagcctccgc   26940
accagtcgca gcggcaaata aacatgctaa aatgaaaagt gcttttctga tcatggttcg   27000
ctgtggccta cgtttgaaac ggtatcttcc gatgtctgat aggaggtgac aaccagacct   27060
gccgggttgg ttagtctcaa tctgccgggc aagctggtca ccttttcgta gcgaactgtc   27120
gcggtccacg tactcaccac aggcattttg ccgtcaacga cgagggtcct tttatagcga   27180
atttgctgcg tgcttggagt tacatcattt gaagcgatgt gctcgacctc cacccctgccg  27240
cgtttgccaa gaatgacttg aggcgaactg ggattgggat agttgaagaa ttgctggtaa   27300
tcctggcgca ctgttgggc actgaagttc gataccaggt cgtaggcgta ctgagcggtg    27360
tcggcatcat aactctcgcg caggcgaacg tactcccaca atgaggcgtt aacgacggcc   27420
tcctcttgag ttgcaggcaa tcgcgagaca gacacctcgc tgtcaacggt gccgtccggc   27480
```

```
cgtatccata gatatacggg cacaagcctg ctcaacggca ccattgtggc tatagcgaac   27540
gcttgagcaa catttcccaa aatcgcgata gctgcgacag ctgcaatgag tttggagaga   27600
cgtcgcgccg atttcgctcg cgcggtttga aaggcttcta cttccttata gtgctcggca   27660
aggctttcgc gcgccactag catggcatat tcaggccccg tcatagcgtc cacccgaatt   27720
gccgagctga agatctgacg gagtaggctg ccatcgcccc acattcagcg ggaagatcgg   27780
gcctttgcag ctcgctaatg tgtcgtttgt ctggcagccg ctcaaagcga caactaggca   27840
cagcaggcaa tacttcatag aattctccat tgaggcgaat ttttgcgcga cctagcctcg   27900
ctcaacctga gcgaagcgac ggtacaagct gctggcagat tgggttgcgc cgctccagta   27960
actgcctcca atgttgccgg cgatcgccgg caaagcgaca atgagcgcat ccctgtcag   28020 aaaaaacata tcgagttcgt aaagaccaat gatcttggcc gcggtcgtac cggcgaaggt   28080
gattacacca agcataaggg tgagcgcagt cgcttcggtt aggatgacga tcgttgccac   28140
gaggtttaag aggagaagca agagaccgta ggtgataagt tgcccgatcc acttagctgc   28200
gatgtcccgc gtgcgatcaa aaatatatcc gacgaggatc agaggcccga tcgcgagaag   28260
cactttcgtg agaattccaa cggcgtcgta aactccgaag gcagaccaga gcgtgccgta   28320
aaggacccac tgtgcccctt ggaaagcaag gatgtcctgg tcgttcatcg gaccgatttc   28380
ggatgcgatt ttctgaaaaa cggcctgggt cacggcgaac attgtatcca actgtgccgg   28440
aacagtctgc agaggcaagc cggttacact aaactgctga acaaagtttg ggaccgtctt   28500
ttcgaagatg gaaaccacat agtcttggta gttagcctgc ccaacaatta gagcaacaac   28560
gatggtgacc gtgatcaccc gagtgatacc gctacgggta tcgacttcgc cgcgtatgac   28620
taaaataccc tgaacaataa tccaaagagt gacacaggcg atcaatggcg cactcaccgc   28680
ctcctggata gtctcaagca tcgagtccaa gcctgtcgtg aaggctacat cgaagatcgt   28740
atgaatggcc gtaaacggcg ccggaatcgt gaaattcatc gattggacct gaacttgact   28800
ggtttgtcgc ataatgttgg ataaaatgag ctcgcattcg gcgaggatgc gggcggatga   28860
acaaatcgcc cagccttagg ggagggcacc aaagatgaca gcggtctttt gatgctcctt   28920
gcgttgagcg gccgcctctt ccgcctcgtg aaggccggcc tgcgcggtag tcatcgttaa   28980
taggcttgtc gcctgtacat tttgaatcat tgcgtcatgg atctgcttga gaagcaaacc   29040
attggtcacg gttgcctgca tgatattgcg agatcgggaa agctgagcag acgtatcagc   29100
attcgccgtc aagcgtttgt ccatcgtttc cagattgtca gccgcaatgc cagcgctgtt   29160
tgcggaaccg gtgatctgcg atcgcaacag gtccgcttca gcatcactac ccacgactgc   29220
acgatctgta tcgctggtga tcgcacgtgc cgtggtcgac attggcattc gcggcgaaaa   29280
catttcattg tctaggtcct tcgtcgaagg atactgattt ttctggttga gcgaagtcag   29340
tagtccagta acgccgtagg ccgacgtcaa catcgtaacc atcgctatag tctgagtgag   29400
attctccgca gtcgcgagcg cagtcgcgag cgtctcagcc tccgttgccg ggtcgctaac   29460
aacaaactgc gcccgcgcgg gctgaatata tagaaagctg caggtcaaaa ctgttgcaat   29520
aagttgcgtc gtcttcatcg tttcctacct tatcaatctt ctgcctcgtg gtgacgggcc   29580
atgaattcgc tgagccagcc agatgagttg ccttcttgtg cctcgcgtag tcgagttgca   29640
aagcgcaccg tgttggcacg ccccgaaagc acggcgacat attcacgcat atcccgcaga   29700
tcaaattcgc agatgacgct tccactttct cgtttaagaa gaaacttacg gctgccgacc   29760
gtcatgtctt cacggatcgc ctgaaattcc ttttcggtac atttcagtcc atcgacataa   29820
```

```
gccgatcgat ctgcggttgg tgatggatag aaaatcttcg tcatacattg cgcaaccaag    29880
ctggctccta gcggcgattc cagaacatgc tctggttgct gcgttgccag tattagcatc    29940
ccgttgtttt ttcgaacggt caggaggaat tgtcgacga cagtcgaaaa tttagggttt    30000
aacaaatagg cgcgaaactc atcgcagctc atcacaaaac ggcggccgtc gatcatggct    30060
ccaatccgat gcaggagata tgctgcagcg ggagcgcata cttcctcgta ttcgagaaga    30120
tgcgtcatgt cgaagccggt aatcgacgga tctaacttta cttcgtcaac ttcgccgtca    30180
aatgcccagc caagcgcatg gccccggcac cagcgttgga gccgcgctcc tgcgccttcg    30240
gcgggcccat gcaacaaaaa ttcacgtaac cccgcgattg aacgcatttg tggatcaaac    30300
gagagctgac gatggatacc acggaccaga cggcggttct cttccggaga atcccaccc    30360 cgaccatcac tctcgatgag agccacgatc cattcgcgca gaaaatcgtg tgaggctgct    30420
gtgttttcta ggccacgcaa cggcgccaac ccgctgggtg tgcctctgtg aagtgccaaa    30480
tatgttcctc ctgtggcgcg aaccagcaat tcgccacccc ggtccttgtc aaagaacacg    30540
accgtacctg cacggtcgac catgctctgt tcgagcatgg ctagaacaaa catcatgagc    30600
gtcgtcttac ccctcccgat aggcccgaat attgccgtca tgccaacatc gtgctcatgc    30660
gggatatagt cgaaaggcgt tccgccattg gtacgaaatc gggcaatcgc gttgccccag    30720
tggcctgagc tggcgccctc tggaaagttt tcgaaagaga caaaccctgc gaaattgcgt    30780
gaagtgattg cgcagggcg tgtgcgccac ttaaaattcc ccggcaattg ggaccaatag    30840
gccgcttcca taccaatacc ttcttggaca accacggcac ctgcatccgc cattcgtgtc    30900
cgagcccgcg cgccctgtc cccaagacta ttgagatcgt ctgcatagac gcaaaggctc    30960
aaatgatgtg agcccataac gaattcgttg ctcgcaagtg cgtcctcagc ctcggataat    31020
ttgccgattt gagtcacggc tttatcgccg gaactcagca tctggctcga tttgaggcta    31080
agtttcgcgt gcgcttgcgg gcgagtcagg aacgaaaaac tctgcgtgag aacaagtgga    31140
aaatcgaggg atagcagcgc gttgagcatg cccggccgtg ttttgcagg gtattcgcga    31200 aacgaataga tggatccaac gtaactgtct tttggcgttc tgatctcgag tcctcgcttg    31260
ccgcaaatga ctctgtcggt ataaatcgaa gcgccgagtg agccgctgac gaccggaacc    31320
ggtgtgaacc gaccagtcat gatcaaccgt agcgcttcgc caatttcggt gaagagcaca    31380
ccctgcttct cgcggatgcc aagacgatgc aggccatacg cttaagaga gccagcgaca    31440 acatgccaaa gatcttccat gttcctgatc tggcccgtga gatcgttttc ccttttccg    31500 cttagcttgg tgaacctcct ctttacttc cctaaagccg cctgtgggta gacaatcaac    31560
gtaaggaagt gttcattgcg gaggagttgg ccggagagca cgcgctgttc aaaagcttcg    31620
ttcaggctag cggcgaaaac actacggaag tgtcgcggcg ccgatgatgg cacgtcggca    31680
tgacgtacga ggtgagcata tattgacaca tgatcatcag cgatattgcg caacagcgtg    31740
ttgaacgcac gacaacgcgc attgcgcatt tcagtttcct caagctcgaa tgcaacgcca    31800
tcaattctcg caatggtcat gatcgatccg tcttcaagaa ggacgatatg gtcgctgagg    31860
tggccaatat aagggagata gatctcaccg gatctttcgg tcgttccact cgcgccgagc    31920
atcacaccat tcctctccct cgtgggggaa ccctaattgg atttgggcta acagtagcgc    31980 cccccaaac tgcactatca atgcttcttc ccgcggtccg caaaaatagc aggacgacgc    32040
tcgccgcatt gtagtctcgc tccacgatga gccgggctgc aaaccataac ggcacgagaa    32100
cgacttcgta gagcgggttc tgaacgataa cgatgacaaa gccggcgaac atcatgaata    32160
accctgccaa tgtcagtggc accccaagaa acaatgcggg ccgtgtggct gcgaggtaaa    32220
```

-continued

```
gggtcgattc ttccaaacga tcagccatca actaccgcca gtgagcgttt ggccgaggaa   32280
gctcgcccca aacatgataa caatgccgcc gacgacgccg gcaaccagcc caagcgaagc   32340
ccgcccgaac atccaggaga tcccgatagc gacaatgccg agaacagcga gtgactggcc   32400
gaacggacca aggataaacg tgcatatatt gttaaccatt gtggcggggt cagtgccgcc   32460
acccgcagat tgcgctgcgg cgggtccgga tgaggaaatg ctccatgcaa ttgcaccgca   32520
caagcttggg gcgcagctcg atatcacgcg catcatcgca ttcgagagcg agaggcgatt   32580
tagatgtaaa cggtatctct caaagcatcg catcaatgcg cacctcctta gtataagtcg   32640
aataagactt gattgtcgtc tgcggatttg ccgttgtcct ggtgtggcgg tggcggagcg   32700
attaaaccgc cagcgccatc ctcctgcgag cggcgctgat atgaccccca acatcccac   32760 gtctcttcgg attttagcgc ctcgtgatcg tcttttggag gctcgattaa cgcgggcacc   32820
agcgattgag cagctgtttc aacttttcgc acgtagccgt ttgcaaaacc gccgatgaaa   32880
ttaccggtgt tgtaagcgga gatcgcccga cgaagcgcaa attgcttctc gtcaatcgtt   32940
tcgccgcctg cataacgact tttcagcatg tttgcagcgg cagataatga tgtgcacgcc   33000
tggagcgcac cgtcaggtgt cagaccgagc atagaaaaat ttcgagagtt tatttgcatg   33060
aggccaacat ccagcgaatg ccgtgcatcg agacggtgcc tgacgacttg ggttgcttgg   33120
ctgtgatctt gccagtgaag cgtttcgccg gtcgtgttgt catgaatcgc taaaggatca   33180
aagcgactct ccaccttagc tatcgccgca agcgtagatg tcgcaactga tggggcacac   33240
ttgcgagcaa catggtcaaa ctcagcagat gagagtggcg tggcaaggct cgacgaacag   33300
aaggagacca tcaaggcaag agaaagcgac cccgatctct taagcatacc ttatctcctt   33360
agctcgcaac taacaccgcc tctcccgttg gaagaagtgc gttgttttat gttgaagatt   33420
atcgggaggg tcggttactc gaaaattttc aattgcttct ttatgatttc aattgaagcg   33480
agaaacctcg cccggcgtct tggaacgcaa catggaccga gaaccgcgca tccatgacta   33540
agcaaccgga tcgacctatt caggccgcag ttggtcaggt caggctcaga acgaaaatgc   33600
tcggcgaggt tacgctgtct gtaaacccat tcgatgaacg ggaagcttcc ttccgattgc   33660
tcttggcagg aatattggcc catgcctgct tgcgctttgc aaatgctctt atcgcgttgg   33720
tatcatatgc cttgtccgcc agcagaaacg cactctaagc gattatttgt aaaaatgttt   33780
cggtcatgcg gcggtcatgg gcttgacccg ctgtcagcgc aagacggatc ggtcaaccgt   33840
cggcatcgac aacagcgtga atcttggtgg tcaaaccgcc acgggaacgt cccatacagc   33900
catcgtcttg atcccgctgt ttcccgtcgc cgcatgttgg tggacgcgga cacaggaact   33960
gtcaatcatg acgacattct atcgaaagcc ttggaaatca cactcagaat atgatcccag   34020
acgtctgcct cacgccatcg tacaaagcga ttgtagcagg ttgtacagga accgtatcga   34080
tcaggaacgt ctgcccaggg cgggcccgtc cggaagcgcc acaagatgac attgatcacc   34140
cgcgtcaacg cgcggcacgc gacgcggctt atttgggaac aaaggactga acaacagtcc   34200
attcgaaatc ggtgacatca aagcggggac gggttatcag tggcctccaa gtcaagcctc   34260
aatgaatcaa aatcagaccg atttgcaaac ctgatttatg agtgtgcggc ctaaatgatg   34320
aaatcgtcct tctagatcgc ctccgtggtg tagcaacacc tcgcagtatc gccgtgctga   34380
ccttggccag ggaattgact ggcaaggggtg ctttcacatg accgctcttt tggccgcgat   34440
agatgatttc gttgctgctt tgggcacgta aaggagaga agtcatatcg gagaaattcc   34500
tcctggcgcg agagcctgct ctatcgcgac ggcatcccac tgtcgggaac agaccggatc   34560
```

```
attcacgagg cgaaagtcgt caacacatgc gttataggca tcttcccttg aaggatgatc   34620
ttgttgctgc caatctggag gtgcggcagc cgcaggcaga tgcgatctca gcgcaacttg   34680
cggcaaaaca tctcactcac ctgaaaacca ctagcgagtc tcgcgatcag acgaaggcct   34740
tttacttaac gacacaatat ccgatgtctg catcacaggc gtcgctatcc cagtcaatac   34800
taaagcggtg caggaactaa agattactga tgacttaggc gtgccacgag gcctgagacg   34860
acgcgcgtag acagtttttt gaaatcatta tcaaagtgat ggcctccgct gaagcctatc   34920
acctctgcgc cggtctgtcg gagagatggg caagcattat tacggtcttc gcgcccgtac   34980
atgcattgga cgattgcagg gtcaatggat ctgagatcat ccagaggatt gccgcccttc   35040
ccttccgttt cgagttggag ccagccccta aatgagacga catagtcgac ttgatgtgac   35100
aatgccaaga gagagatttg cttaacccga tttttttgct caagcgtaag cctattgaag   35160
cttgccggca tgacgtccgc gccgaaagaa tatcctacaa gtaaaacatt ctgcacaccg   35220
aaatgcttgg tgtagacatc gattatgtga ccaagatcct tagcagtttc gcttggggac   35280
cgctccgacc agaaataccg aagtgaactg acgccaatga caggaatccc ttccgtctgc   35340
agataggtac catcgataga tctgctgcct cgcgcgtttc ggtgatgacg gtgaaaacct   35400
ctgacacatg cagctcccgg agacggtcac agcttgtctg taagcggatg ccgggagcag   35460
acaagcccgt cagggcgcgt cagcgggtgt tggcgggtgt cggggcgcag ccatgaccca   35520
gtcacgtagc gatagcggag tgtatactgg cttaactatg cggcatcaga gcagattgta   35580
ctgagagtgc accatatgcg gtgtgaaata ccgcacagat gcgtaaggag aaaataccgc   35640
atcaggcgct cttccgcttc ctcgctcact gactcgctgc gctcggtcgt tcggctgcgg   35700
cgagcggtat cagctcactc aaaggcggta atacggttat ccacagaatc aggggataac   35760
gcaggaaaga acatgtgagc aaaaggccag caaaaggcca ggaaccgtaa aaaggccgcg   35820
ttgctggcgt ttttccatag gctccgcccc cctgacgagc atcacaaaaa tcgacgctca   35880
agtcagaggt ggcgaaaccc gacaggacta taaagatacc aggcgtttcc ccctggaagc   35940
tccctcgtgc gctctcctgt tccgaccctg ccgcttaccg gatacctgtc cgcctttctc   36000
ccttcgggaa gcgtggcgct ttctcatagc tcacgctgta ggtatctcag ttcggtgtag   36060
gtcgttcgct ccaagctggg ctgtgtgcac gaaccccccg ttcagcccga ccgctgcgcc   36120
ttatccggta actatcgtct tgagtccaac ccggtaagac acgacttatc gccactggca   36180
gcagccactg gtaacaggat tagcagagcg aggtatgtag gcggtgctac agagttcttg   36240
aagtggtggc ctaactacgg ctacactaga aggacagtat ttggtatctg cgctctgctg   36300
aagccagtta ccttcggaaa aagagttggt agctcttgat ccggcaaaca aaccaccgct   36360
ggtagcggtg gttttttttgt ttgcaagcag cagattacgc gcagaaaaaa aggatctcaa   36420
gaagatcctt tgatcttttc tacggggtct gacgctcagt ggaacgaaaa ctcacgttaa   36480
gggattttgg tcatgagatt atcaaaaagg atcttcacct agatcctttt aaattaaaaa   36540
tgaagtttta aatcaatcta agtatatat gagtaaactt ggtctgacag ttaccaatgc   36600
ttaatcagtg aggcacctat ctcagcgatc tgtctatttc gttcatccat agttgcctga   36660
ctccccgtcg tgtagataac tacgatacgg gagggcttac catctggccc cagtgctgca   36720
atgataccgc gagacccacg ctcaccggct ccagatttat cagcaataaa ccagccagcc   36780
ggaagggccg agcgcagaag tggtcctgca actttatccg cctccatcca gtctattaat   36840
tgttgccggg aagctagagt aagtagttcg ccagttaata gtttgcgcaa cgttgttgcc   36900
attgctgcag gggggggggg gggggggac ttccattgtt cattccacgg acaaaaacag   36960
```

```
agaaaggaaa cgacagaggc caaaaagcct cgctttcagc acctgtcgtt tcctttcttt    37020
tcagagggta ttttaaataa aaacattaag ttatgacgaa gaagaacgga aacgccttaa    37080
accggaaaat tttcataaat agcgaaaacc cgcgaggtcg ccgccccgta acctgtcgga    37140
tcaccggaaa ggacccgtaa agtgataatg attatcatct acatatcaca acgtgcgtgg    37200
aggccatcaa accacgtcaa ataatcaatt atgacgcagg tatcgtatta attgatctgc    37260
atcaacttaa cgtaaaaaca acttcagaca atacaaatca gcgacactga atacggggca    37320
acctcatgtc ccccccccc ccccccctgc aggcatcgtg gtgtcacgct cgtcgtttgg    37380
tatggcttca ttcagctccg gttcccaacg atcaaggcga gttacatgat ccccatgtt    37440 gtgcaaaaaa gcggttagct ccttcggtcc tccgatcgtt gtcagaagta agttggccgc    37500
agtgttatca ctcatggtta tggcagcact gcataattct cttactgtca tgccatccgt    37560
aagatgcttt tctgtgactg gtgagtactc aaccaagtca ttctgagaat agtgtatgcg    37620
gcgaccgagt tgctcttgcc cggcgtcaac acgggataat accgcgccac atagcagaac    37680
tttaaaagtg ctcatcattg gaaaacgttc ttcggggcga aaactctcaa ggatcttacc    37740
gctgttgaga tccagttcga tgtaacccac tcgtgcaccc aactgatctt cagcatcttt    37800
tactttcacc agcgtttctg ggtgagcaaa aacaggaagg caaaatgccg caaaaaaggg    37860
aataagggcg acacggaaat gttgaatact catactcttc cttttcaat attattgaag    37920 catttatcag ggttattgtc tcatgagcgg atacatattt gaatgtattt agaaaaataa    37980
acaaataggg gttccgcgca catttccccg aaaagtgcca cctgacgtct aagaaaccat    38040
tattatcatg acattaacct ataaaaatag gcgtatcacg aggccctttc gtcttcaaga    38100
attggtcgac gatcttgctg cgttcggata ttttcgtgga gttcccgcca cagacccgga    38160
ttgaaggcga gatccagcaa ctcgcgccag atcatcctgt gacggaactt tggcgcgtga    38220
tgactggcca ggacgtcggc cgaaagagcg acaagcagat cacgcttttc gacagcgtcg    38280
gatttgcgat cgaggatttt tcggcgctgc gctacgtccg cgaccgcgtt gagggatcaa    38340
gccacagcag cccactcgac cttctagccg acccagacga gccaagggat ctttttggaa    38400
tgctgctccg tcgtcaggct ttccgacgtt tgggtggttg aacagaagtc attatcgtac    38460
ggaatgccaa gcactcccga ggggaacccct gtggttggca tgcacataca aatggacgaa    38520
cggataaacc ttttcacgcc cttttaaata tccgttattc taataaacgc tcttttctct    38580
taggtttacc cgccaatata tcctgtcaaa cactgatagt ttaaactgaa ggcgggaaac    38640
gacaatctga tcatgagcgg agaattaagg gagtcacgtt atgaccccg ccgatgacgc    38700 gggacaagcc gttttacgtt tggaactgac agaaccgcaa cgttgaagga gccactcagc    38760
aagctggtac gattgtaata cgactcacta tagggcgaat tgagcgctgt ttaaacgctc    38820
ttcaactgga agagcggtta cccggaccga agcttgaagt tcctattccg aagttcctat    38880
tctctagaaa gtataggaac ttcagatctc gatgctcacc ctgttgtttg tgttacttc    38940 tgcaggtcga ctctagagga tccaccatga gcccagaacg acgcccggcc gacatccgcc    39000
gtgccaccga gcggacatg ccggcggtct gcaccatcgt caaccactac atcgagacaa    39060
gcacggtcaa cttccgtacc gagccgcagg aaccgcagga ctggacgac gacctcgtcc    39120 gtctgcggga gcgctatccc tggctcgtcg ccgaggtgga cggcgaggtc gccggcatcg    39180
cctacgcggg ccccctggaag gcacgcaacg cctacgactg gacggccgag tcgaccgtgt    39240
acgtctcccc ccgccaccag cggacgggac tgggctccac gctctacacc cacctgctga    39300
```

```
agtccctgga ggcacagggc ttcaagagcg tggtcgctgt catcgggctg cccaacgacc  39360
cgagcgtgcg catgcacgag gcgctcggat atgcccccg cggcatgctg cgggcggccg  39420
gcttcaagca cgggaactgg catgacgtgg gtttctggca gctggacttc agcctgccgg  39480
taccgccccg tccggtcctg cccgtcaccg agatctgatc cgtcgaccaa cctagacttg  39540
tccatcttct ggattggcca acttaattaa tgtatgaaat aaaaggatgc acacatagtg  39600
acatgctaat cactataatg tgggcatcaa agttgtgtgt tatgtgtaat tactagttat  39660
ctgaataaaa gagaaagaga tcatccatat ttcttatcct aaatgaatgt cacgtgtctt  39720
tataattctt tgatgaacca gatgcatttc attaaccaaa tccatataca tataaatatt  39780
aatcatatat aattaatatc aattgggtta gcaaacaaa tctagtctag gtgtgttttg  39840
cgaattgcgg ccgcgatctg gggaattccc atggacaccg tgtgcagcg tgacccggtc  39900 gtgcccctct ctagagataa tgagcattgc atgtctaagt tataaaaaat taccacatat  39960 ttttttgtc acacttgttt gaagtgcagt ttatctatct ttatacatat atttaaactt  40020
tactctacga ataatataat ctatagtact acaataatat cagtgtttta gagaatcata  40080
taaatgaaca gttagacatg gtctaaagga caattgagta ttttgacaac aggactctac  40140
agttttatct ttttagtgtg catgtgttct ccttttttt tgcaaatagc ttcacctata  40200
taatacttca tccattttat tagtacatcc atttaggggtt tagggttaat ggttttata  40260 gactaatttt tttagtacat ctattttatt ctattttagc ctctaaatta agaaaactaa  40320
aactctattt tagttttttt atttaataat ttagatataa aatagaataa aataaagtga  40380
ctaaaaatta aacaaatacc ctttaagaaa ttaaaaaaac taaggaaaca tttttcttgt  40440
ttcgagtaga taatgccagc ctgttaaacg ccgtcgacga gtctaacgga caccaaccag  40500
cgaaccagca gcgtcgcgtc gggccaagcg aagcagacgg cacggcatct ctgtcgctgc  40560
ctctggaccc ctctcgagag ttccgctcca ccgttggact tgctccgctg tcggcatcca  40620
gaaattgcgt ggcggagcgg cagacgtgag ccggcacggc aggcggcctc ctcctcctct  40680
cacggcaccg gcagctacgg gggattcctt tcccaccgct ccttcgcttt cccttcctcg  40740
cccgccgtaa taaatagaca cccctccac accctctttc cccaacctcg tgttgttcgg  40800
agcgcacaca cacacaacca gatctccccc aaatccaccc gtcggcacct ccgcttcaag  40860
gtacgccgct cgtcctcccc cccccccctc tctaccttct ctagatcggc gttccggtcc  40920
atgcatggtt agggcccggt agttctactt ctgttcatgt ttgtgttaga tccgtgtttg  40980
tgttagatcc gtgctgctag cgttcgtaca cggatgcgac ctgtacgtca gacacgttct  41040
gattgctaac ttgccagtgt ttctctttgg ggaatcctgg gatggctcta gccgttccgc  41100
agacgggatc gatttcatga tttttttgt ttcgttgcat agggtttggt ttgcccttt  41160 cctttatttc aatatatgcc gtgcacttgt ttgtcgggtc atcttttcat gcttttttt  41220 gtcttggttg tgatgatgtg gtctggttgg gcggtcgttc tagatcggag tagaattctg  41280
tttcaaacta cctggtggat ttattaattt tggatctgta tgtgtgtgcc atacatattc  41340
atagttacga attgaagatg atggatggaa atatcgatct aggataggta tacatgttga  41400
tgcgggtttt actgatgcat atacagagat gcttttgtt cgcttggttg tgatgatgtg  41460
gtgtggttgg gcggtcgttc attcgttcta gatcggagta gaatactgtt tcaaactacc  41520
tggtgtattt attaattttg gaactgtatg tgtgtgtcat acatcttcat agttacgagt  41580
ttaagatgga tggaaatatc gatctaggat aggtatacat gttgatgtgg gttttactga  41640
tgcatataca tgatggcata tgcagcatct attcatatgc tctaaccttg agtacctatc  41700
```

```
tattataata aacaagtatg ttttataatt attttgatct tgatatactt ggatgatggc   41760
atatgcagca gctatatgtg gattttttta gccctgcctt catacgctat ttatttgctt   41820
ggtactgttt cttttgtcga tgctcaccct gttgttggt gttacttctg caggtaccgg    41880
tctctacgta cagtccggac tggcgccttg gcgcgccgat catccacaag tttgtacaaa   41940
aaagctgaac gagaaacgta aaatgatata aatatcaata tattaaatta gattttgcat   42000
aaaaaacaga ctacataata ctgtaaaaca caacatatcc agtcactatg gcggccgcat   42060
taggcacccc aggctttaca ctttatgctt ccggctcgta taatgtgtgg attttgagtt   42120
aggatttaaa tacgcgttga tccggcttac taaaagccag ataacagtat gcgtatttgc   42180
gcgctgattt ttgcggtata agaatatata ctgatatgta tacccgaagt atgtcaaaaa   42240
gaggtatgct atgaagcagc gtattacagt gacagttgac agcgacagct atcagttgct   42300
caaggcatat atgatgtcaa tatctccggt ctggtaagca caaccatgca gaatgaagcc   42360
cgtcgtctgc gtgccgaacg ctggaaagcg gaaaatcagg aagggatggc tgaggtcgcc   42420
cggtttattg aaatgaacgg ctcttttgct gacgagaaca ggggctggtg aaatgcagtt   42480
taaggtttac acctataaaa gagagagccg ttatcgtctg tttgtggatg tacagagtga   42540
tatcattgac acgcccggtc gacggatggt gatcccctg gccagtgcac gtctgctgtc    42600
agataaagtc tcccgtgaac tttacccggt ggtgcatatc ggggatgaaa gctgcgcat    42660 gatgaccacc gatatggcca gtgtgccggt ctccgttatc ggggaagaag tggctgatct   42720
cagccaccgc gaaaatgaca tcaaaaacgc cattaacctg atgttctggg aatataaat    42780 gtcaggctcc cttatacaca gccagtctgc aggtcgacca tagtgactgg atatgttgtg   42840
ttttacagta ttatgtagtc tgttttttat gcaaaatcta atttaatata ttgatattta   42900
tatcatttta cgtttctcgt tcagctttct tgtacaaagt ggtgttaacc tagacttgtc   42960
catcttctgg attggccaac ttaattaatg tatgaaataa aaggatgcac acatagtgac   43020
atgctaatca ctataatgtg ggcatcaaag ttgtgtgtta tgtgtaatta ctagttatct   43080
gaataaaaga gaaagagatc atccatattt cttatcctaa atgaatgtca cgtgtcttta   43140
taattctttg atgaaccaga tgcatttcat taaccaaatc catatacata taaatattaa   43200
tcatatataa ttaatatcaa ttgggttagc aaaacaaatc tagtctaggt gtgttttgcg   43260
aattgcggcc gccaccgcgg tggagctcga attccggtcc gggtcacctt tgtccaccaa   43320
gatggaactg cggccgctca ttaattaagt caggcgcgcc tctagttgaa gacacgttca   43380
tgtcttcatc gtaagaagac actcagtagt cttcggccag aatggccatc tggattcagc   43440
aggcctagaa ggccatttaa atcctgagga tctggtcttc ctaaggaccc gggatatcgg   43500
accgattaaa ctttaattcg gtccgaagct tgaagttcct attccgaagt tcctattctc   43560
cagaaagtat aggaacttcg catgcctgca gtgcagcgtg acccggtcgt gcccctctct   43620
agagataatg agcattgcat gtctaagtta taaaaaatta ccacatattt ttttgtcac    43680 acttgtttga agtgcagttt atctatcttt atacatatat ttaaacttta ctctacgaat   43740
aatataatct atagtactac aataatatca gtgttttaga gaatcatata aatgaacagt   43800
tagacatggt ctaaaggaca attgagtatt ttgacaacag gactctacag ttttatcttt   43860
ttagtgtgca tgtgttctcc ttttttttg caaatagctt cacctatata atacttcatc    43920 catttttatta gtcatccat ttagggttta gggttaatgg tttttataga ctaatttttt   43980
tagtacatct attttattct attttagcct ctaaattaag aaaactaaaa ctctatttta   44040
```

```
gttttttttat ttaataattt agatataaaa tagaataaaa taaagtgact aaaaattaaa    44100
caaatacccct ttaagaaatt aaaaaaacta aggaaacatt tttcttgttt cgagtagata    44160
atgccagcct gttaaacgcc gtcgacgagt ctaacggaca ccaaccagcg aaccagcagc    44220
gtcgcgtcgg gccaagcgaa gcagacggca cggcatctct gtcgctgcct ctggacccct    44280
ctcgagagtt ccgctccacc gttggacttg ctccgctgtc ggcatccaga aattgcgtgg    44340
cggagcggca gacgtgagcc ggcacggcag gcggcctcct cctcctctca cggcaccggc    44400
agctacgggg gattcctttc ccaccgctcc ttcgctttcc cttcctcgcc cgccgtaata    44460
aatagacacc ccctccacac cctctttccc aacctcgtg ttgttcggag cgcacacaca    44520
cacaaccaga tctcccccaa atccacccgt cggcacctcc gcttcaaggt acgccgctcg    44580
tcctcccccc ccccctctc taccttctct agatcggcgt tccggtccat gcatggttag    44640
ggcccggtag ttctacttct gttcatgttt gtgttagatc cgtgtttgtg ttagatccgt    44700
gctgctagcg ttcgtacacg gatgcgacct gtacgtcaga cacgttctga ttgctaactt    44760
gccagtgttt ctctttgggg aatcctggga tggctctagc cgttccgcag acgggatcga    44820
tttcatgatt ttttttgttt cgttgcatag ggtttggttt gcccttttcc tttatttcaa    44880
tatatgccgt gcacttgttt gtcgggtcat cttttcatgc ttttttttgt cttggttgtg    44940
atgatgtggt ctggttgggc ggtcgttcta gatcggagta gaattctgtt tcaaactacc    45000
tggtggattt ttaattttg gatctgtatg tgtgtgccat acatattcat agttacgaat    45060
tgaagatgat ggatggaaat atcgatctag ataggtata catgttgatg cgggttttac    45120
tgatgcatat acagagatgc ttttgttcg cttggttgtg atgatgtggt gtggttgggc    45180
ggtcgttcat tcgttctaga tcggagtaga atactgtttc aaactacctg gtgtatttat    45240
taattttgga actgtatgtg tgtgtcatac atcttcatag ttacgagttt aagatggatg    45300
gaaatatcga tctaggatag gtatacatgt tgatgtgggt tttactgatg catatacatg    45360
atggcatatg cagcatctat tcatatgctc taaccttgag tacctatcta ttataataaa    45420
caagtatgtt ttataattat tttgatcttg atatacttgg atgatggcat atgcagcagc    45480
tatatgtgga tttttttagc cctgccttca tacgctattt atttgcttgg tactgtttct    45540
tttgtcgatg ctcaccctgt tgtttggtgt tacttctgca ggtcgacttt aacttagcct    45600
aggatccaca cgacaccatg atagaggtga aaccgattaa cgcagaggat acctatgaac    45660
taaggcatag aatactcaga ccaaaccagc cgatagaagc gtgtatgttt gaaagcgatt    45720
tacttcgtgg tgcatttcac ttaggcggct attacggggg caaactgatt tccatagctt    45780
cattccacca ggccgagcac tcagaactcc aaggccagaa acagtaccag ctccgaggta    45840
tggctacctt ggaaggttat cgtgagcaga aggcgggatc gagtctaatt aaacacgctg    45900
aagaaattct tcgtaagagg ggggcggact tgctttggtg taatgcgcgg acatccgcct    45960
caggctacta caaaaagtta ggcttcagcg agcaggaga ggtattcgac acgccgccag    46020
taggacctca catcctgatg tataaaagga tcacataact agctagtcag ttaacctaga    46080
cttgtccatc ttctggattg gccaacttaa ttaatgtatg aaataaaagg atgcacacat    46140
agtgacatgc taatcactat aatgtgggca tcaaagttgt gtgttatgtg taattactag    46200
ttatctgaat aaaagagaaa gagatcatcc atatttctta tcctaaatga atgtcacgtg    46260
tctttataat tctttgatga accagatgca tttcattaac caaatccata tacatataaa    46320
tattaatcat atataattaa tatcaattgg gttagcaaaa caaatctagt ctaggtgtgt    46380
tttgcgaatt cagagctcga attcattccg attaatcgtg gcctcttgct cttcaggatg    46440
```

| | | | | | |
|---|---|---|---|---|---|
| aagagctatg | tttaaacgtg | caagcgctac | tagacaattc | agtacattaa | aaacgtccgc | 46500 |
| aatgtgttat | taagttgtct | aagcgtcaat | ttgtttacac | cacaatatat | cctgccacca | 46560 |
| gccagccaac | agctccccga | ccggcagctc | ggcacaaaat | caccactcga | tacaggcagc | 46620 |
| ccatcagtcc | gggacggcgt | cagcgggaga | gccgttgtaa | ggcggcagac | tttgctcatg | 46680 |
| ttaccgatgc | tattcggaag | aacggcaact | aagctgccgg | gtttgaaaca | cggatgatct | 46740 |
| cgcggagggt | agcatgttga | ttgtaacgat | gacagagcgt | tgctgcctgt | gatcaaatat | 46800 |
| catctccctc | gcagagatcc | gaattatcag | ccttcttatt | catttctcgc | ttaaccgtga | 46860 |
| caggctgtcg | atcttgagaa | ctatgccgac | ataataggaa | atcgctggat | aaagccgctg | 46920 |
| aggaagctga | gtggcgctat | ttctttagaa | gtgaacgttg | acgatcgtcg | accgtacccc | 46980 |
| gatgaattaa | ttcggacgta | cgttctgaac | acagctggat | acttacttgg | gcgattgtca | 47040 |
| tacatgacat | caacaatgta | cccgtttgtg | taaccgtctc | ttggaggttc | gtatgacact | 47100 |
| agtggttccc | ctcagcttgc | gactagatgt | tgaggcctaa | cattttatta | gagagcaggc | 47160 |
| tagttgctta | gatacatgat | cttcaggccg | ttatctgtca | gggcaagcga | aaattggcca | 47220 |
| tttatgacga | ccaatgcccc | gcagaagctc | ccatctttgc | cgccatagac | gccgcgcccc | 47280 |
| ccttttgggg | tgtagaacat | cctttttgcca | gatgtggaaa | agaagttcgt | tgtcccattg | 47340 |
| ttggcaatga | cgtagtagcc | ggcgaaagtg | cgagacccat | ttgcgctata | tataagccta | 47400 |
| cgatttccgt | tgcgactatt | gtcgtaattg | gatgaactat | tatcgtagtt | gctctcagag | 47460 |
| ttgtcgtaat | ttgatggact | attgtcgtaa | ttgcttatgg | agttgtcgta | gttgcttgga | 47520 |
| gaaatgtcgt | agttggatgg | ggagtagtca | tagggaagac | gagcttcatc | cactaaaaca | 47580 |
| attggcaggt | cagcaagtgc | ctgccccgat | gccatcgcaa | gtacgaggct | tagaaccacc | 47640 |
| ttcaacagat | cgcgcatagt | cttccccagc | tctctaacgc | ttgagttaag | ccgcgccgcg | 47700 |
| aagcggcgtc | ggcttgaacg | aattgttaga | cattatttgc | cgactacctt | ggtgatctcg | 47760 |
| cctttcacgt | agtgaacaaa | ttcttccaac | tgatctgcgc | gcgaggccaa | gcgatcttct | 47820 |
| tgtccaagat | aagcctgcct | agcttcaagt | atgacgggct | gatactgggc | cggcaggcgc | 47880 |
| tccattgccc | agtcggcagc | gacatccttc | ggcgcgattt | tgccggttac | tgcgctgtac | 47940 |
| caaatgcggg | acaacgtaag | cactacattt | cgctcatcgc | cagcccagtc | gggcggcgag | 48000 |
| ttccatagcg | ttaaggtttc | atttagcgcc | tcaaatagat | cctgttcagg | aaccggatca | 48060 |
| aagagttcct | ccgccgctgg | acctaccaag | gcaacgctat | gttctcttgc | ttttgtcagc | 48120 |
| aagatagcca | gatcaatgtc | gatcgtggct | ggctcgaaga | tacctgcaag | aatgtcattg | 48180 |
| cgctgccatt | ctccaaattg | cagttcgcgc | ttagctggat | aacgccacgg | aatgatgtcg | 48240 |
| tcgtgcacaa | caatggtgac | ttctacagcg | cggagaatct | cgctctctcc | aggggaagcc | 48300 |
| gaagtttcca | aaaggtcgtt | gatcaaagct | cgccgcgttg | tttcatcaag | ccttacagtc | 48360 |
| accgtaacca | gcaaatcaat | atcactgtgt | ggcttcaggc | cgccatccac | tgcggagccg | 48420 |
| tacaaatgta | cggccagcaa | cgtcggttcg | agatggcgct | cgatgacgcc | aactacctct | 48480 |
| gatagttgag | tcgatacttc | ggcgatcacc | gcttccctca | tgatgtttaa | ctcctgaatt | 48540 |
| aagccgcgcc | gcgaagcggt | gtcggcttga | atgaattgtt | aggcgtcatc | ctgtgctccc | 48600 |
| gagaaccagt | accagtacat | cgctgtttcg | ttcgagactt | gaggtctagt | tttatacgtg | 48660 |
| aacaggtcaa | tgccgccgag | agtaaagcca | catttttgcgt | acaaattgca | ggcaggtaca | 48720 |
| ttgttcgttt | gtgtctctaa | tcgtatgcca | aggagctgtc | tgcttagtgc | ccacttttttc | 48780 |

-continued

```
gcaaattcga tgagactgtg cgcgactcct ttgcctcggt gcgtgtgcga cacaacaatg    48840
tgttcgatag aggctagatc gttccatgtt gagttgagtt caatcttccc gacaagctct    48900
tggtcgatga atgcgccata gcaagcagag tcttcatcag agtcatcatc cgagatgtaa    48960
tccttccggt aggggctcac acttctggta gatagttcaa agccttggtc ggataggtgc    49020
acatcgaaca cttcacgaac aatgaaatgg ttctcagcat ccaatgtttc cgccacctgc    49080
tcagggatca ccgaaatctt catatgacgc ctaacgcctg gcacagcgga tcgcaaacct    49140
ggcgcggctt ttggcacaaa aggcgtgaca ggtttgcgaa tccgttgctg ccacttgtta    49200
acccttttgc cagatttggt aactataatt tatgttagag gcgaagtctt gggtaaaaac    49260
tggcctaaaa ttgctgggga tttcaggaaa gtaaacatca ccttccggct cgatgtctat    49320
tgtagatata tgtagtgtat ctacttgatc gggggatctg ctgcctcgcg cgtttcggtg    49380
atgacggtga aaacctctga cacatgcagc tcccggagac ggtcacagct tgtctgtaag    49440
cggatgccgg gagcagacaa gcccgtcagg gcgcgtcagc gggtgttggc gggtgtcggg    49500
gcgcagccat gacccagtca cgtagcgata gcggagtgta tactggctta actatgcggc    49560
atcagagcag attgtactga gagtgcacca tatgcggtgt gaaataccgc acagatgcgt    49620
aaggagaaaa taccgcatca ggcgctcttc cgcttcctcg ctcactgact cgctgcgctc    49680
ggtcgttcgg ctgcggcgag cggtatcagc tcactcaaag gcggtaatac ggttatccac    49740
agaatcaggg gataacgcag gaaagaacat gtgagcaaaa ggccagcaaa aggccaggaa    49800
ccgtaaaaag gccgcgttgc tggcgttttt ccataggctc cgccccctg acgagcatca    49860
caaaaatcga cgctcaagtc agaggtggcg aaacccgaca ggactataaa gataccaggc    49920
gtttccccct ggaagctccc tcgtgcgctc tcctgttccg accctgccgc ttaccggata    49980
cctgtccgcc tttctccctt cgggaagcgt ggcgctttct catagctcac gctgtaggta    50040
tctcagttcg gtgtaggtcg ttcgctccaa gctgggctgt gtgcacgaac cccccgttca    50100
gcccgaccgc tgcgccttat ccggtaacta tcgtcttgag tccaacccgg taagacacga    50160
cttatcgcca ctggcagcag ccactggtaa caggattagc agagcgaggt atgtaggcgg    50220
tgctacagag ttcttgaagt ggtggcctaa ctacggctac actagaagga cagtatttgg    50280
tatctgcgct ctgctgaagc cagttacctt cggaaaaaga gttggtagct cttgatccgg    50340
caaacaaacc accgctggta gcggtggttt ttttgtttgc aagcagcaga ttacgcgcag    50400
aaaaaaagga tctcaagaag atcctttgat cttttctacg gggtctgacg ctcagtggaa    50460
cgaaaactca cgttaaggga ttttggtcat gagattatca aaaaggatct tcacctagat    50520
ccttttaaat taaaatgaa gttttaaatc aatctaaagt atatatgagt aaacttggtc    50580
tgacagttac caatgcttaa tcagtgaggc acctatctca gcgatctgtc tatttcgttc    50640
atccatagtt gcctgactcc ccgtcgtgta gataactacg atacgggagg gcttaccatc    50700
tggccccagt gctgcaatga taccgcgaga cccacgctca ccggctccag atttatcagc    50760
aataaaccag ccagccggaa gggccgagcg cagaagtggt cctgcaactt tatccgcctc    50820
catccagtct attaattgtt gccgggaagc tagagtaagt agttcgccag ttaatagttt    50880
gcgcaacgtt gttgccattg ctgca                                          50905
```

<210> SEQ ID NO 17
<211> LENGTH: 606
<212> TYPE: DNA
<213> ORGANISM: Arabidopsis thaliana

<400> SEQUENCE: 17

```
ggcttcctca acaaatcacc aattcatttc catgctaatc acagttctag ttatcttcaa    60
aacatcgtta gcgtttgaaa acttttcatc tgtcgatggt aatttcccgt tctcacctaa   120
acatgttata atcatcaaca ctttgcaccc acatggaaaa ttatacgtgc actgtaggaa   180
taaaggggaa gatttagggc ttcataagat agaatatcga gaacaaatag atttcaggtt   240
tcgtgtcaat ctacgcagaa caacaacata cacttgtaaa ttctcgtggc aggaaatga    300
aaagacgttc gatattttta gagcggatag agacgatagt tcaaaaagta caagtggaat   360
atgtagagaa tgtatttggt atatttgtga gacaggtcca tgtcgtgcta gacgcgatgg   420
agggatcca ttctgttttt catggacatc ttagagattg actggtatat cagattaaca    480
gatgaaaaga caattatga aatatcggaa tcaataaaaa gatggcactt ttaaattgaa    540
tatatatgtt ttttttcaa atgccaaaaa ttaatattta gtagatgaat aaagtgtctt    600
tagttt                                                              606
```

```
<210> SEQ ID NO 18
<211> LENGTH: 140
<212> TYPE: PRT
<213> ORGANISM: Arabidopsis thaliana

<400> SEQUENCE: 18

Met Leu Ile Thr Val Leu Val Ile Phe Lys Thr Ser Leu Ala Phe Glu
1               5                   10                  15
Asn Phe Ser Ser Val Asp Gly Asn Phe Pro Phe Ser Pro Lys His Val
            20                  25                  30
Ile Ile Ile Asn Thr Leu His Pro His Gly Lys Leu Tyr Val His Cys
        35                  40                  45
Arg Asn Lys Gly Glu Asp Leu Gly Leu His Lys Ile Glu Tyr Arg Glu
    50                  55                  60
Gln Ile Asp Phe Arg Phe Arg Val Asn Leu Arg Arg Thr Thr Thr Tyr
65                  70                  75                  80
Thr Cys Lys Phe Ser Trp Pro Gly Asn Glu Lys Thr Phe Asp Ile Phe
                85                  90                  95
Arg Ala Asp Arg Asp Asp Ser Ser Lys Ser Thr Ser Gly Ile Cys Arg
            100                 105                 110
Glu Cys Ile Trp Tyr Ile Cys Glu Thr Gly Pro Cys Arg Ala Arg Arg
        115                 120                 125
Asp Gly Asp Pro Phe Cys Phe Ser Trp Thr Ser
    130                 135                 140
```

```
<210> SEQ ID NO 19
<211> LENGTH: 551
<212> TYPE: DNA
<213> ORGANISM: Arabidopsis thaliana

<400> SEQUENCE: 19
aatacatcca tggcttcctt aacaaatcac caattcattt ccgtgctaat cacaactcta    60
gttatcttca aacgtcatt agcgtttgaa aactatacat ctgtcgatgt tgatcttccg    120
tttgcaccta acatgttat aatcatcaac acattgaacc cacatgaaag attggtcgtg    180
cactgtagga ataaagggaa agatctaggg gttcatgcgt agaacctca agaacaaata    240
gatttcaggt ttcgggtcaa tctacgcaga acaacaacat acacttgtac attctcgtgg   300
ccaggaaatg caaagacatt tgatattttt agagtagata gagacgataa ttcaaaaagt   360
acatgtggaa tatgtagaga atgtatttgg tatatttgtg agacaggtcc atgtcgtgct   420
```

```
agacgcgatg gagggctcc tttctgtttt tcatggacat cttagagatt gaatggtata      480
tcatattaac agatgaatag accaattgtg aaatatcgga atcaatagaa taacgacact      540
tttaaattga a                                                          551
```

```
<210> SEQ ID NO 20
<211> LENGTH: 151
<212> TYPE: PRT
<213> ORGANISM: Arabidopsis thaliana

<400> SEQUENCE: 20
```

```
Met Ala Ser Leu Thr Asn His Gln Phe Ile Ser Val Leu Ile Thr Thr
1               5                   10                  15

Leu Val Ile Phe Lys Thr Ser Leu Ala Phe Glu Asn Tyr Thr Ser Val
            20                  25                  30

Asp Val Asp Leu Pro Phe Ala Pro Lys His Val Ile Ile Asn Thr
        35                  40                  45

Leu Asn Pro His Glu Arg Leu Val Val His Cys Arg Asn Lys Gly Lys
    50                  55                  60

Asp Leu Gly Val His Ala Leu Glu Pro Gln Glu Gln Ile Asp Phe Arg
65                  70                  75                  80

Phe Arg Val Asn Leu Arg Arg Thr Thr Thr Tyr Thr Cys Thr Phe Ser
                85                  90                  95

Trp Pro Gly Asn Ala Lys Thr Phe Asp Ile Phe Arg Val Asp Arg Asp
            100                 105                 110

Asp Asn Ser Lys Ser Thr Cys Gly Ile Cys Arg Glu Cys Ile Trp Tyr
        115                 120                 125

Ile Cys Glu Thr Gly Pro Cys Arg Ala Arg Arg Asp Gly Gly Ala Pro
    130                 135                 140

Phe Cys Phe Ser Trp Thr Ser
145                 150
```

```
<210> SEQ ID NO 21
<211> LENGTH: 530
<212> TYPE: DNA
<213> ORGANISM: Arabidopsis thaliana

<400> SEQUENCE: 21
cacacatggc ttcttcaagc aatcaaaatt tcattttctt gttaattttc tttctcgctg      60
tccacaaaac atcgtcatca tttggaaatt attcgtccac cgaaggagtc ttactattct     120
cacctaaaca tgttatcatc atcaacaaat tggtcacact tgcaacgttg attgtgcatt     180
gtaggaacaa agggacgat ttaggggtaa taagcctcca acatttagct cgttttcatt      240
tcaggtttcg cgtcaatctt cgtaaaacaa caaagtacac ttgcagtttc gagtggcccg     300
gcaatacagc tacgtttgat attttagag ctgatagaga cgataatcca agaagtaaat     360
atggagtttg cagcgaatgt atttggagta tttatgagcc agctccttgt cgtgatagac     420
gtgatggagg ccagcctcag tgttttcctt gggcttctta gtcatttaaa atatttttcc     480
cttcatttac tttagtaata atataaataa aataatttgg tgtttgaatt                530
```

```
<210> SEQ ID NO 22
<211> LENGTH: 151
<212> TYPE: PRT
<213> ORGANISM: Arabidopsis thaliana

<400> SEQUENCE: 22
```

```
Met Ala Ser Ser Ser Asn Gln Asn Phe Ile Phe Leu Leu Ile Phe Phe
1               5                   10                  15

Leu Ala Val His Lys Thr Ser Ser Phe Gly Asn Tyr Ser Ser Thr
            20                  25                  30

Glu Gly Val Leu Leu Phe Ser Pro Lys His Val Ile Ile Asn Lys
                35                  40                  45

Leu Val Thr Leu Ala Thr Leu Ile Val His Cys Arg Asn Lys Gly Asp
    50                  55                  60

Asp Leu Gly Val Ile Ser Leu Gln His Leu Ala Arg Phe His Phe Arg
65                  70                  75                  80

Phe Arg Val Asn Leu Arg Lys Thr Thr Lys Tyr Thr Cys Ser Phe Glu
                85                  90                  95

Trp Pro Gly Asn Thr Ala Thr Phe Asp Ile Phe Arg Ala Asp Arg Asp
                100                 105                 110

Asp Asn Pro Arg Ser Lys Tyr Gly Val Cys Ser Glu Cys Ile Trp Ser
                115                 120                 125

Ile Tyr Glu Pro Ala Pro Cys Arg Asp Arg Arg Asp Gly Gly Gln Pro
    130                 135                 140

Gln Cys Phe Pro Trp Ala Ser
145                 150
```

<210> SEQ ID NO 23
<211> LENGTH: 574
<212> TYPE: DNA
<213> ORGANISM: Arabidopsis thaliana

<400> SEQUENCE: 23

```
attattatct cacaaattct taaaagtaaa acacactcat ggctttctca accaatcaaa      60
attttatttt tgtattattc ttattttttct ttatcctcaa acgtcagca tcattaacaa    120
atcactcgtc ccccgatggg cttttaccat tcgcacgtaa acatgttatc atcatcaaca    180
aattggtcac acgtgcaacg ttgattgtac attgtactaa caaaggggaa gatttagggg    240
taataagact caaccctcta gatcgttttg atttcaggtt tcgtgtcaat ctccgtaaaa    300
caacaacata cacttgcagt ttcgagtggc ccggcaatac agctacgttt gatatttta    360
gagctgatag agacgataat ccaagcggta atatggagt ttgcagcgaa tgtatatgga    420
gtatttatga gccagctcct tgtcgtgata gacgtgatgg aggccaacct cagtgttttc    480
cttgggcttc ttagtcatct aaaaatattt aagatatttg tattttccct ttcatttact    540
ttagtaataa taaaataaaa taattttgtg tttg                                 574
```

<210> SEQ ID NO 24
<211> LENGTH: 151
<212> TYPE: PRT
<213> ORGANISM: Arabidopsis thaliana

<400> SEQUENCE: 24

```
Met Ala Phe Ser Thr Asn Gln Asn Phe Ile Phe Val Leu Phe Leu Phe
1               5                   10                  15

Phe Phe Ile Leu Lys Thr Ser Ala Ser Leu Thr Asn His Ser Ser Pro
            20                  25                  30

Asp Gly Leu Leu Pro Phe Ala Arg Lys His Val Ile Ile Asn Lys
                35                  40                  45

Leu Val Thr Arg Ala Thr Leu Ile Val His Cys Thr Asn Lys Gly Glu
    50                  55                  60

Asp Leu Gly Val Ile Arg Leu Asn Pro Leu Asp Arg Phe Asp Phe Arg
```

```
                65                  70                  75                  80
Phe Arg Val Asn Leu Arg Lys Thr Thr Thr Tyr Thr Cys Ser Phe Glu
                    85                  90                  95

Trp Pro Gly Asn Thr Ala Thr Phe Asp Ile Phe Arg Ala Asp Arg Asp
                    100                 105                 110

Asp Asn Pro Ser Gly Lys Tyr Gly Val Cys Ser Glu Cys Ile Trp Ser
                    115                 120                 125

Ile Tyr Glu Pro Ala Pro Cys Arg Asp Arg Arg Asp Gly Gly Gln Pro
130                 135                 140

Gln Cys Phe Pro Trp Ala Ser
145                 150

<210> SEQ ID NO 25
<211> LENGTH: 453
<212> TYPE: DNA
<213> ORGANISM: Arabidopsis thaliana

<400> SEQUENCE: 25
atgaaaaaca tcctaaaaac acaagttcat gtggtggtaa tatatctact catcaaaata      60
gctttctcac aagtgaaaac cgattttgat gttaattggt ctacttcaaa atggtgagg     120 atcacaaacc gccttggtga tggtttgacc ttaaaccttc attgtaagtc cgcagatgac    180
gatcttggcc tcaaaatcct cgctccgaat ggttcttggt cgtttaagtt tagaacaagt    240
attgttggaa cgacactttt ctattgtcat ttcacatggc ctggacaatc aaaaaggttt    300
gacatttacg atgatgacag agatggtgtt cgtagtcata tttcatgcat caattgtatc    360
tgggatataa gcatacaagg gccatgcatg tttagtgaaa gtgatcatgc atttaatata    420
tgttatgatt ggaatgggaa tctaaggaca taa                                 453

<210> SEQ ID NO 26
<211> LENGTH: 150
<212> TYPE: PRT
<213> ORGANISM: Arabidopsis thaliana

<400> SEQUENCE: 26

Met Lys Asn Ile Leu Lys Thr Gln Val His Val Val Ile Tyr Leu
1               5                   10                  15

Leu Ile Lys Ile Ala Phe Ser Gln Val Lys Thr Asp Phe Asp Val Asn
                20                  25                  30

Trp Ser Thr Ser Lys Met Val Arg Ile Thr Asn Arg Leu Gly Asp Gly
            35                  40                  45

Leu Thr Leu Asn Leu His Cys Lys Ser Ala Asp Asp Leu Gly Leu
50                  55                  60

Lys Ile Leu Ala Pro Asn Gly Ser Trp Ser Phe Lys Phe Arg Thr Ser
65                  70                  75                  80

Ile Val Gly Thr Thr Leu Phe Tyr Cys His Phe Thr Trp Pro Gly Gln
                85                  90                  95

Ser Lys Arg Phe Asp Ile Tyr Asp Asp Arg Asp Gly Val Arg Ser
                    100                 105                 110

His Ile Ser Cys Ile Asn Cys Ile Trp Asp Ile Ser Ile Gln Gly Pro
                    115                 120                 125

Cys Met Phe Ser Glu Ser Asp His Ala Phe Asn Ile Cys Tyr Asp Trp
                    130                 135                 140

Asn Gly Asn Leu Arg Thr
145                 150
```

<210> SEQ ID NO 27
<211> LENGTH: 594
<212> TYPE: DNA
<213> ORGANISM: Arabidopsis thaliana

<400> SEQUENCE: 27

```
aatttacaga accatggctt ccattactaa ttctcattat atattgttgt ttcttatctt      60
ttttactttt attgtattta ctttagcatt agatttatca atgttgcag cagaagcacc     120
agacggcttg ttacctctgt ccaaaaagca cgttttaatt cgcaacactg ttcagaacgg    180
acaagttttg aatatacatt gcaaatccag tgaggatgat ttggggcata tccgtcttaa    240
acatggggat acttggggtt tcagatttcg tgttaacatg gcactaacta cgagatttcg    300
ttgtcacttt tggtggtatg cacgcgacca tctaggccat tatagttact ggtttgatat    360
atttactgta tacagagacg ataatccatt tggaaaatat ccaatttgcg atgaatgcgt    420
ttggaatatg tacgaattaa gtgaaaactt tatttgtcgt ataaatcgtg atcaatctgg    480
atggtgtttt aaaatggaca gagaaaatta agaagaaaac acattatcgt tcgatgtatc    540
ttatcctaat acaatcatta aaattgattg aataaaataa aatcgttgat acta          594
```

<210> SEQ ID NO 28
<211> LENGTH: 165
<212> TYPE: PRT
<213> ORGANISM: Arabidopsis thaliana

<400> SEQUENCE: 28

Met Ala Ser Ile Thr Asn Ser His Tyr Ile Leu Leu Phe Leu Ile Phe
1               5                   10                  15

Phe Thr Phe Ile Val Phe Thr Leu Ala Leu Asp Leu Ser Asn Val Ala
            20                  25                  30

Ala Glu Ala Pro Asp Gly Leu Leu Pro Leu Ser Lys Lys His Val Leu
        35                  40                  45

Ile Arg Asn Thr Val Gln Asn Gly Gln Val Leu Asn Ile His Cys Lys
    50                  55                  60

Ser Ser Glu Asp Asp Leu Gly His Ile Arg Leu Lys His Gly Asp Thr
65                  70                  75                  80

Trp Gly Phe Arg Phe Arg Val Asn Met Ala Leu Thr Thr Arg Phe Arg
                85                  90                  95

Cys His Phe Trp Trp Tyr Ala Arg Asp His Leu Gly His Tyr Ser Tyr
            100                 105                 110

Trp Phe Asp Ile Phe Thr Val Tyr Arg Asp Asp Asn Pro Phe Gly Lys
        115                 120                 125

Tyr Pro Ile Cys Asp Glu Cys Val Trp Asn Met Tyr Glu Leu Ser Glu
    130                 135                 140

Asn Phe Ile Cys Arg Ile Asn Arg Asp Gln Ser Gly Trp Cys Phe Lys
145                 150                 155                 160

Met Asp Arg Glu Asn
            165

<210> SEQ ID NO 29
<211> LENGTH: 456
<212> TYPE: DNA
<213> ORGANISM: Arabidopsis lyrata

<400> SEQUENCE: 29

```
atggcttcct caacaaataa ccacttcact ttcctgcttc tctcattttt atttatccca      60
```

```
aaaaaatcgt catctttggg aaatcattcg tccatcgatg gaattttact gttttcacct    120
aaacatgtcg tgatctacaa cacattgacc acacgtgcaa cattggtcgt acattgcatg    180
aataaagaga aagatttggg gataaaaaag ctcccaattg gagctagttt tgatttcagg    240
tttcatgtca attttcgtaa aacaacaacg tataattgca ctttcgagtg gcccggaagt    300
aaagagaaat ttgatatttt tagggcagac agagacgaca gtgcaacaag tcctattggg    360
gtctgtagag aatgtatatg gtacatttat gaaccagccc cttgtcgtga aaaacgtgac    420
ggaggccatt ctatatgctt ttcatgggat ccatag                              456
```

```
<210> SEQ ID NO 30
<211> LENGTH: 151
<212> TYPE: PRT
<213> ORGANISM: Arabidopsis lyrata

<400> SEQUENCE: 30

Met Ala Ser Ser Thr Asn Asn His Phe Thr Phe Leu Leu Ser Phe
1               5                   10                  15

Leu Phe Ile Pro Lys Lys Ser Ser Leu Gly Asn His Ser Ser Ile
                20                  25                  30

Asp Gly Ile Leu Leu Phe Ser Pro Lys His Val Val Ile Tyr Asn Thr
            35                  40                      45

Leu Thr Thr Arg Ala Thr Leu Val Val His Cys Met Asn Lys Glu Lys
        50                  55                  60

Asp Leu Gly Ile Lys Lys Leu Pro Ile Gly Ala Ser Phe Asp Phe Arg
65                  70                  75                  80

Phe His Val Asn Phe Arg Lys Thr Thr Thr Tyr Asn Cys Thr Phe Glu
                85                  90                  95

Trp Pro Gly Ser Lys Glu Lys Phe Asp Ile Phe Arg Ala Asp Arg Asp
                100                 105                 110

Asp Ser Ala Thr Ser Pro Ile Gly Val Cys Arg Glu Cys Ile Trp Tyr
            115                 120                 125

Ile Tyr Glu Pro Ala Pro Cys Arg Glu Lys Arg Asp Gly Gly His Ser
        130                 135                 140

Ile Cys Phe Ser Trp Asp Pro
145                 150
```

```
<210> SEQ ID NO 31
<211> LENGTH: 435
<212> TYPE: DNA
<213> ORGANISM: Populus balsamifera subsp. trichocarpa

<400> SEQUENCE: 31
atgatttctt tcaccagcca tttcgcccta ctgatattat tatccgtgtt gctgctgatc     60
atagctacgt gtgatgcagg ttgtctatgg aaaccaacac gtttgaatat caataatgac    120
ttgggcccag gcctggacct tacaatccat tgcaaatcca aaaacgacga tcttgggcag    180
catgtagtcc cttctggtgg cgaatataca attgattttt gctccaactt tggagaagc     240 acactgttct tctgtggcct gtcatggtca ggaaaattcc attggtttga tgtctacgat    300
gcttccaggg attctagtcg ctgtggaaat tgcaattgga caatacatgc aactgggcca    360
tgcatggatt attataatta ttataccaag gaatttgtat gttatccttg gaatgacaag    420
gcatatctcc agtaa                                                     435
```

```
<210> SEQ ID NO 32
<211> LENGTH: 144
```

```
<212> TYPE: PRT
<213> ORGANISM: Populus balsamifera subsp. trichocarpa

<400> SEQUENCE: 32

Met Ile Ser Phe Thr Ser His Phe Ala Leu Leu Ile Leu Leu Ser Val
1               5                   10                  15

Leu Leu Leu Ile Ile Ala Thr Cys Asp Ala Gly Cys Leu Trp Lys Pro
            20                  25                  30

Thr Arg Leu Asn Ile Asn Asn Asp Leu Gly Pro Gly Leu Asp Leu Thr
        35                  40                  45

Ile His Cys Lys Ser Lys Asn Asp Asp Leu Gly Gln His Val Val Pro
    50                  55                  60

Ser Gly Gly Glu Tyr Thr Ile Asp Phe Cys Ser Asn Phe Trp Arg Ser
65                  70                  75                  80

Thr Leu Phe Phe Cys Gly Leu Ser Trp Ser Gly Lys Phe His Trp Phe
                85                  90                  95

Asp Val Tyr Asp Ala Ser Arg Asp Ser Ser Arg Cys Gly Asn Cys Asn
            100                 105                 110

Trp Thr Ile His Ala Thr Gly Pro Cys Met Asp Tyr Tyr Asn Tyr Tyr
        115                 120                 125

Thr Lys Glu Phe Val Cys Tyr Pro Trp Asn Asp Lys Ala Tyr Leu Gln
    130                 135                 140

<210> SEQ ID NO 33
<211> LENGTH: 486
<212> TYPE: DNA
<213> ORGANISM: Vitis vinifera

<400> SEQUENCE: 33
atgttgtcat tggataggta tttgttttca tttgtgctgc ttgtgttttct tgttcgtttg    60
tgtgatgggg gtcctggggt tgtcgaaaag aaagtggatt taaagatcat caatggcctt   120
gacgctggca cagatcttaa tgtccactgt aaatccaaaa acgatgacct tggcgctcat   180
gtcctggcct ttgatcaatt cttttgaattc cgtttccgac caaacttctg ggggactacc   240
ttatacttct gtaggttctg gtggaacagt gaatcccatt ggtttgacat atacgttcag   300
aagagggatg caggccgatg taacaagaag tgctggtggt atgtgggagc cgatggtcct   360
tgcttactga atgataaaat tggagtatac gatatttgcg aaaactgaa ggatggcggt   420
tcaagtcaag aagggactgg aaacgacaca gctagaatct acaatgaaat atttggaggg   480
cagtga                                                              486

<210> SEQ ID NO 34
<211> LENGTH: 161
<212> TYPE: PRT
<213> ORGANISM: Vitis vinifera

<400> SEQUENCE: 34

Met Leu Ser Leu Asp Arg Tyr Leu Phe Ser Phe Val Leu Leu Val Phe
1               5                   10                  15

Leu Val Arg Leu Cys Asp Gly Gly Pro Gly Val Val Glu Lys Lys Val
            20                  25                  30

Asp Leu Lys Ile Ile Asn Gly Leu Asp Ala Gly Thr Asp Leu Asn Val
        35                  40                  45

His Cys Lys Ser Lys Asn Asp Asp Leu Gly Ala His Val Leu Ala Phe
    50                  55                  60

Asp Gln Phe Phe Glu Phe Arg Phe Arg Pro Asn Phe Trp Gly Thr Thr
```

```
                65                  70                  75                  80
Leu Tyr Phe Cys Arg Phe Trp Trp Asn Ser Glu Ser His Trp Phe Asp
                    85                  90                  95
Ile Tyr Val Gln Lys Arg Asp Ala Gly Arg Cys Asn Lys Lys Cys Trp
                100                 105                 110
Trp Tyr Val Gly Ala Asp Gly Pro Cys Leu Leu Asn Asp Lys Ile Gly
                115                 120                 125
Val Tyr Asp Ile Cys Glu Asn Trp Lys Asp Gly Ser Ser Gln Glu
130                 135                 140
Gly Thr Gly Asn Asp Thr Ala Arg Ile Tyr Asn Glu Ile Phe Gly Gly
145                 150                 155                 160
Gln

<210> SEQ ID NO 35
<211> LENGTH: 151
<212> TYPE: PRT
<213> ORGANISM: Arabidopsis thaliana

<400> SEQUENCE: 35

Met Ala Phe Ser Thr Asn Gln Asn Phe Ile Phe Val Leu Phe Leu Phe
1               5                   10                  15
Phe Phe Ile Leu Lys Thr Ser Ala Ser Leu Thr Asn His Ser Ser Pro
                20                  25                  30
Asp Gly Leu Leu Pro Phe Ala Arg Lys His Val Ile Ile Asn Lys
            35                  40                  45
Leu Val Thr Arg Ala Thr Leu Ile Val His Cys Thr Asn Lys Gly Glu
50                  55                  60
Asp Leu Gly Val Ile Arg Leu Asn Pro Leu Asp Arg Phe Asp Phe Arg
65                  70                  75                  80
Phe Arg Val Asn Leu Arg Lys Thr Thr Thr Tyr Thr Cys Ser Phe Glu
                85                  90                  95
Trp Pro Gly Asn Thr Ala Thr Phe Asp Ile Phe Arg Ala Asp Arg Asp
                100                 105                 110
Asp Asn Pro Ser Gly Lys Tyr Gly Val Cys Ser Glu Cys Ile Trp Ser
            115                 120                 125
Ile Tyr Glu Pro Ala Pro Cys Arg Asp Arg Asp Gly Gly Gln Pro
130                 135                 140
Gln Cys Phe Pro Trp Ala Ser
145                 150

<210> SEQ ID NO 36
<211> LENGTH: 150
<212> TYPE: PRT
<213> ORGANISM: Arabidopsis thaliana

<400> SEQUENCE: 36

Met Lys Asn Ile Leu Lys Thr Gln Val His Val Val Ile Tyr Leu
1               5                   10                  15
Leu Ile Lys Ile Ala Phe Ser Gln Val Lys Thr Asp Phe Asp Val Asn
                20                  25                  30
Trp Ser Thr Ser Lys Met Val Arg Ile Thr Asn Arg Leu Gly Asp Gly
            35                  40                  45
Leu Thr Leu Asn Leu His Cys Lys Ser Ala Asp Asp Leu Gly Leu
50                  55                  60
Lys Ile Leu Ala Pro Asn Gly Ser Trp Ser Phe Lys Phe Arg Thr Ser
65                  70                  75                  80
```

```
Ile Val Gly Thr Thr Leu Phe Tyr Cys His Phe Thr Trp Pro Gly Gln
                85                  90                  95

Ser Lys Arg Phe Asp Ile Tyr Asp Asp Arg Asp Gly Val Arg Ser
            100                 105                 110

His Ile Ser Cys Ile Asn Cys Ile Trp Asp Ile Ser Ile Gln Gly Pro
            115                 120                 125

Cys Met Phe Ser Glu Ser Asp His Ala Phe Asn Ile Cys Tyr Asp Trp
    130                 135                 140

Asn Gly Asn Leu Arg Thr
145             150

<210> SEQ ID NO 37
<211> LENGTH: 166
<212> TYPE: PRT
<213> ORGANISM: Arabidopsis thaliana

<400> SEQUENCE: 37

Met Ala Ser Ile Thr Asn Ser His Leu Thr Leu Leu Phe Leu Ile Ser
1               5                   10                  15

Ser Thr Phe Ile Ile Phe Thr Leu Ala Leu Glu Phe Ser Asp Val Thr
            20                  25                  30

Ala Glu Ala Pro Asp Gly Phe Leu Pro Leu Ala Lys Lys His Val Val
        35                  40                  45

Ile Arg Asn Thr Val Lys Asn Gly Glu Glu Leu Asn Ile His Cys Lys
    50                  55                  60

Ser Ser Glu Asn Asn Leu Gly His Ile His Leu Lys His Gly His Thr
65                  70                  75                  80

Trp Asp Phe Arg Phe Leu Val Asn Ile Ser Lys Ser Thr Lys Phe Arg
                85                  90                  95

Cys His Phe Trp Trp Tyr Ala Gly Asn Lys Lys Phe Phe Asn Tyr Trp
            100                 105                 110

Phe Asp Ile Phe Thr Val Ser Arg Asp Asp Lys Pro Ser Gly Arg Tyr
            115                 120                 125

Pro Val Cys Gln Glu Cys Ile Trp Asp Leu Ser Asp Tyr Gly Pro Glu
    130                 135                 140

Gly Tyr Ile Cys Arg Ile Asn Arg Asp Lys Ser Glu Pro Trp Cys Phe
145                 150                 155                 160

Pro Met Asp Asp Glu Pro
                165

<210> SEQ ID NO 38
<211> LENGTH: 161
<212> TYPE: PRT
<213> ORGANISM: Arabidopsis thaliana

<400> SEQUENCE: 38

Met Asp Ile Pro Lys Gln Tyr Leu Ser Leu Phe Ile Leu Ile Ile Phe
1               5                   10                  15

Ile Thr Thr Lys Leu Ser Gln Ala Asp His Lys Asn Asp Ile Pro Val
            20                  25                  30

Pro Asn Asp Pro Ser Ser Thr Asn Ser Val Phe Pro Thr Ser Lys Arg
        35                  40                  45

Thr Val Glu Ile Asn Asn Asp Leu Gly Asn Gln Leu Thr Leu Leu Tyr
    50                  55                  60

His Cys Lys Ser Lys Asp Asp Leu Gly Asn Arg Thr Leu Gln Pro
65                  70                  75                  80
```

```
Gly Glu Ser Trp Ser Phe Ser Phe Gly Arg Gln Phe Gly Arg Thr
                85                  90                  95

Leu Tyr Phe Cys Ser Phe Ser Trp Pro Asn Glu Ser His Ser Phe Asp
            100                 105                 110

Ile Tyr Lys Asp His Arg Asp Ser Gly Gly Asp Asn Lys Cys Glu Ser
            115                 120                 125

Asp Arg Cys Val Trp Lys Ile Arg Arg Asn Gly Pro Cys Arg Phe Asn
130                 135                 140

Asp Glu Thr Lys Gln Phe Asp Leu Cys Tyr Pro Trp Asn Lys Ser Leu
145                 150                 155                 160

Tyr
```

<210> SEQ ID NO 39
<211> LENGTH: 153
<212> TYPE: PRT
<213> ORGANISM: Arabidopsis thaliana

<400> SEQUENCE: 39

```
Met Gly Ser Leu Val Glu Leu Val Ala Phe Leu Val Thr Met Cys Val
1               5                   10                  15

Ser Val Thr Ile Ser Arg Gly Gln Lys Asp Ser Ile Pro Pro Thr Pro
                20                  25                  30

Thr Ser Gly Phe Asp Asn Pro Arg Thr Thr Val Val Ile Tyr Asn Asp
            35                  40                  45

Leu Gly Gly His Leu Pro Leu Arg Tyr His Cys Lys Ser Lys Asn Asp
        50                  55                  60

Asp Leu Gly Asp Arg Asn Met Ala Val Asn Gly Thr Trp Ser Phe Glu
65                  70                  75                  80

Phe Arg Pro Ser Val Phe Gly Thr Leu Phe Cys Gly Phe Ile
                85                  90                  95

Trp Asp Lys Glu Leu His Trp Phe Asp Ile Tyr Lys Gln Ser Arg Asp
            100                 105                 110

Arg Glu Phe Ala Glu Phe Gly Cys Arg Arg Cys Glu Trp Lys Ile Arg
        115                 120                 125

Lys Asp Gly Pro Cys Lys Leu Asn Lys Asn Ser Asn Met Phe Asp Val
130                 135                 140

Cys Leu Pro Trp Asn Ser Gln Ser Leu
145                 150
```

<210> SEQ ID NO 40
<211> LENGTH: 477
<212> TYPE: PRT
<213> ORGANISM: Arabidopsis lyrata

<400> SEQUENCE: 40

```
Met Ala Ser Ser Thr Asn Gln Phe Phe Ile Phe Val Leu Phe Leu Phe
1               5                   10                  15

Leu Phe Val Leu Lys Thr Ser Ala Ser Leu Ala Tyr His Ser Ser Pro
                20                  25                  30

Asp Gly Leu Leu Pro Phe Ser Ser Lys His Val Ile Ile Asn Lys
            35                  40                  45

Leu Val Thr Arg Ala Thr Leu Ile Val His Cys Thr Asn Lys Gly Asp
        50                  55                  60

Asp Leu Gly Val Ile Arg Leu Asn Pro Leu Asp Ser Phe Asp Phe Arg
65                  70                  75                  80
```

```
Phe Arg Val Asn Leu Arg Lys Thr Thr Thr Tyr Thr Cys Ser Phe Glu
                85                  90                  95
Trp Pro Gly Asn Thr Ala Thr Phe Asp Ile Phe Arg Ala Asp Arg Asp
           100                 105                 110
Asp Asn Pro Lys Ser Lys Tyr Gly Val Cys Ser Glu Cys Ile Trp Arg
       115                 120                 125
Phe Phe Pro Phe Ala Ser Lys His Val Ile Ile Asn Lys Leu Val
130                 135                 140
Thr Leu Ala Thr Leu Ile Val His Cys Arg Asn Lys Gly Asp Asp Leu
145                 150                 155                 160
Gly Val Ile Ser Leu Gln His Leu Ala Arg Phe Asp Phe Arg Phe Arg
                165                 170                 175
Val Asn Leu Arg Lys Thr Thr Thr Tyr Thr Cys Ser Phe Glu Trp Pro
                180                 185                 190
Gly Asn Thr Ala Thr Phe Asp Ile Phe Arg Ala Asp Arg Asp Asp Asn
            195                 200                 205
Pro Arg Ala Phe Gly Asn Phe Leu Ser Val Asp Gly Gly Phe Pro Phe
        210                 215                 220
Ser Pro Lys His Val Val Ile Ile Asn Thr Leu Asn Ser His Glu Ile
225                 230                 235                 240
Leu Val Val His Cys Arg Asn Lys Gly Lys Asp Leu Gly Phe Arg Ala
                245                 250                 255
Leu Gln Ser Gln Glu Gln Ile Asp Phe Arg Phe His Val Asn Leu Arg
                260                 265                 270
Arg Thr Thr Thr Tyr Thr Cys Thr Phe Ser Trp Pro Gly Asn Ala Lys
        275                 280                 285
Thr Phe Asp Ile Phe Arg Val Asp Arg Asp Asp Asn Ser Lys Ser Thr
    290                 295                 300
Cys Gly Ile Cys Lys Glu Cys Ile Cys Lys Glu Lys Tyr Cys Val Thr
305                 310                 315                 320
Lys Pro Leu Asn Pro Ser Met Ala Ser Ser Thr Asn Asn His Phe Thr
                325                 330                 335
Phe Leu Leu Leu Ser Phe Leu Phe Ile Pro Lys Lys Ser Ser Ser Leu
                340                 345                 350
Gly Asn His Ser Ser Ile Asp Gly Ile Leu Leu Phe Ser Pro Lys His
            355                 360                 365
Val Val Ile Tyr Asn Thr Leu Thr Thr Arg Ala Thr Leu Val Val His
    370                 375                 380
Cys Met Asn Lys Glu Lys Asp Leu Gly Ile Lys Lys Leu Pro Ile Gly
385                 390                 395                 400
Ala Ser Phe Asp Phe Arg Phe His Val Asn Phe Arg Lys Thr Thr Thr
                405                 410                 415
Tyr Asn Cys Thr Phe Glu Trp Pro Gly Ser Lys Glu Lys Phe Asp Ile
            420                 425                 430
Phe Arg Ala Asp Arg Asp Asp Ser Ala Thr Ser Pro Ile Gly Val Cys
        435                 440                 445
Arg Glu Cys Ile Trp Tyr Ile Tyr Glu Pro Ala Pro Cys Arg Glu Lys
    450                 455                 460
Arg Asp Gly Gly His Ser Ile Cys Phe Ser Trp Asp Pro
465                 470                 475
```